US012696683B2

(12) United States Patent
Lee et al.

(10) Patent No.: US 12,696,683 B2
(45) Date of Patent: Jul. 28, 2026

(54) ORGANIC ELECTROLUMINESCENT COMPOUND, A PLURALITY OF HOST MATERIALS, AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Su-Hyun Lee, Gyeonggi-do (KR); So-Young Jung, Gyeonggi-do (KR); Sang-Hee Cho, Gyeonggi-do (KR); Jin-Ri Hong, Gyeonggi-do (KR); So-Mi Park, Gyeonggi-do (KR); Hae-Yeon Kim, Gyeonggi-do (KR); Tae-Jun Han, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 961 days.

(21) Appl. No.: 17/500,575

(22) Filed: Oct. 13, 2021

(65) Prior Publication Data

US 2022/0131083 A1 Apr. 28, 2022

(30) Foreign Application Priority Data

Oct. 26, 2020 (KR) ........................ 10-2020-0139106
Mar. 2, 2021 (KR) ........................ 10-2021-0027268
Oct. 7, 2021 (KR) ........................ 10-2021-0133134

(51) Int. Cl.

| | |
|---|---|
| ***H10K 85/60*** | (2023.01) |
| ***C07C 211/61*** | (2006.01) |
| ***C07D 307/91*** | (2006.01) |
| ***C07D 403/10*** | (2006.01) |
| ***C07D 405/04*** | (2006.01) |
| ***C07D 405/10*** | (2006.01) |
| ***C07D 405/14*** | (2006.01) |
| ***C07D 413/04*** | (2006.01) |
| ***C07D 413/14*** | (2006.01) |
| ***C09K 11/06*** | (2006.01) |
| ***H10K 50/11*** | (2023.01) |
| ***H10K 101/00*** | (2023.01) |
| ***H10K 101/10*** | (2023.01) |

(52) U.S. Cl.

CPC .......... *H10K 85/654* (2023.02); *C07C 211/61* (2013.01); *C07D 307/91* (2013.01); *C07D 403/10* (2013.01); *C07D 405/04* (2013.01); *C07D 405/10* (2013.01); *C07D 405/14* (2013.01); *C07D 413/04* (2013.01); *C07D 413/14* (2013.01); *C09K 11/06* (2013.01); *H10K 85/615* (2023.02); *H10K 85/622* (2023.02); *H10K 85/626* (2023.02); *H10K 85/633* (2023.02); *H10K 85/636* (2023.02); *H10K 85/657* (2023.02); *H10K 85/6572* (2023.02); *H10K 85/6574* (2023.02); *C07C 2603/18* (2017.05); *C07C 2603/48* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 2101/10* (2023.02); *H10K 2101/90* (2023.02)

(58) Field of Classification Search

CPC ............. H10K 2101/90; H10K 85/631; H10K 85/633; H10K 85/636; H10K 85/654

See application file for complete search history.

(56) References Cited

U.S. PATENT DOCUMENTS

| | | | | |
|---|---|---|---|---|
| 11,856,843 | B2 * | 12/2023 | Mun | H10K 85/6574 |
| 2010/0096982 | A1 | 4/2010 | Eum et al. | |
| 2011/0037381 | A1 | 2/2011 | Rostovtsev et al. | |
| 2011/0147718 | A1 * | 6/2011 | Howard, Jr. | H10K 85/633 252/301.16 |
| 2011/0288292 | A1 † | 11/2011 | Parham | |
| 2018/0053898 | A1 | 2/2018 | Kim et al. | |
| 2021/0135142 | A1 * | 5/2021 | Li | H10K 85/658 |
| 2021/0184129 | A1 * | 6/2021 | Mun | C07D 409/14 |
| 2021/0359216 | A1 * | 11/2021 | Kim | H10K 85/626 |
| 2022/0123233 | A1 * | 4/2022 | Lee | H10K 85/6574 |

FOREIGN PATENT DOCUMENTS

| | | | | |
|---|---|---|---|---|
| JP | 2000012229 | A2 † | 1/2000 | |
| KR | 20190005522 | A * | 1/2019 | C09K 11/06 |
| WO | 08149968 | A1 † | 12/2008 | |
| WO | WO-2010068865 | A2 * | 6/2010 | C09B 57/008 |
| WO | WO-2011019360 | A1 * | 2/2011 | C09K 11/06 |
| WO | WO-2020045976 | A1 * | 3/2020 | C09K 11/06 |
| WO | WO-2020080693 | A1 * | 4/2020 | C07D 405/10 |

OTHER PUBLICATIONS

Notification of Third Party Observation from Korean Intellectual Property Office, Application No. 10-2021-0133134 Application Date: Oct. 7, 2021.

* cited by examiner
† cited by third party

*Primary Examiner* — Vu A Nguyen
(74) *Attorney, Agent, or Firm* — G. Creston Campbell

(57) ABSTRACT

The present disclosure relates to a plurality of host materials comprising a first host material including a compound represented by formula 1 and a second host material including a compound represented by formula 2, and an organic electroluminescent device comprising the same. By comprising the organic electroluminescent compound and/or a specific combination of compounds according to the present disclosure as host materials, an organic electroluminescent device having high luminous efficiency and long lifespan property can be provided.

6 Claims, No Drawings

ORGANIC ELECTROLUMINESCENT COMPOUND, A PLURALITY OF HOST MATERIALS, AND ORGANIC ELECTROLUMINESCENT DEVICE COMPRISING THE SAME

TECHNICAL FIELD

The present disclosure relates to an organic electroluminescent compound, a plurality of host materials, and an organic electroluminescent device comprising the same.

BACKGROUND ART

The organic electroluminescent device (OLED) was first developed by Eastman Kodak in 1987, by using small aromatic diamine molecules and aluminum complexes as materials for forming a light-emitting layer [Appl. Phys. Lett. 51, 913, 1987].

The most important factor determining luminous efficiency in an OLED is light-emitting materials. The light-emitting material is classified into a host material and a dopant material in a functional aspect. A light-emitting material can be used as a combination of a host and a dopant to improve color purity, luminous efficiency, and stability. Generally, a device having excellent electroluminescent (EL) characteristics has a structure comprising a light-emitting layer formed by doping a dopant to a host. When using such a dopant/host material system as a light-emitting material, their selection is important since host materials greatly influence the efficiency and lifespan of the light-emitting device.

Recently, an urgent task is the development of an OLED having high efficiency and long lifespan property. In particular, the development of highly excellent light-emitting material over conventional light-emitting materials is urgently required, considering the EL properties necessary for medium and large-sized OLED panels.

Korean Patent No. 10-1545774 discloses an organic electronic device comprising a compound having a chrysene moiety in the light-emitting layer. However, said reference does not specifically disclose a specific combination of host materials as described in the present disclosure. In addition, there is still a need for development of a light-emitting material having improved performances, such as improved luminous efficiency, and lifespan property, compared to the conventional disclosed specific combination of compounds.

DISCLOSURE OF THE INVENTION

Problems to be Solved

The object of the present disclosure is firstly, to provide a plurality of host materials which is able to produce an organic electroluminescent device having high luminous efficiency and long lifespan property, and secondly, to provide an organic electroluminescent device comprising the host materials.

The other object of the present disclosure is to provide a novel structure of an organic electroluminescent compound suitable for use as organic electroluminescent material.

Solution to Problems

As a result of intensive studies to solve the technical problem above, the present inventors found that the aforementioned objective can be achieved by a plurality of host materials comprising a first host material including a compound represented by the following formula 1 and a second host material including a compound represented by the following formula 2, so that the present invention was completed.

(1)

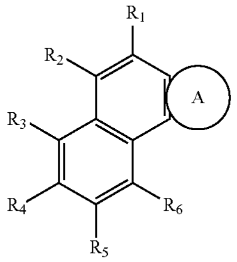

In formula 1,

Ring A represents a substituted or unsubstituted benzene ring or a substituted or unsubstituted naphthalene ring;

$R_1$ to $R_6$ each independently represent, hydrogen, deuterium, halogen, cyano, a substituted or unsubstituted (C1-C30)alkyl, a substituted or unsubstituted (C3-C30)cycloalkyl, a substituted or unsubstituted (3- to 7-membered) heterocycloalkyl, a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or *-$L_1$-$NAr_1Ar_2$; provided that at least one of $R_1$ to $R_6$ is *-$L_1$-$NAr_1Ar_2$;

$L_1$ represents a single bond, a substituted or unsubstituted (C6-C30)arylene, or a substituted or unsubstituted (3- to 30-membered)heteroarylene; and $Ar_1$ and $Ar_2$ each independently represent, a substituted or unsubstituted (C1-C30)alkyl, a substituted or unsubstituted (C2-C30)alkenyl, a substituted or unsubstituted (C6-C30) aryl, or a substituted or unsubstituted (3- to 30-membered) heteroaryl;

$$(Ar_{11}\text{-}L_{11})_a\text{-}HAr \quad (2)$$

in formula 2,

HAr represents a substituted or unsubstituted nitrogen-containing (3- to 20-membered)heteroaryl;

$L_{11}$ represents a single bond, a substituted or unsubstituted (C6-C30)arylene, or a substituted or unsubstituted (3- to 30-membered)heteroarylene;

$Ar_{11}$ represents a substituted or unsubstituted (C1-C30) alkyl, a substituted or unsubstituted (C3-C30)cycloalkyl, a substituted or unsubstituted (3- to 7-membered)heterocycloalkyl, a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or*-$L_{21}$-$NAr_{21}Ar_{22}$;

$L_{21}$ represents a single bond, a substituted or unsubstituted (C6-C30)arylene, or a substituted or unsubstituted (3- to 30-membered)heteroarylene.

$Ar_{21}$ and $Ar_{22}$ each independently represent, a substituted or unsubstituted (C1-C30)alkyl, a substituted or unsubstituted (C2-C30)alkenyl, a substituted or unsubstituted (C6-C30)aryl, or a substituted or unsubstituted (3- to 30-membered)heteroaryl; and a represents an integer of 1 to 3, and when a represents an integer of 2 or more, each of $-(L_{11}-Ar_{11})$ may be the same or different.

Advantageous Effects of Invention

By comprising an organic electroluminescent compound and/or the specific combination of the compounds according to the present disclosure as host materials, an organic electroluminescent device having a high luminous efficiency and long lifespan property can be manufactured.

EMBODIMENTS OF THE INVENTION

Hereinafter, the present disclosure will be described in detail. However, the following description is intended to explain the invention, and is not meant in any way to restrict the scope of the invention.

The present disclosure relates to a plurality of host materials comprising a first host material including at least one compound represented by the formula 1 and a second host material including at least one compound represented by the formula 2, and an organic electroluminescent device comprising the host materials.

The present disclosure relates to an organic electroluminescent compound represented by formula 1-1' and/or an organic electroluminescent compound represented by formula 1-2', and an organic electroluminescent device comprising the organic electroluminescent compound.

The term "organic electroluminescent compound" in the present disclosure means a compound that may be used in an organic electroluminescent device, and may be comprised in any material layer constituting an organic electroluminescent device, as necessary.

Herein, "organic electroluminescent material" means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (containing host and dopant materials), an electron buffer material, a hole blocking material, an electron transport material, or an electron injection material, etc.

The term "a plurality of organic electroluminescent materials" in the present disclosure means an organic electroluminescent material comprising a combination of at least two compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials may be a combination of at least two compounds, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. Such at least two compounds may be comprised in the same layer or different layers, and may be mixture-evaporated or co-evaporated, or may be individually evaporated.

Herein, "a plurality of host materials" means an organic electroluminescent material comprising a combination of at least two host materials. It may mean both a material before being comprised in an organic electroluminescent device (e.g., before vapor deposition) and a material after being comprised in an organic electroluminescent device (e.g., after vapor deposition). A plurality of host materials of the present disclosure may be comprised in any light-emitting layer constituting an organic electroluminescent device. The at least two compounds comprised in a plurality of host materials may be comprised together in one light-emitting layer, or may each be comprised in separate light-emitting layers. When at least two compounds are comprised in one light-emitting layer, the at least two compounds may be mixture-evaporated to form a layer or may be individually and simultaneously co-evaporated to form a layer.

Herein, "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, sec-butyl, etc. Herein, the term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. Herein, "(C6-C30)aryl(ene)" is a monocyclic or fused ring radical derived from an aromatic hydrocarbon having 6 to 30 ring backbone carbon atoms, in which the number of the ring backbone carbon atoms is preferably 6 to 20, more preferably 6 to 15, may be partially saturated, and may include a spiro structure. Examples of the aryl specifically may be phenyl, biphenyl, terphenyl, quaterphenyl, naphthyl, binaphthyl, phenyinaphthyl, naphthylphenyl, fluorenyl, phenylfluorenyl, dimethyifluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, tolyl, xylyl, mesityl, cumenyl spiro[fluoren-fluoren]yl, spiro[fluoren-benzofluoren]yl, azulenyl, tetramethyl-dihydrophenanthrenyl, etc. More specifically, the aryl may be o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenyl, 4''-t-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, benzofluoranthenyl, 11,11-dimethyl-1-benzo[a]

fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc. Herein. "(3- to 30-membered) heteroaryl(ene)" is an aryl having 3 to 30 ring backbone atoms including at least one, preferably 1 to 4 heteroatoms selected from the group consisting of B, N, O, S, Si, P, Se, and Ge, in which the number of the ring backbone carbon atoms is preferably 3 to 30, more preferably 5 to 20. The above heteroaryl(ene) may be a monocyclic ring, or a fused ring condensed with at least one benzene ring: and may be partially saturated. Also, the above heteroaryl or heteroarylene herein may be one formed by linking at least one heteroaryl or aryl group to a heteroaryl group via a single bond(s) and may include a spiro structure. Examples of the heteroaryl specifically may be a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, dibenzoselenophenyl, benzofuroquinolinyl, benzofuroquinazolinyl, benzofuronaphthiridinyl, benzofuropyrimidinyl, naphthofuropyrimidinyl, benzothienoquinolinyl, benzothienoquinazolinyl, benzothienonaphthiridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzoimidazolyl, benzothiazolyl, benzoisothiazolyl, benzoisoxazolyl, benzoxazolyl, imidazopyridinyl, isoindolyl, indolyl, benzoindolyl, indazolyl, benzothiadiazolyl, quinolyl, isoquinolyl, cinnolinyl, quinazolinyl, quinoxalinyl, carbazolyl, azacarbazolyl, benzocarbazolyl, dibenzocarbazolyl, phenoxazinyl, phenanthridinyl, benzodioxolyl, indolizidinyl, acridinyl, silafluorenyl, germafluorenyl, benzotriazolyl, phenazinyl, imidazopyridinyl, chromenoquinazolinyl, thiochromenoquinazolinyl, dimethylbenzopyrimidinyl, indolocarbazolyl, indenocarbazolyl, etc. More specifically, the heteroaryl may be 1-pyrrolyl, 2-pyrrolyl, 3-pyrrolyl, 2-pyridinyl, 3-pyridinyl, 4-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolizidinyl, 2-indolizidinyl, 3-indolizidinyl, 5-indolizidinyl, 6-indolizidinyl, 7-indolizidinyl, 8-indolizidinyl, 2-imidazopyridinyl, 3-imidazopyridinyl, 5-imidazopyridinyl, 6-imidazopyridinyl, 7-imidazopyridinyl, 8-imidazopyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazol-1-yl, azacarbazol-2-yl, azacarbazol-3-yl, azacarbazol-4-yl, azacarbazol-5-yl, azacarbazol-6-yl, azacarbazol-7-yl, azacarbazol-8-yl, azacarbazol-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-

[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. Herein, the term “a fused ring of (C3-C30) aliphatic ring and (C6-C30) aromatic ring” means a ring formed by fusing at least one aliphatic ring having 3 to 30 ring backbone carbon atoms in which the carbon atoms number is preferably 3 to 25, more preferably 3 to 18, and at least one aromatic ring having 6 to 30 ring backbone carbon atoms in which the carbon atoms number is preferably 6 to 25, more preferably 6 to 18. For example, the fused ring may be a fused ring of at least one benzene and at least one cyclohexane, or a fused ring of at least one naphthalene and at least one cyclopentane, etc. Herein, the carbon atoms in the fused ring of (C3-C30) aliphatic ring and (C6-C30) aromatic ring may be replaced with at least one heteroatoms selected from B. N, O, S, Si and P, preferably at least one heteroatoms selected from N, O and S. The term “Halogen” in the present disclosure includes F, Cl, Br, and I.

In addition, “ortho (o),” “meta (m),” and “para (p)” are meant to signify the substitution position of all substituents. Ortho position is a compound with substituents, which are adjacent to each other, e.g., at the 1 and 2 positions on benzene. Meta position is the next substitution position of the immediately adjacent substitution position, e.g., a compound with substituents at the 1 and 3 positions on benzene. Para position is the next substitution position of the meta position, e.g., a compound with substituents at the 1 and 4 positions on benzene.

Herein, “a ring formed in linking to an adjacent substituent” means a substituted or unsubstituted (3- to 30-membered) mono- or polycyclic, alicyclic, aromatic ring, or a combination thereof, formed by linking or fusing two or more adjacent substituents, preferably may be a substituted or unsubstituted (5- to 25-membered) mono- or polycyclic, alicyclic, aromatic ring, or a combination thereof. Further, the formed ring may include at least one heteroatom selected from the group consisting of B, N, O, S, Si and P, preferably, N, O and S. According to one embodiment of the present disclosure, the number of atoms in the ring skeleton is 5 to 20; according to another embodiment of the present disclosure, the number of atoms in the ring skeleton is 5 to 15. In one embodiment, the fused ring may be, for example, a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzofluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, a substituted or unsubstituted carbazole ring, etc.

In addition, “substituted” in the expression “substituted or unsubstituted” means that a hydrogen atom in a certain functional group is replaced with another atom or functional group, i.e., a substituent, and substituted with a group to which two or more substituents are connected among the substituents. For example, “a substituent to which two or more substituents are connected” may be pyridine-triazine. That is, pyridine-triazine may be heteroaryl or may be interpreted as one substituent in which two heteroaryls are connected. The substituents of the substituted alkyl, the substituted alkenyl, the substituted heterocycloalkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, and the substituted fused ring of the aliphatic ring and the aromatic ring, the substituted mono- or di-alkylamino, the substituted mono- or di-alkenylamino, the substituted alkylalkenylamino, the substituted mono- or di-arylamino, the substituted alkylarylamino, the substituted mono- or di-heteroarylamino, the substituted alkylheteroarylamino, the substituted alkenylarylamino, the substituted alkenylheteroarylamino, and the substituted arylheteroarylamino in the formulas of the present disclosure, each independently represent, at least one selected from the group consisting of deuterium; halogen; cyano; carboxyl; nitro; hydroxyl; phosphine oxide; (C1-C30)alkyl; halo(C1-C30)alkyl; (C2-C30)alkenyl; (C2-C30)alkynyl; (C1-C30)alkoxy; (C1-C30)alkylthio; (C3-C30)cycloalkyl; (C3-C30)cycloalkenyl; (3- to 7-membered)heterocycloalkyl; (C6-C30)aryloxy; (C6-C30)arylthio; (3- to 30-membered)heteroaryl unsubstituted or substituted with at least one of (C1-C30)alkyl and (C6-C30)aryl; (C6-C30)aryl unsubstituted or substituted with at least one of deuterium, cyano, (C1-C30)alkyl, (C3-C30)cycloalkyl, tri(C1-C30)alkylsilyl, (C6-C30)aryl and (3- to 30-membered)heteroaryl; tri(C1-C30)alkylsilyl; tri(C6-C30)arylsilyl; di(C1-C30)alkyl(C6-C30)arylsilyl; (C1-C30)alkyldi(C6-C30)arylsilyl; a substituted or unsubstituted fused ring of (C3-C30) aliphatic ring and (C6-C30) aromatic ring; amino; mono- or di-(C1-C30)alkylamino; mono- or di-(C2-C30)alkenylamino; (C1-C30)alkyl(C2-C30)alkenylamino; mono- or di-(C6-C30)arylamino; (C1-C30)alkyl(C6-C30)arylamino; mono- or di-(3- to 30-membered)heteroarylamino; (C1-C30)alkyl(3- to 30-membered)heteroarylamino; (C2-C30)alkenyl(C6-C30)arylamino; (C2-C30)alkenyl(3- to 30-membered)heteroarylamino; (C6-C30)aryl(3- to 30-membered)heteroarylamino; (C1-C30)alkylcarbonyl; (C1-C30)alkoxycarbonyl; (C6-C30)arylcarbonyl; (C6-C30)arylphosphinyl; di(C6-C30)arylboronyl; di(C1-C30)alkylboronyl; (C1-C30)alkyl(C6-C30)arylboronyl; (C6-C30)ar(C1-C30)alkyl; and (C1-C30)

alkyl(C6-C30)aryl. For example, the substituents of the substituted groups may be deuterium, methyl, tert-butyl, a substituted or unsubstituted phenyl, unsubstituted biphenyl, a substituted or unsubstituted naphthyl, a substituted or unsubstituted pyridyl, triphenylsilane, a substituted or unsubstituted isobenzofuranyl, or a substituted or unsubstituted carbazolyl, etc.

Hereinafter, the host materials according to one embodiment will be described.

The plurality of host materials according to one embodiment comprise a first host material including a compound represented by the above formula 1 and a second host material including a compound represented by the above formula 2; and the plurality of host materials may be contained in the light-emitting layer of an organic electroluminescent device according to one embodiment.

The host material represented by the above formula 2 according to one embodiment has slow hole mobility due to the very deep HOMO (Highest Occupied Molecular Orbital) level, but has rapid electron mobility by including a nitrogen-containing heteroaryl group, for example, a triazine moiety, so that it has fast electron mobility, which may negatively affect the efficiency and lifespan of the device due to the imbalance of hole and electron mobility. However, the plurality of host materials according to one embodiment include not only the host material of the above formula 2, but also the hole host of the above formula 1 having fast hole mobility, thereby exhibiting balanced hole/electron mobility. As a result, the plurality of host materials according to the present disclosure can provide an organic electroluminescent device having high luminous efficiency and long lifespan property by increasing exciton formation in the light-emitting layer.

The first host material as the host material according to one embodiment may be represented by the following formula 1.

(1)

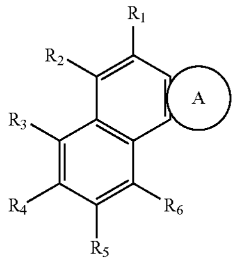

In formula 1,

Ring A represents a substituted or unsubstituted benzene ring or a substituted or unsubstituted naphthalene ring;

$R_1$ to $R_6$ each independently represent, hydrogen, deuterium, halogen, cyano, a substituted or unsubstituted (C1-C30)alkyl, a substituted or unsubstituted (C3-C30)cycloalkyl, a substituted or unsubstituted (3- to 7-membered) heterocycloalkyl, a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsiyl, a substituted or unsubstituted tri(C6-C30)arylsilyl, or *-$L_1$-$NAr_1Ar_2$; provided that at least one of $R_1$ to $R_6$ is *-$L_1$-$NAr_1Ar_2$;

$L_1$ represents a single bond, a substituted or unsubstituted (C6-C30)arylene, or a substituted or unsubstituted (3- to 30-membered)heteroarylene; and $Ar_1$ and $Ar_2$ each independently represent, a substituted or unsubstituted (C1-C30)alkyl, a substituted or unsubstituted (C2-C30)alkenyl, a substituted or unsubstituted (C6-C30) aryl, or a substituted or unsubstituted (3- to 30-membered) heteroaryl.

In one embodiment, Ring A may be a substituted or unsubstituted benzene ring or a substituted or unsubstituted naphthalene ring, for example, the compound represented by the above formula 1 may be represented by any one of the following formulas 1-1 to 1-4.

(1-1)

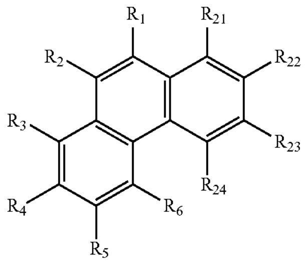

(1-2)

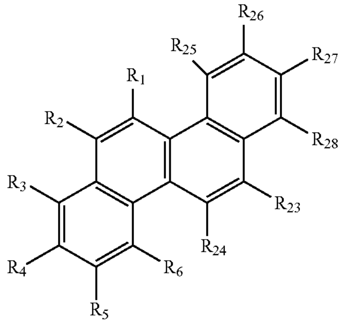

(1-3)

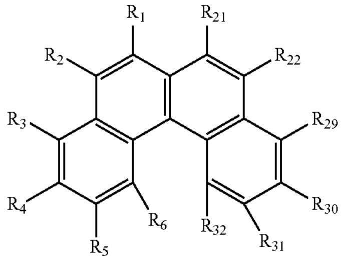

(1-4)

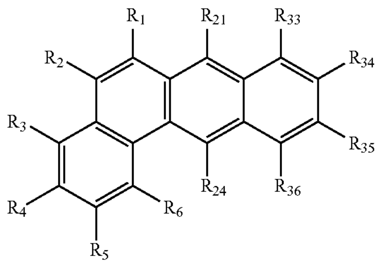

In formulas 1-1 to 1-4, $R_1$ to $R_6$ are as defined in formula 1; and $R_{21}$ to $R_{36}$ each independently represent, hydrogen, deuterium, halogen, cyano, a substituted or unsubstituted (C1-C30)alkyl, a substituted or unsubstituted (C3-C30)cycloalkyl, a substituted or unsubstituted (3- to 7-membered) heterocycloalkyl, a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30)alkenylamino, a substituted or unsubstituted (C1-C30)alkyl (C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl (3- to 30-membered)heteroarylamino.

In one embodiment, $R_1$ to $R_6$ each independently may be hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, or $*-L_1-NAr_1Ar_2$; provided that at least one of $R_1$ to $R_6$ is $*-L_1-NAr_1Ar_2$.

In one embodiment, $L_1$ may be a single bond, a substituted or unsubstituted (C6-C30)arylene, or a substituted or unsubstituted (5- to 30-membered)heteroarylene, preferably, a single bond, a substituted or unsubstituted (C6-C25)arylene, or a substituted or unsubstituted (5- to 25-membered)heteroarylene, more preferably, a single bond, a substituted or unsubstituted (C6-C18)arylene, or a substituted or unsubstituted (5- to 25-membered)heteroarylene. For example, $L_1$ may be a single bond, a substituted or unsubstituted phenylene, a substituted or unsubstituted p-biphenylene, a substituted or unsubstituted m-biphenylene, a substituted or unsubstituted o-biphenylene, a substituted or unsubstituted terphenylene, a substituted or unsubstituted naphthalenylene, a substituted or unsubstituted phenylnaphthalenylene, a substituted or unsubstituted naphthylphenylene, a substituted or unsubstituted binaphthalenylene, a substituted or unsubstituted pyrimidylphenylene, a substituted or unsubstituted phenanthrenylene, a substituted or unsubstituted triphenylenylene, a substituted or unsubstituted chrysenylene, a substituted or unsubstituted fluorenylene, a substituted or unsubstituted pyridylene, a substituted or unsubstituted pyrimidylene, a substituted or unsubstituted dibenzofuranylene, a substituted or unsubstituted phenanthrooxazolylene, a substituted or unsubstituted phenanthrothiazolylene, a substituted or unsubstituted triazinylene, a substituted or unsubstituted quinoxalinylene, a substituted or unsubstituted quinazolinylene, or a substituted or unsubstituted benzoquinoxalinylene, for example, a single bond, a substituted or unsubstituted phenylene, a substituted or unsubstituted p-biphenylene, a substituted or unsubstituted m-biphenylene, a substituted or unsubstituted o-biphenylene, a substituted or unsubstituted naphthalenylene, or a substituted or unsubstituted naphthylphenylene.

In one embodiment. $Ar_1$ and $Ar_2$ each independently may be a substituted or unsubstituted (C6-C30)aryl or a substituted or unsubstituted (5- to 30-membered)heteroaryl, preferably, a substituted or unsubstituted (C6-C25)aryl or a substituted or unsubstituted (5- to 25-membered)heteroaryl, more preferably, a substituted or unsubstituted (C6-C25)aryl or a substituted or unsubstituted (5- to 18-membered)heteroaryl. For example, $Ar_1$ and $Ar_2$ each independently may be a substituted or unsubstituted phenyl, a substituted or unsubstituted naphthyl, a substituted or unsubstituted naphthylphenyl, a substituted or unsubstituted p-biphenyl, a substituted or unsubstituted m-biphenyl, a substituted or unsubstituted o-biphenyl, a substituted or unsubstituted p-terphenyl, a substituted or unsubstituted m-terphenyl, a substituted or unsubstituted o-terphenyl, a substituted or unsubstituted fluorenyl, a substituted or unsubstituted spirobifluorenyl, a substituted or unsubstituted phenanthrenyl, a substituted or unsubstituted chrysenyl, a substituted or unsubstituted dibenzofuranyl, a substituted or unsubstituted dibenzothiophenyl, a substituted or unsubstituted carbazolyl, a substituted or unsubstituted benzofluorenyl, or a substituted or unsubstituted dihydrophenanthrenyl, for example, a substituted or unsubstituted phenyl, a substituted or unsubstituted naphthyl, a substituted or unsubstituted p-biphenyl, a substituted or unsubstituted m-biphenyl, a substituted or unsubstituted o-biphenyl, a substituted or unsubstituted p-terphenyl, a substituted or unsubstituted m-terphenyl, a substituted or unsubstituted o-terphenyl, a substituted or unsubstituted fluorenyl, a substituted or unsubstituted spirobifluorenyl, a substituted or unsubstituted phenanthrenyl, a substituted or unsubstituted dibenzofuranyl, or a substituted or unsubstituted dibenzothiophenyl. The substituents of the substituted groups may be for example, methyl; tert-butyl; phenyl unsubstituted or substituted with deuterium or tert-butyl; naphthyl; phenylpyridyl; triphenylsilane; phenanthrenyl; or isobenzofuranyl substituted with phenyl.

In one embodiment, $R_{21}$ to $R_{38}$ each independently may be hydrogen, deuterium, a substituted or unsubstituted (C6-C30)aryl, a substituted or unsubstituted (5- to 30-membered) heteroaryl, or a substituted or unsubstituted mono- or di-(C6-C30)arylamino, preferably, hydrogen, deuterium, a substituted or unsubstituted (C6-C25)aryl, a substituted or unsubstituted (5- to 25-membered)heteroaryl, or a substituted or unsubstituted di(C6-C25)arylamino, more preferably, hydrogen, deuterium, a substituted or unsubstituted (C6-C18)aryl, a substituted or unsubstituted (5- to 18-membered)heteroaryl, or a substituted or unsubstituted di(C6-C18)arylamino. For example, $R_{21}$ to $R_{36}$ each independently may be a substituted or unsubstituted phenyl, a substituted or unsubstituted naphthyl, a substituted or unsubstituted pyridyl, a substituted or unsubstituted triphenylenyl, a substituted or unsubstituted quinolinyl, a substituted or unsubstituted dibenzofuranyl, or a substituted or unsubstituted diphenylamino.

In one embodiment, the first host material represented by the above formula 1 may be more specifically illustrated by the following compounds, but is not limited thereto.

-continued
H1-1
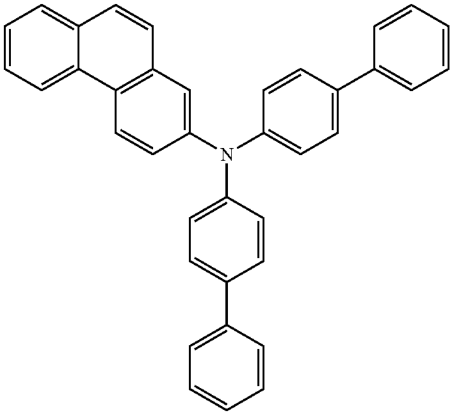
H1-2
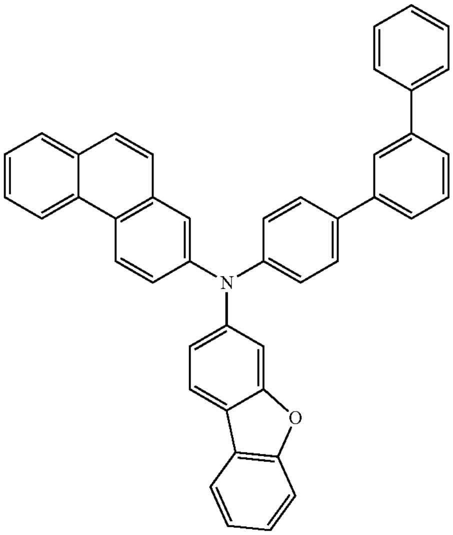
H1-3
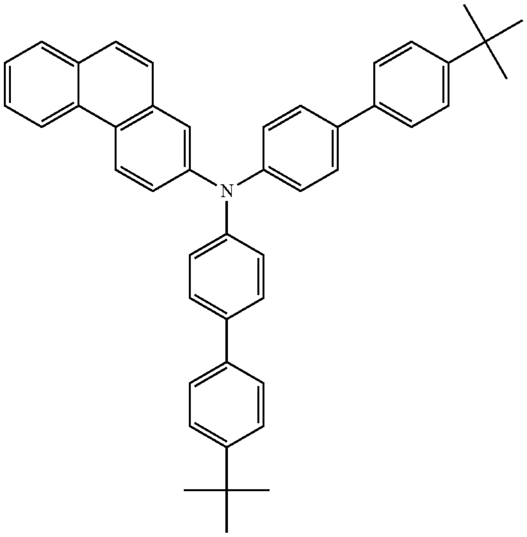
H1-4
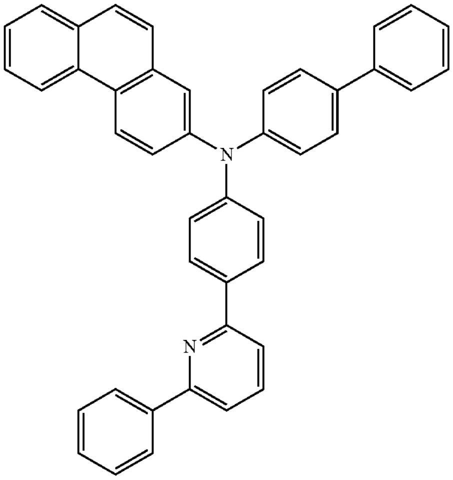
H1-5
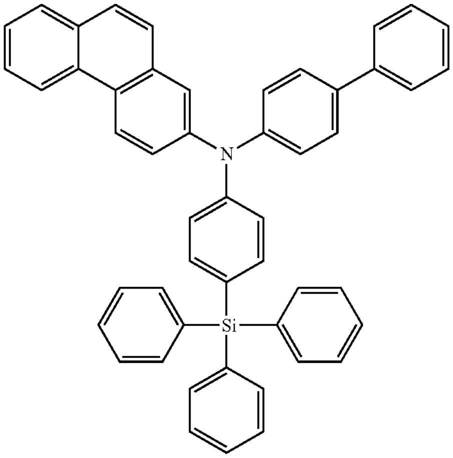
H1-6
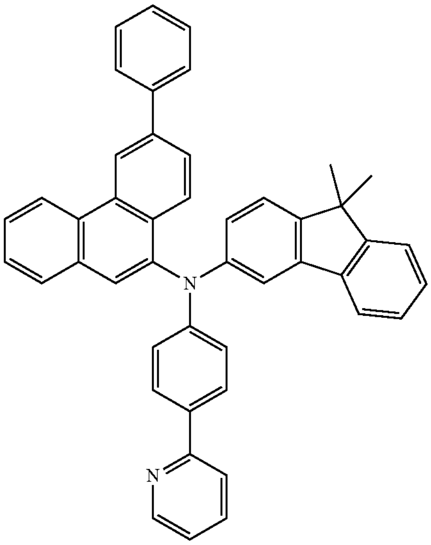

-continued
H1-7
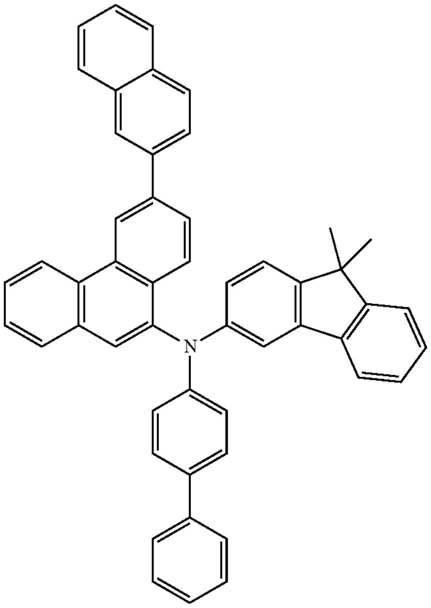
H1-8
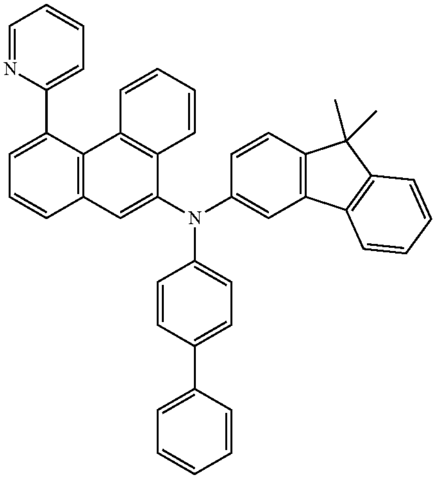
H1-9
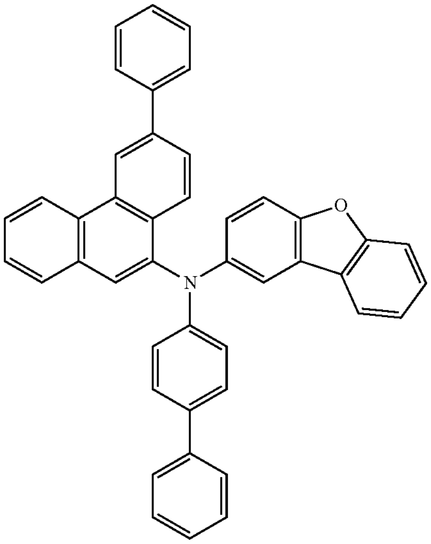
-continued
H1-10
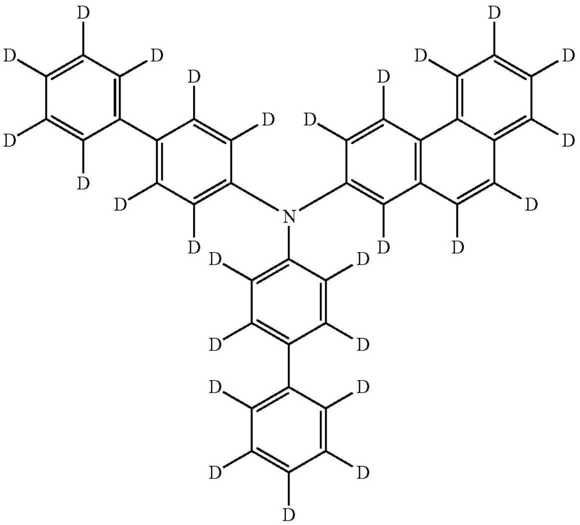
H1-11
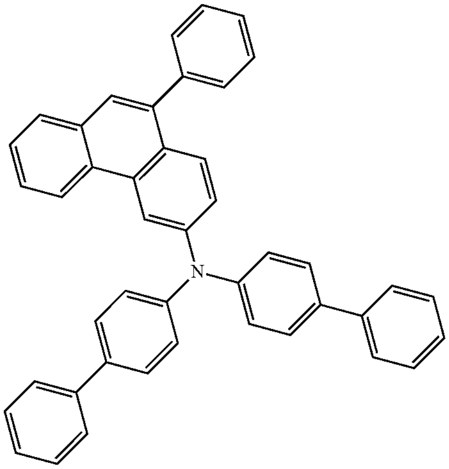
H1-12
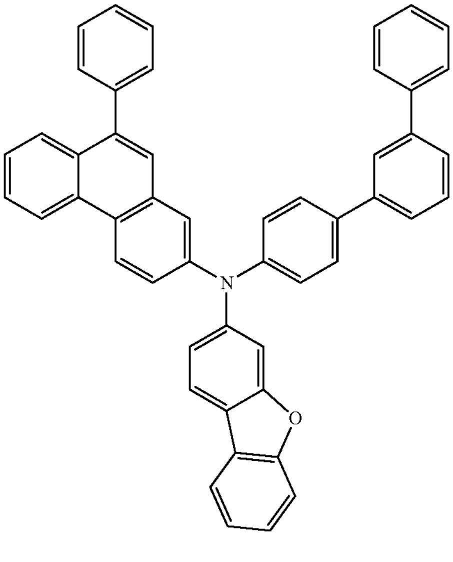

-continued
H1-13
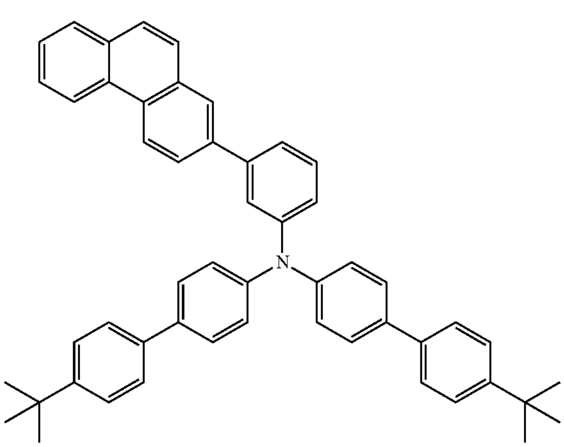
H1-14
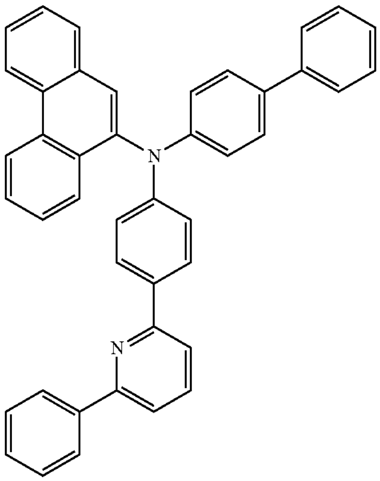
H1-15
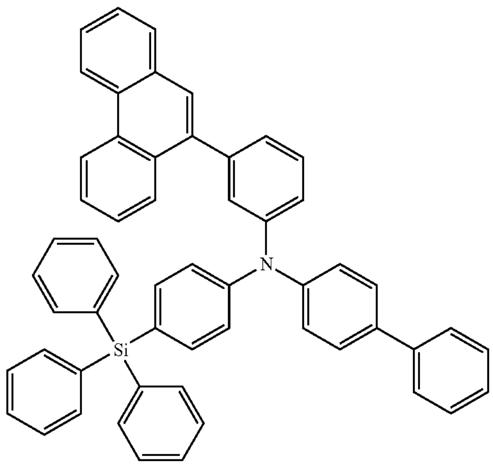
-continued
H1-16
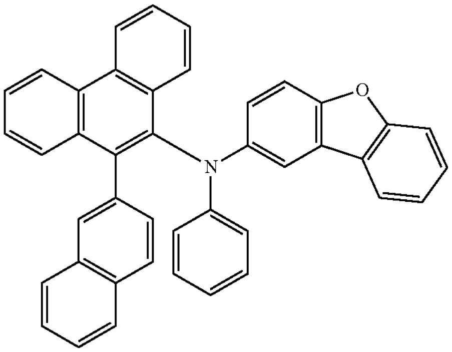
H1-17
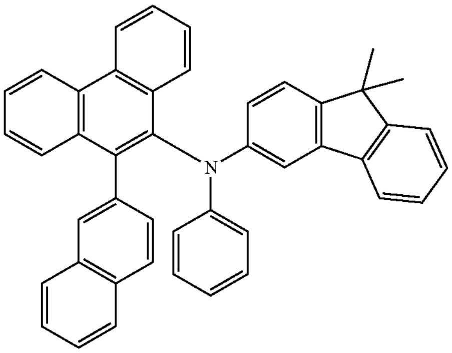
H1-18
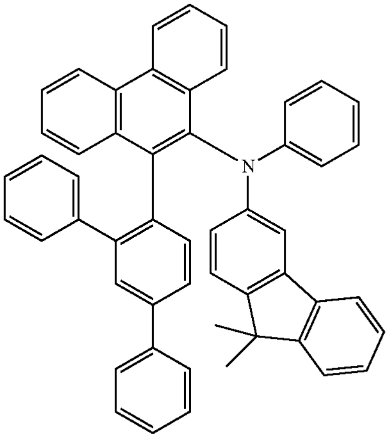
H1-19
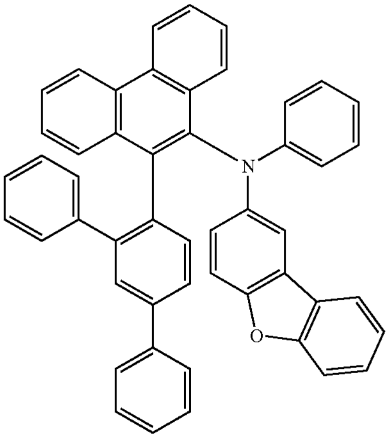

-continued
H1-20
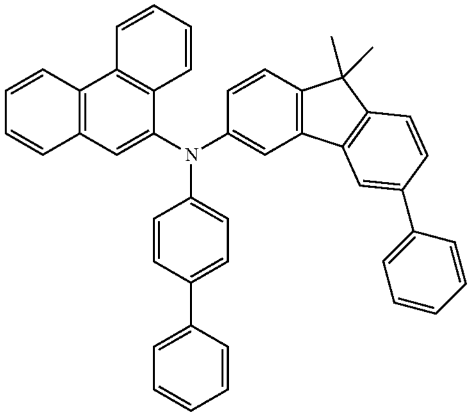
H1-21
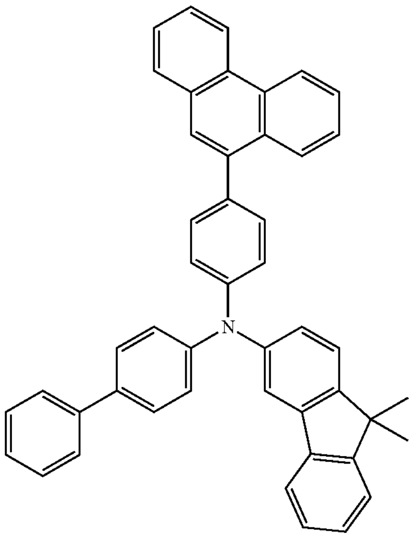
H1-22
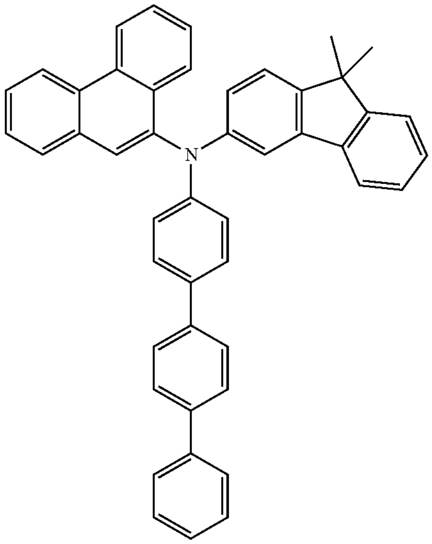
-continued
H1-23
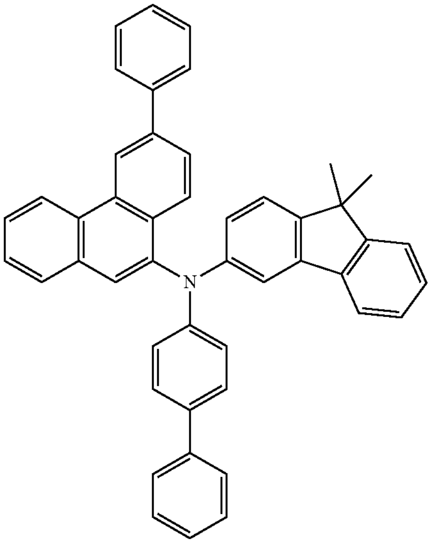
H1-24
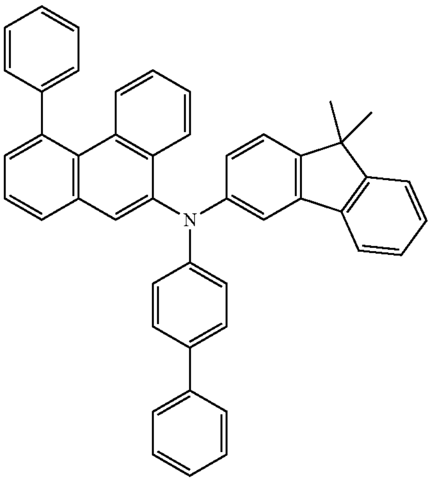
H1-25
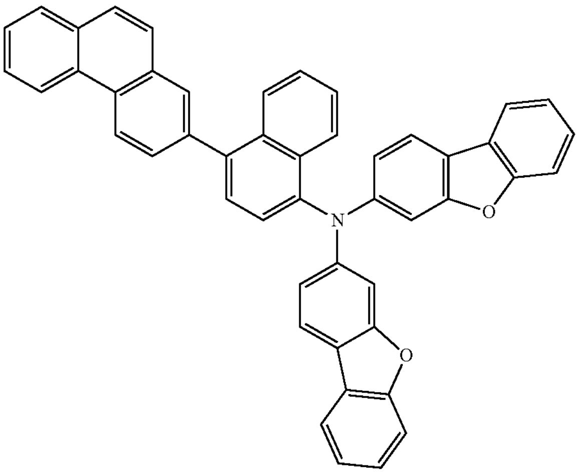

-continued
H1-26
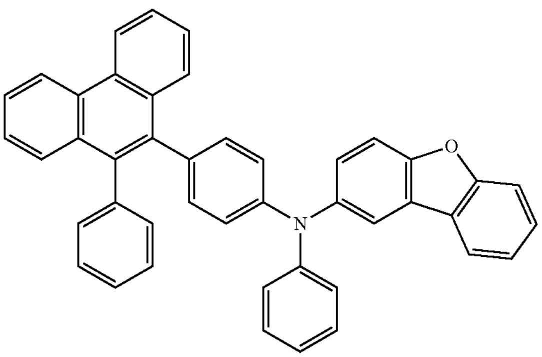
H1-27
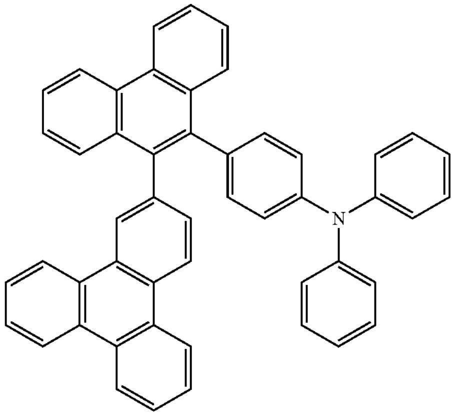
H1-28
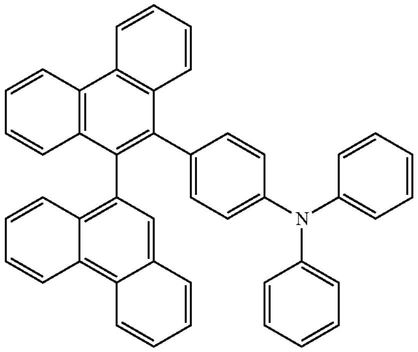
H1-29
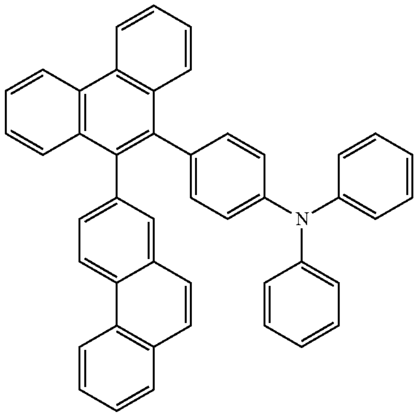
-continued
H1-30
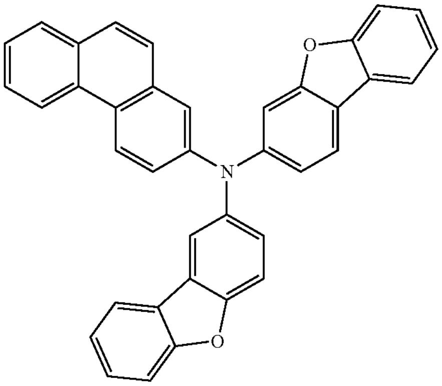
H1-31
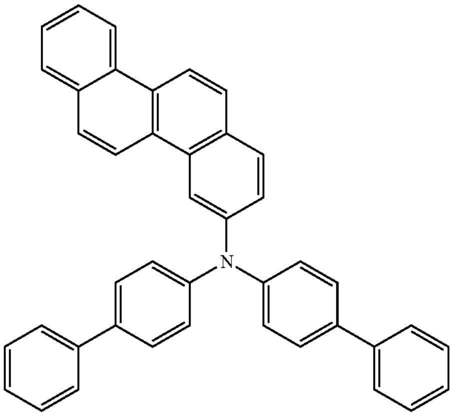
H1-32
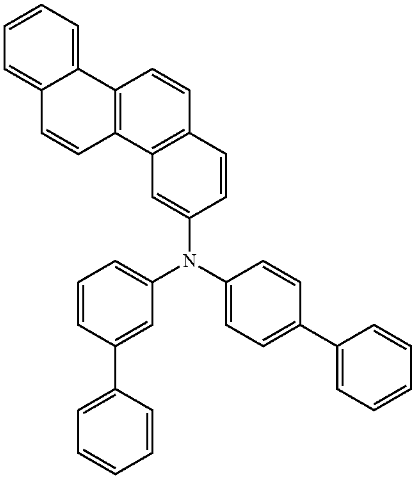

-continued
H1-33
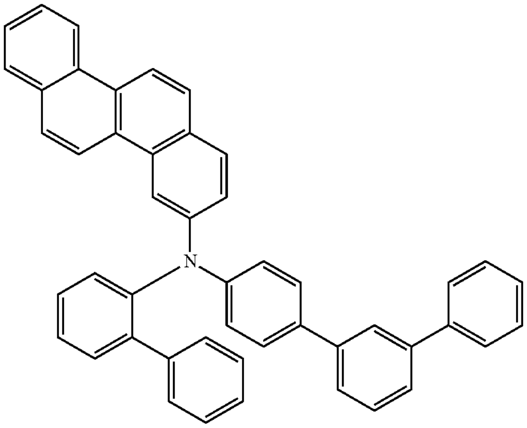
H1-34
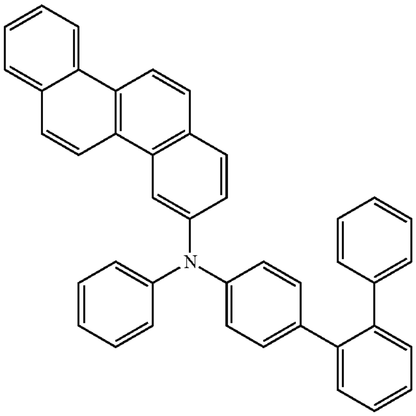
H1-35
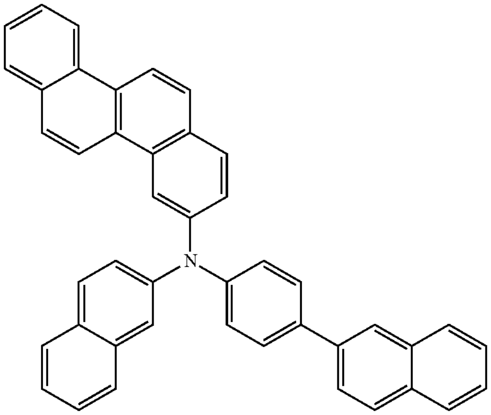
-continued
H1-36
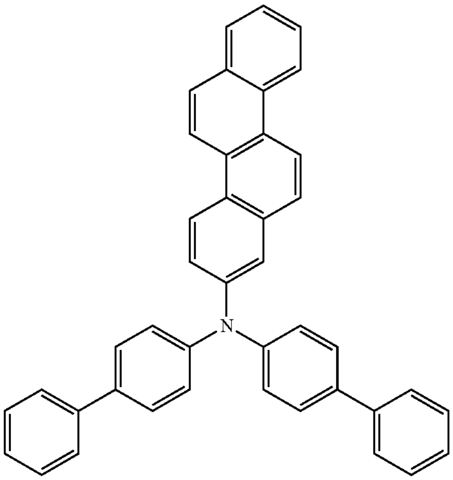
H1-37
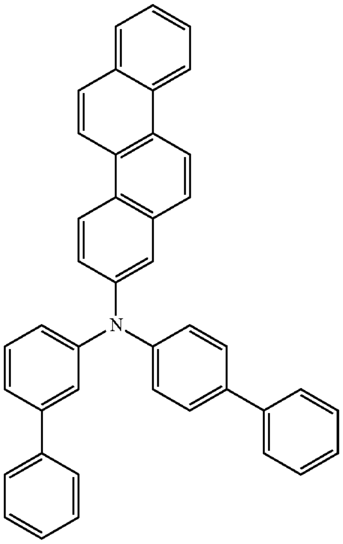
H1-38
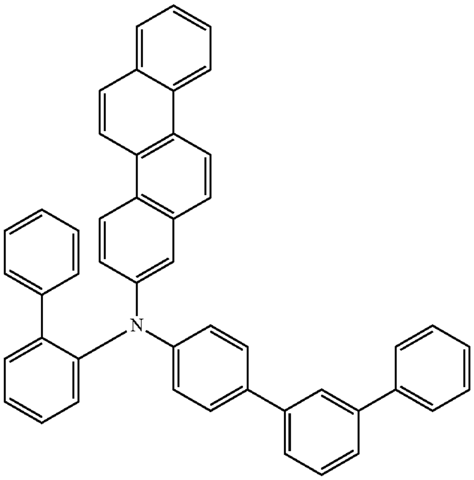

-continued
H1-39
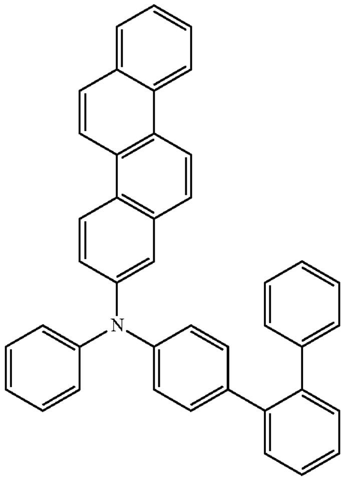
H1-40
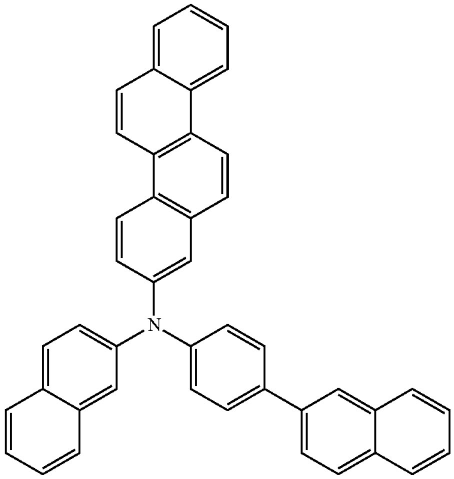
H1-41
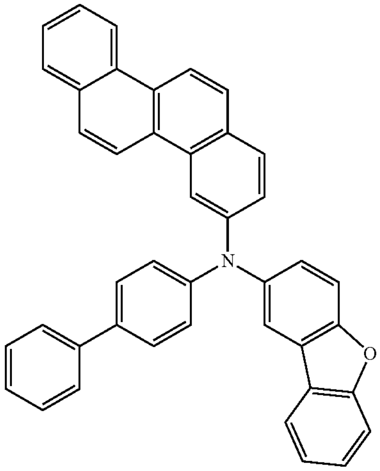
-continued
H1-42
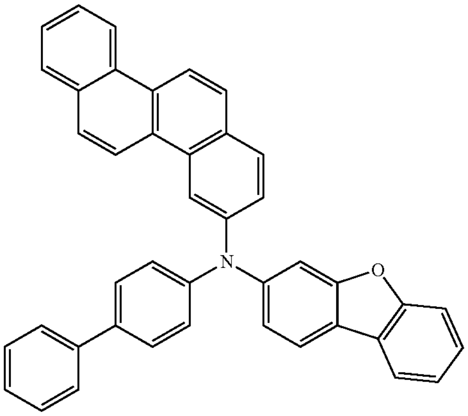
H1-43
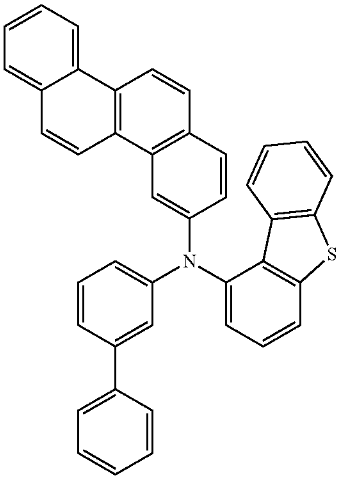
H1-44
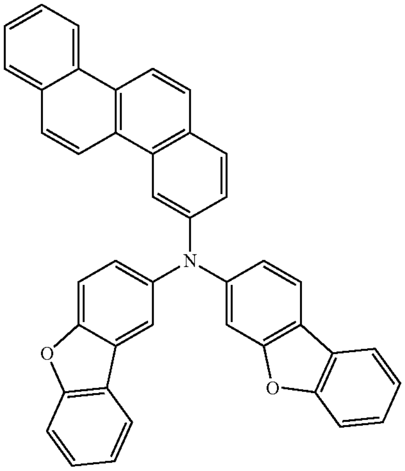

-continued
H1-45
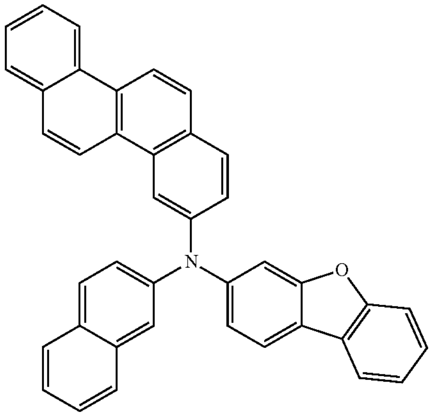
H1-46
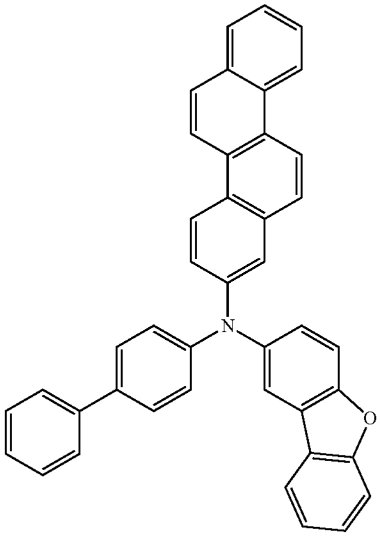
H1-47
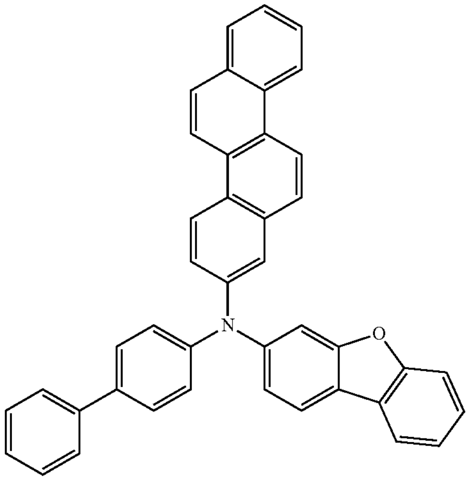
-continued
H1-48
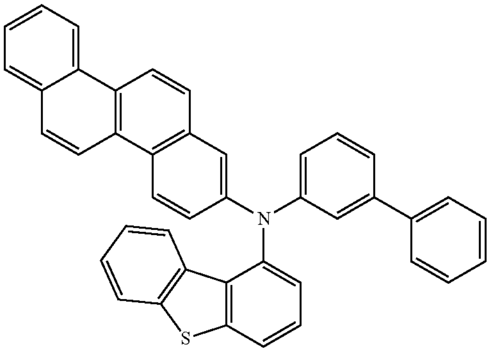
H1-49
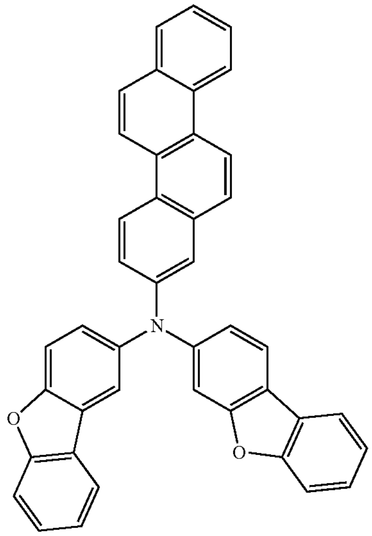
H1-50
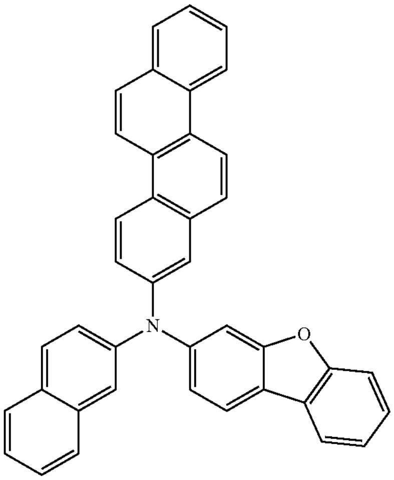

-continued
H1-51
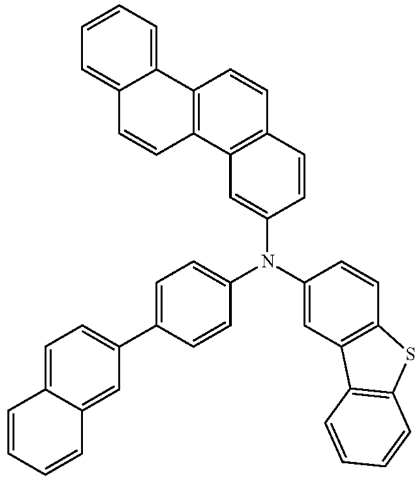
H1-52
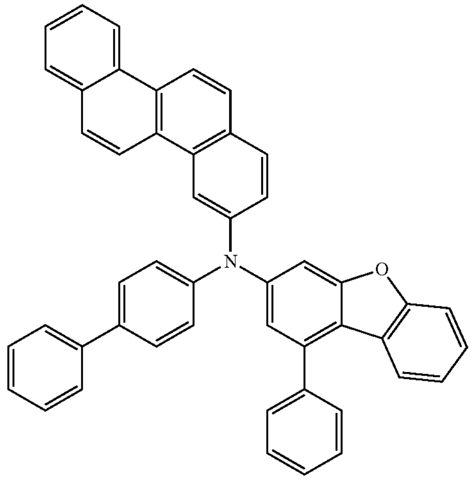
H1-53
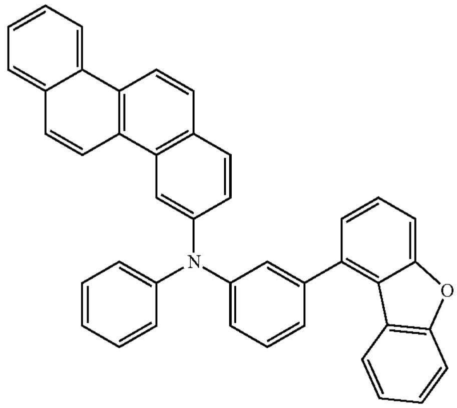
-continued
H1-54
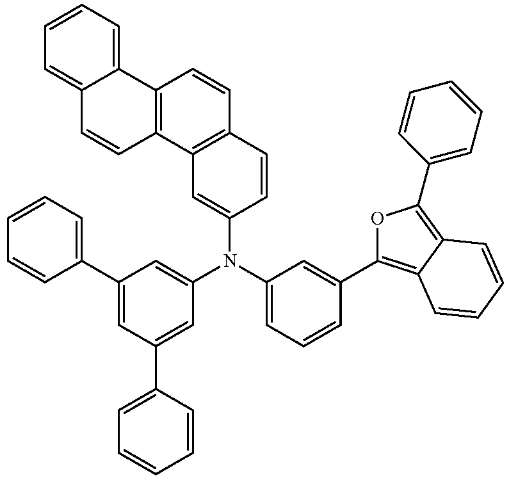
H1-55
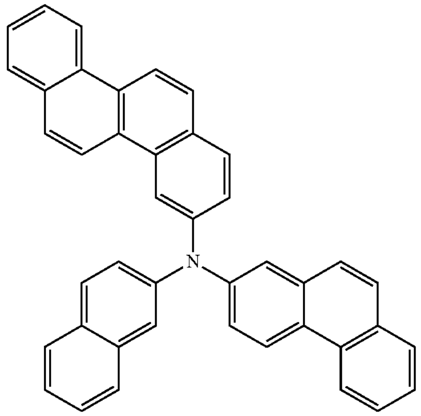
H1-56
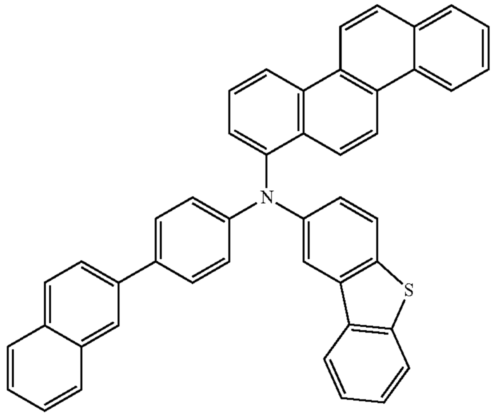

-continued
H1-57
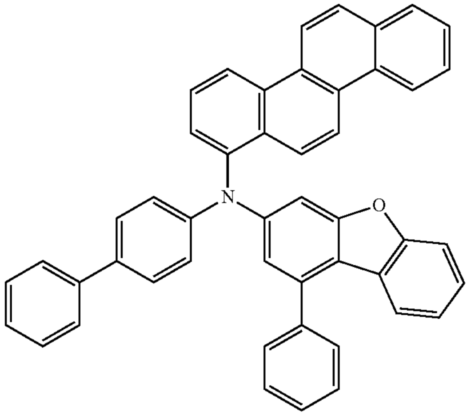
H1-58
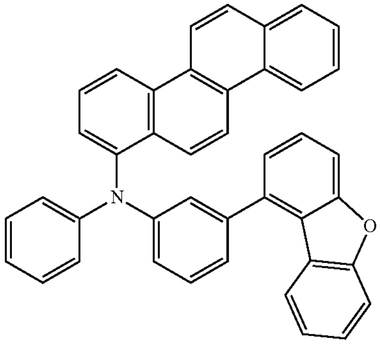
H1-59
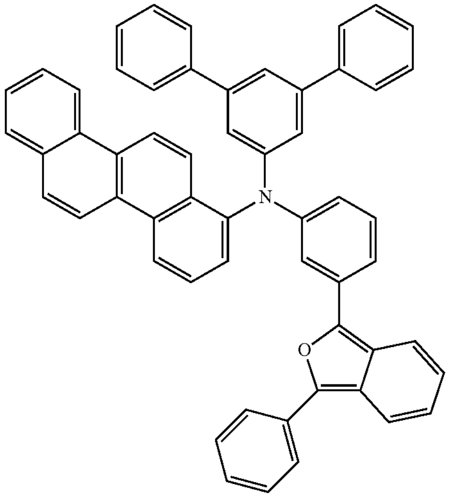
H1-60
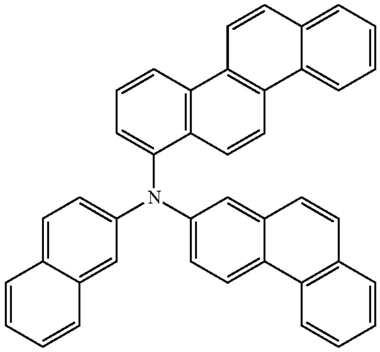
-continued
H1-61
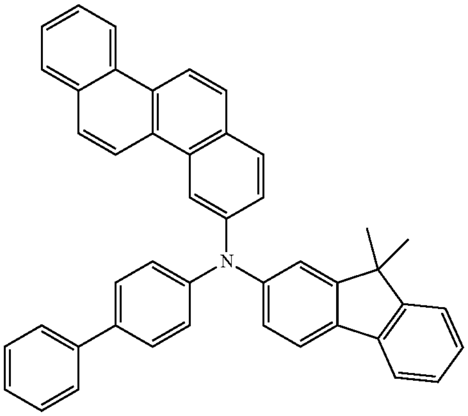
H1-62
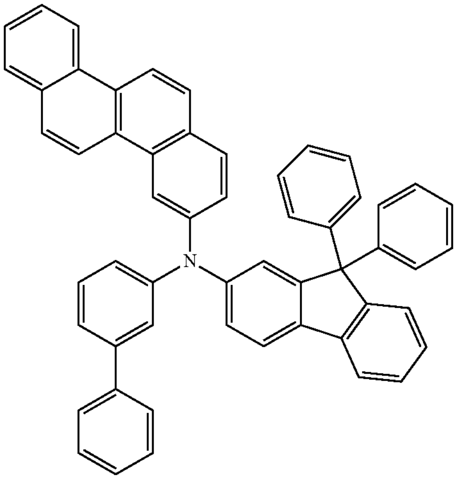
H1-63
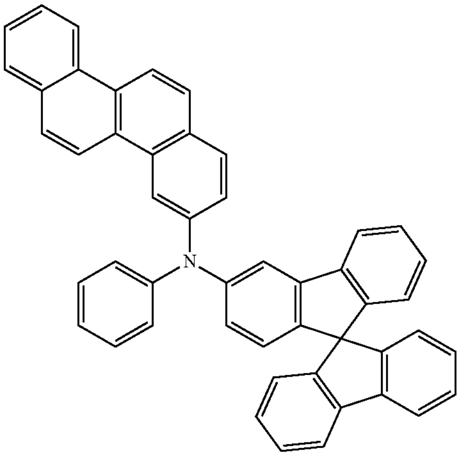

-continued
H1-64
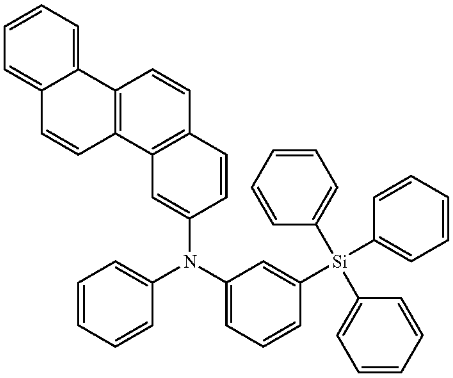
H1-65
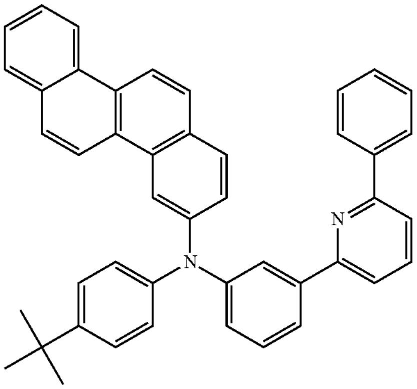
H1-66
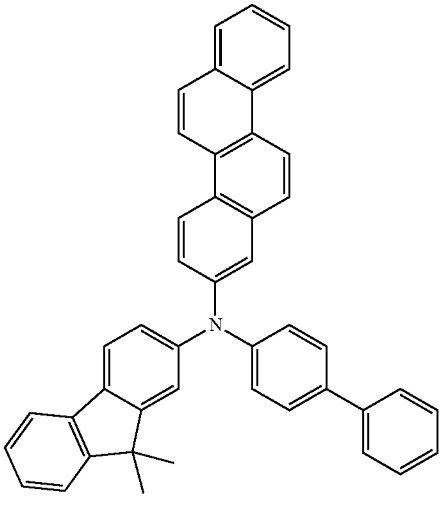
-continued
H1-67
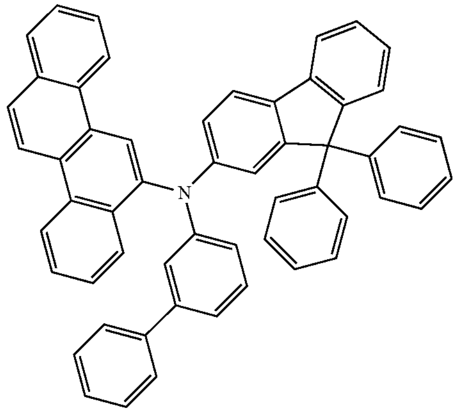
H1-68
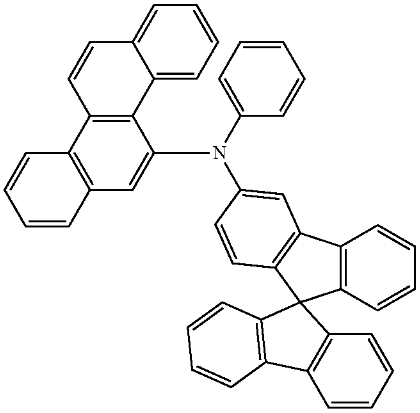
H1-69
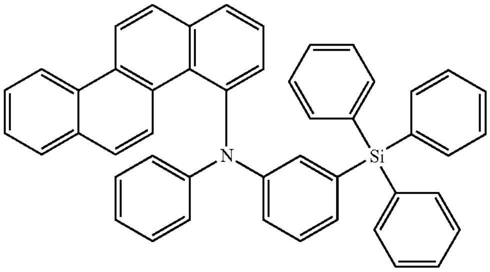
H1-70
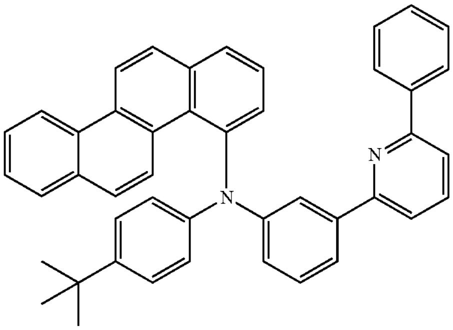

-continued
H1-71
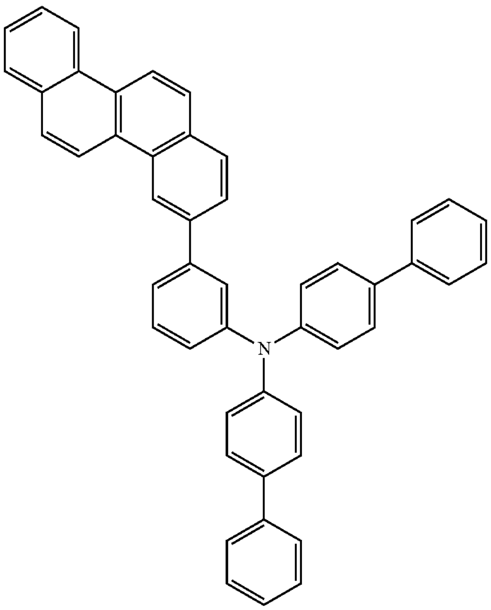
H1-72
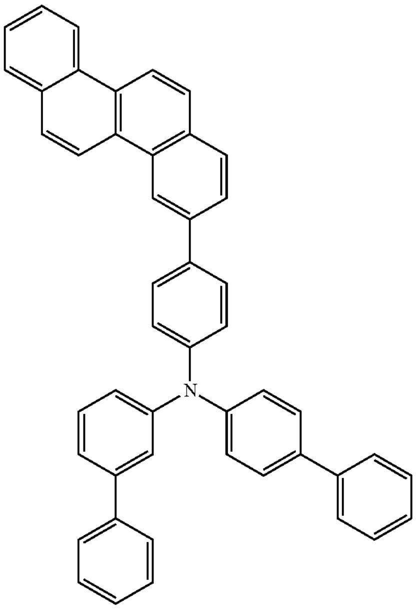
-continued
H1-73
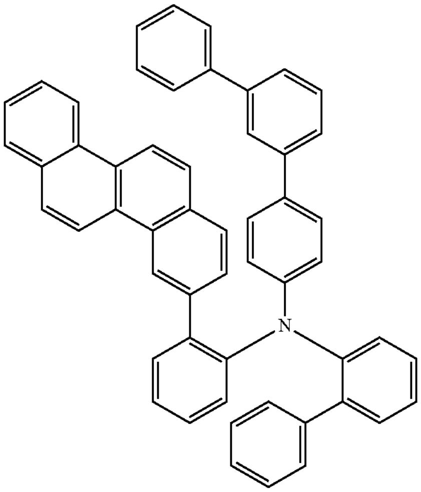
H1-74
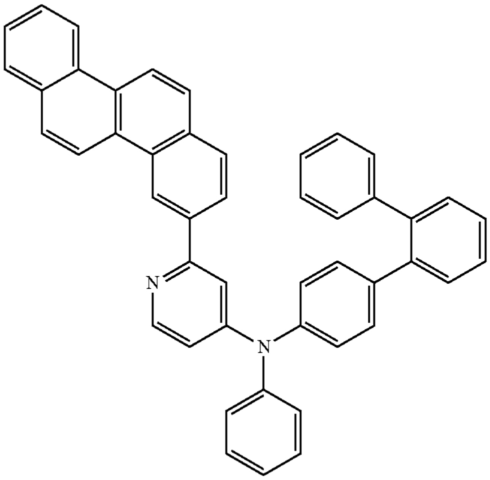
H1-75
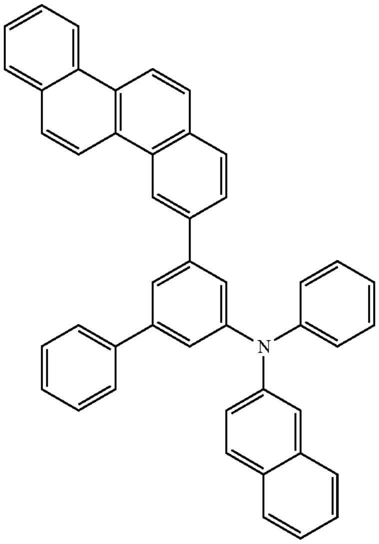

-continued
H1-76
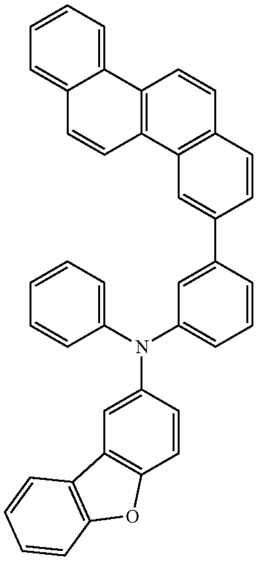
H1-77
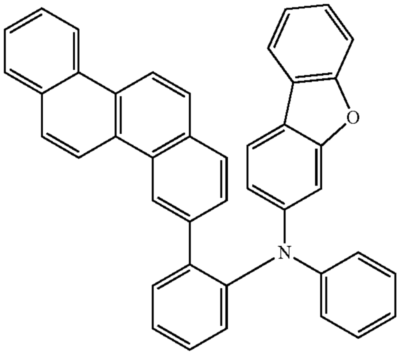
H1-78
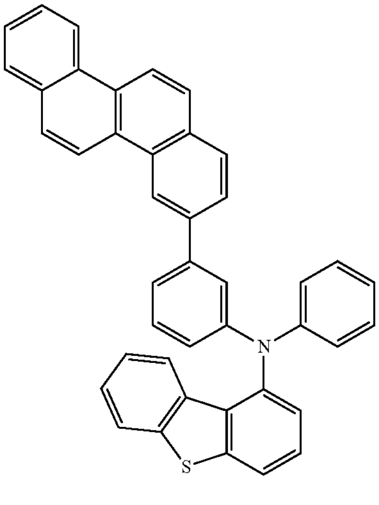
-continued
H1-79
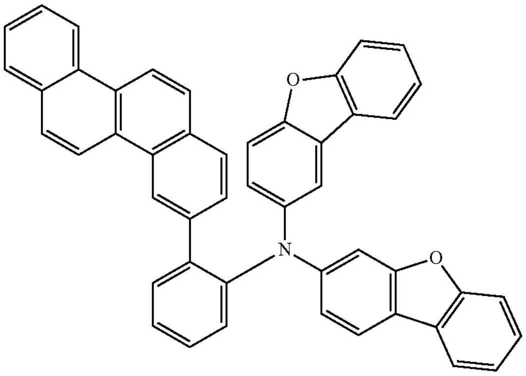
H1-80
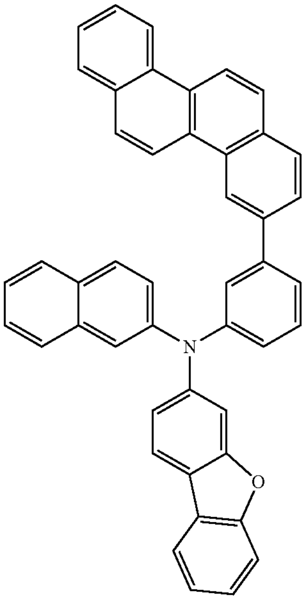
H1-81
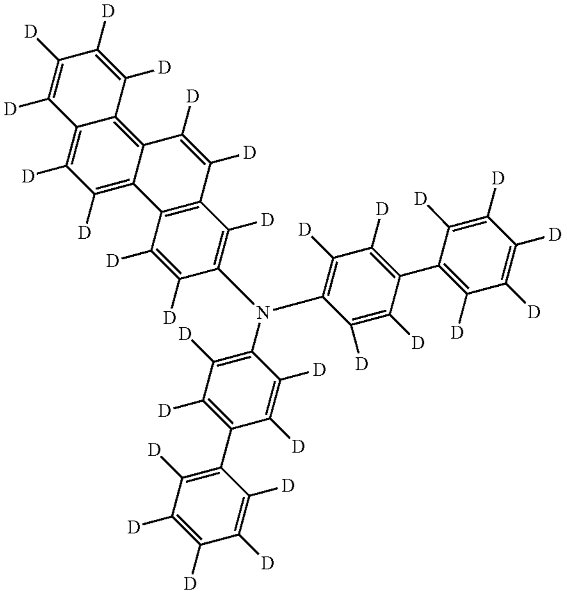

-continued
H1-82
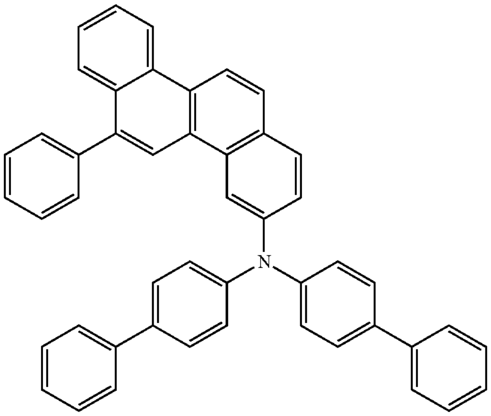
H1-83
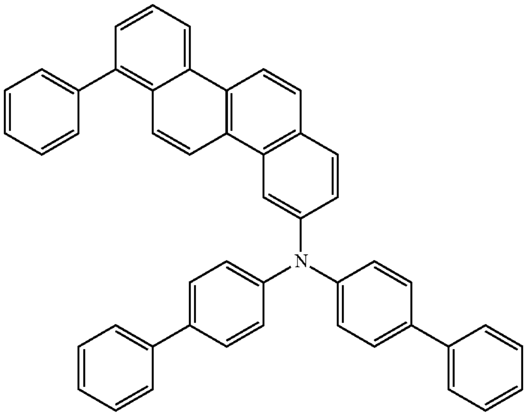
H1-84
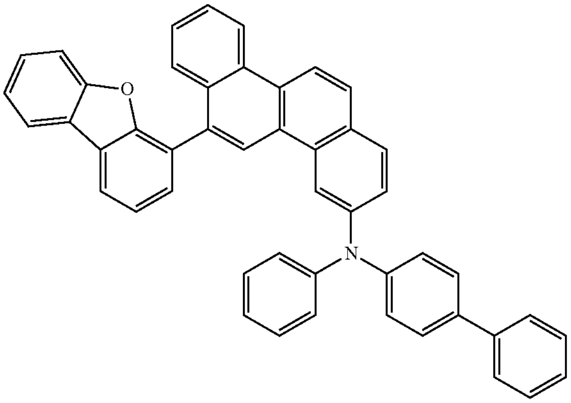
H1-85
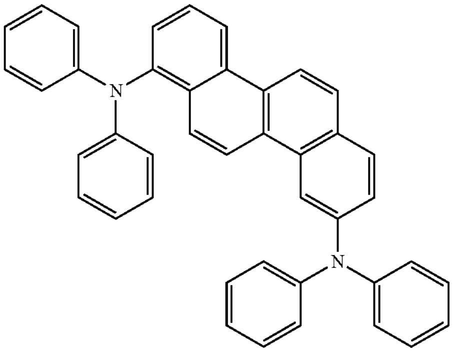
-continued
H1-86
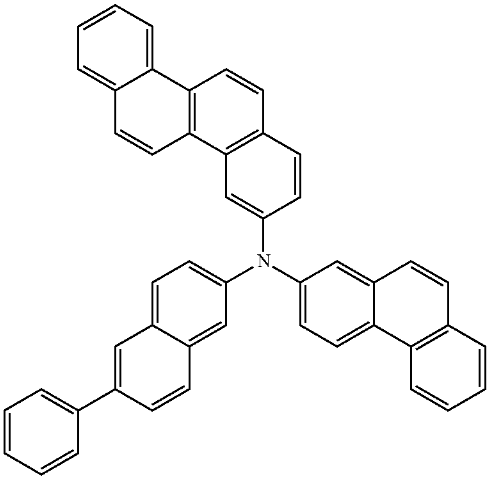
H1-87
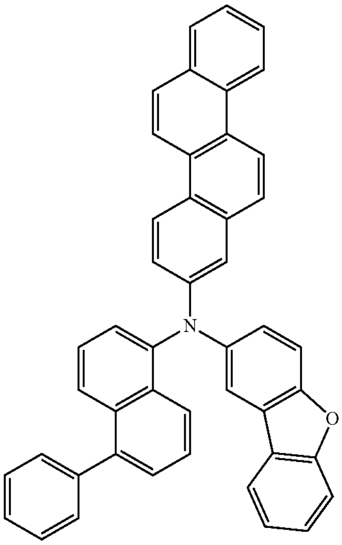
H1-88
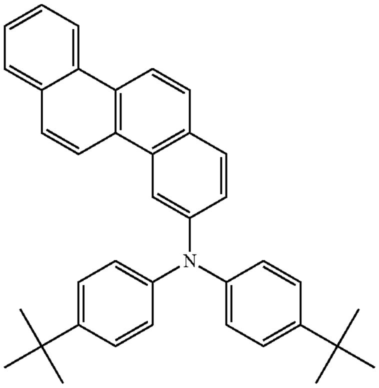

-continued
H1-89
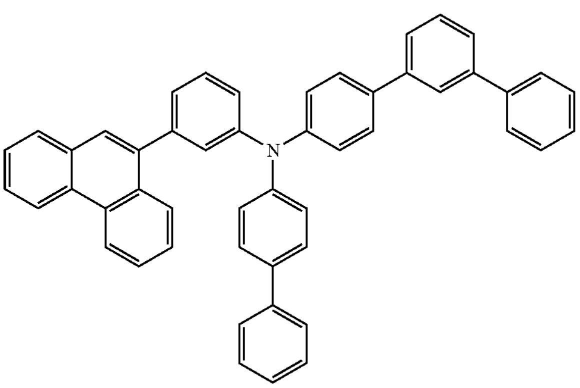
H1-90
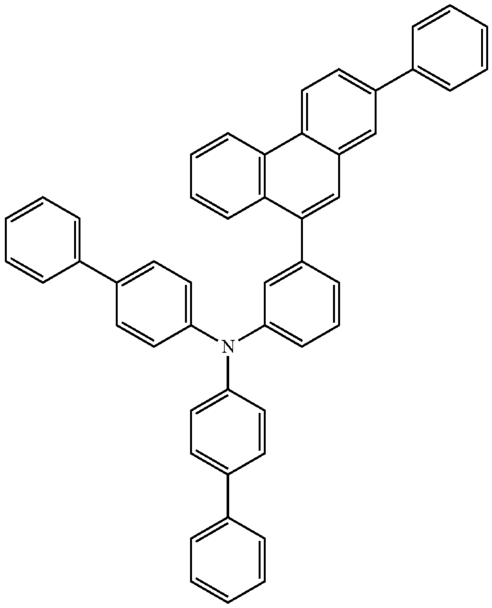
H1-91
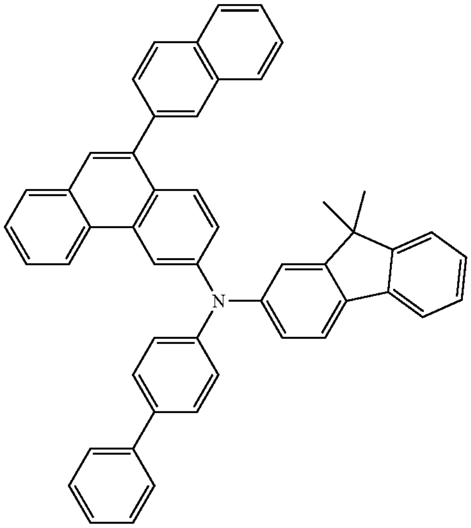
-continued
H1-92
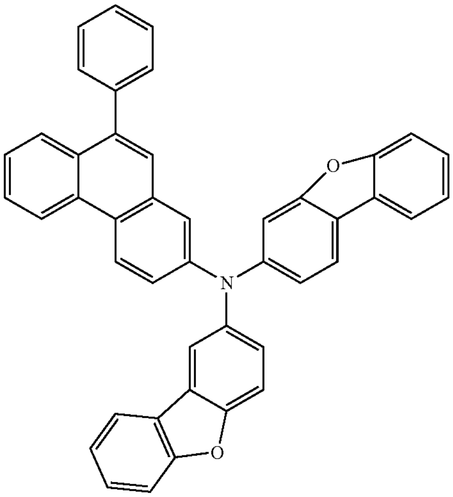
H1-93
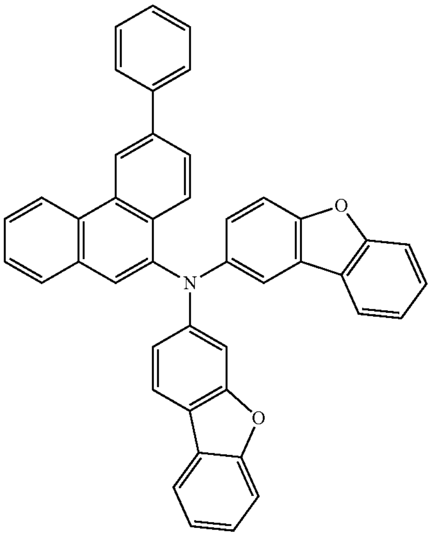
H1-94
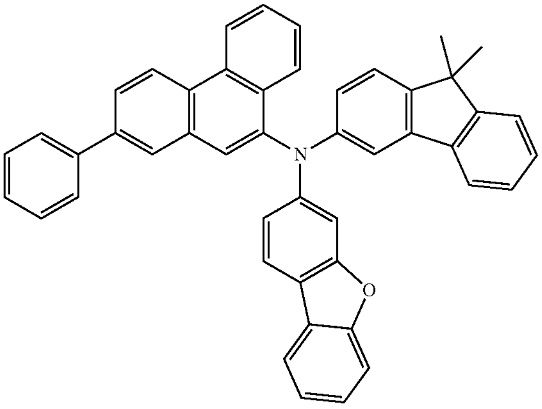

-continued
H1-95
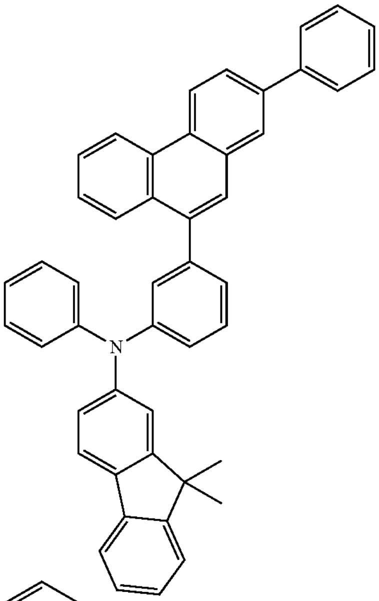
H1-96
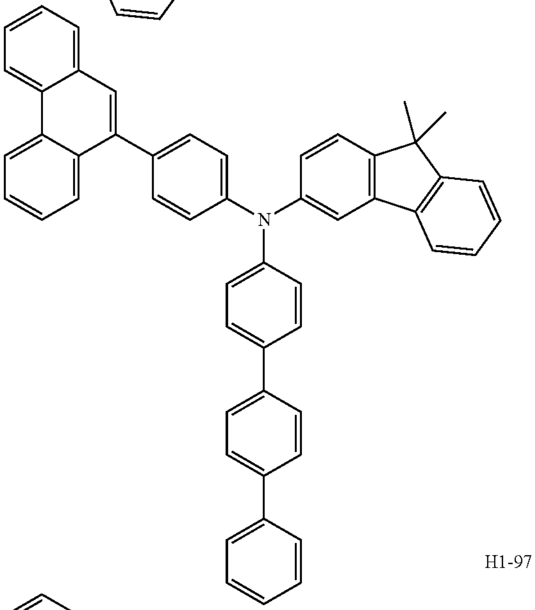
H1-97
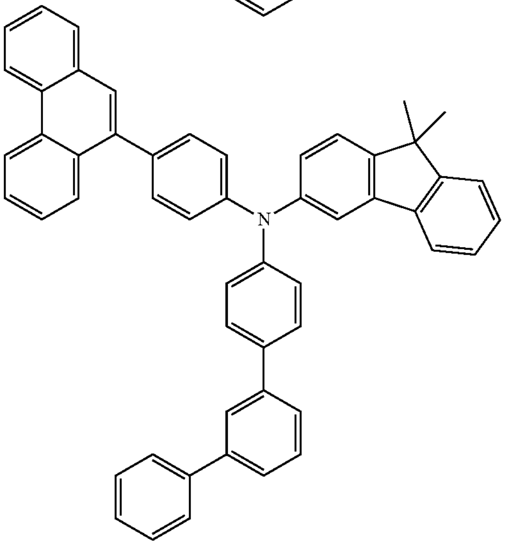
-continued
H1-98
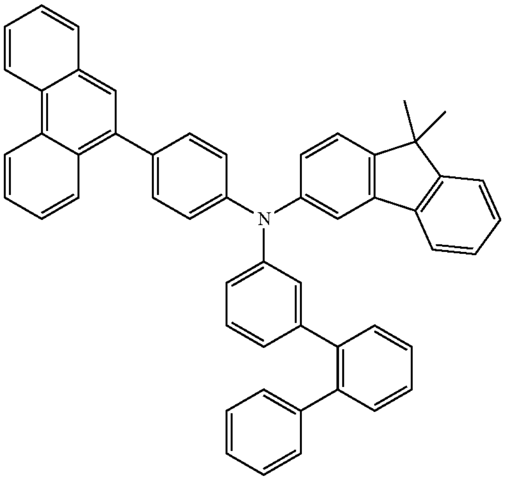
H1-99
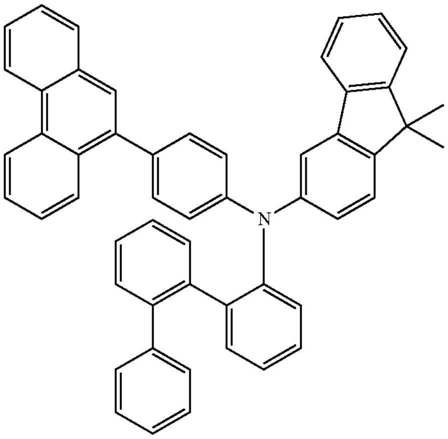
H1-100
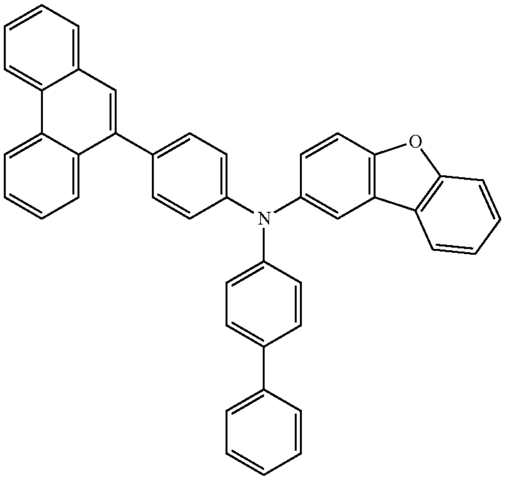

-continued
H1-101
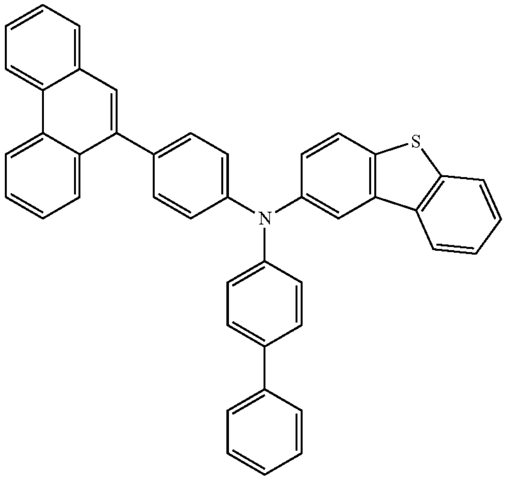
H1-102
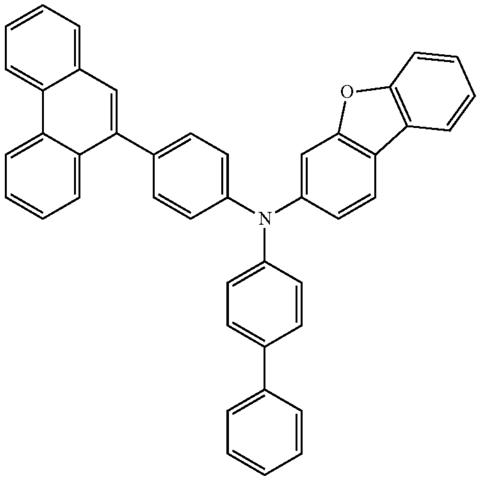
H1-103
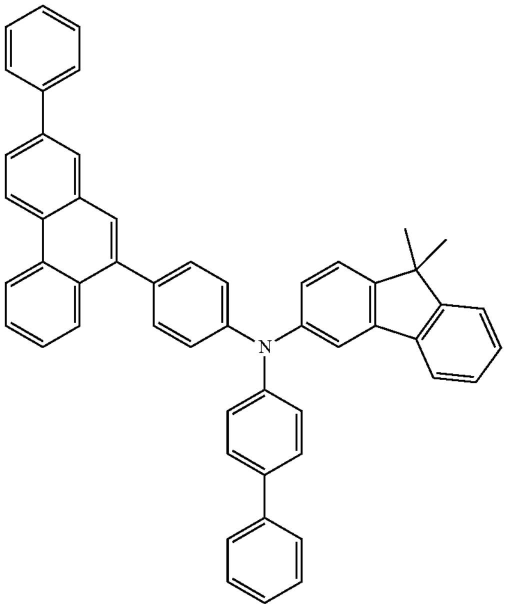
-continued
H1-104
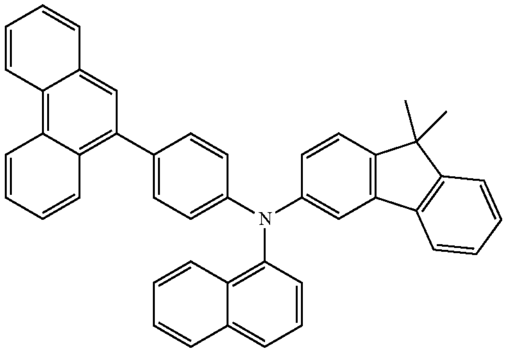
H1-105
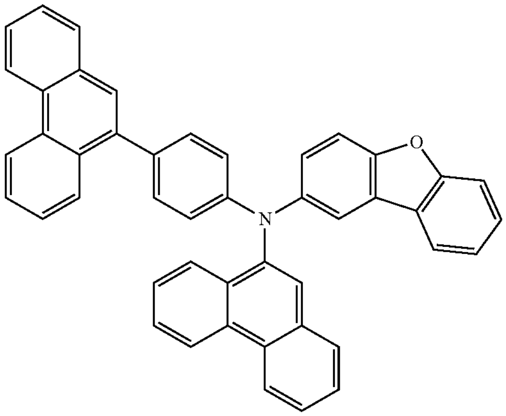
H1-106
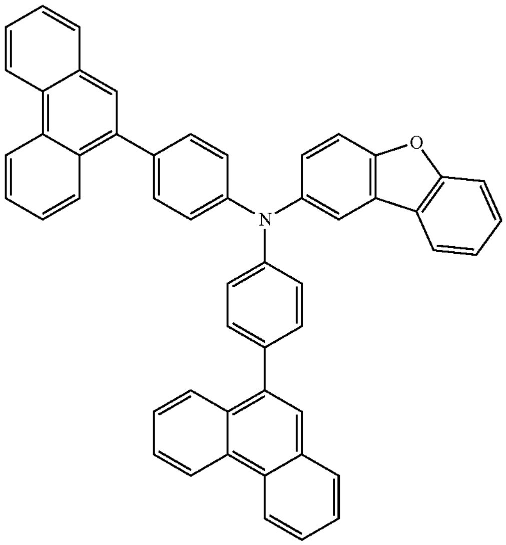

-continued
H1-107
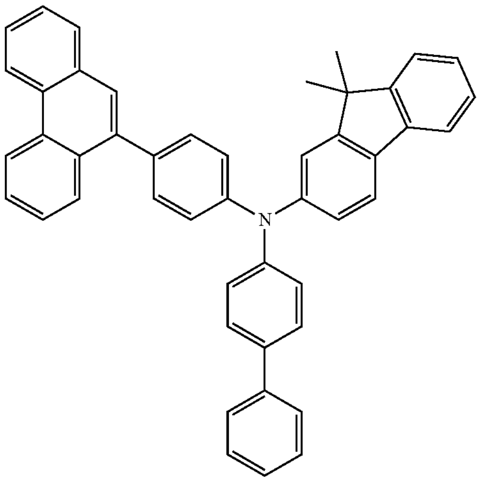
H1-108
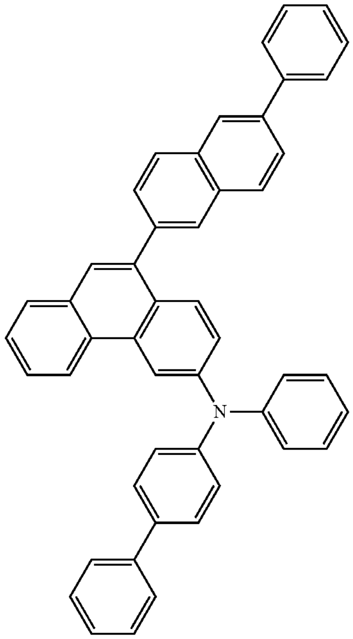
-continued
H1-109
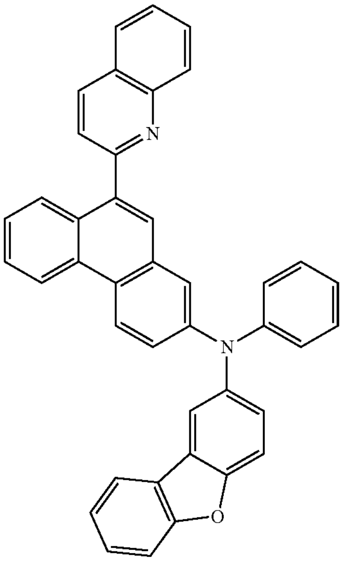
H1-110
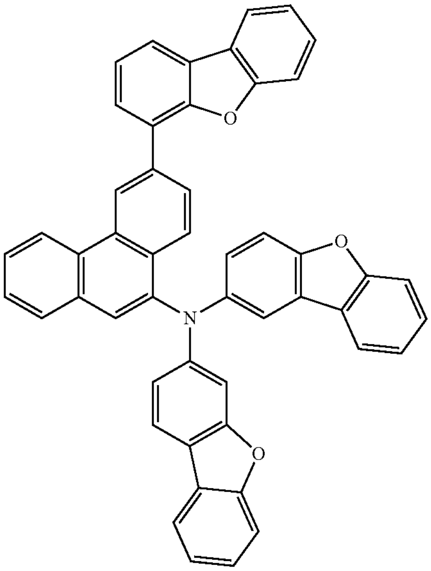
H1-111
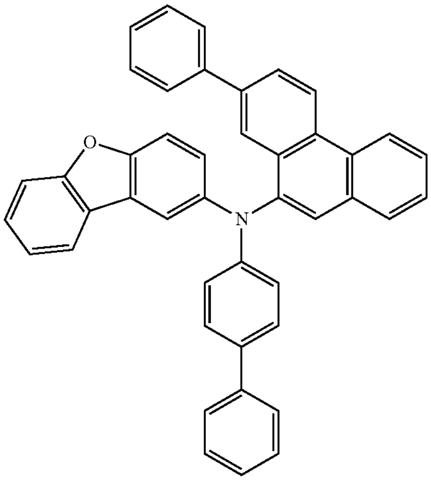

-continued
H1-112
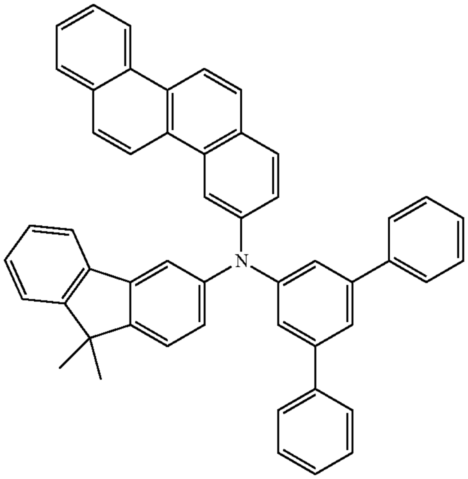
H1-113
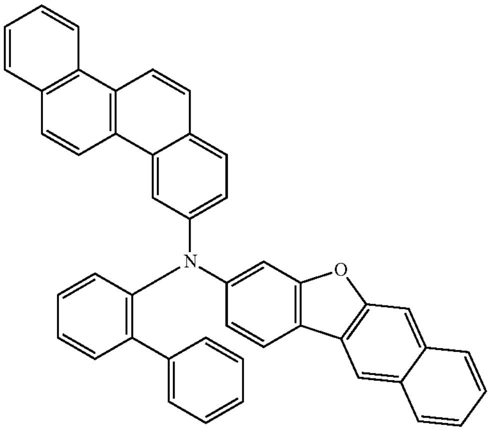
H1-114
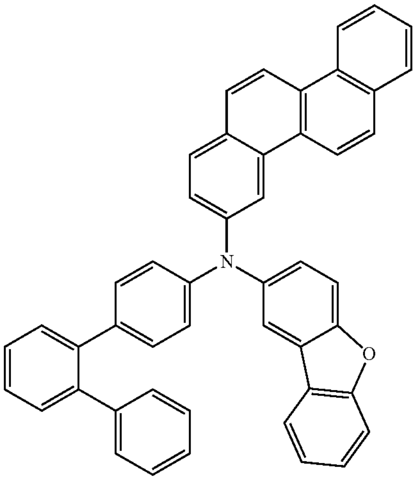
-continued
H1-115
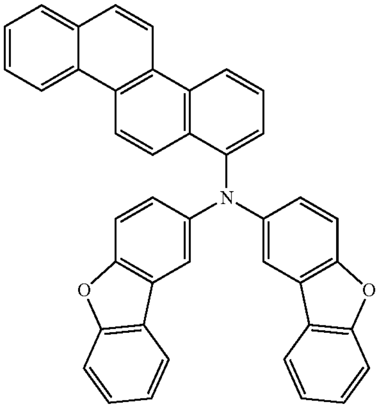
H1-116
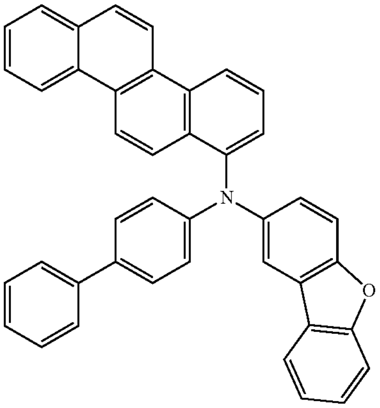
H1-117
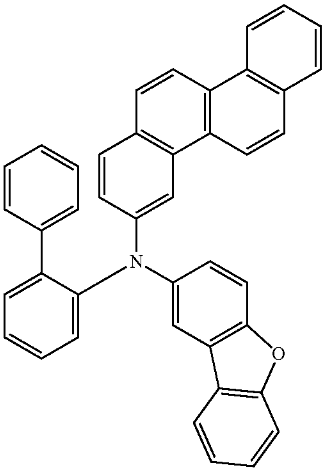

-continued
H1-118
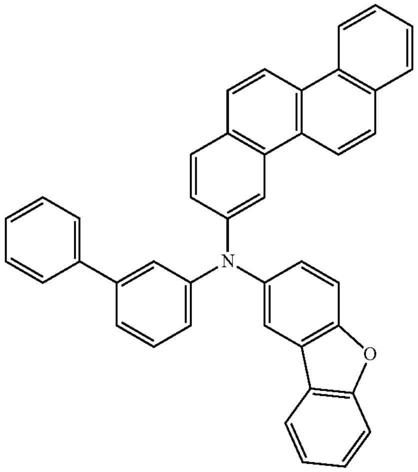
H1-119
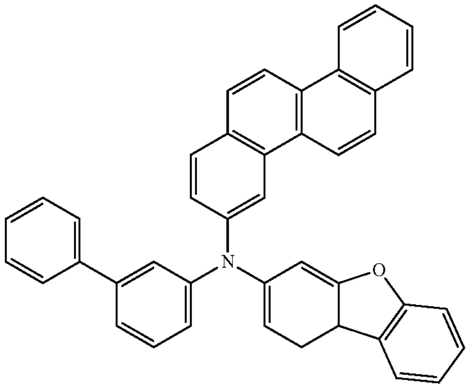
H1-120
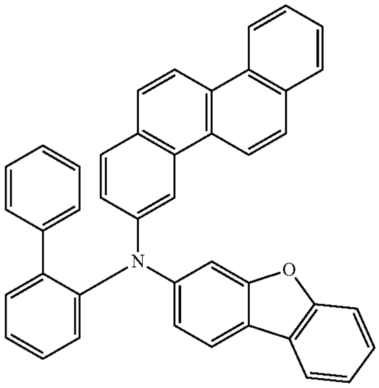
-continued
H1-121
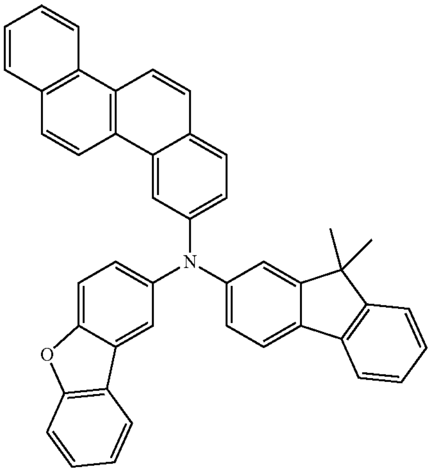
H1-122
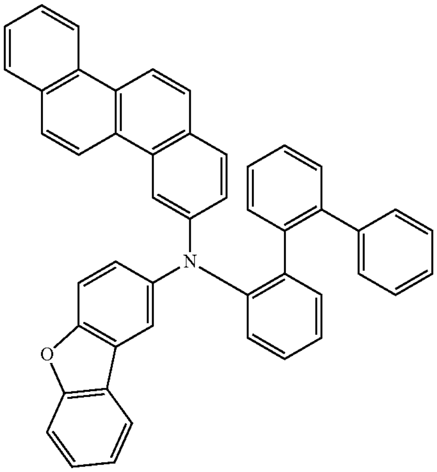
H1-123
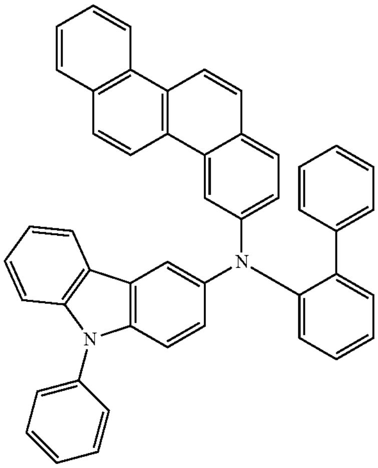

-continued
H1-124
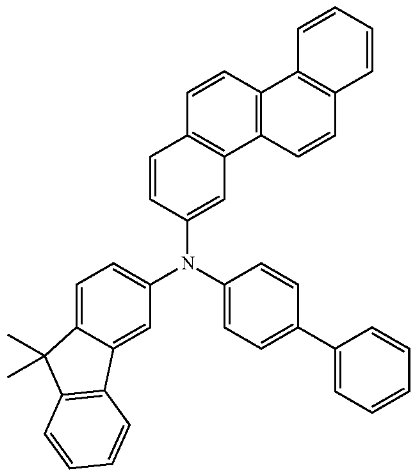
H1-125
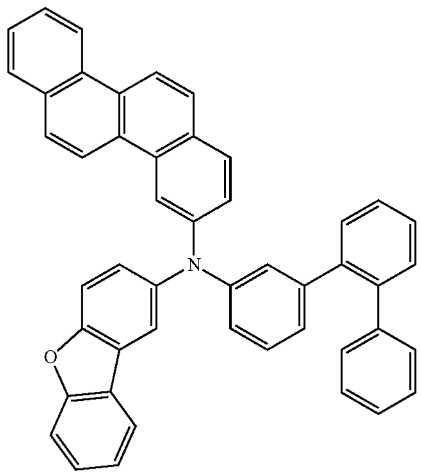
H1-121
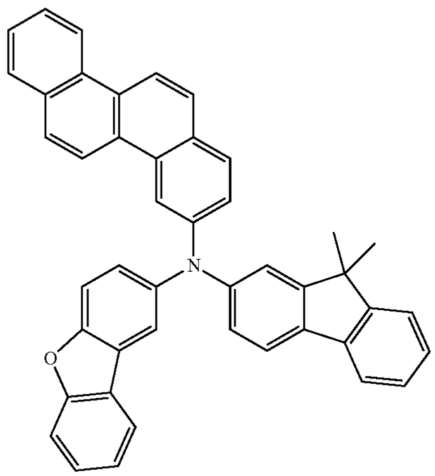
-continued
H1-122
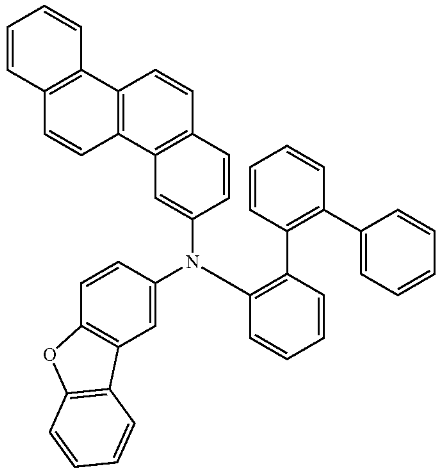
H1-123
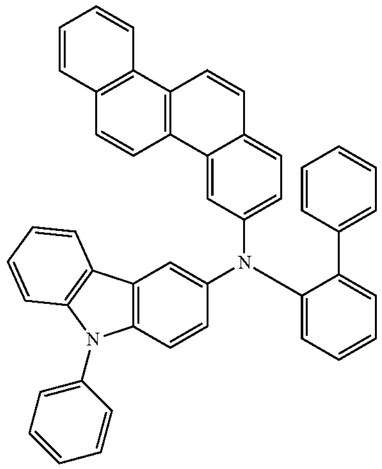
H1-124
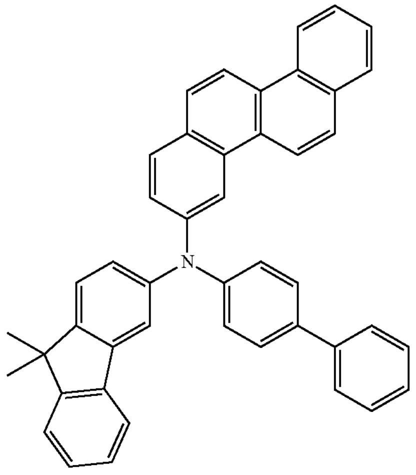

-continued
H1-125
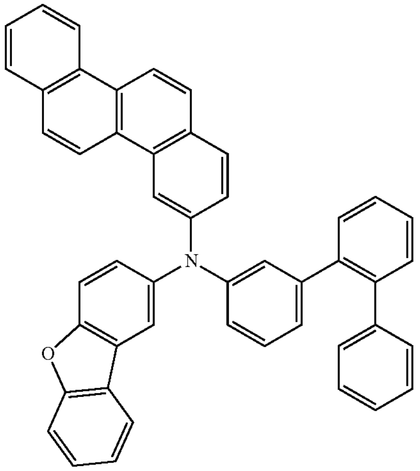
H1-126
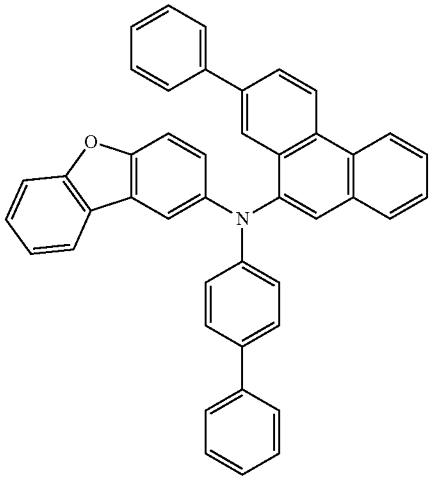
H1-127
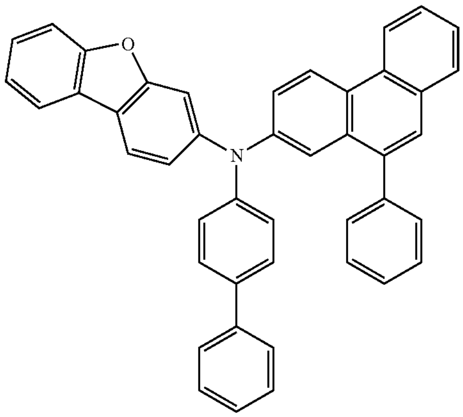
-continued
H1-128
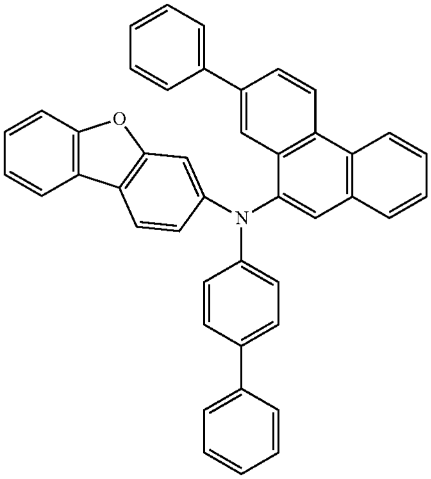
H1-129
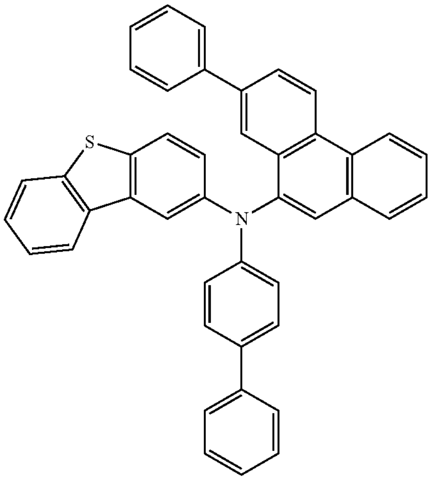
H1-130
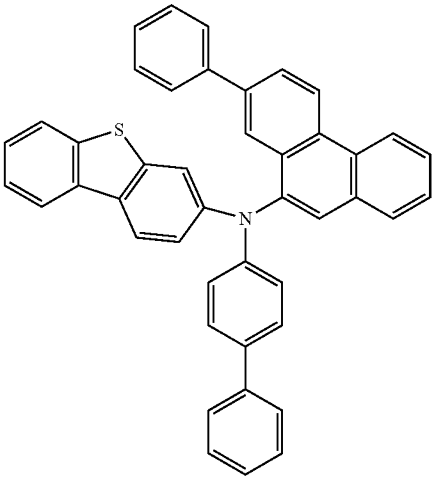

-continued
H1-131
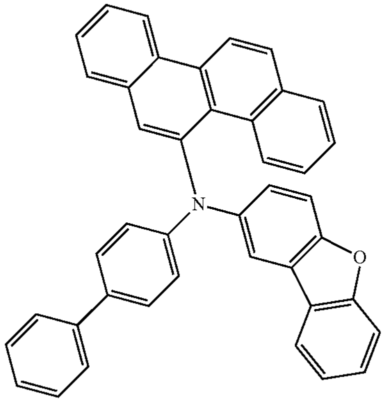
H1-132
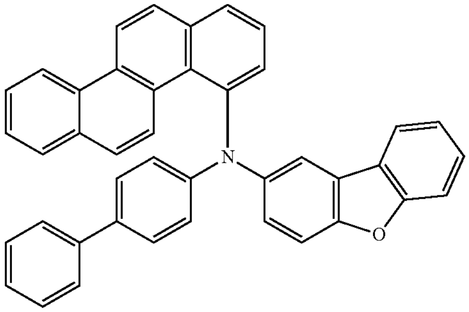
H1-133
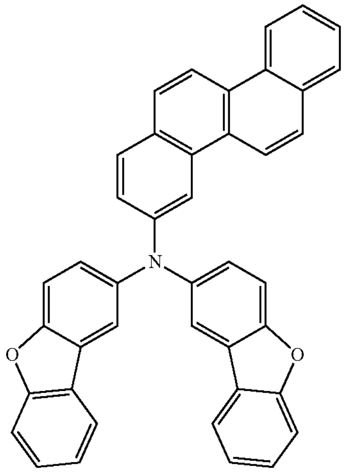
H1-134
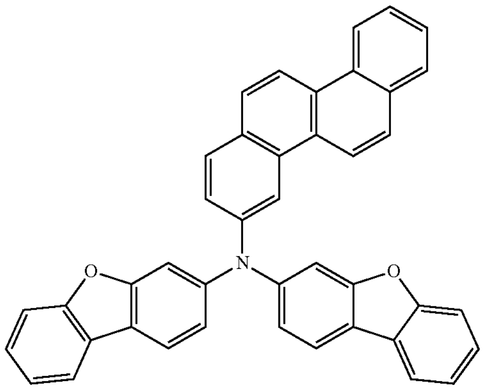
-continued
H1-135
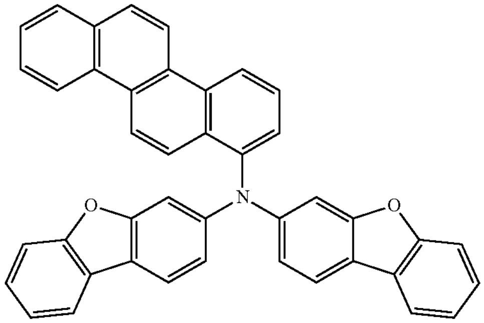
H1-136
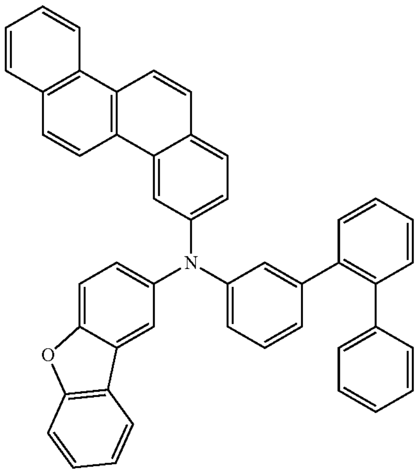
H1-137
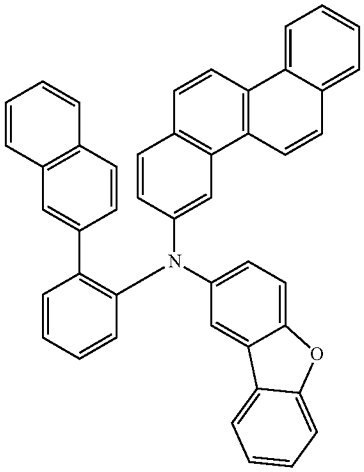

-continued
H1-138
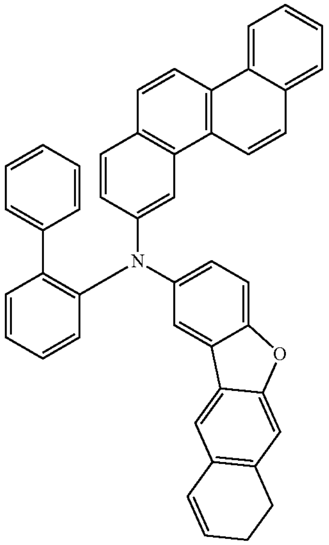
H1-139
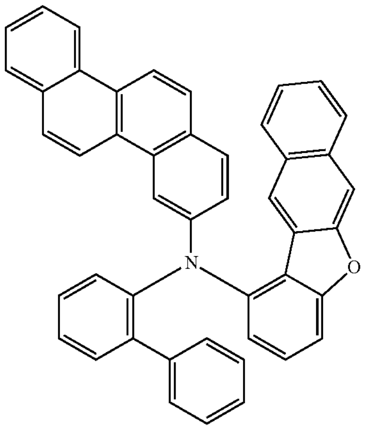
H1-140
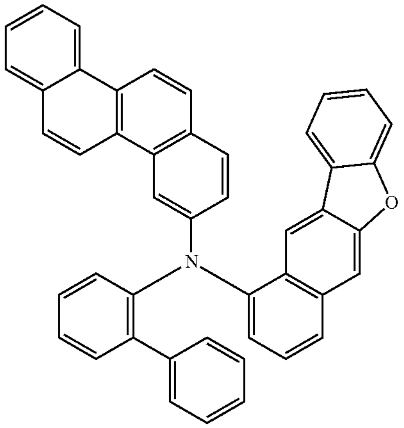
-continued
H1-141
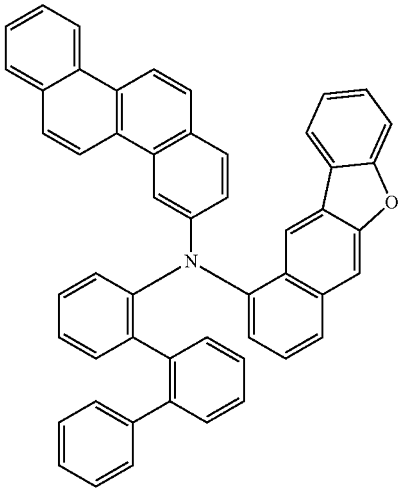
H1-142
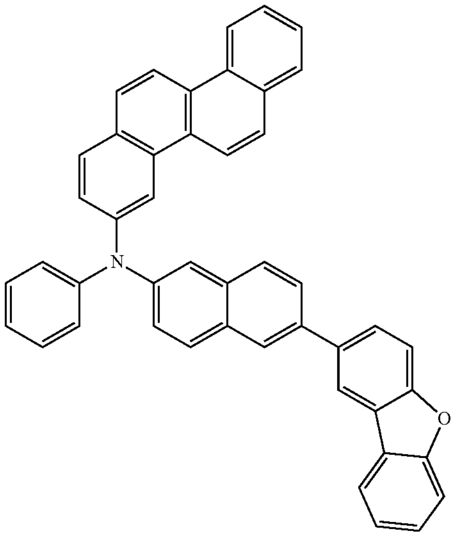
H1-143
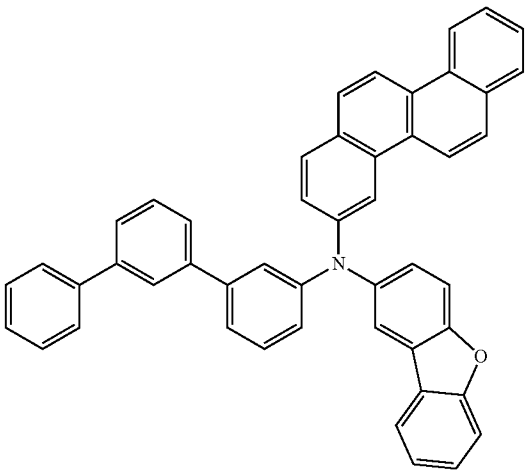

-continued

H1-144

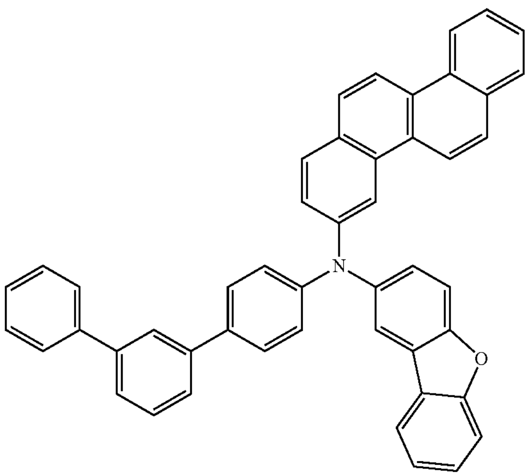

H1-145

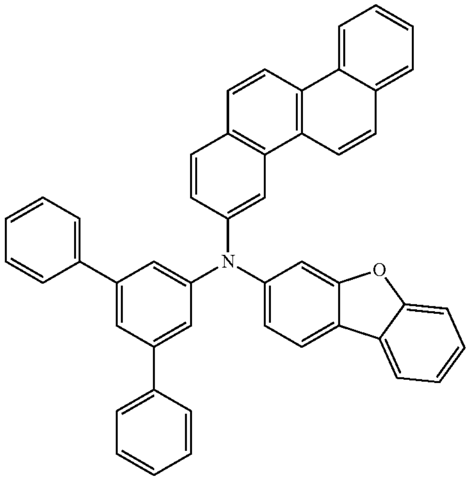

The compound represented by the formula 1 according to the present disclosure may be produced by a synthetic method known to a person skilled in the art.

The second host compound as another host material according to one embodiment may be represented by the following formula 2.

$$(Ar_{11}\text{-}L_{11})_a\text{-}HAr \quad (2)$$

In formula 2.

HAr represents a substituted or unsubstituted nitrogen-containing (3- to 20-membered)heteroaryl;

$L_{11}$ represents a single bond, a substituted or unsubstituted (C6-C30)arylene, or a substituted or unsubstituted (3- to 30-membered)heteroarylene;

$Ar_{11}$ represents a substituted or unsubstituted (C1-C30) alkyl, a substituted or unsubstituted (C3-C30)cycloalkyl, a substituted or unsubstituted (3- to 7-membered)heterocycloalkyl, a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or *-$L_{21}$-$NAr_{21}Ar_{22}$;

$L_{21}$ represents a single bond, a substituted or unsubstituted (C6-C30)arylene, or a substituted or unsubstituted (3- to 30-membered)heteroarylene:

$Ar_{21}$ and $Ar_2$ each independently represent, a substituted or unsubstituted (C1-C30)alkyl, a substituted or unsubstituted (C2-C30)alkenyl, a substituted or unsubstituted (C6-C30)aryl, or a substituted or unsubstituted (3- to 30-membered)heteroaryl; and a represent an integer of 1 to 3, and when a represent an integer of 2 or more, each of -($L_{11}$-$Ar_{11}$) may be the same or different.

In one embodiment, HAr may be a substituted or unsubstituted nitrogen-containing (5- to 20-membered)heteroaryl, preferably, a substituted or unsubstituted (5- to 20-membered)heteroaryl containing at least one nitrogen, more preferably a substituted or unsubstituted (5- to 20-membered)heteroaryl containing at least two nitrogens, even more preferably a (5- to 20-membered)heteroaryl containing at least three nitrogens. For example, HAr may be a substituted or unsubstituted pyridyl, a substituted or unsubstituted pyrimidyl, a substituted or unsubstituted triazinyl, a substituted or unsubstituted pyrazinyl, a substituted or unsubstituted quinolinyl, a substituted or unsubstituted quinazolinyl, a substituted or unsubstituted quinoxalinyl, a substituted or unsubstituted benzoquinolinyl, a substituted or unsubstituted benzoquinazolinyl, a substituted or unsubstituted benzoquinoxalinyl, a substituted or unsubstituted dibenzoquinolinyl, a substituted or unsubstituted dibenzoquinazolinyl, a substituted or unsubstituted dibenzoquinoxalinyl, a substituted or unsubstituted indenopyridyl, a substituted or unsubstituted indenopyrimidyl, a substituted or unsubstituted indenopyrazinyl, a substituted or unsubstituted benzofuropyridyl, a substituted or unsubstituted benzofuropyrimidyl, a substituted or unsubstituted benzofuropyrazinyl, a substituted or unsubstituted benzothiopyridyl, a substituted or unsubstituted benzothiopyrimidyl, or a substituted or unsubstituted benzothiopyrazinyl, for example, a substituted or unsubstituted pyridyl, a substituted or unsubstituted pyrimidyl, or a substituted or unsubstituted triazinyl.

In one embodiment, $L_{11}$ may be a single bond, a substituted or unsubstituted (C6-C30)arylene, or a substituted or unsubstituted (5- to 30-membered)heteroarylene, preferably, a single bond, a substituted or unsubstituted (C6-C25) arylene, or a substituted or unsubstituted (5- to 25-membered)heteroarylene, more preferably, a single bond, a substituted or unsubstituted (C6-C18)arylene, or a substituted or unsubstituted (5- to 25-membered)heteroarylene. For example, $L_{11}$ may be a single bond, a substituted or unsubstituted phenylene, a substituted or unsubstituted p-biphenylene, a substituted or unsubstituted m-biphenylene, a substituted or unsubstituted o-biphenylene, a substituted or unsubstituted terphenylene, a substituted or unsubstituted naphthalenylene, a substituted or unsubstituted phenylnaphthalenylene, a substituted or unsubstituted naphthylphenylene, a substituted or unsubstituted binaphthalenylene, a substituted or unsubstituted pyrimidylphenylene, a substituted or unsubstituted phenanthrenylene, a substituted or unsubstituted triphenylenylene, a substituted or unsubstituted chrysenylene, a substituted or unsubstituted fluorenylene, a substituted or unsubstituted pyridylene, a substituted or unsubstituted pyrimidylene, a substituted or unsubstituted dibenzofuranylene, a substituted or unsubstituted phenanthrooxazolylene, a substituted or unsubstituted phenanthrothiazolylene, a substituted or unsubstituted triazinylene, a substituted or unsubstituted quinoxalinylene, a substituted or unsubstituted quinazolinylene, or a substituted or unsubstituted benzoquinoxalinylene, for example, a single bond, a substituted or unsubstituted phenylene, a substituted or unsubstituted p-biphenylene, a substituted or unsubstituted m-biphenylene, a substituted or unsubstituted naphthalenylene, a substituted or unsubstituted naphthylphenylene, a substituted or unsubstituted binaphthalenylene, a substituted or unsubstituted phenanthrenylene, a substituted or unsubstituted chrysenylene, a substituted or unsubstituted pyridylene, a substituted or unsubstituted pyrimidylene, a substituted or unsubstituted dibenzofuranylene, a substituted or unsubstituted phenanthrooxazolylene, or a substituted or unsubstituted phenanthrothiazolylene.

In one embodiment, $Ar_{11}$ may be a substituted or unsubstituted (C1-C30)alkyl, a substituted or unsubstituted (C3-C30)cycloalkyl, a substituted or unsubstituted (C6-C30)aryl, a substituted or unsubstituted (5- to 30-membered)heteroaryl, or a substituted or unsubstituted tri(C6-C30)arylsilyl, preferably a substituted or unsubstituted (C1-C10)alkyl, a substituted or unsubstituted (C3-C12)cycloalkyl, a substituted or unsubstituted (C6-C25)aryl, a substituted or unsubstituted (5- to 25-membered)heteroaryl, or a substituted or unsubstituted tri(C6-C25)arylsilyl, more preferably a substituted or unsubstituted (C1-C4)alkyl, a substituted or unsubstituted (C5-C12)cycloalkyl, a substituted or unsubstituted (C6-C18)aryl, a substituted or unsubstituted (5- to 25-membered)heteroaryl, or a substituted or unsubstituted tri(C6-C18)arylsilyl. For example, $Ar_{11}$ may be a substituted or unsubstituted methyl, a substituted or unsubstituted tert-butyl, a substituted or unsubstituted cyclohexyl, a substituted or unsubstituted phenyl, a substituted or unsubstituted m-biphenyl, a substituted or unsubstituted p-biphenyl, a substituted or unsubstituted o-terphenyl, a substituted or unsubstituted m-terphenyl, a substituted or unsubstituted p-terphenyl, a substituted or unsubstituted naphthyl, a substituted or unsubstituted phenanthrenyl, a substituted or unsubstituted triphenylenyl, a substituted or unsubstituted fluorenyl, a substituted or unsubstituted spirobifluorenyl, a substituted or unsubstituted triphenylsilanyl, a substituted or unsubstituted pyridyl, a substituted or unsubstituted triazinyl, a substituted or unsubstituted quinoxalinyl, a substituted or unsubstituted quinazolinyl, or a substituted or unsubstituted benzoquinoxalinyl, a substituted or unsubstituted carbazolyl, a substituted or unsubstituted benzocarbazolyl, a substituted or unsubstituted dibenzocarbazolyl, a substituted or unsubstituted dibenzofuranyl, a substituted or unsubstituted benzonaphthofuranyl, a substituted or unsubstituted dibenzothiophenyl, a substituted or unsubstituted benzonaphthothiophenyl, a substituted or unsubstituted phenanthrooxazolyl, a substituted or unsubstituted phenanthrothiazolyl, a substituted or unsubstituted naphthocarbazolyl, a substituted or unsubstituted benzophenanthrofuranyl, a substituted or unsubstituted benzophenanthrothiophenyl, a substituted or unsubstituted indenophenanthrenyl, or a substituted or unsubstituted carbazolyl or benzocarbazolyl fused with indole, benzofuran, benzothiophene, indeno, or benzoindole, for example, a substituted or unsubstituted methyl, a substituted or unsubstituted tert-butyl, a substituted or unsubstituted cyclohexyl, a substituted or unsubstituted phenyl, a substituted or unsubstituted m-biphenyl, a substituted or unsubstituted p-biphenyl, a substituted or unsubstituted o-terphenyl, a substituted or unsubstituted m-terphenyl, a substituted or unsubstituted p-terphenyl, a substituted or unsubstituted naphthyl, a substituted or unsubstituted triphenylenyl, a substituted or unsubstituted fluorenyl, a substituted or unsubstituted spirobifluorenyl, a substituted or unsubstituted triphenylsilanyl, a substituted or unsubstituted triazinyl, a substituted or unsubstituted carbazolyl, a substituted or unsubstituted benzocarbazolyl, a substituted or unsubstituted dibenzofuranyl, a substituted or unsubstituted benzonaphthofuranyl, a substituted or unsubstituted benzophenanthrofuranyl, a substituted or unsubstituted benzonaphthothiophenyl, a substituted or unsubstituted phenanthrooxazolyl, or a substituted or unsubstituted phenanthrothiazolyl. The substituents of the substituted groups may be for example, deuterium; tert-butyl; phenyl; naphthyl; or carbazolyl.

In one embodiment, the second host material represented by the above formula 2 may be more specifically illustrated by the following compounds, but is not limited thereto.

H2-1

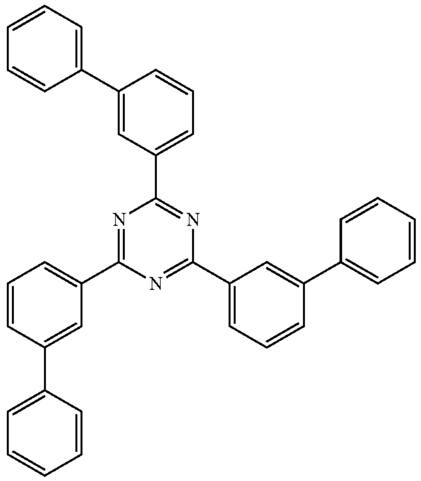

H2-2

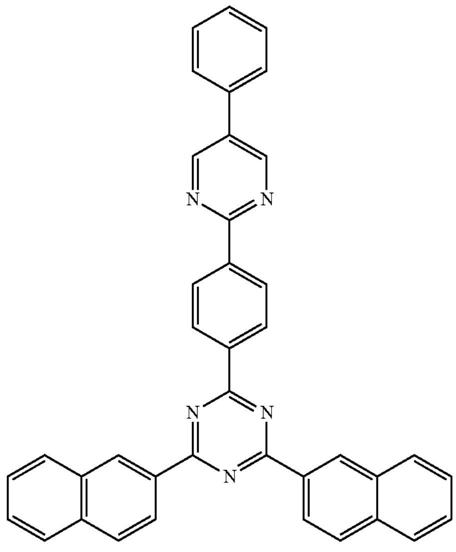

-continued
H2-3
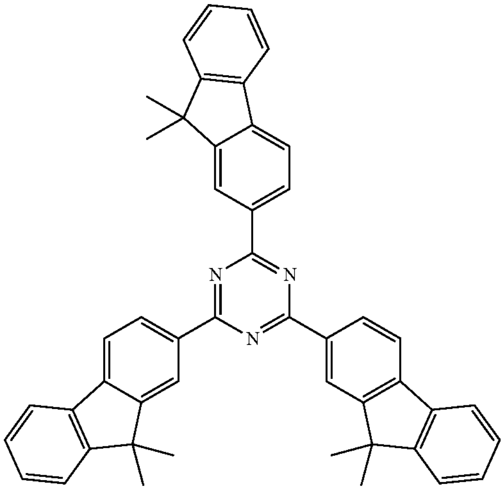
H2-4
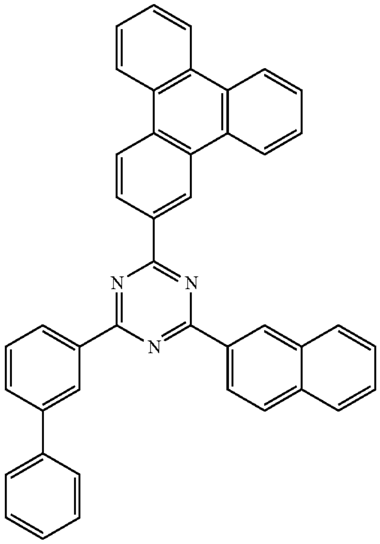
H2-5
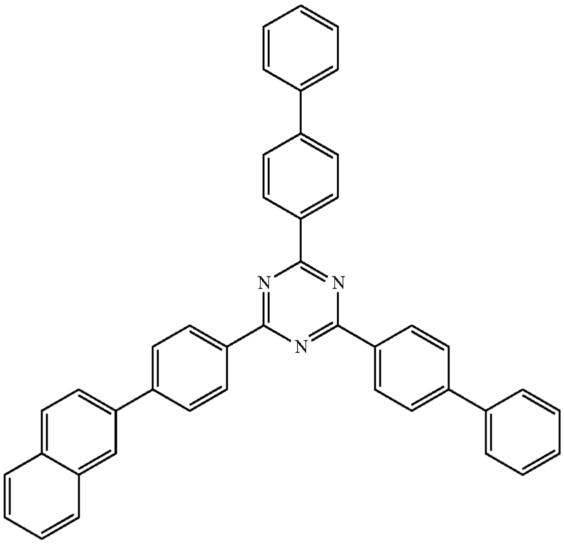
-continued
H2-6
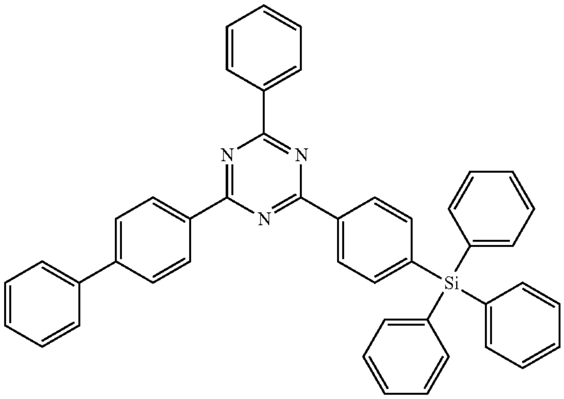
H2-7
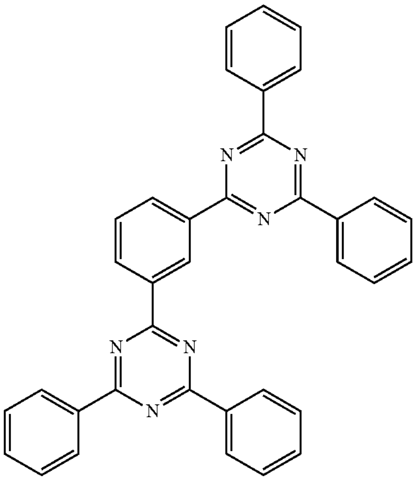
H2-8
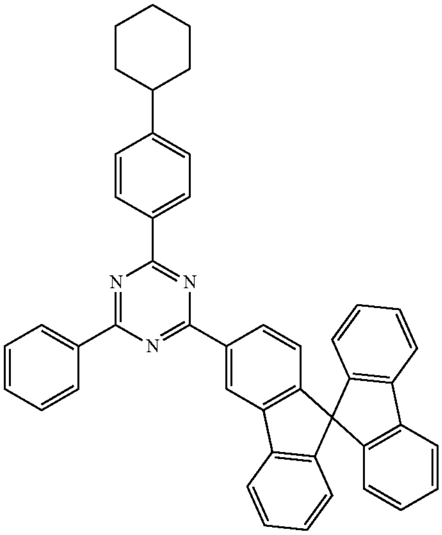

-continued
H2-9
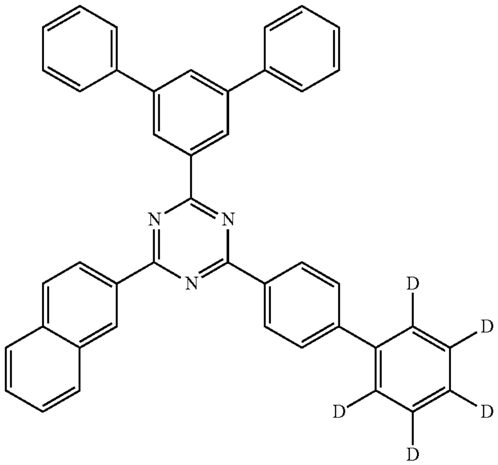
H2-10
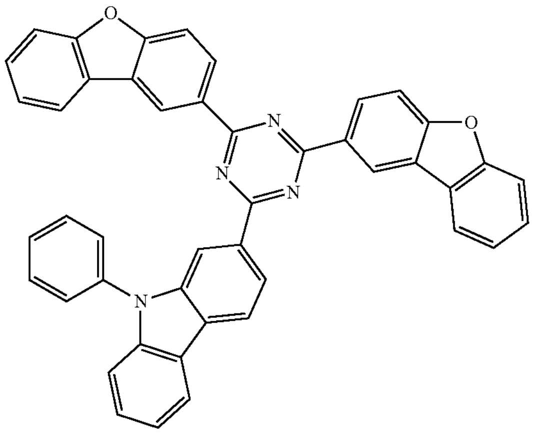
H2-11
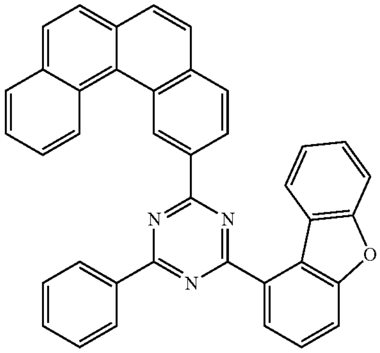
H2-12
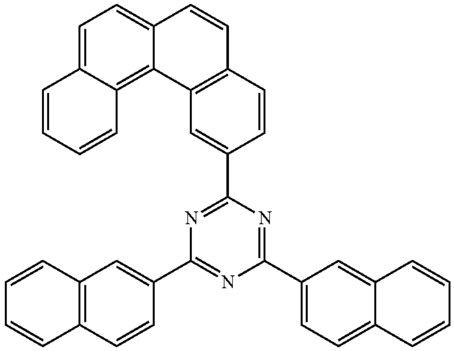
-continued
H2-13
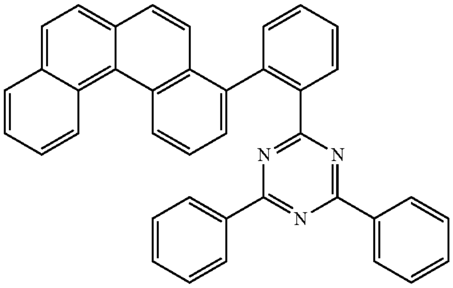
H2-14
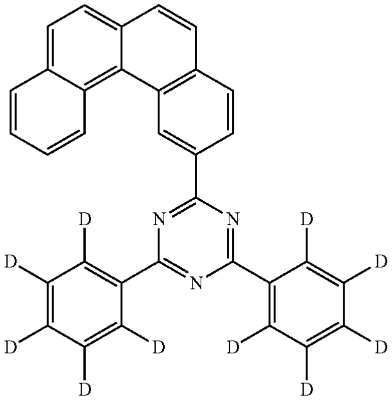
H2-15
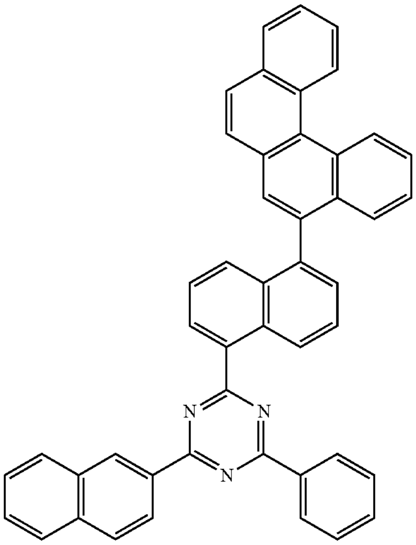
H2-16
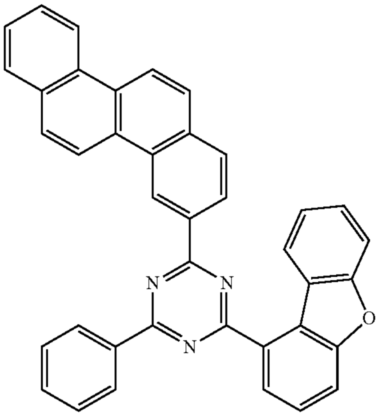

-continued
H2-17
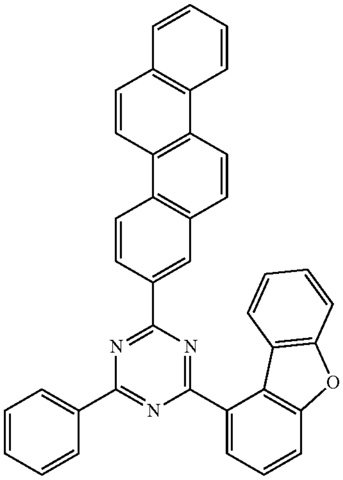
H2-18
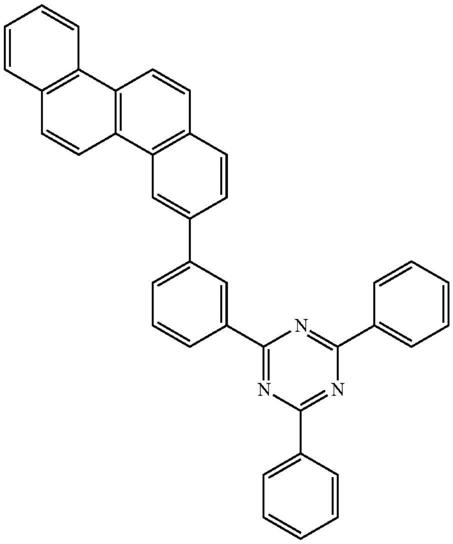
H2-19
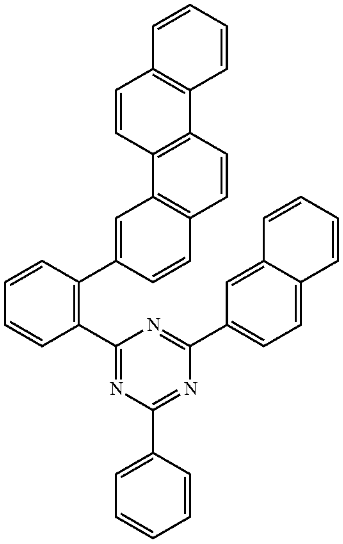
-continued
H2-20
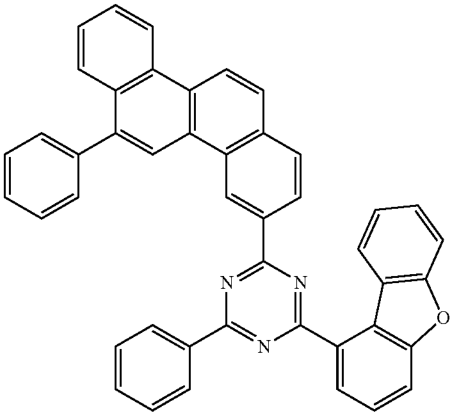
H2-21
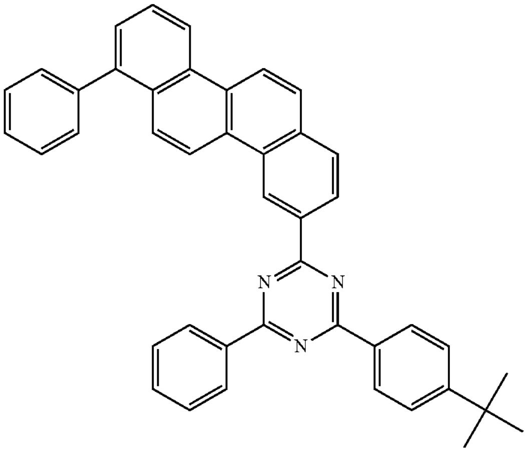
H2-22
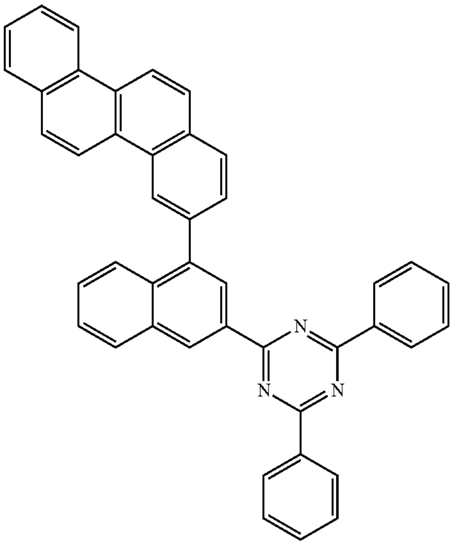

-continued
H2-23
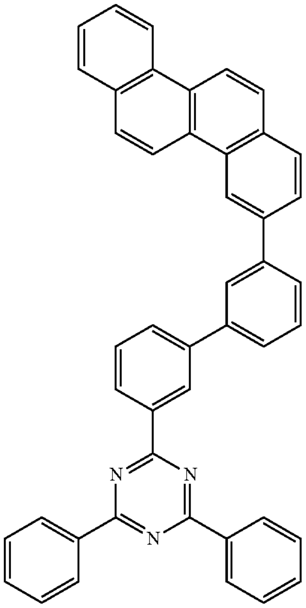
H2-24
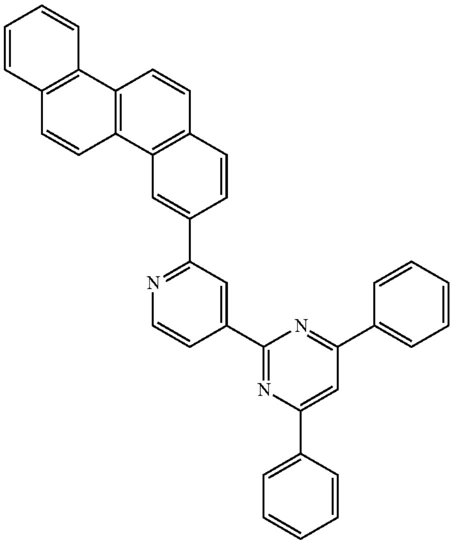
H2-25
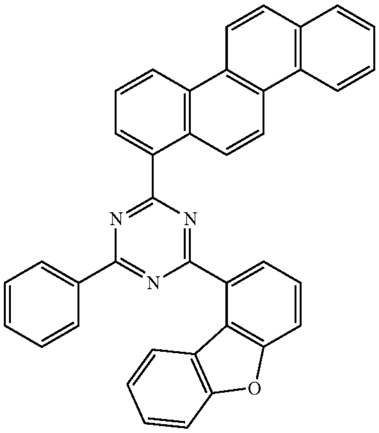
-continued
H2-26
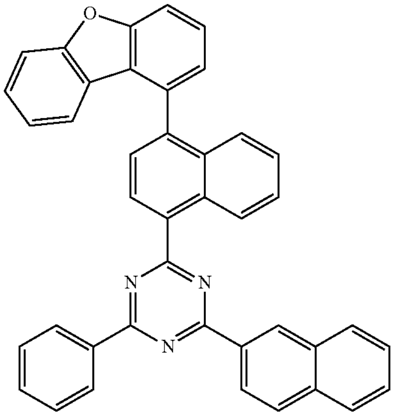
H2-27
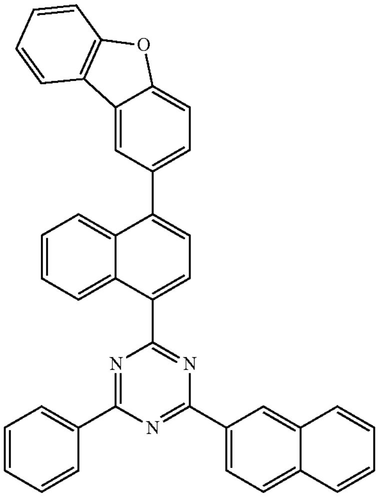
H2-28
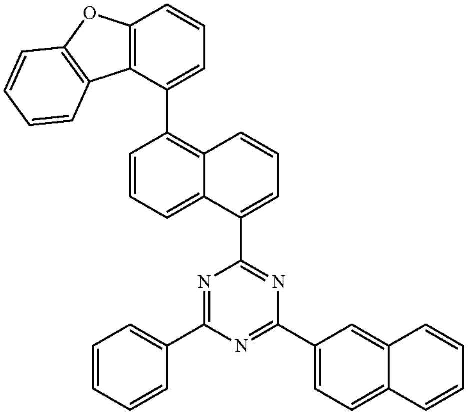

-continued
H2-29
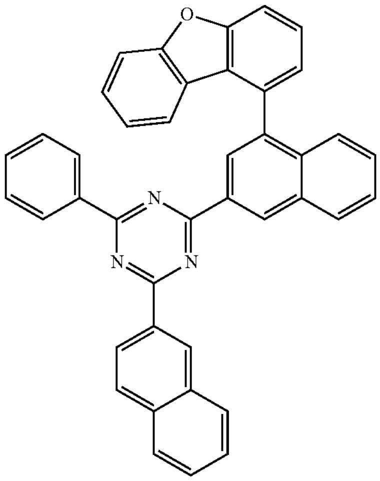
H2-30
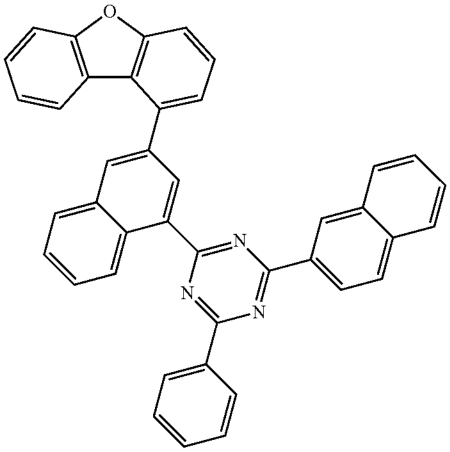
H2-31
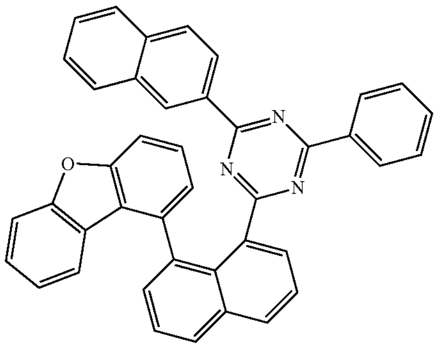
H2-32
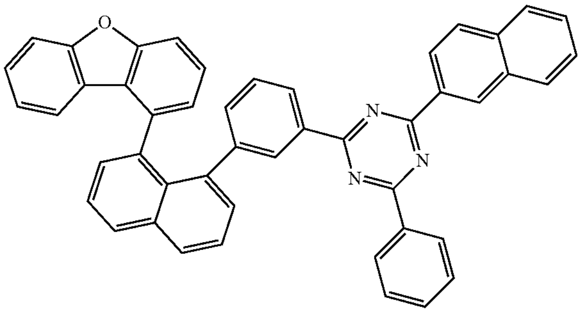
-continued
H2-33
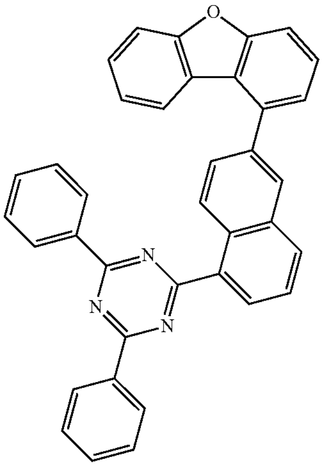
H2-34
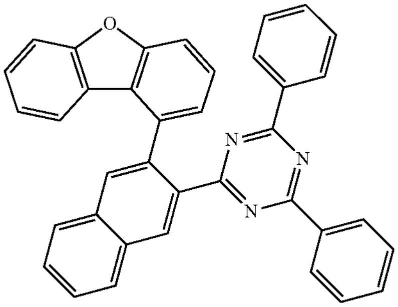
H2-35
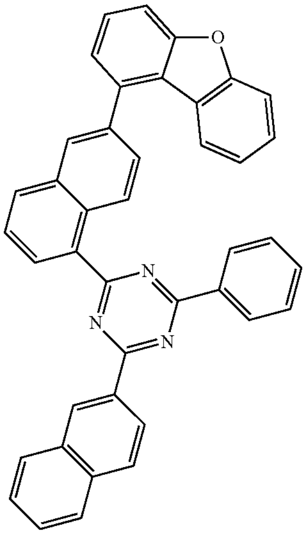

-continued
H2-36
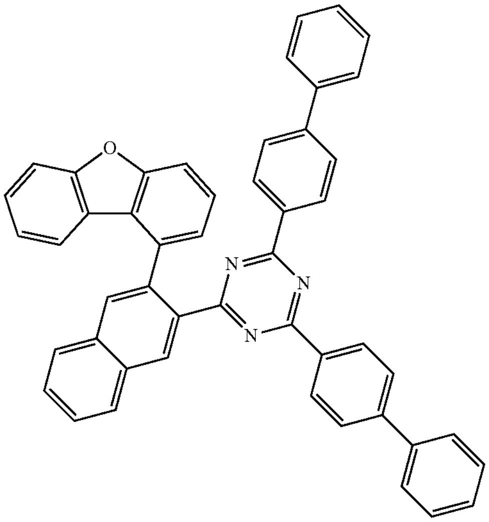
H2-37
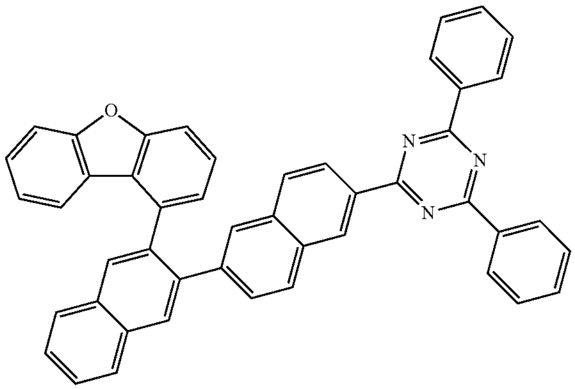
H2-38
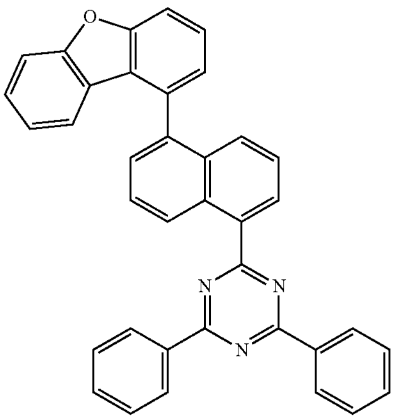
-continued
H2-39
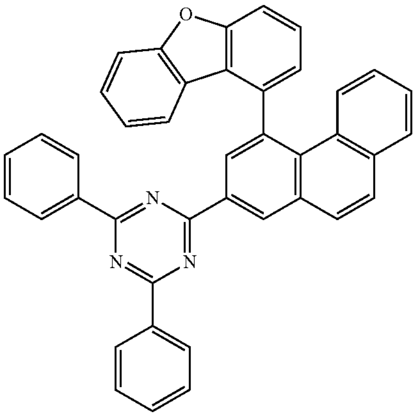
H2-40
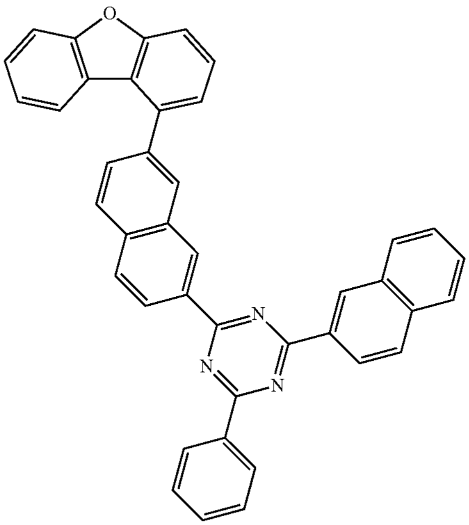
H2-41
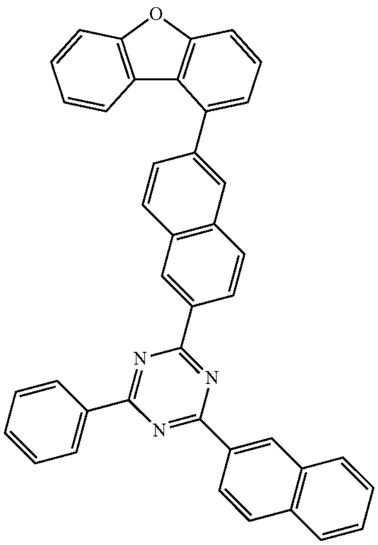

-continued
H2-42
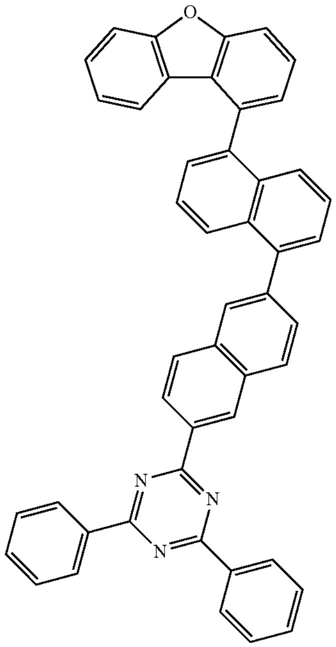
H2-43
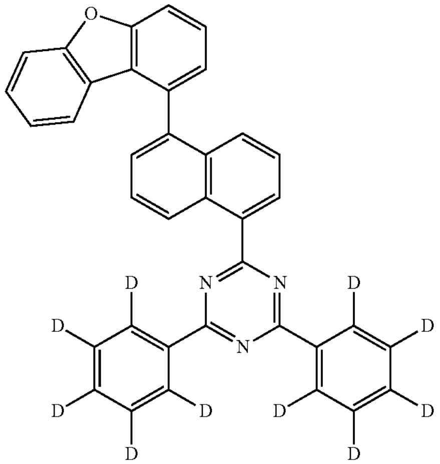
H2-44
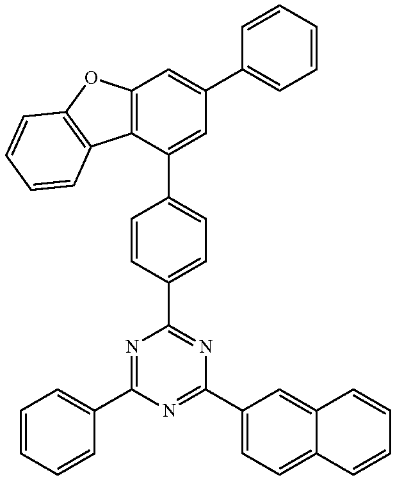
-continued
H2-45
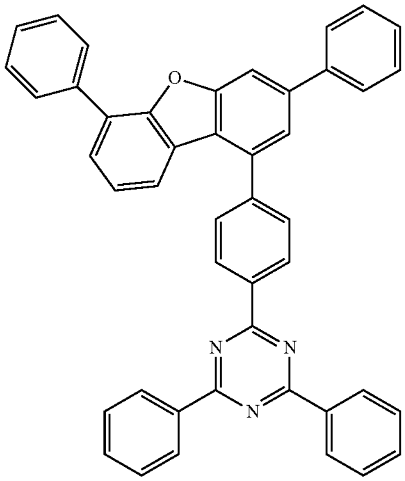
H2-46
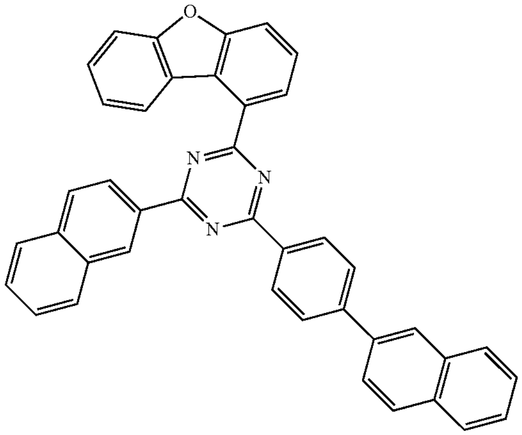
H2-47
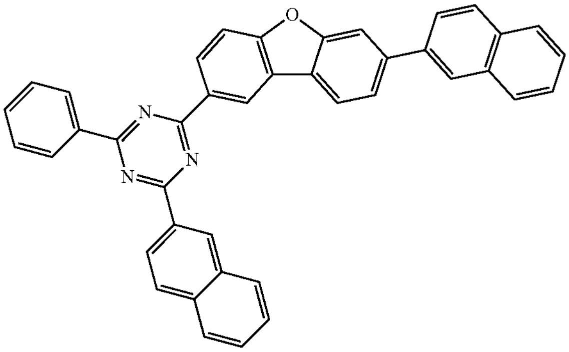

-continued
H2-48
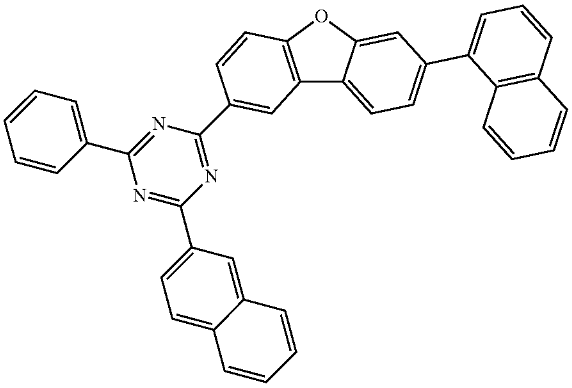
H2-49
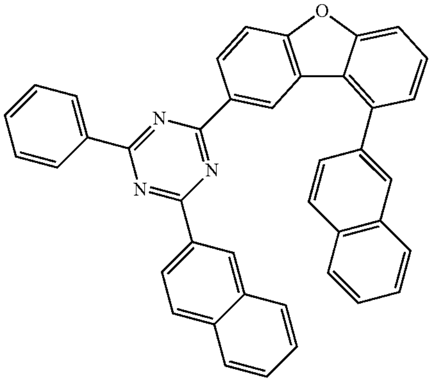
H2-50
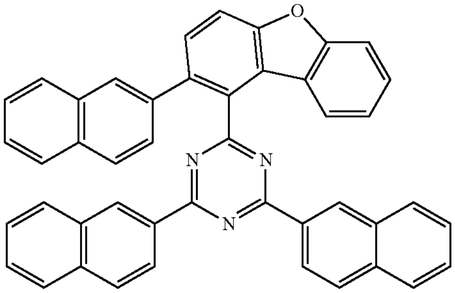
H2-51
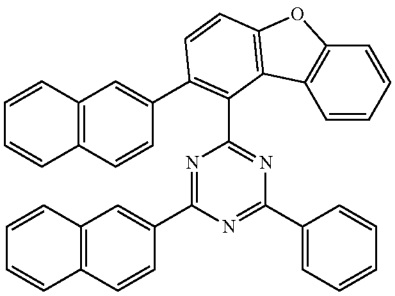
-continued
H2-52
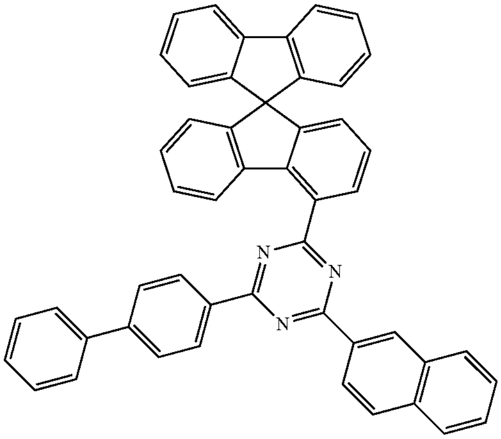
H2-53
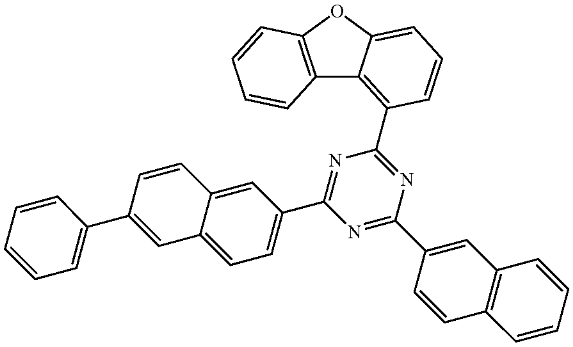
H2-54
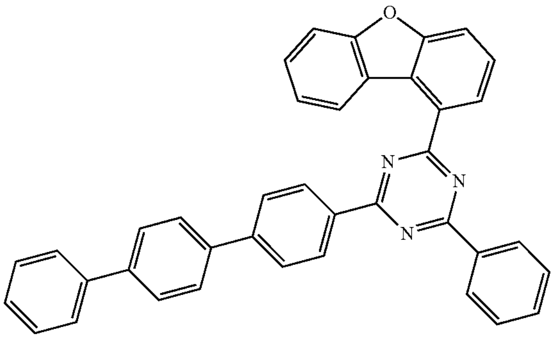
H2-55
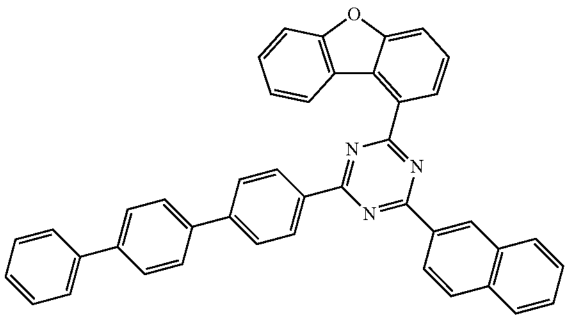

-continued
H2-56
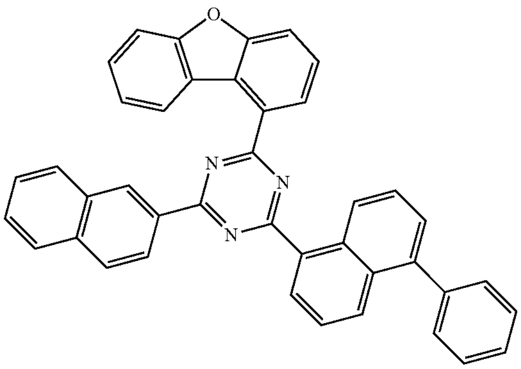
H2-57
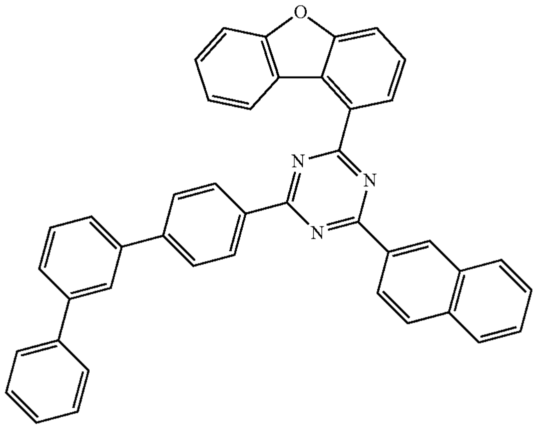
H2-58
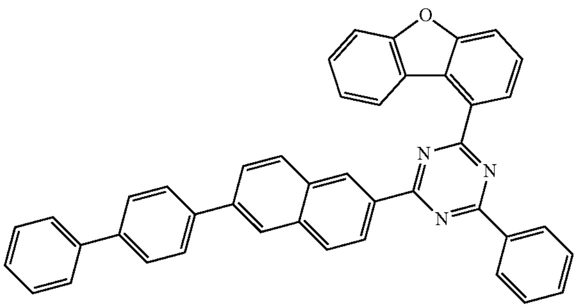
H2-59
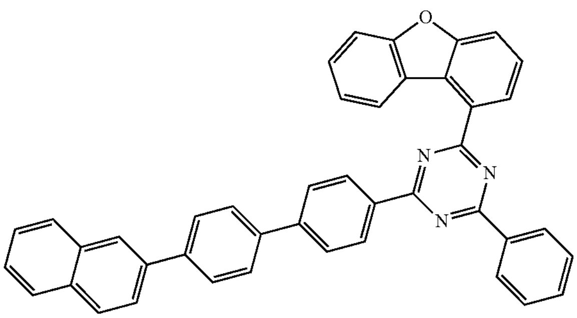
-continued
H2-60
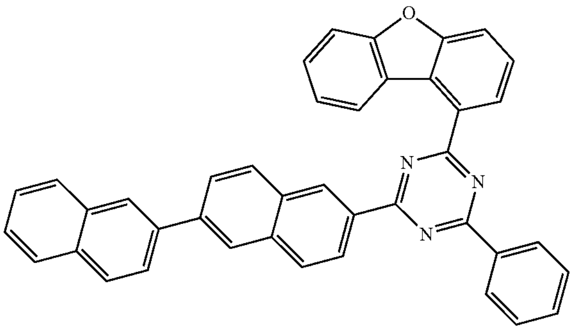
H2-61
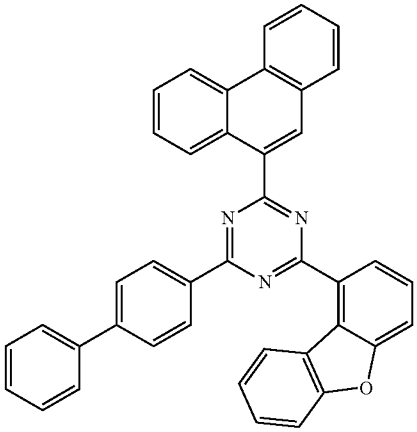
H2-62
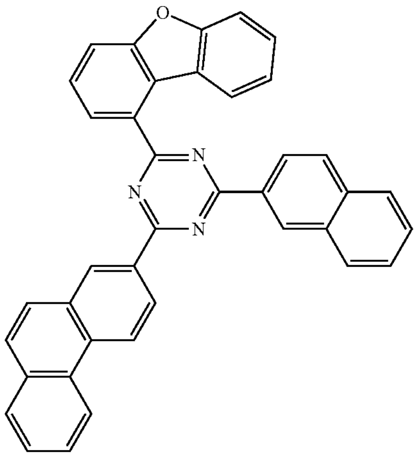
H2-63
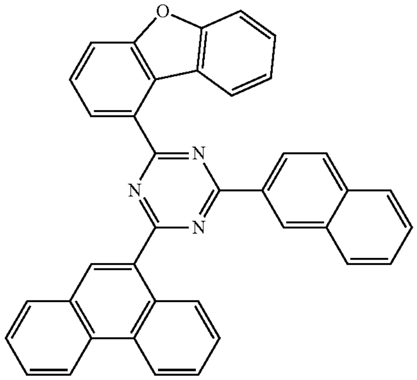

-continued
H2-64
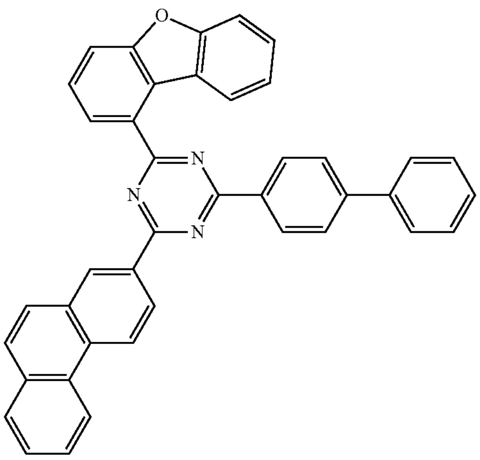
H2-65
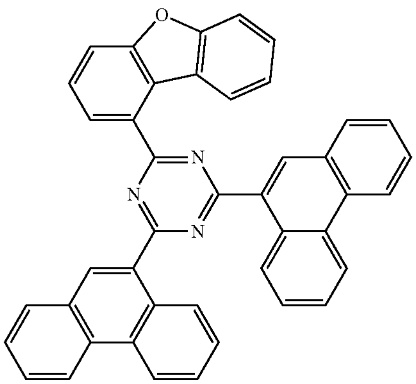
H2-66
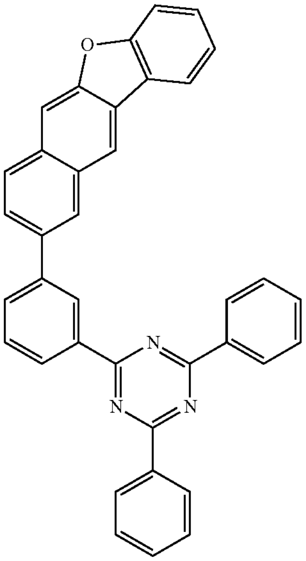
-continued
H2-67
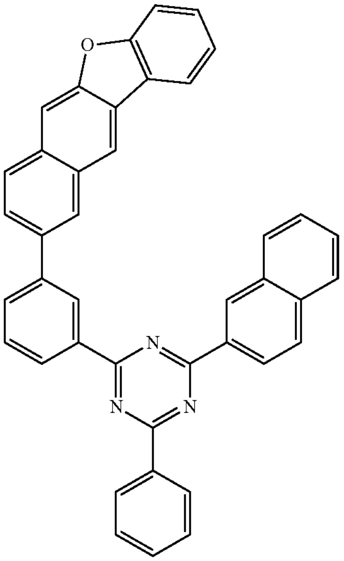
H2-68
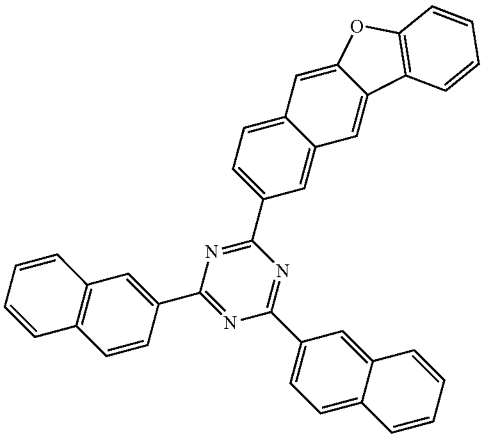
H2-69
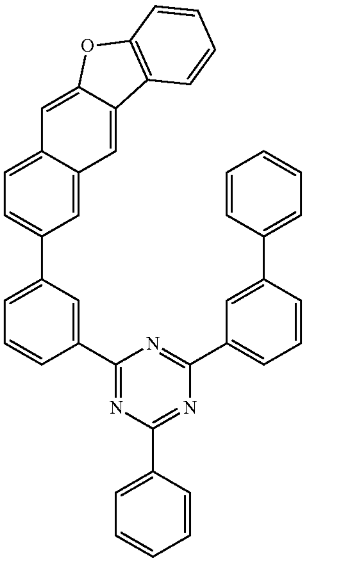

-continued
H2-70
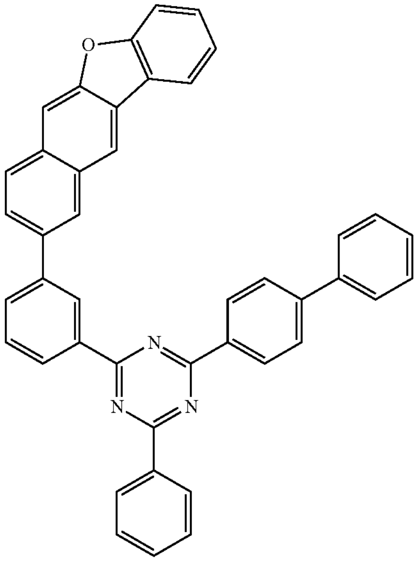
H2-71
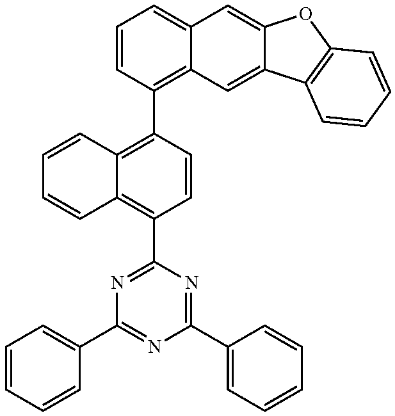
H2-72
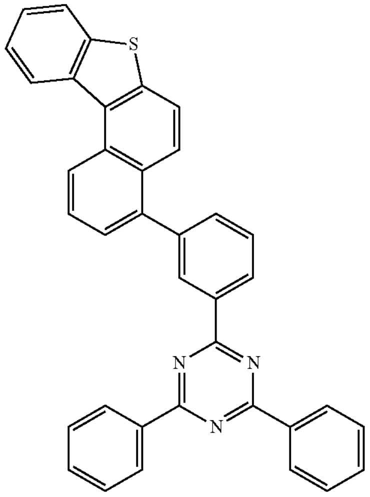
-continued
H2-73
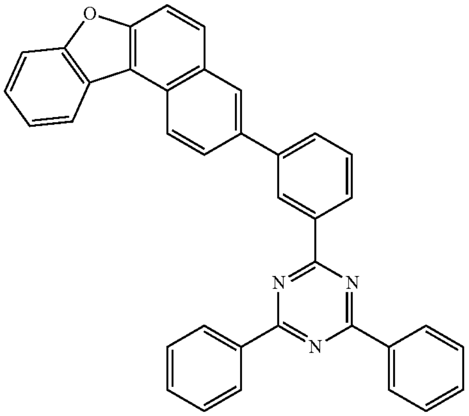
H2-74
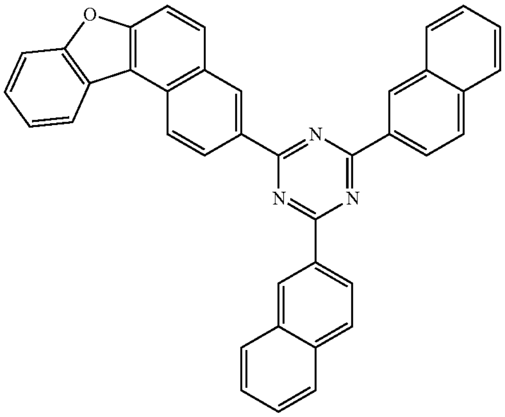
H2-75
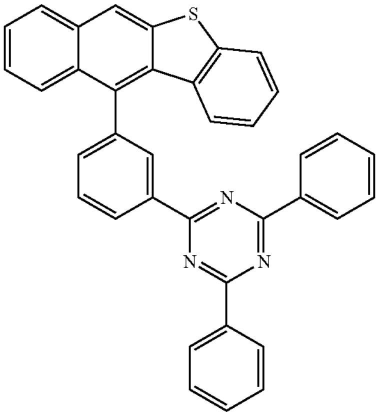
H2-76
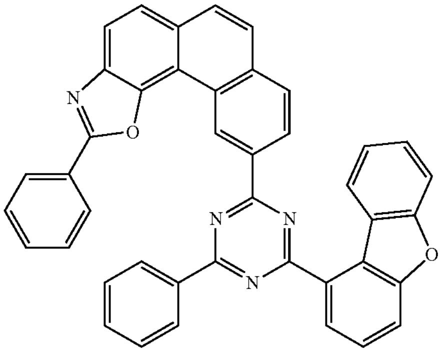

-continued
H2-77
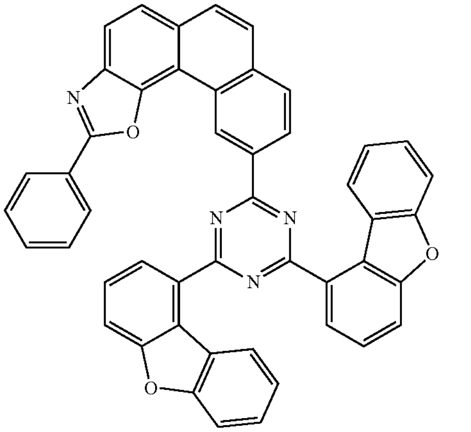
H2-78
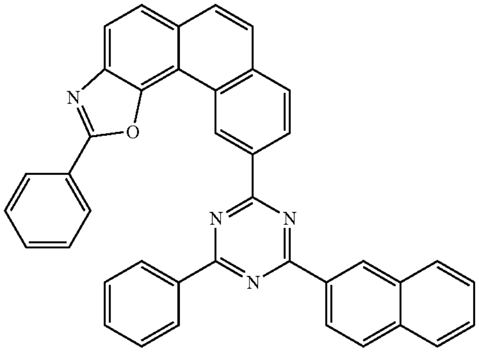
H2-79
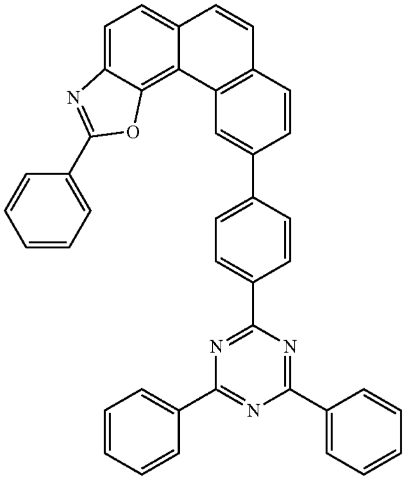
-continued
H2-80
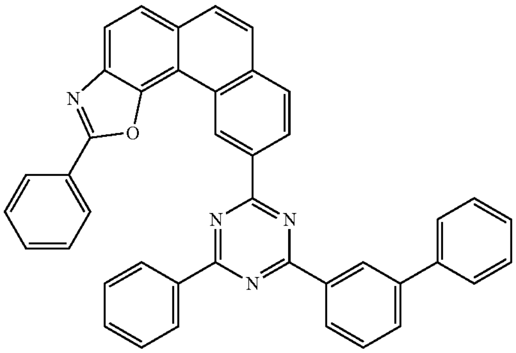
H2-81
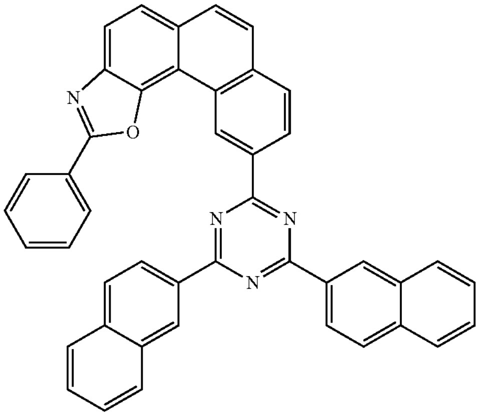
H2-82
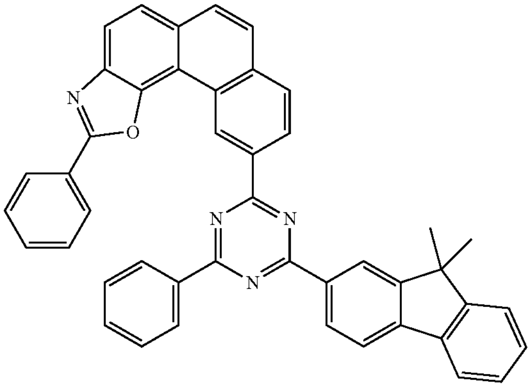
H2-83
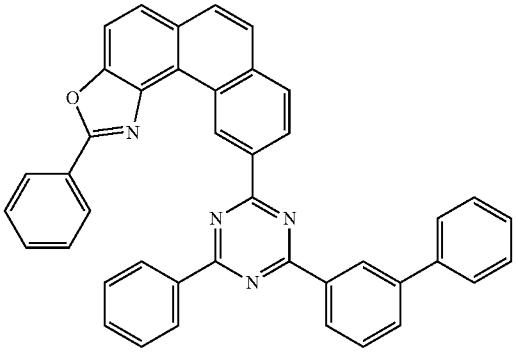

-continued
H2-84
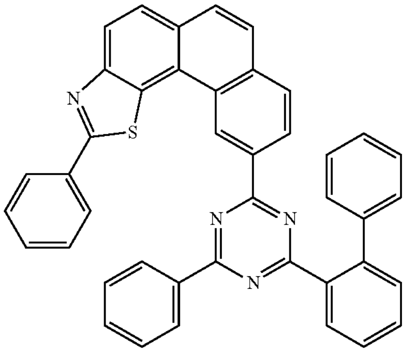
H2-85
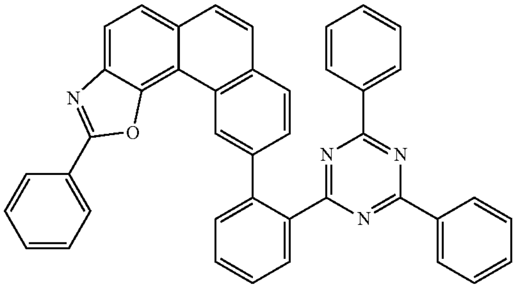
H2-86
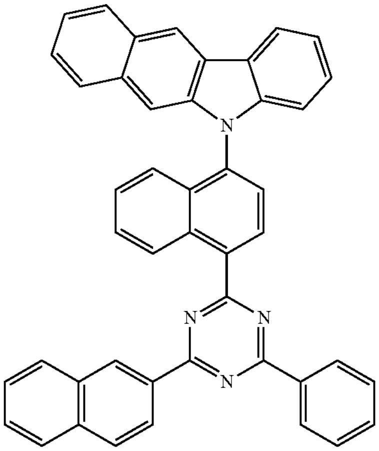
H2-87
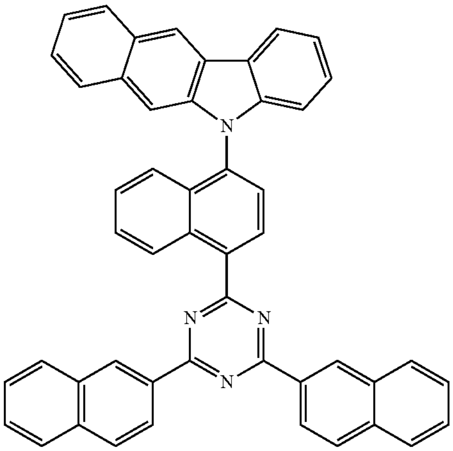
-continued
H2-88
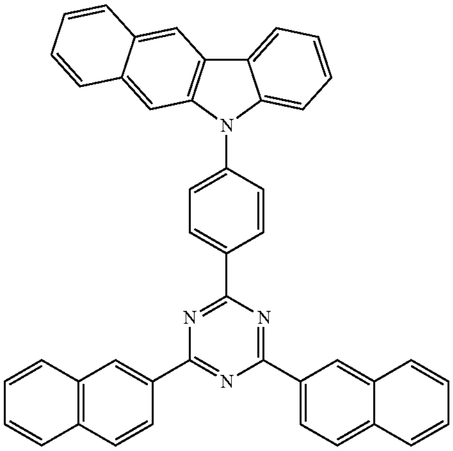
H2-89
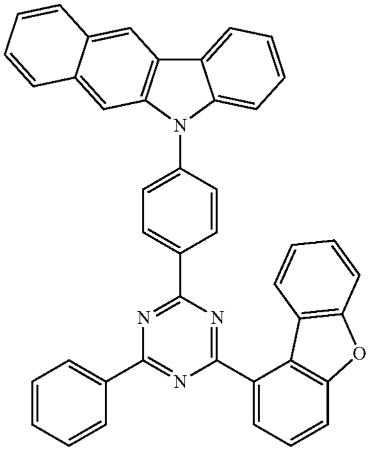
H2-90
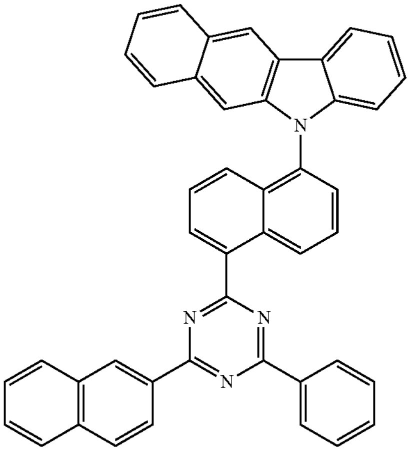

-continued
H2-91
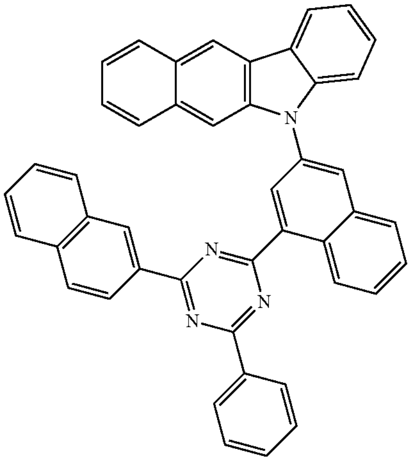
H2-92
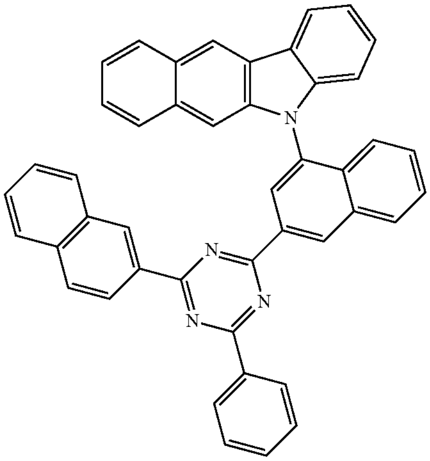
H2-93
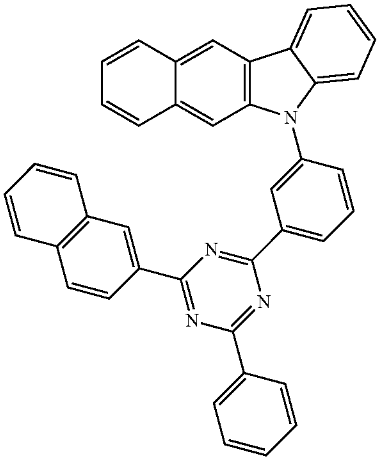
-continued
H2-94
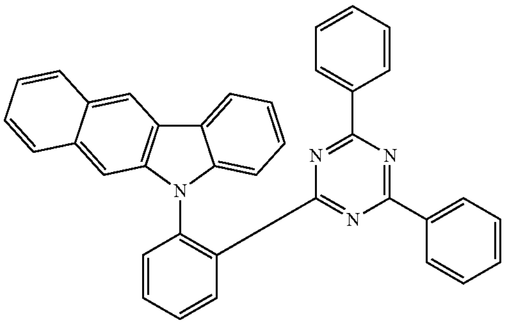
H2-95
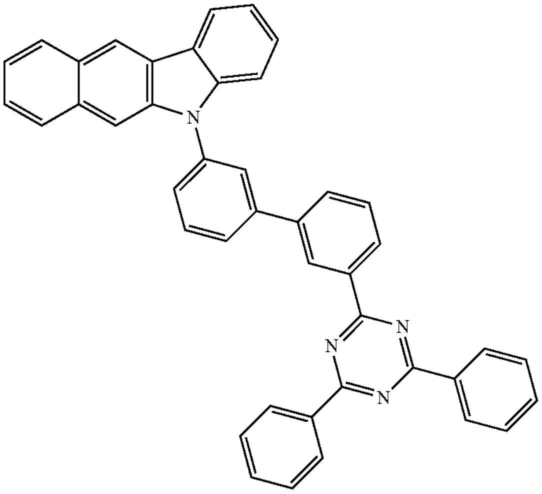
H2-96
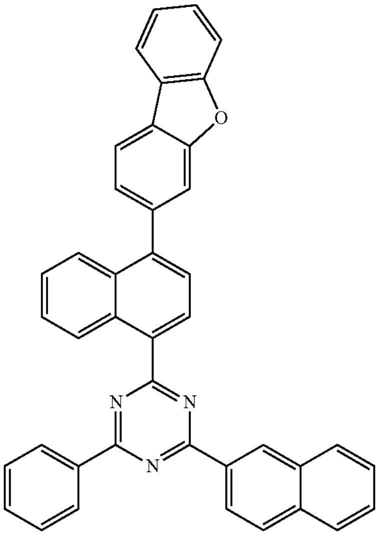

-continued
H2-97
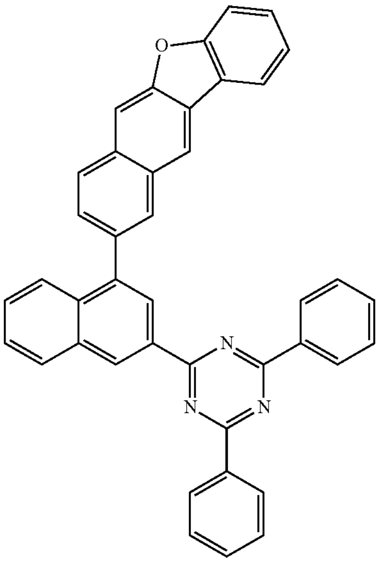
H2-98
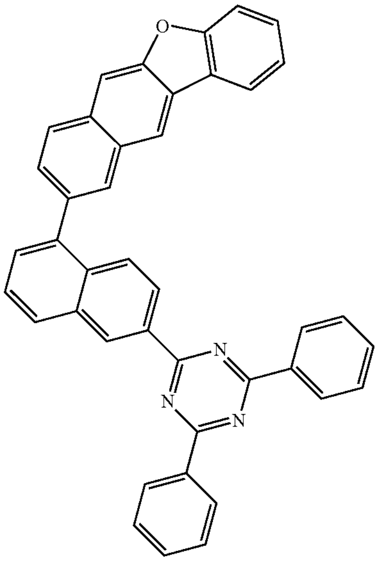
H2-99
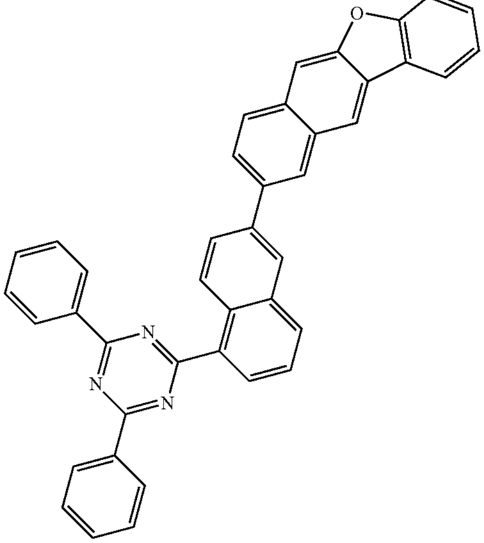
-continued
H2-100
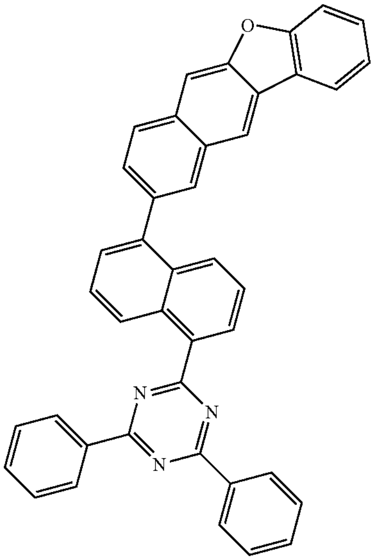
H2-101
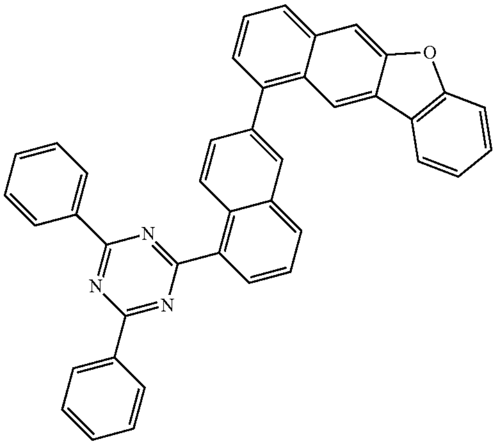
H2-102
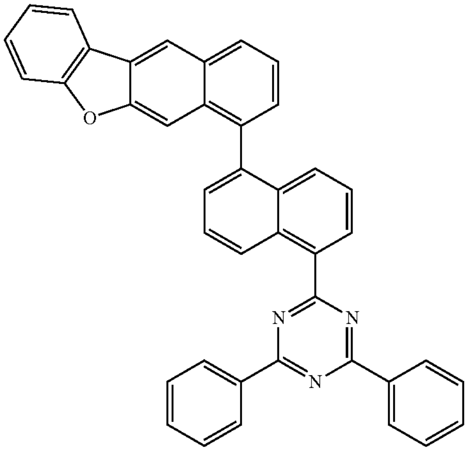

-continued
H2-103
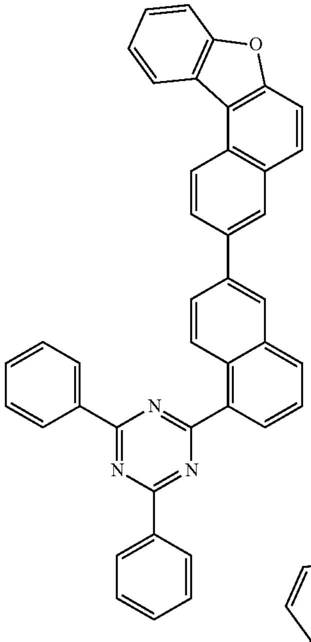
H2-104
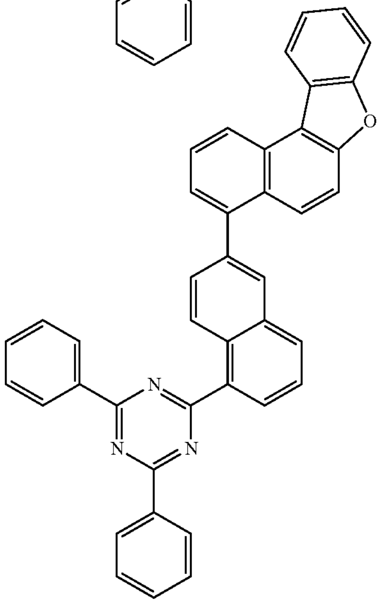
H2-105
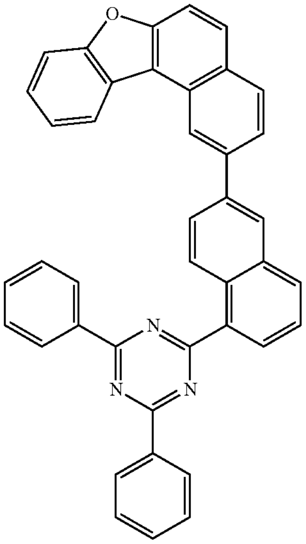
-continued
H2-106
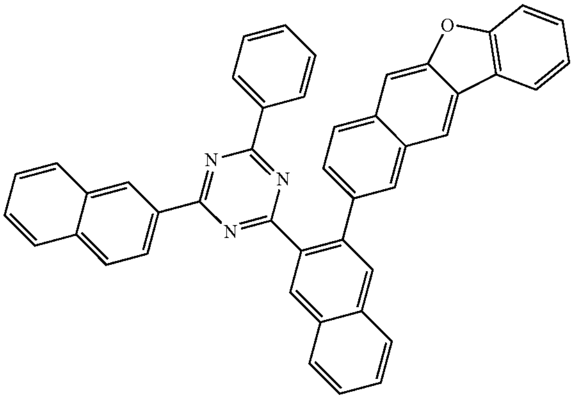
H2-107
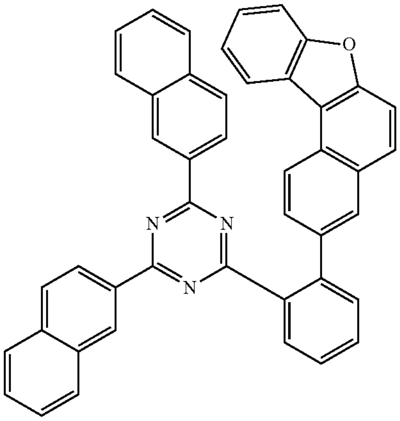
H2-108
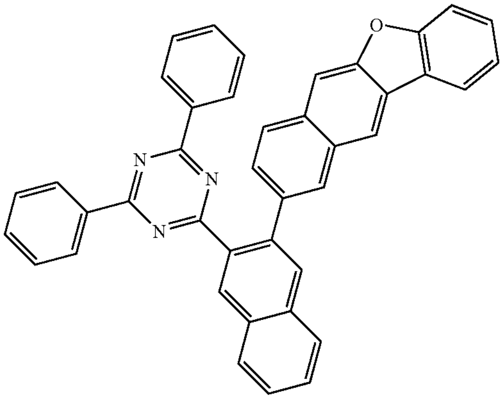
H2-109
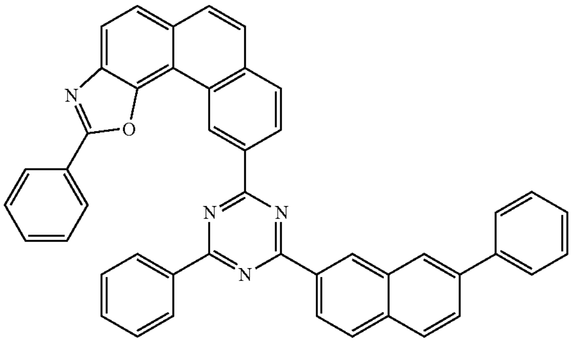

-continued
H2-110
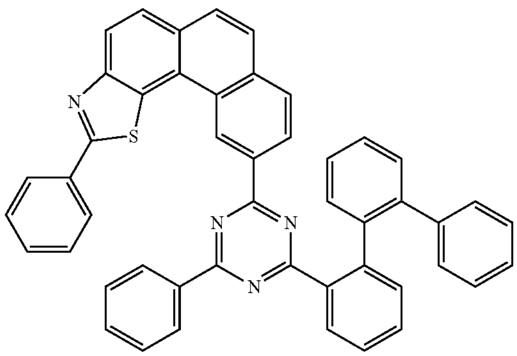
H2-111
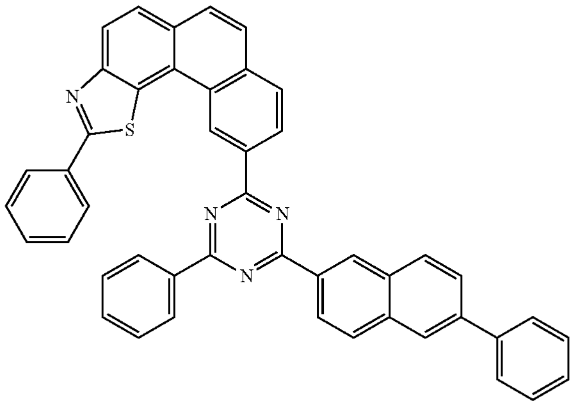
H2-112
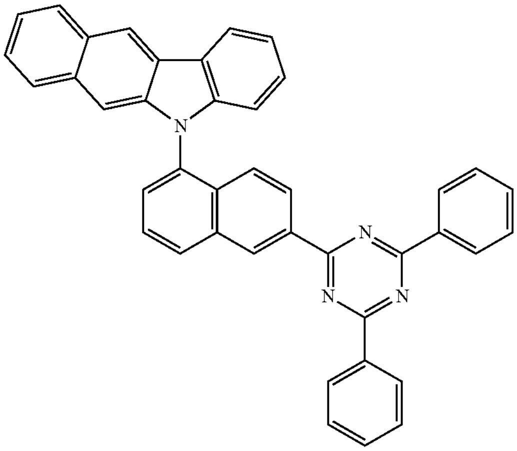
-continued
H2-113
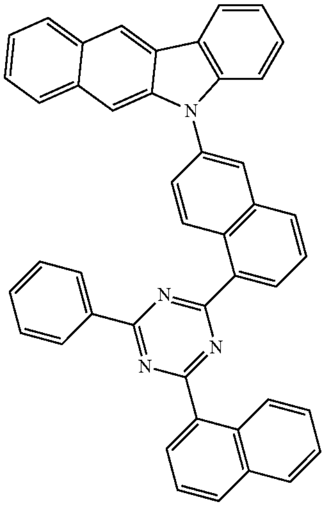
H2-114
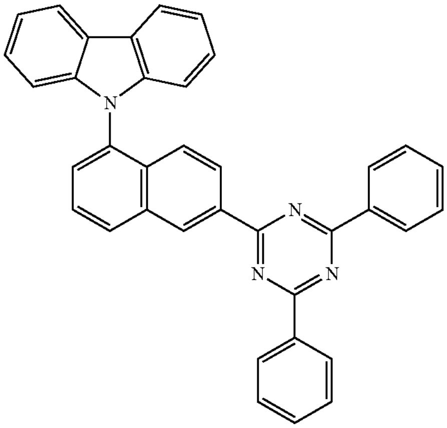
H2-115
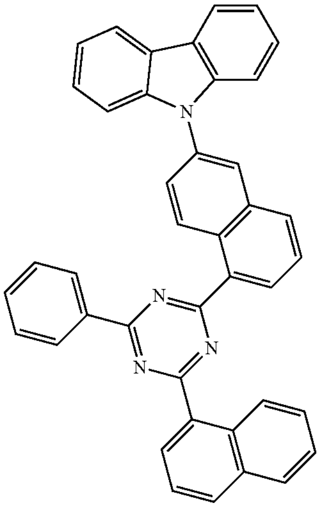

-continued
H2-116
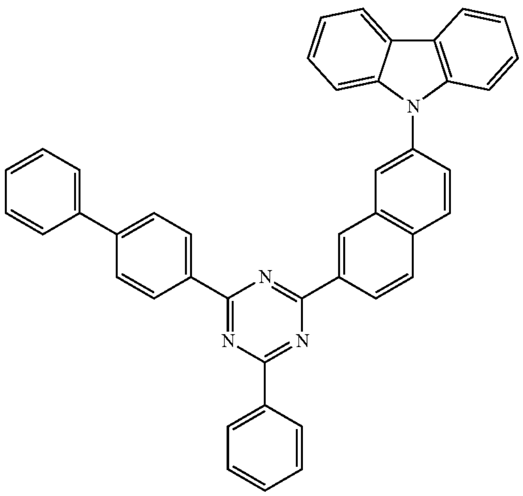
H2-117
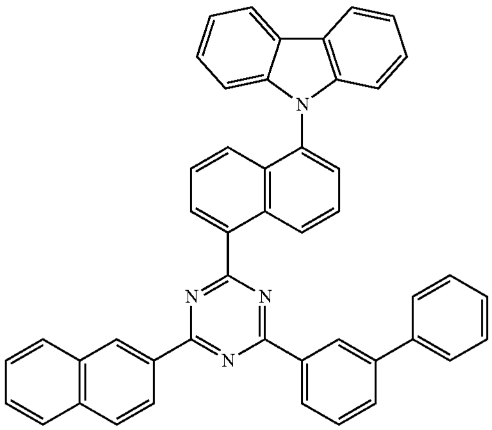
H2-118
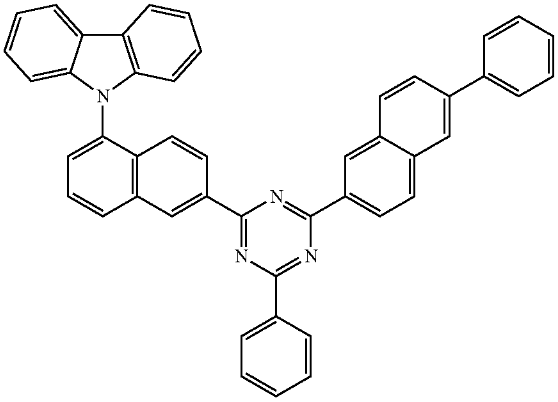
-continued
H2-119
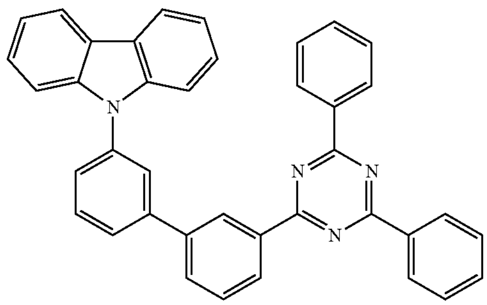
H2-120
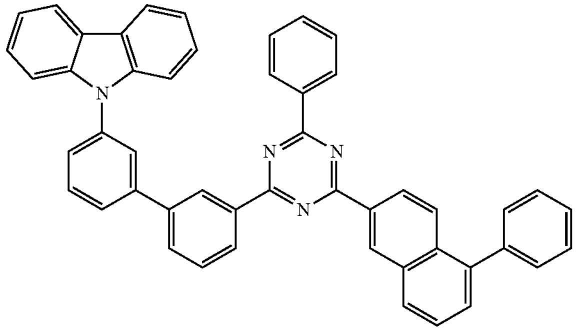
H2-121
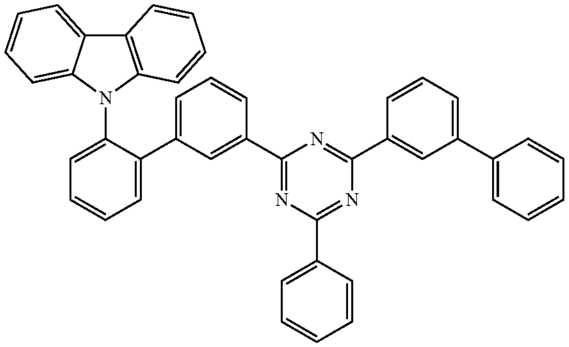
H2-122
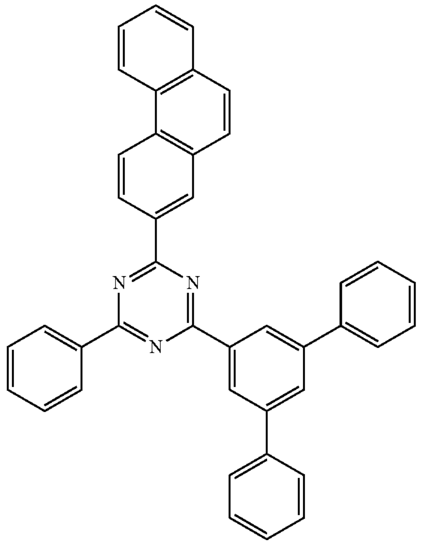

-continued
H2-123
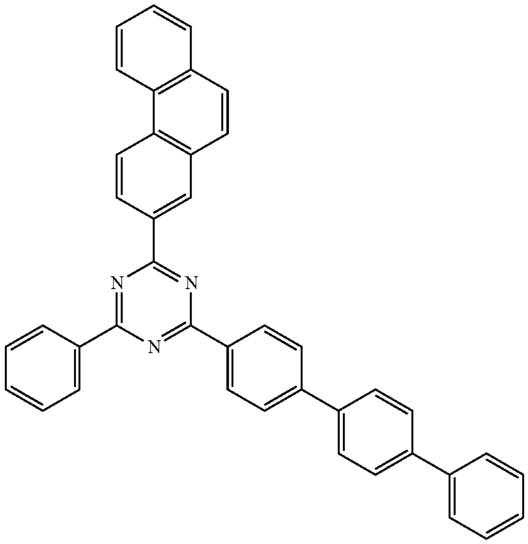
H2-124
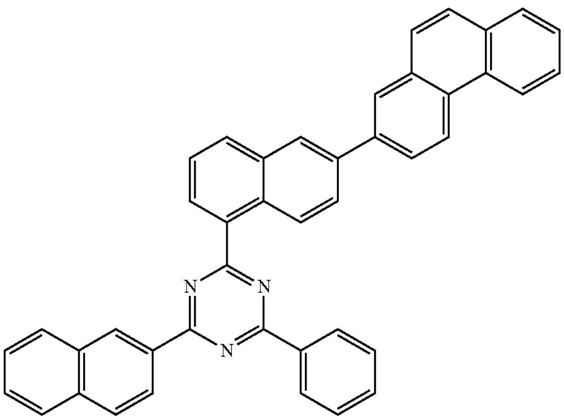
H2-125
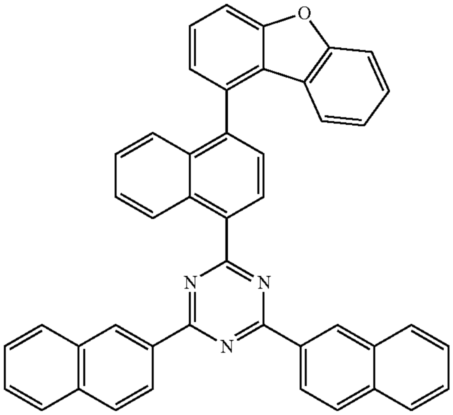
-continued
H2-126
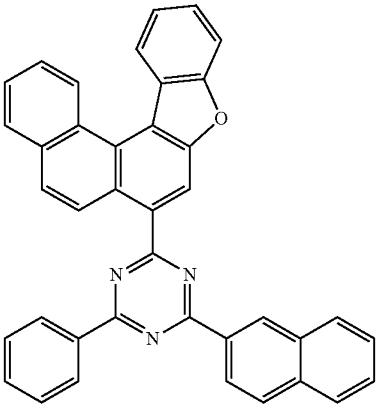
H2-127
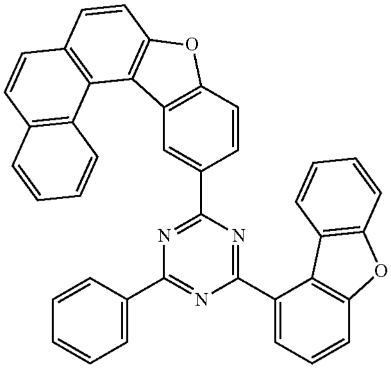
H2-128
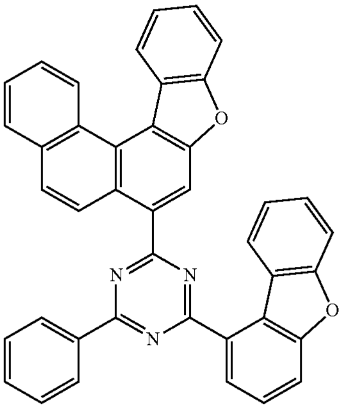

-continued
H2-129
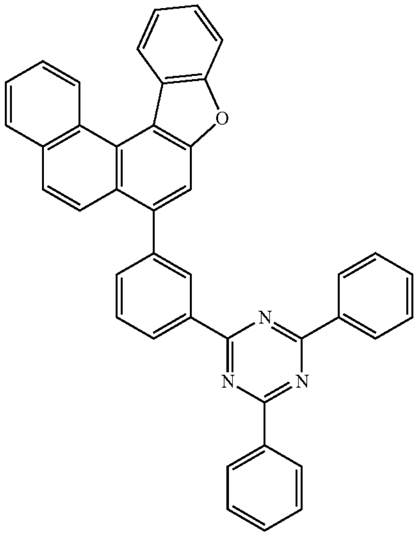
H2-130
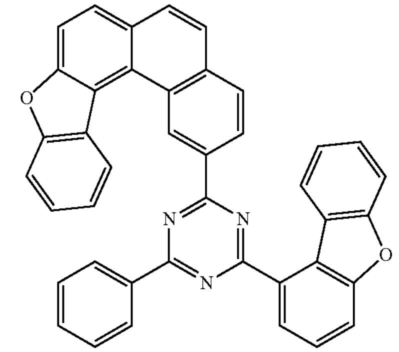
H2-131
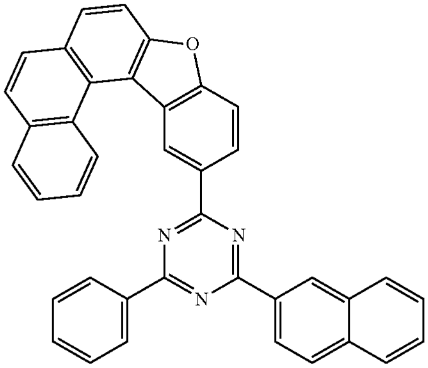
H2-132
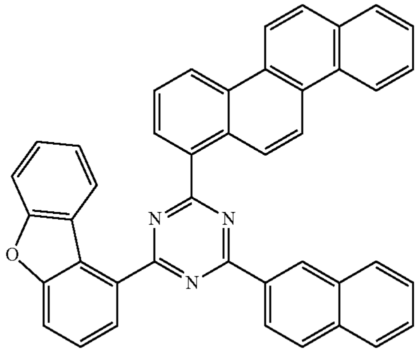
-continued
H2-133
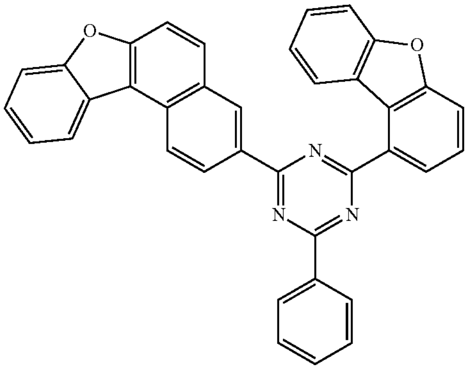
H2-134
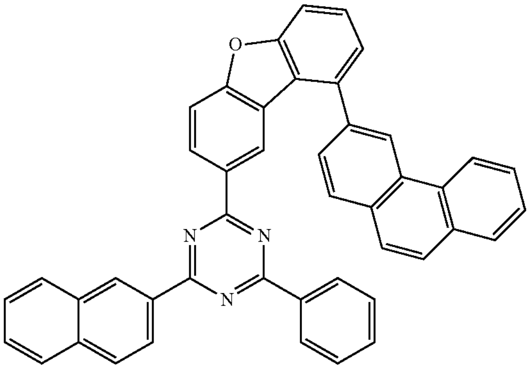
H2-135
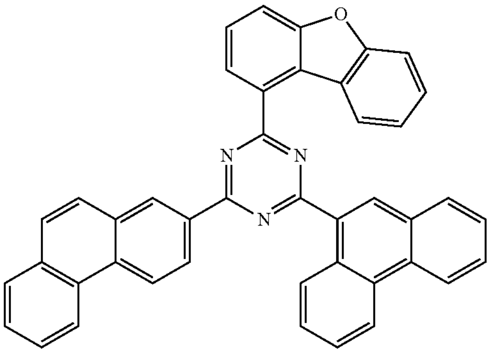
H2-136
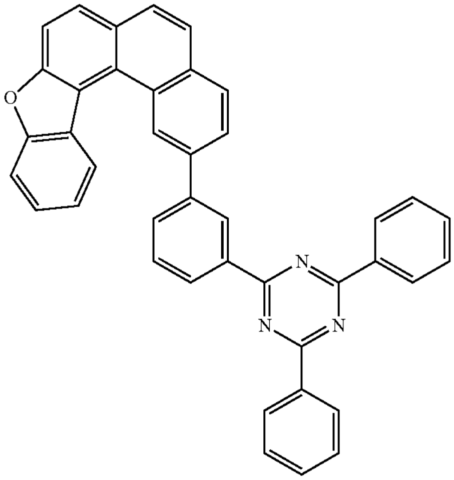

-continued
H2-137
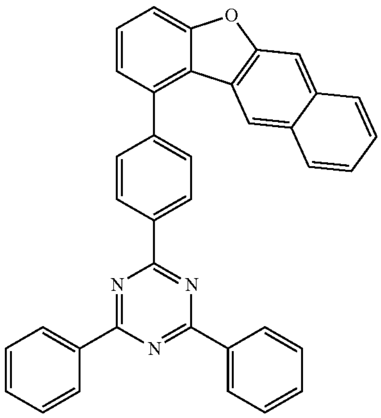
H2-138
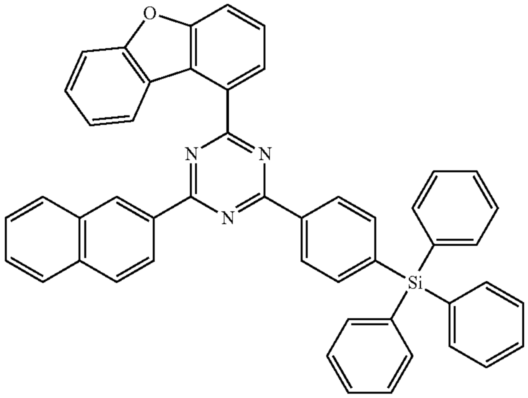
H2-139
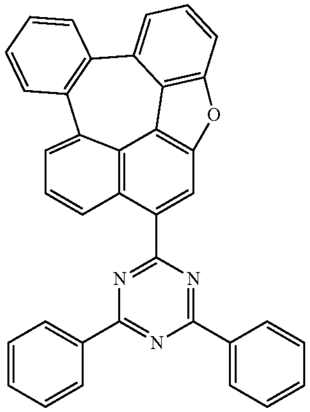
-continued
H2-140
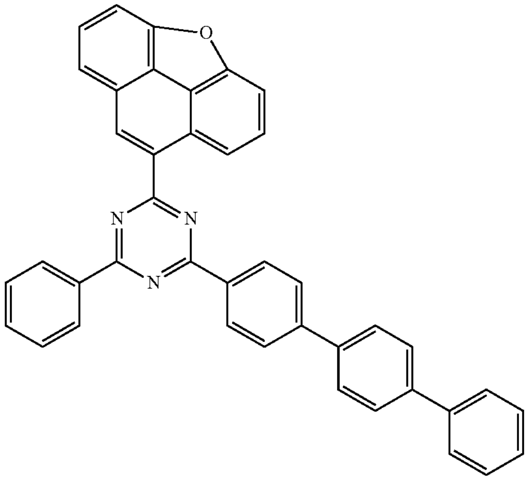
H2-141
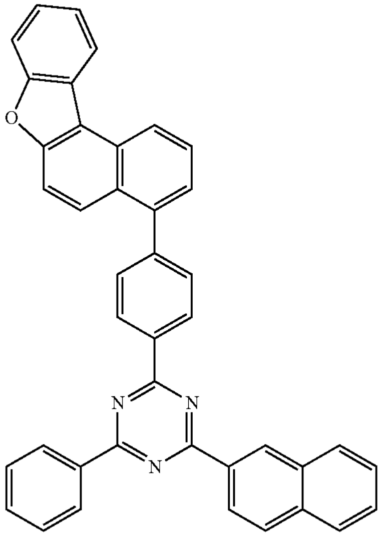
H2-142
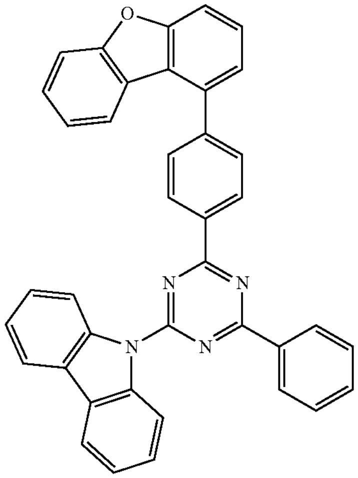

-continued

H2-143

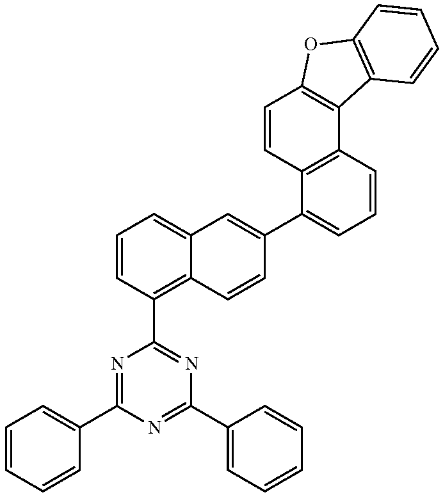

H2-144

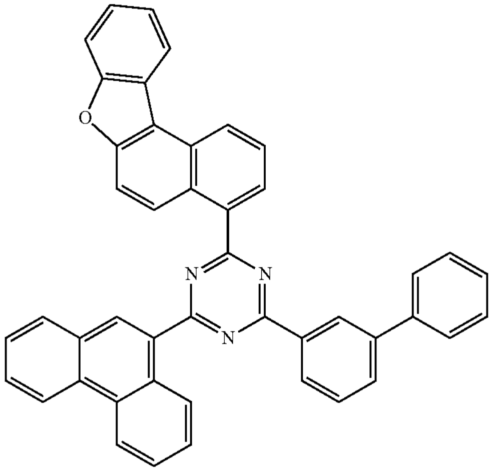

H2-145

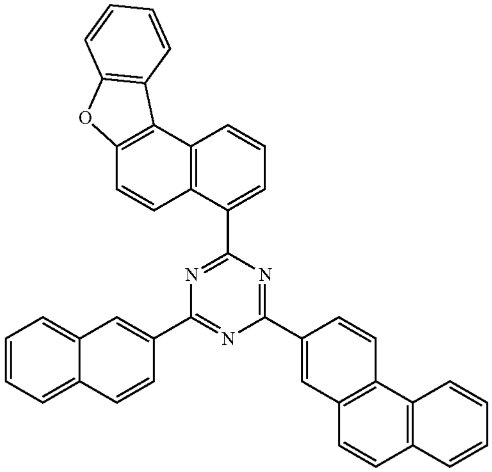

The compound represented by the above formula 2 according to one embodiment may be produced with reference to a synthetic method known to a person skilled in the art.

An organic electroluminescent compound according to another embodiment of the present disclosure may be represented by the following formula 1-2'.

(1-2')

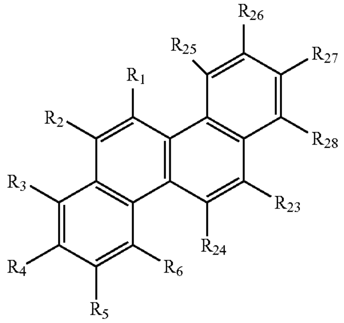

In formula 1-2, $R_1$ to $R_6$ and $R_{23}$ to $R_{28}$ each independently represent, hydrogen, deuterium, halogen, cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or *-$L_1$-$NAr_1Ar_2$; provided that at least one of $R_3$ to $R_6$ is *-$L_1$-$NAr_1Ar_2$;

$L_1$ represents a single bond, a substituted or unsubstituted (C6-C30)arylene, or a substituted or unsubstituted (3- to 30-membered)heteroarylene; and $Ar_1$ and $Ar_2$ each independently represent, a substituted or unsubstituted (C1-C30)alkyl, a substituted or unsubstituted (C2-C30)alkenyl, a substituted or unsubstituted (C6-C30) aryl, or a substituted or unsubstituted (3- to 30-membered) heteroaryl;

provided that the following compounds are excluded from the formula 1-2':

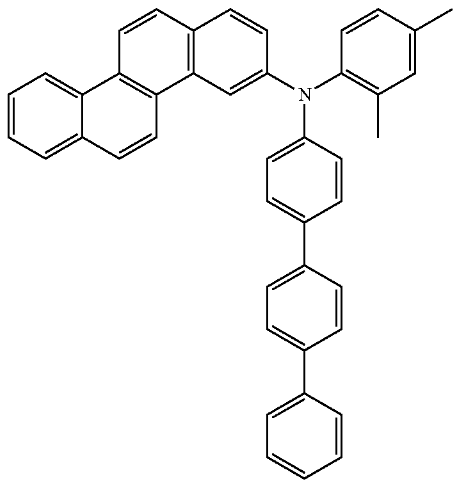
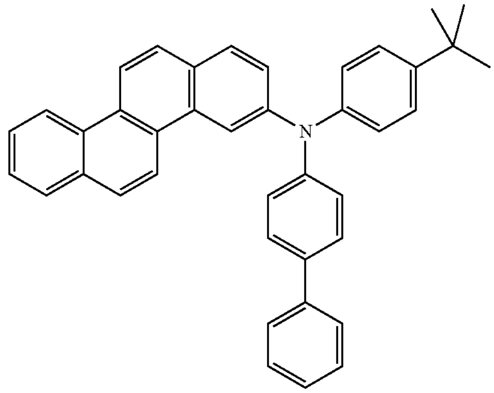
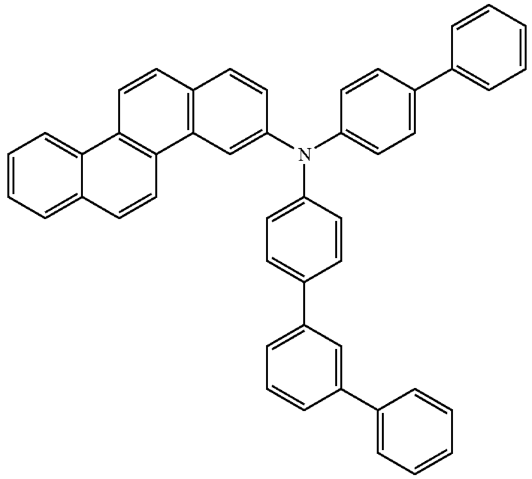
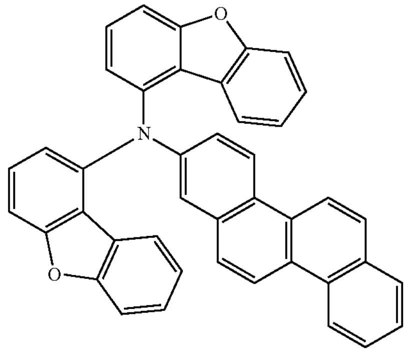
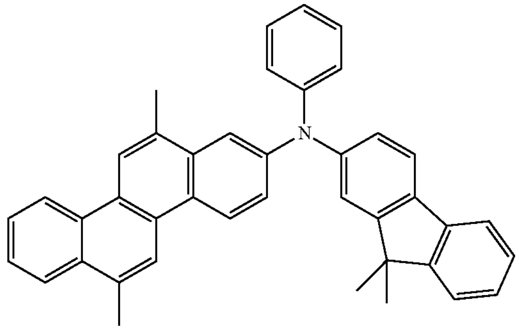

-continued

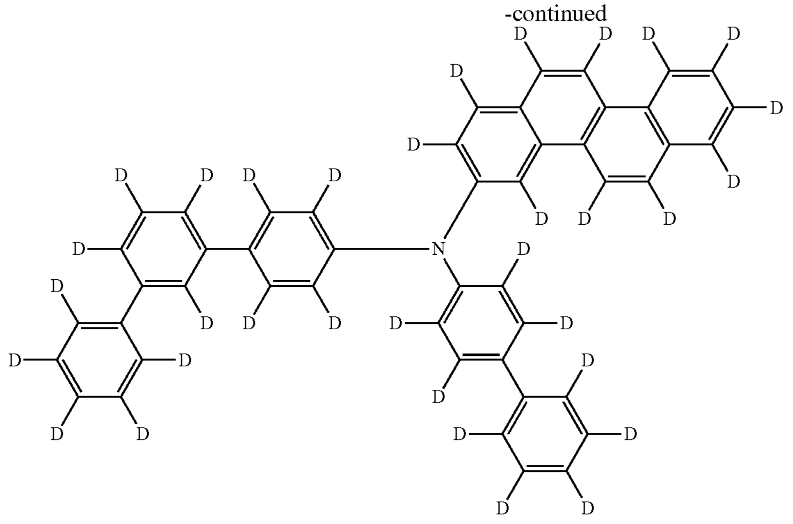

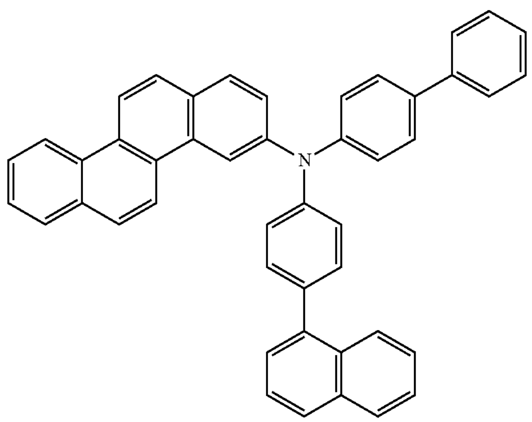

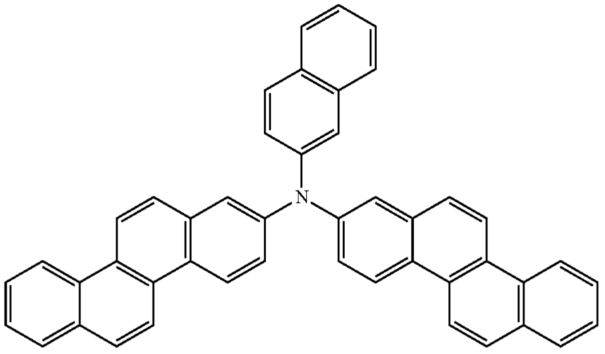

In one embodiment, $R_1$ to $R_6$ and $R_{23}$ to $R_{28}$ in the formula 1-2' each independently may be hydrogen, deuterium, a substituted or unsubstituted (C6-C30)aryl, a substituted or unsubstituted (5- to 30-membered)heteroaryl, or $*L_1NAr_1Ar_2$, preferably hydrogen, deuterium, a substituted or unsubstituted (C6-C25)aryl, a substituted or unsubstituted (5- to 25-membered)heteroaryl, or$*$-$L_1$-$NAr_1Ar_2$, more preferably hydrogen, deuterium, a substituted or unsubstituted (C6-C18)aryl, a substituted or unsubstituted (5- to 18-membered)heteroaryl, or $*$-$L_1$-$NAr_1Ar_2$, provided that at least one of $R_3$ to $R_6$ is $*$-$L_1$-$NAr_1Ar_2$. For example, $R_1$ to $R_6$ and $R_{23}$ to $R_{28}$ each independently may be hydrogen, deuterium, a substituted or unsubstituted phenyl, a substituted or unsubstituted dibenzofuranyl, or$*$-$L_1$-$NAr_1Ar_2$.

In one embodiment. $L_1$ in the formula 1-2' may be a single bond, a substituted or unsubstituted (C6-C30)arylene, or a substituted or unsubstituted (5- to 30-membered)heteroarylene, preferably a single bond, a substituted or unsubstituted (C6-C25)arylene, or a substituted or unsubstituted (5- to 25-membered)heteroarylene, more preferably a single bond, a substituted or unsubstituted (C6-C18)arylene, or a substituted or unsubstituted (5- to 18-membered)heteroarylene. For example, $L_1$ may be a single bond, phenylene unsubstituted or substituted with phenyl, or a substituted or unsubstituted pyridylene.

In one embodiment, $Ar_1$ and $Ar_2$ in the formula 1-2' each independently may be a substituted or unsubstituted (C6-C30)aryl or a substituted or unsubstituted (5- to 30-membered)heteroaryl, preferably a substituted or unsubstituted (C6-C25)aryl or a substituted or unsubstituted (5- to 25-membered)heteroaryl, more preferably a substituted or unsubstituted (C6-C25)aryl or a substituted or unsubstituted (5- to 18-membered)heteroaryl. For example, $Ar_1$ and $Ar_2$ each independently may be a substituted or unsubstituted phenyl, a substituted or unsubstituted naphthyl, a substituted or unsubstituted p-biphenyl, a substituted or unsubstituted m-biphenyl, a substituted or unsubstituted o-biphenyl, a substituted or unsubstituted p-terphenyl, a substituted or unsubstituted m-terphenyl, a substituted or unsubstituted o-terphenyl, a substituted or unsubstituted fluorenyl, a substituted or unsubstituted spirobifluorenyl, a substituted or unsubstituted phenanthrenyl, a substituted or unsubstituted dibenzofuranyl, or a substituted or unsubstituted dibenzothiophenyl. The substituents of the substituted groups may be for example, methyl; tert-butyl; naphthyl; phenylpyridyl; triphenylsilane; or isobenzofuranyl substituted with phenyl.

An organic electroluminescent compound according to another embodiment of the present disclosure may be represented by the following formula 1-1'.

(1-1')

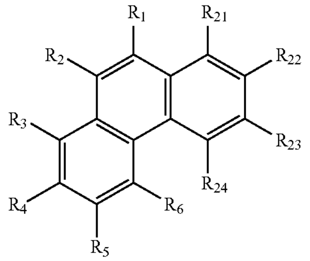

In formula 1-1', $R_1$ to $R_6$ and $R_{21}$ to $R_{24}$ each independently represent, hydrogen, deuterium, halogen, cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, or *-$L_1$-$NAr_1Ar_2$; provided that at least one of $R_1$ to $R_6$ is *-$L_1$-$NAr_1Ar_2$;

$L_1$ represents a single bond, a substituted or unsubstituted (C6-C30)arylene, or a substituted or unsubstituted (3- to 30-membered)heteroarylene; and $Ar_1$ and $Ar_2$ each independently represent, a substituted or unsubstituted (C1-C30)alkyl, a substituted or unsubstituted (C2-C30)alkenyl, a substituted or unsubstituted (C6-C30) aryl, or a substituted or unsubstituted (3- to 30-membered) heteroaryl;

provided that the compounds where $R_1$ to $R_6$ which are not *-$L_1$-$NAr_1Ar_2$, and $R_{21}$ to $R_{24}$ are all hydrogen, are excluded from the formula 1-1', and when $R_1$ is *-$L_1$-$NAr_1Ar_2$, $R_2$ is hydrogen.

In one embodiment, $R_1$ to $R_6$ and $R_{21}$ to $R_{24}$ in the formula 1-1' each independently may be hydrogen, deuterium, a substituted or unsubstituted (C6-C30)aryl, a substituted or unsubstituted (5- to 30-membered)heteroaryl, or *-$L_1$-$NAr_1Ar_2$, preferably hydrogen, deuterium, a substituted or unsubstituted (C6-C25)aryl, a substituted or unsubstituted (5- to 25-membered)heteroaryl, or -$L_1$-$NAr_1Ar_2$, more preferably hydrogen, deuterium, a substituted or unsubstituted (C6-C18)aryl, a substituted or unsubstituted (5- to 18-membered)heteroaryl, or *-$L_1$-$NAr_1Ar_2$; provided that at least one of $R_1$ to $R_6$ is *-$L_1$-$NAr_1Ar_2$. For example, $R_1$ to $R_6$ and $R_{21}$ to $R_{24}$ each independently may be hydrogen, deuterium, a substituted or unsubstituted phenyl, a substituted or unsubstituted naphthyl, a substituted or unsubstituted m-terphenyl, a substituted or unsubstituted triphenylenyl, a substituted or unsubstituted phenanthrenyl, a substituted or unsubstituted quinolinyl, a substituted or unsubstituted dibenzofuranyl, or a substituted or unsubstituted pyridyl, or at least one of $R_1$ to $R_6$ is *-$L_1$-$NAr_1Ar_2$. In this case, the compounds where $R_1$ to $R_6$ which are not *-$L_1$-$NAr_1Ar_2$, and $R_{21}$ to $R_{24}$ are all hydrogen, are excluded from the formula 1-1'. For example, $R_{21}$ to $R_{24}$ in the formula 1-1' each independently may be deuterium, a substituted or unsubstituted phenyl, a substituted or unsubstituted naphthyl, a substituted or unsubstituted dibenzofuranyl, or a substituted or unsubstituted pyridyl. $R_1$ and $R_2$ each independently may be *-$L_1$-$NAr_1Ar_2$, a substituted or unsubstituted phenyl, a substituted or unsubstituted naphthyl, a substituted or unsubstituted m-terphenyl, a substituted or unsubstituted triphenylenyl, a substituted or unsubstituted phenanthrenyl, or a substituted or unsubstituted quinolinyl, and provided that when $R_1$ in the formula 1-1' is *-$L_1$-$NAr_1Ar_2$, $R_2$ is hydrogen.

In one embodiment, $L_1$ in the formula 1-1' may be a single bond or a substituted or unsubstituted (C6-C30)arylene, preferably a single bond or a substituted or unsubstituted (C6-C25)arylene, more preferably a single bond or a substituted or unsubstituted (C6-C18)arylene. For example, $L_1$ may be a single bond, a substituted or unsubstituted phenylene, or a substituted or unsubstituted naphthalenylene.

In one embodiment. $Ar_1$ and $Ar_2$ in the formula 1-1' each independently may be a substituted or unsubstituted (C6-C30)aryl or a substituted or unsubstituted (5- to 30-membered)heteroaryl, preferably a substituted or unsubstituted (C6-C25)aryl or a substituted or unsubstituted (5- to 25-membered)heteroaryl, more preferably a substituted or unsubstituted (C6-C18)aryl or a substituted or unsubstituted (5- to 18-membered)heteroaryl. For example, $Ar_1$ and $Ar_2$ each independently may be a substituted or unsubstituted p-biphenyl, a substituted or unsubstituted terphenyl, a substituted or unsubstituted fluorenyl, or a substituted or unsubstituted dibenzofuranyl. The substituents of the substituted groups may be for example, deuterium; tert-butyl; phenyl unsubstituted or substituted with deuterium or tert-butyl; triphenylsilane; pyridyl; or phenylpyridyl.

In one embodiment, the organic electroluminescent compound represented by the above formula 1-1' may be more specifically illustrated by the following compounds, but is not limited thereto.

H1-6

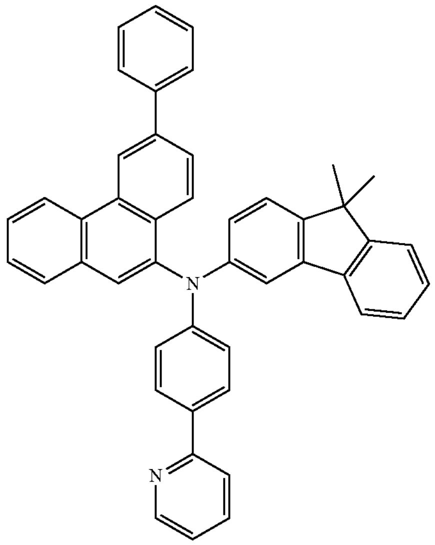

-continued
H1-7
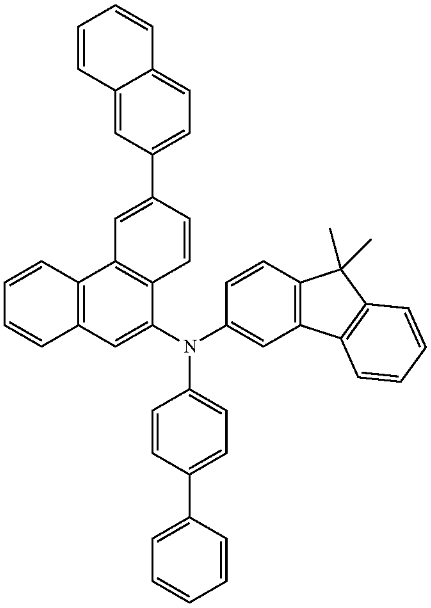
H1-8
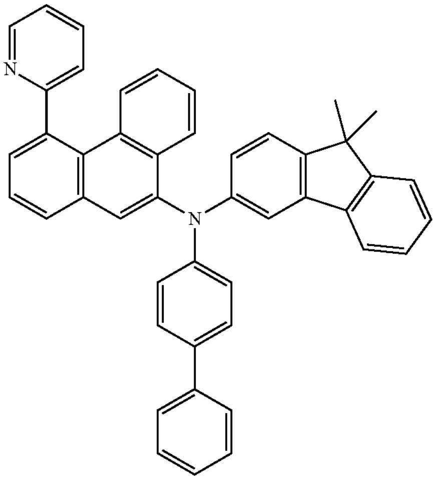
H1-9
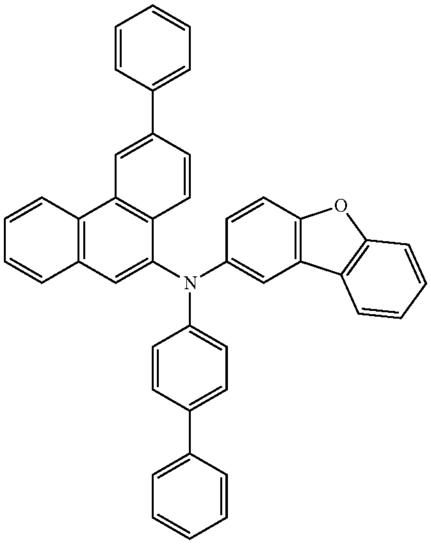
-continued
H1-10
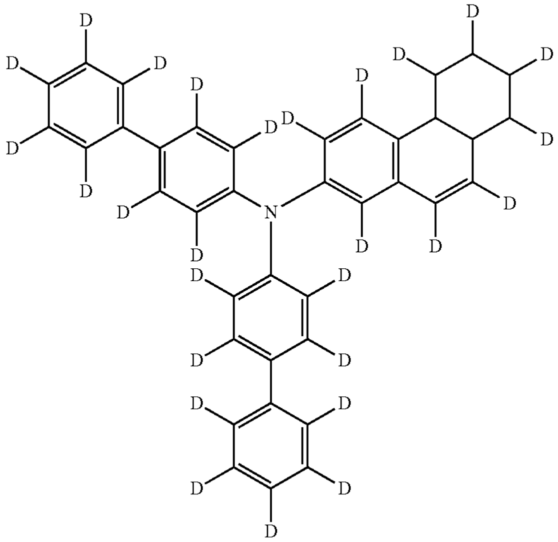
H1-11
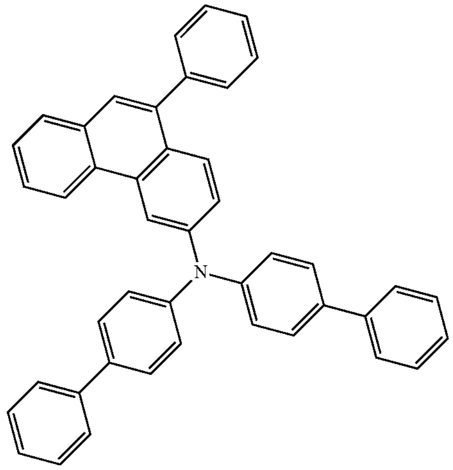
H1-12
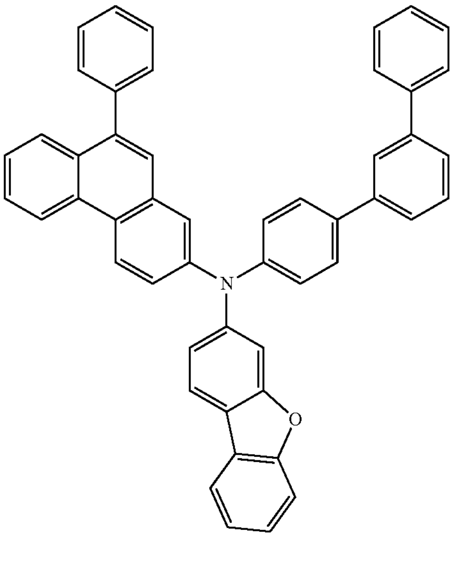

-continued
H1-23
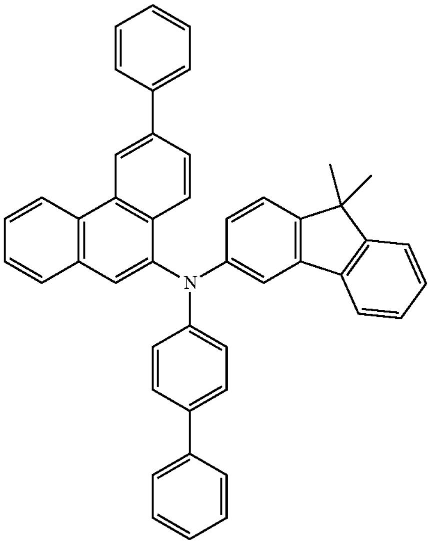
H1-24
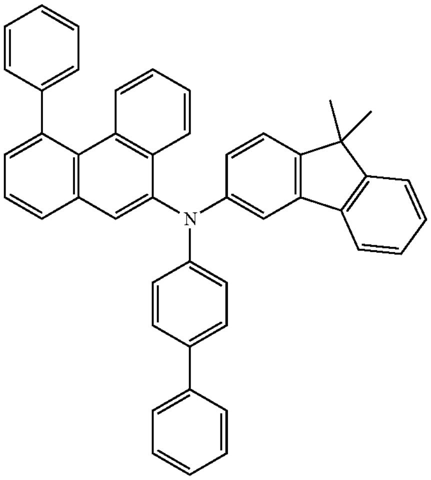
H1-90
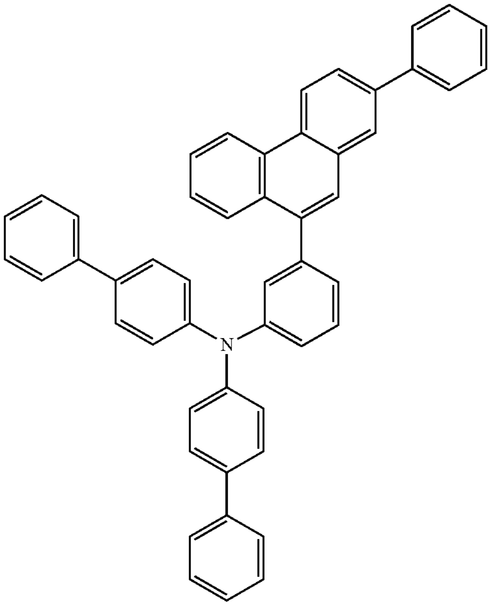
-continued
H1-91
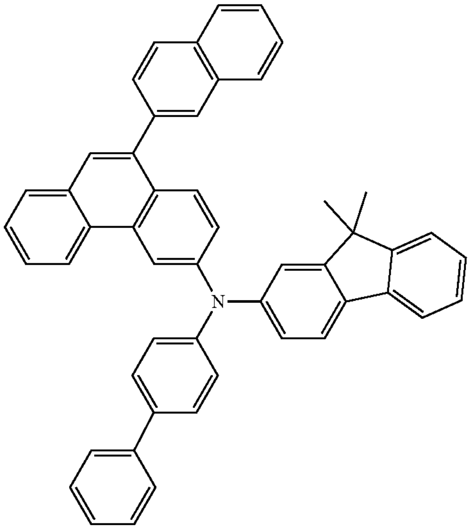
H1-92
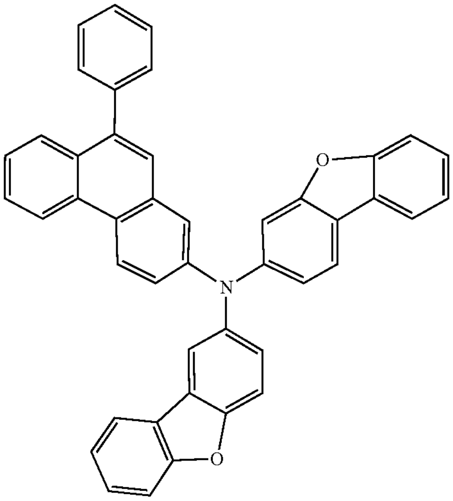
H1-93
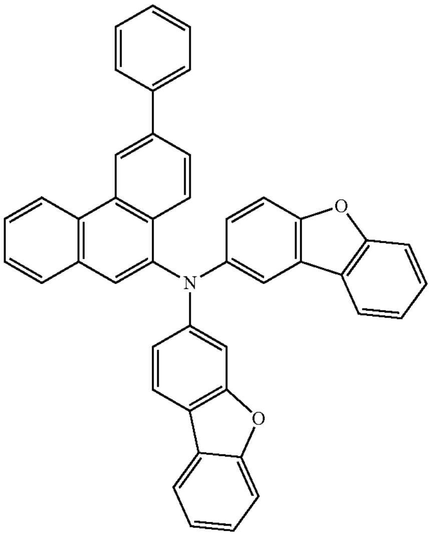

-continued
H1-94
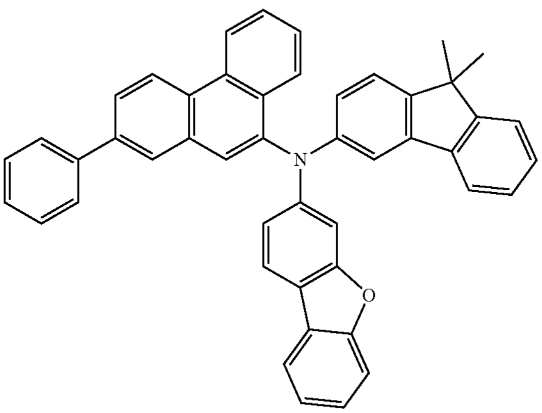
H1-95
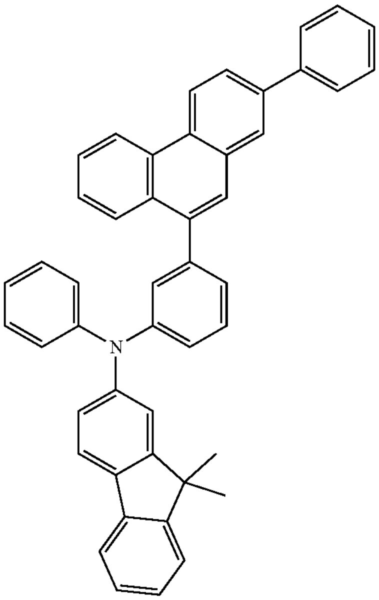
H1-108
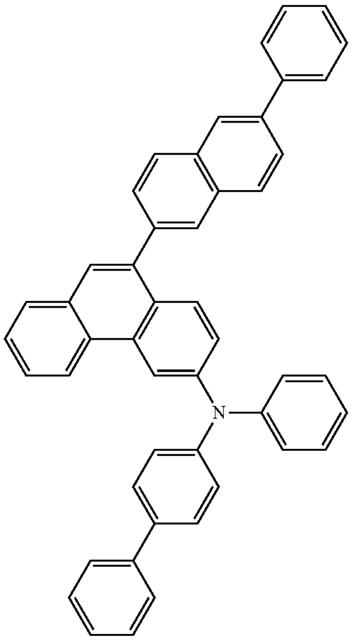
-continued
H1-109
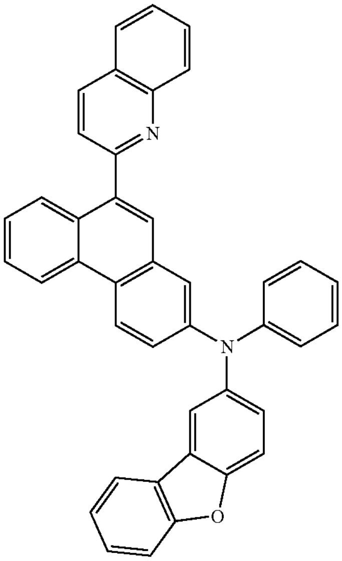
H1-110
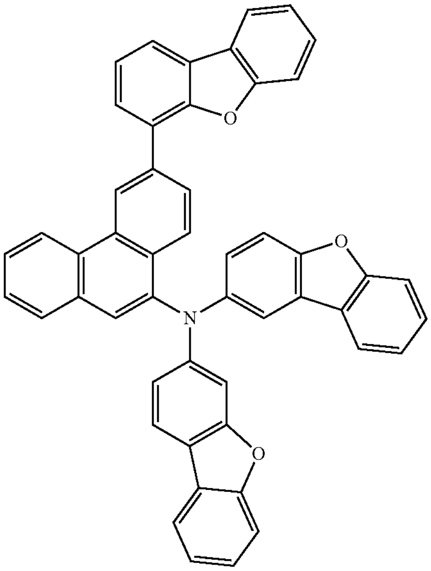
H1-111
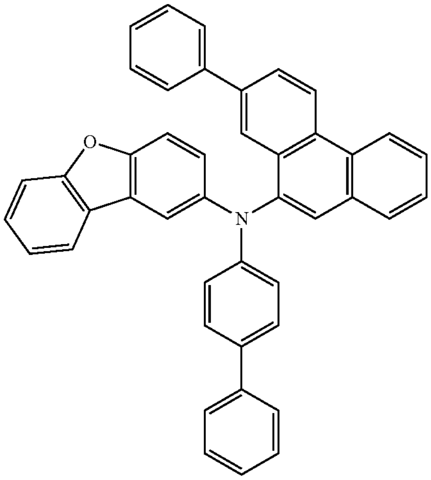

-continued

H1-126

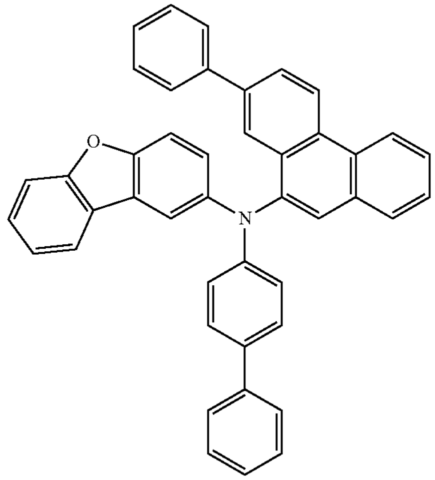

H1-127

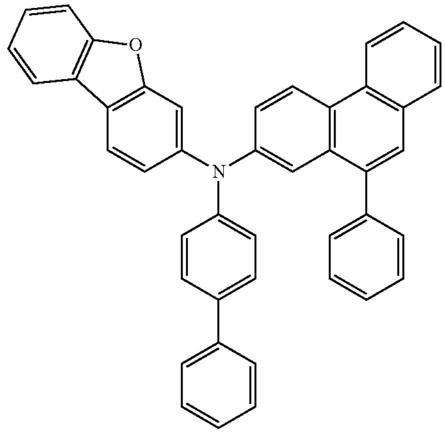

H1-128

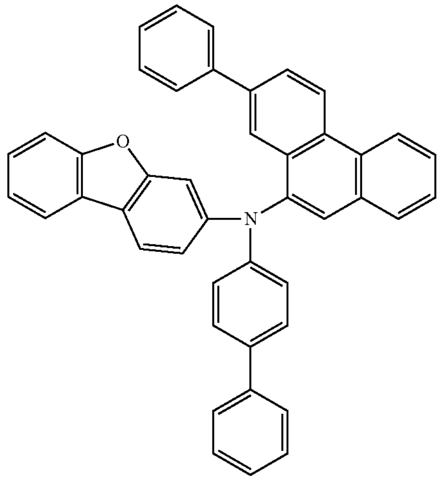

-continued

H1-129

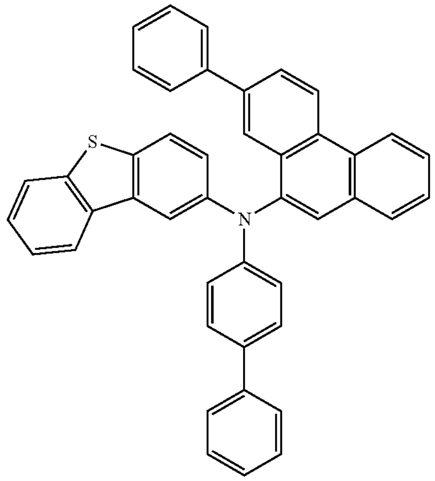

H1-130

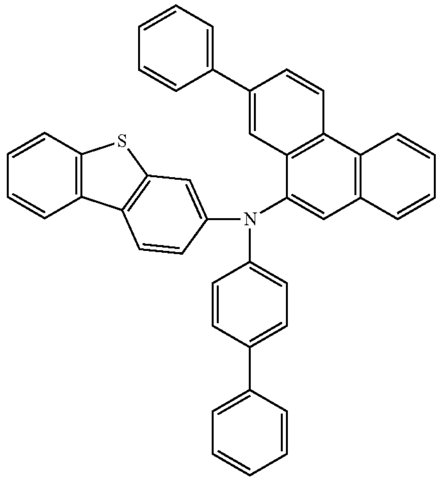

Hereinafter, an organic electroluminescent device to which the aforementioned plurality of host materials and/or the organic electroluminescent compound is(are) applied will be described.

The organic electroluminescent device according to one embodiment includes a first electrode; a second electrode; and at least one organic layer(s) interposed between the first electrode and the second electrode. The organic layer may include a light-emitting layer and a hole transport layer, and the light-emitting layer may comprise a plurality of host materials comprising at least one first host material represented by the above formula 1 and at least one second host material represented by the above formula 2. The organic electroluminescent device according to another embodiment of the present disclosure may include an organic electroluminescent compound represented by the above formula 1-1' and/or an organic electroluminescent compound represented by the above formula 1-2' in a hole transport layer.

According to one embodiment, the organic electroluminescent material of the present disclosure comprises at least one compound(s) of compounds H1-1 to H1-145 as the first host material represented by the above formula 1 and at least one compound(s) of compounds H2-1 to H2-145 as the second host material represented by the above formula 2, and the plurality of host materials may be included in the same organic layer, for example, a light-emitting layer or may be included in different light-emitting layers, respectively. According to another embodiment, the organic electroluminescent material of the present disclosure may comprise a compound represented by the above formula 1-1' and/or a compound represented by the above formula 1-2' alone or in combination of two or more compounds, and the organic electroluminescent material may be included in the organic layer of the organic electroluminescent device, for example, a hole transport layer.

The organic layer may further comprise at least one layer selected from a hole injection layer, a hole auxiliary layer, a light-emitting auxiliary layer, an electron transport layer, an electron injection layer, an interlayer, a hole blocking layer, an electron blocking layer, and an electron buffer layer, in addition to the light-emitting layer and the hole transport layer. The organic layer may further comprise an amine-based compound and/or an azine-based compound other than the light-emitting material according to the present disclosure. Specifically, the hole injection layer, the hole transport layer, the hole auxiliary layer, the light-emitting layer, the light-emitting auxiliary layer, or the electron blocking layer may contain the amine-based compound, e.g., an arylamine-based compound and a styrylarylamine-based compound, etc., as a hole injection material, a hole transport material, a hole auxiliary material, a light-emitting material, a light-emitting auxiliary material, and an electron blocking material. Also, the electron transport layer, the electron injection layer, the electron buffer layer, and the hole blocking layer may contain the azine-based compound as an electron transport material, an electron injection material, an electron buffer material, and a hole blocking material. Also, the organic layer may further comprise at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising such a metal.

A plurality of host materials according to one embodiment may be used as light-emitting materials for a white organic light-emitting device. The white organic light-emitting device has suggested various structures such as a parallel side-by-side arrangement method, a stacking arrangement method, or CCM (color conversion material) method, etc., according to the arrangement of R (Red), G (Green), YG (yellowish green), or B (blue) light-emitting units. In addition, the organic electroluminescent material according to one embodiment may also be applied to the organic electroluminescent device comprising a QD (quantum dot).

One of either the first electrode or the second electrode may be an anode and the other may be a cathode. Wherein, the first electrode and the second electrode may each be formed as a transmissive conductive material, a transflective conductive material, or a reflective conductive material. The organic electroluminescent device may be a top emission type, a bottom emission type, or a both-sides emission type according to the kinds of the material forming the first electrode and the second electrode.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. Also, the hole injection layer may be doped as a p-dopant. Also, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer or the electron blocking layer may be multi-layers, and wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer may be placed between the electron transport layer (or electron injection layer) and the light-emitting layer, and blocks the arrival of holes to the cathode, thereby improving the probability of recombination of electrons and holes in the light-emitting layer. The hole blocking layer or the electron transport layer may also be multi-layers, wherein each layer may use a plurality of compounds. Also, the electron injection layer may be doped as an n-dopant.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as the hole auxiliary layer or the electron blocking layer. The light-emitting auxiliary layer, the hole auxiliary layer, or the electron blocking layer may have an effect of improving the efficiency and/or the lifespan of the organic electroluminescent device.

In the organic electroluminescent device of the present disclosure, preferably, at least one layer (hereinafter, "a surface layer") selected from a chalcogenide layer, a halogenated metal layer, and a metal oxide layer may be placed on an inner surface(s) of one or both electrode(s). Specifically, a chalcogenide (including oxides) layer of silicon and aluminum is preferably placed on an anode surface of an electroluminescent medium layer, and a halogenated metal layer or a metal oxide layer is preferably placed on a cathode surface of an electroluminescent medium layer. The operation stability for the organic electroluminescent device may be obtained by the surface layer. Preferably, the chalcogenide includes $SiO_x(1 \leq X \leq 2)$, $AlO_x(1 \leq X \leq 1.5)$, SiON, SiAlON, etc.: the halogenated metal includes LiF, $MgF_2$, $CaF_2$, a rare earth metal fluoride, etc.; and the metal oxide includes $Cs_2O$, $Li_2O$, MgO, SrO, BaO, CaO, etc.

Further, in the organic electroluminescent device of the present disclosure, preferably, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

The organic electroluminescent device according to one embodiment may further include at least one dopant in the light-emitting layer.

The dopant comprised in the organic electroluminescent device of the present disclosure may be at least one phosphorescent or fluorescent dopant, preferably a phosphorescent dopant. The phosphorescent dopant material applied to the organic electroluminescent device of the present disclosure is not particularly limited, but may be preferably a metallated complex compound(s) of a metal atom(s) selected from iridium (Ir), osmium (Os), copper (Cu), and platinum (Pt), as necessary; more preferably an ortho-metallated complex compound(s) of a metal atom(s) selected from iridium (Ir), osmium (Os), copper (Cu), and platinum (Pt), as necessary; and even more preferably ortho-metallated iridium complex compound(s), as necessary.

The dopant comprised in the organic electroluminescent device of the present disclosure may use the compound represented by the following formula 101, but is not limited thereto.

(101)

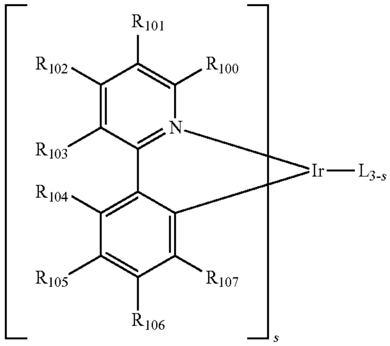

In formula 101,

L is selected from the following structures 1 to 3;

structure (1)

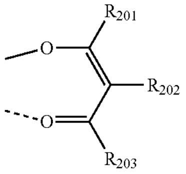

-continued structure (2)

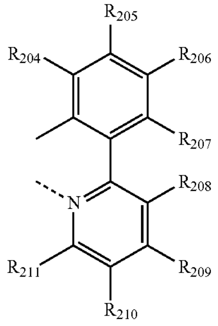

structure (3)

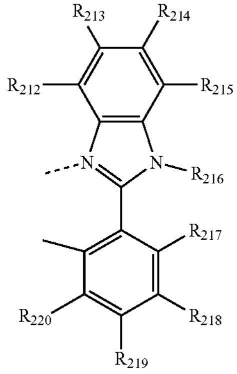

in structures 1 to 3, $R_{100}$ to $R_{103}$ each independently represent, hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, cyano, a substituted or unsubstituted (3- to 30-membered)heteroaryl, or a substituted or unsubstituted (C1-C30)alkoxy; or may be linked to the adjacent substituents to form a ring(s) e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline, together with pyridine;

$R_{104}$ to $R_{107}$ each independently represent, hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, a substituted or unsubstituted (3- to 30-membered)heteroaryl, cyano, or a substituted or unsubstituted (C1-C30)alkoxy; or may be linked to the adjacent substituents to form a a substituted or unsubstituted ring(s), for example, a substituted or unsubstituted naphthyl, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine, together with benzene:

$R_{201}$ to $R_{220}$ each independently represent, hydrogen, deuterium, halogen, (C1-C30)alkyl unsubstituted or substituted with deuterium and/or halogen, a substituted or unsubstituted (C3-C30)cycloalkyl, or a substituted or unsubstituted (C6-C30)aryl; or may be linked to the adjacent substituents to form a substituted or unsubstituted ring(s); and s represents an integer of 1 to 3.

Specifically, the specific examples of the dopant compound include the following, but are not limited thereto.
D-1
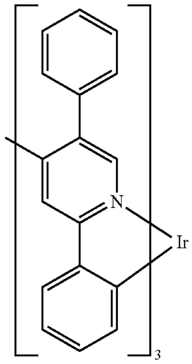
D-2
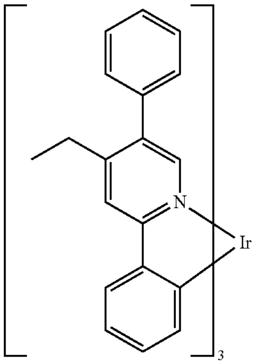
D-3
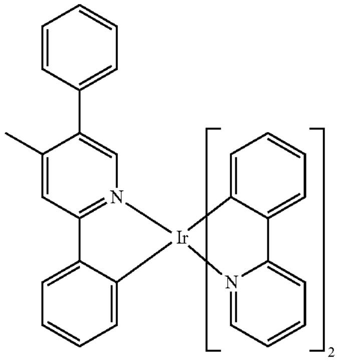
D-4
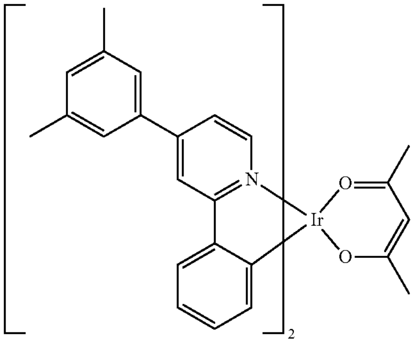
-continued
D-5
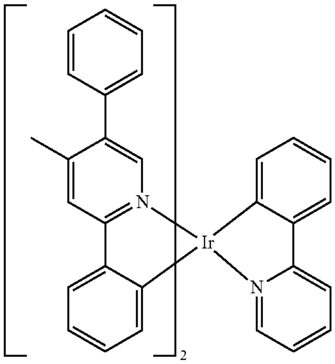
D-6
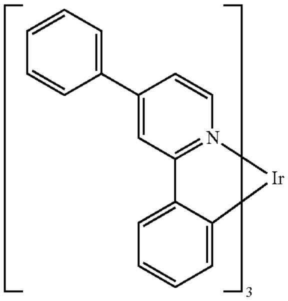
D-7
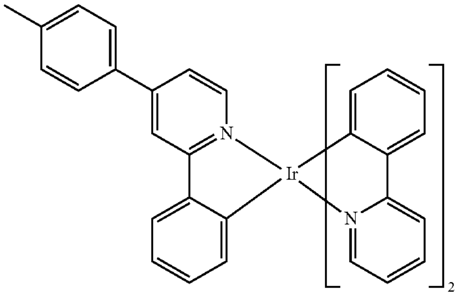
D-8
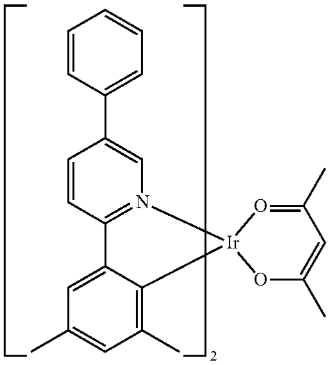

-continued
D-9
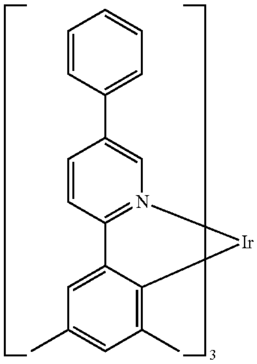
D-10
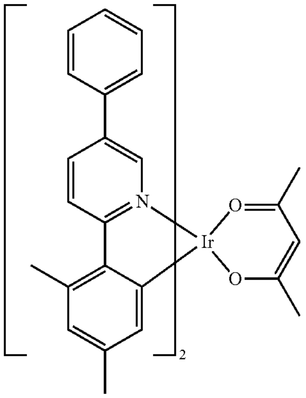
D-11
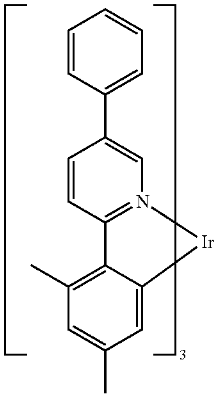
D-12
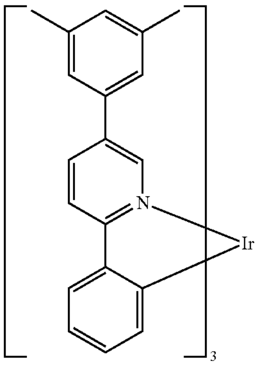
-continued
D-13
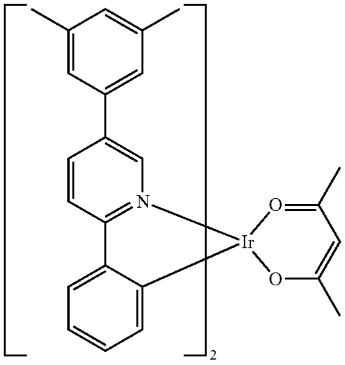
D-14
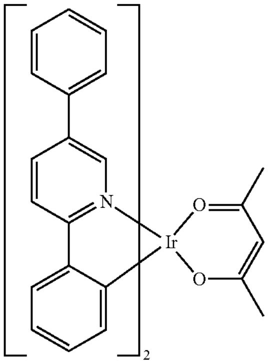
D-15
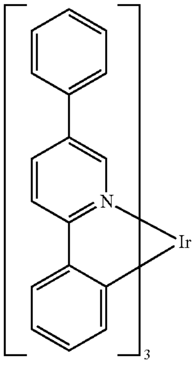
D-16
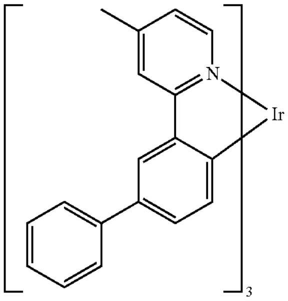

D-17
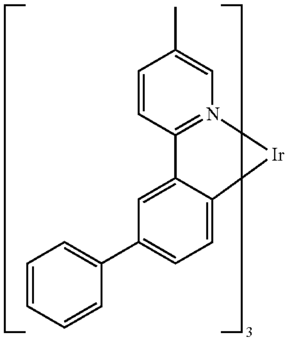
D-18
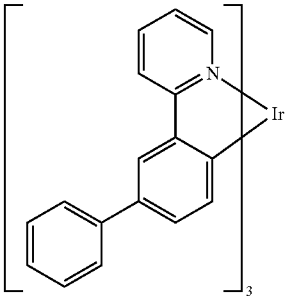
D-19
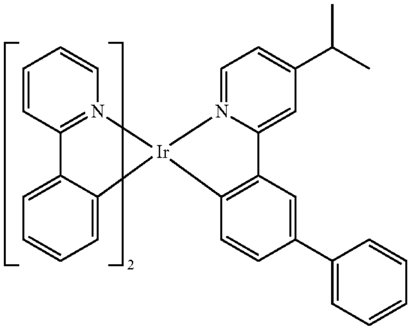
D-20
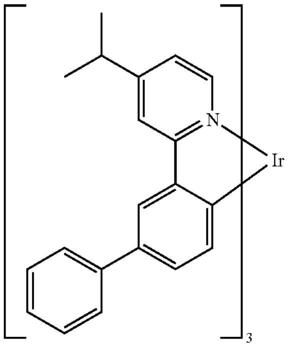
D-21
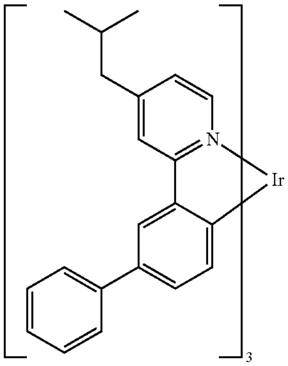
D-22
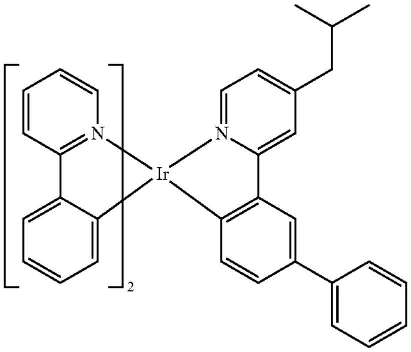
D-23
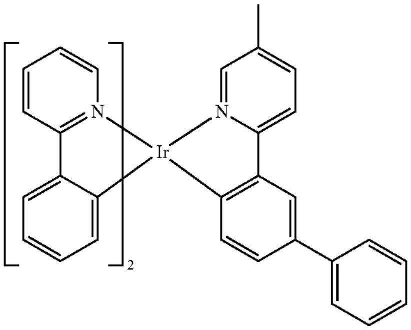
D-24
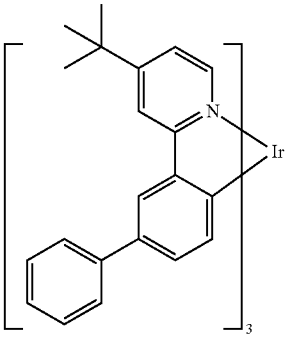

-continued
D-25
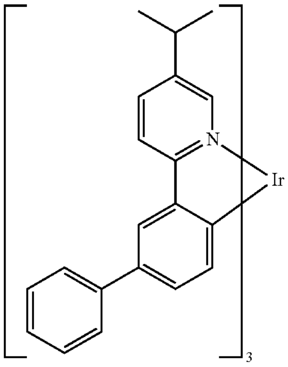
D-26
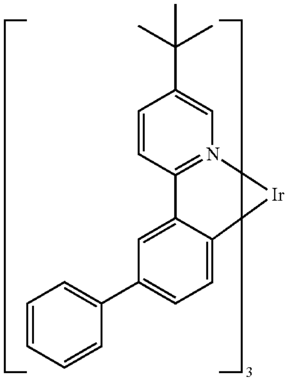
D-27
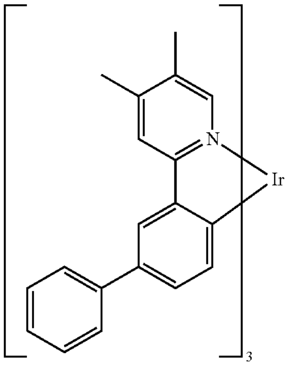
D-28
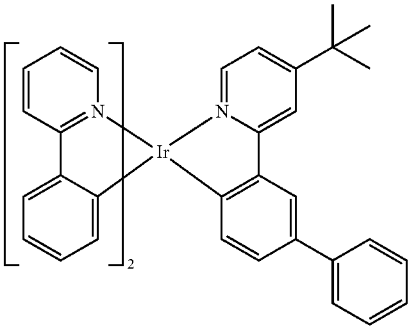
-continued
D-29
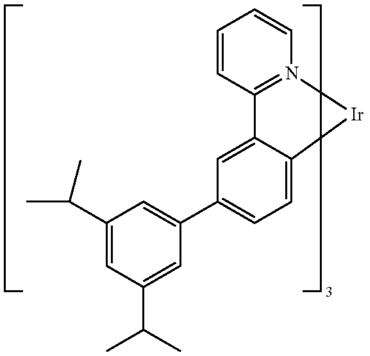
D-30
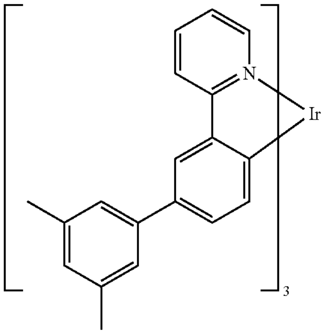
D-31
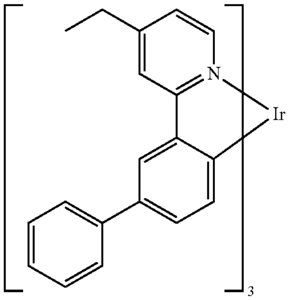
D-32
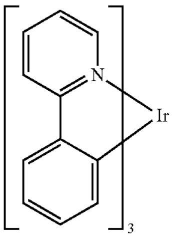
D-33
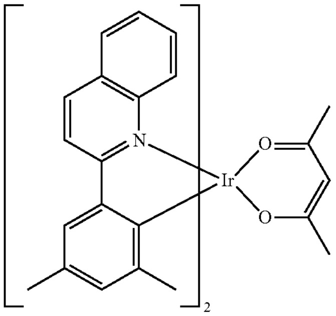

-continued
D-34
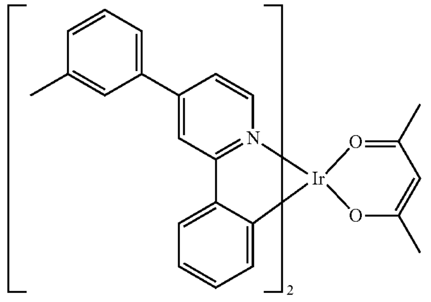
D-35
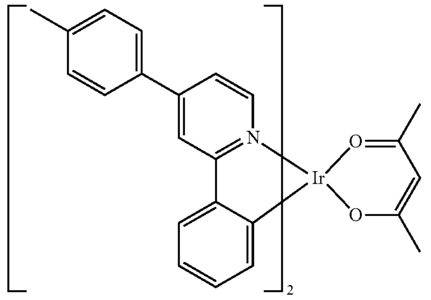
D-36
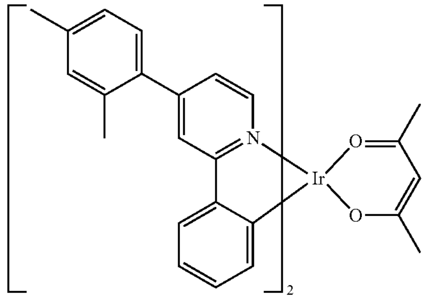
D-37
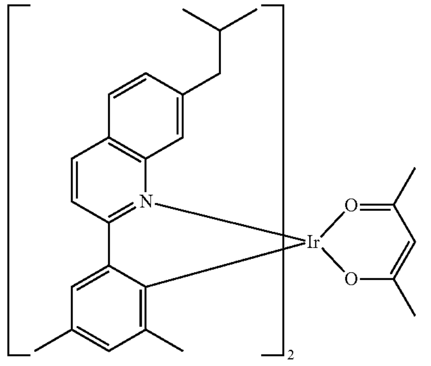
D-38
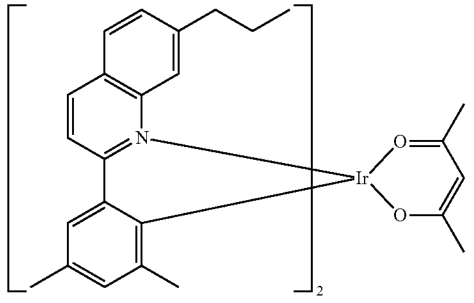
-continued
D-39
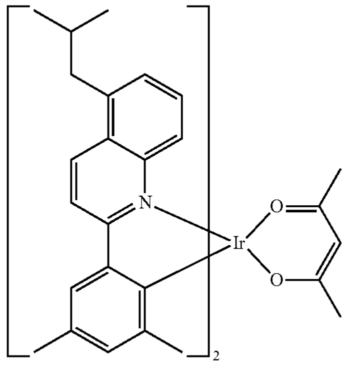
D-40
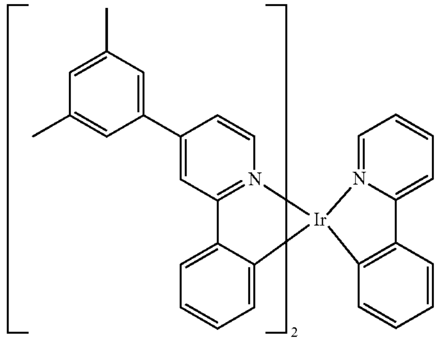
D-41
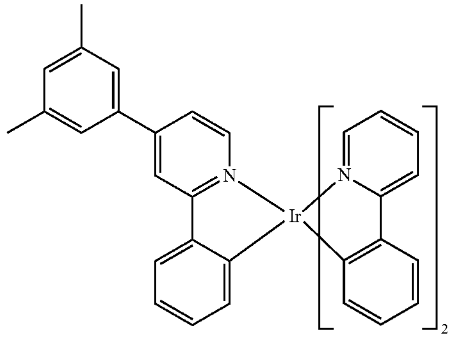
D-42
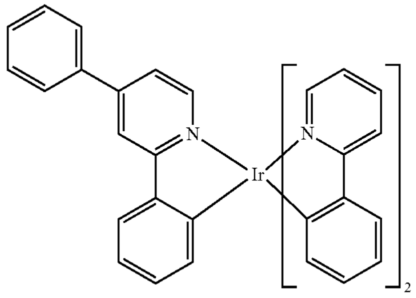

-continued
D-43
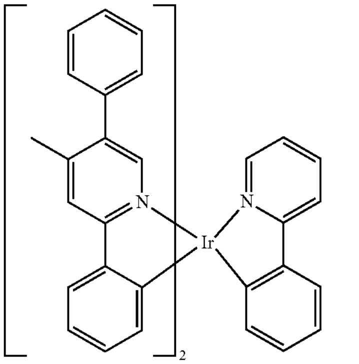
D-44
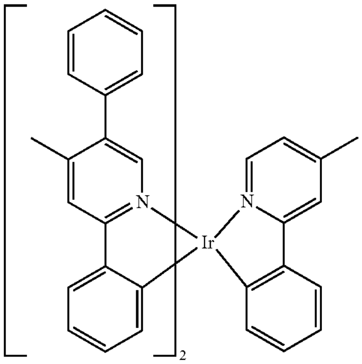
D-45
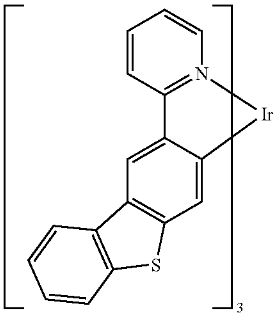
D-46
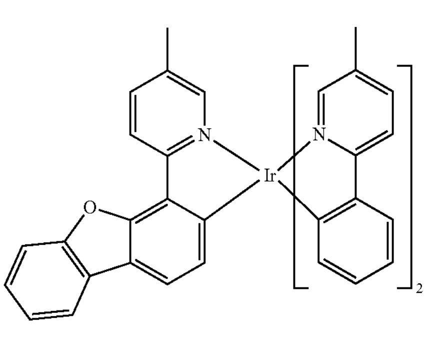
-continued
D-47
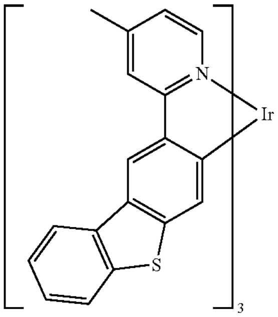
D-48
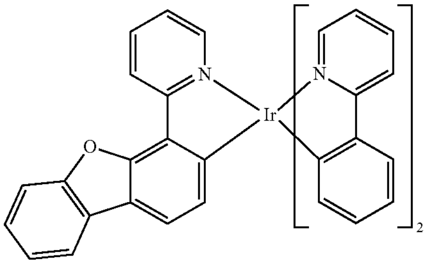
D-49
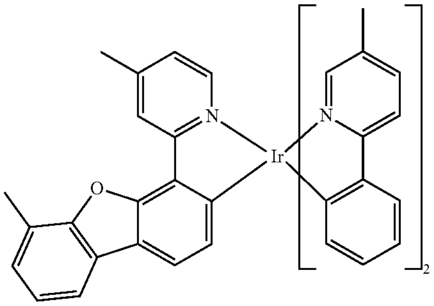
D-50
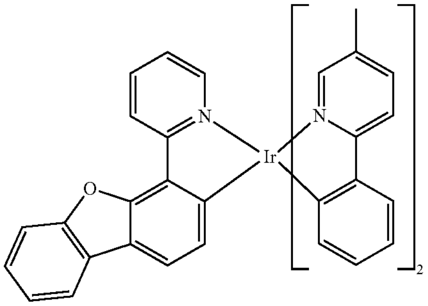
D-51
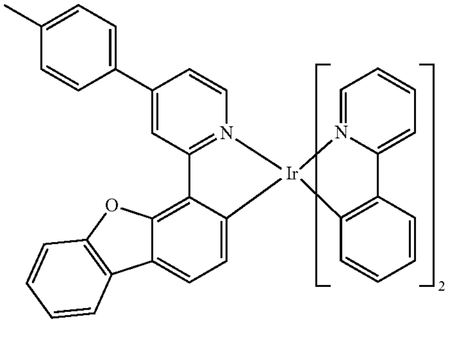

D-52
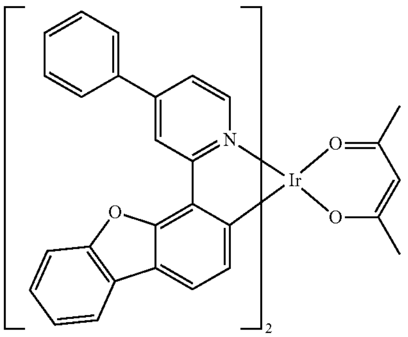
D-53
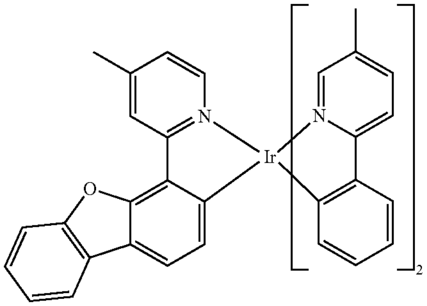
D-54
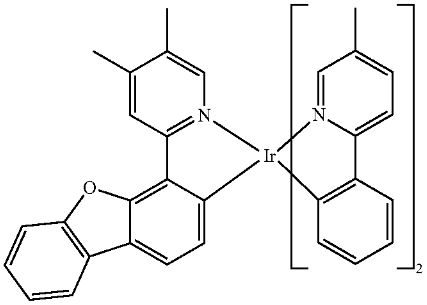
D-55
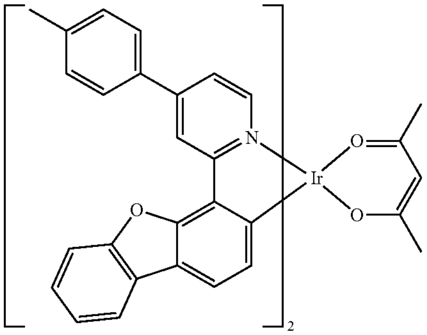
D-56
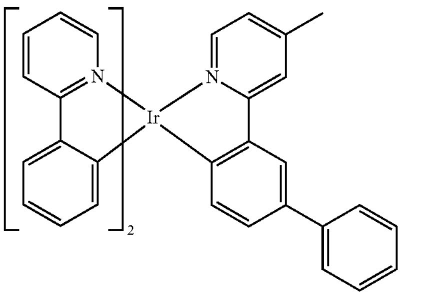
D-57
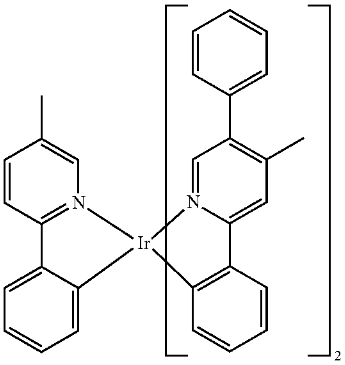
D-58
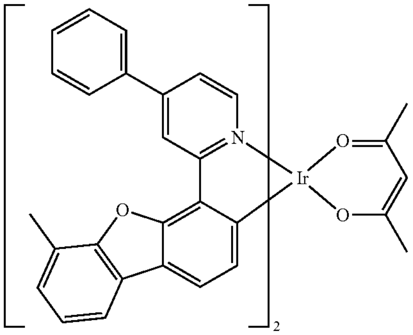
D-59
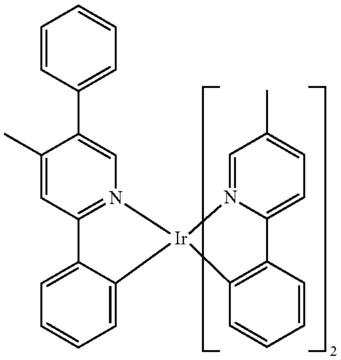
D-60
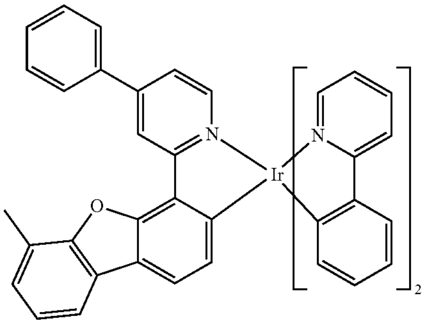

-continued
D-61
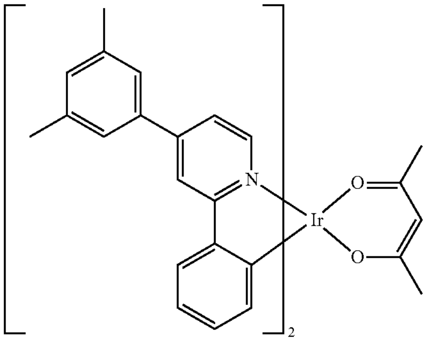
D-62
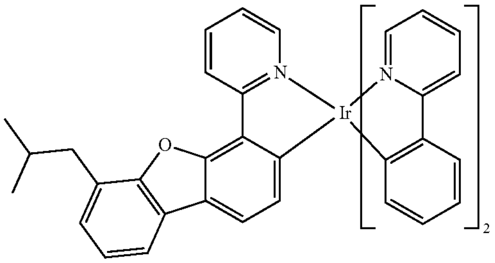
D-63
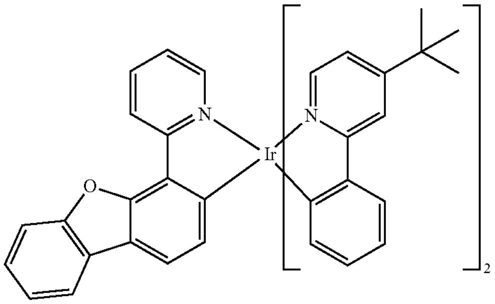
D-64
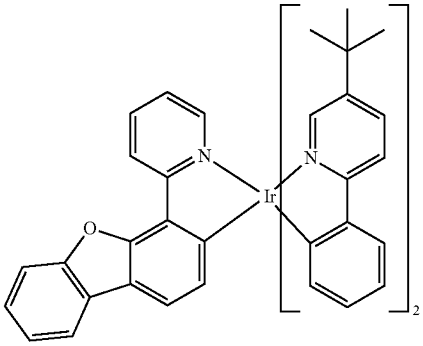
-continued
D-65
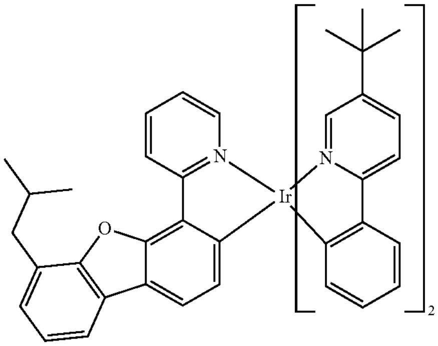
D-66
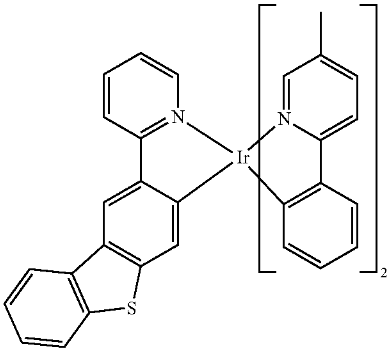
D-67
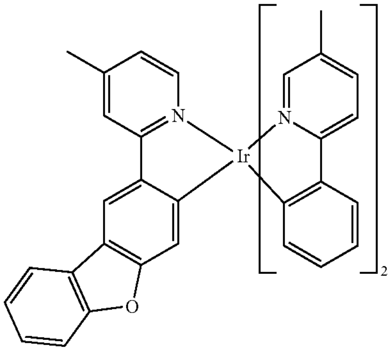
D-68
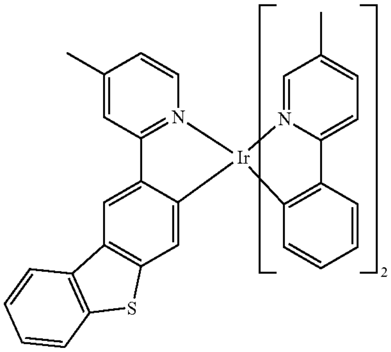

-continued
D-69
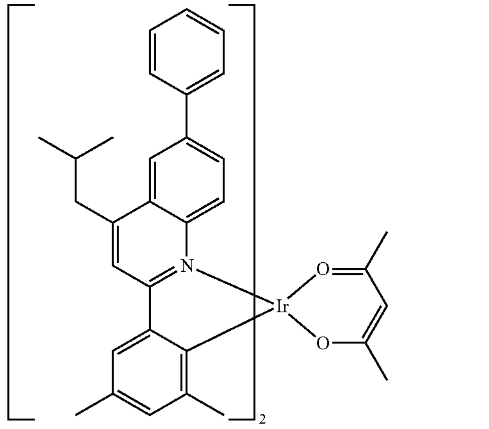
D-70
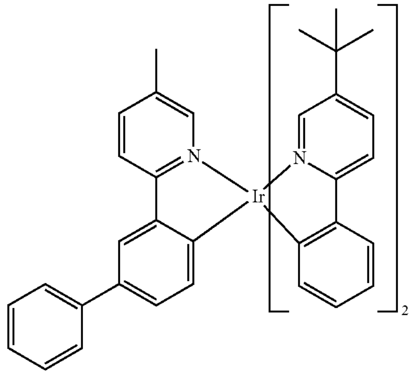
D-71
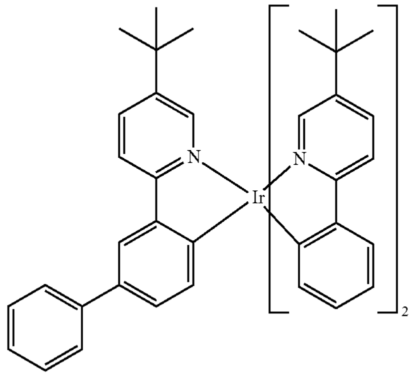
D-72
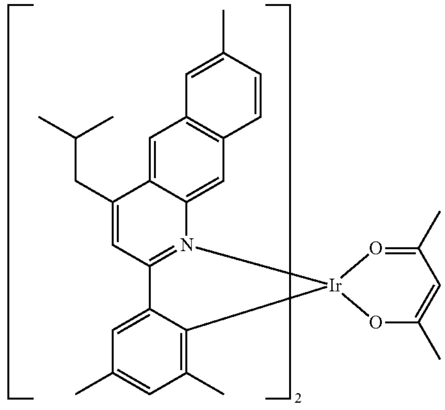
-continued
D-73
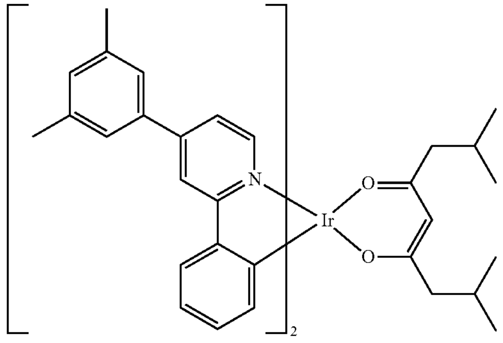
D-74
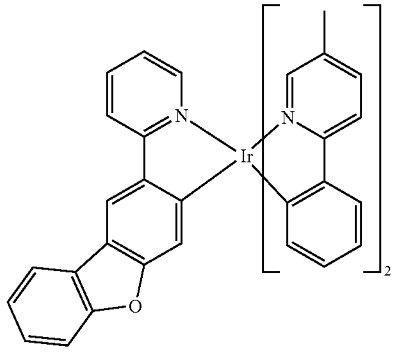
D-75
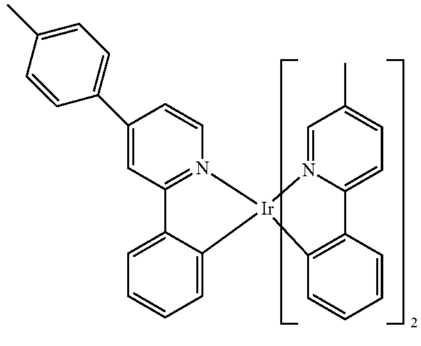
D-76
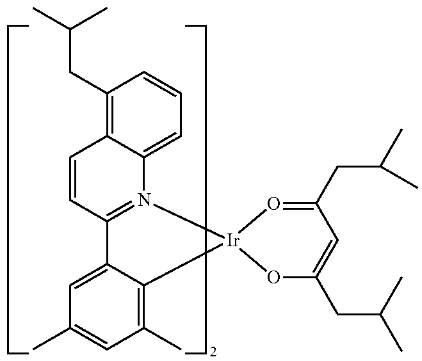

D-77
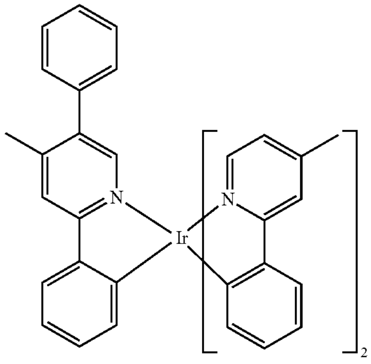
D-78
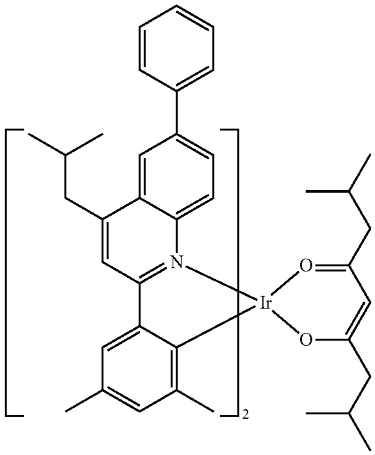
D-79
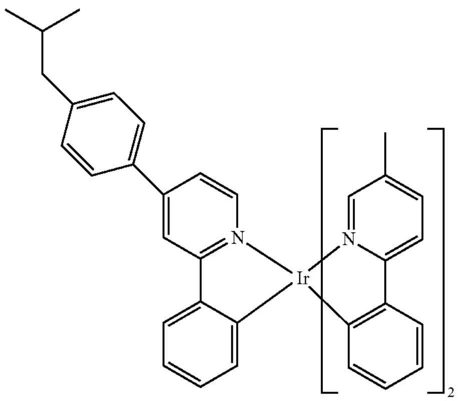
D-80
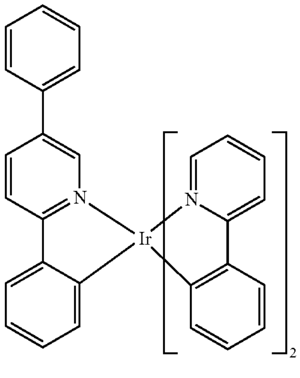
D-81
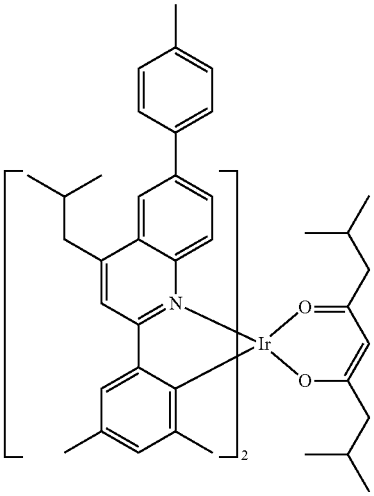
D-82
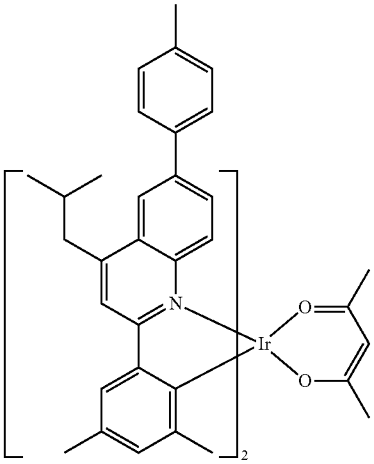
D-83
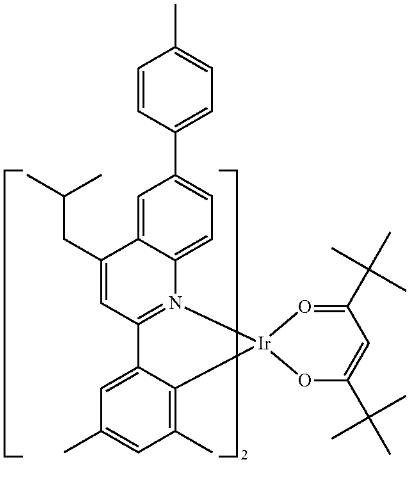

-continued
D-84
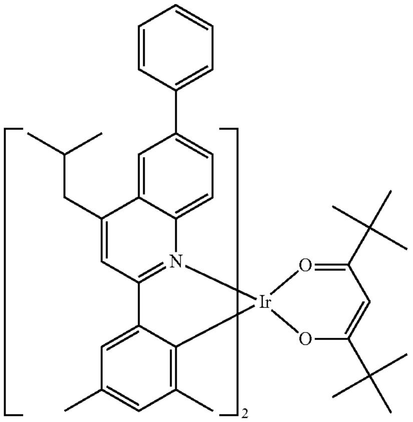
D-85
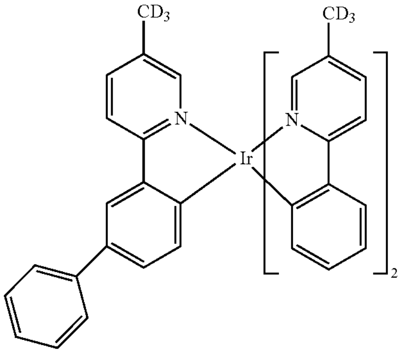
D-86
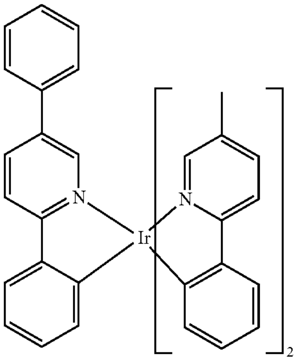
D-87
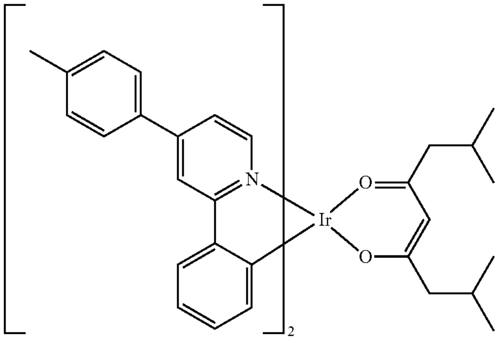
-continued
D-88
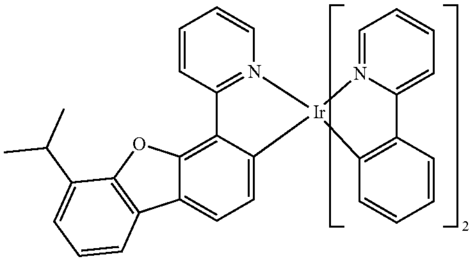
D-89
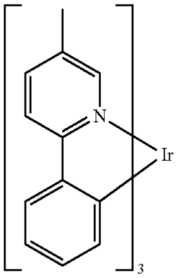
D-90
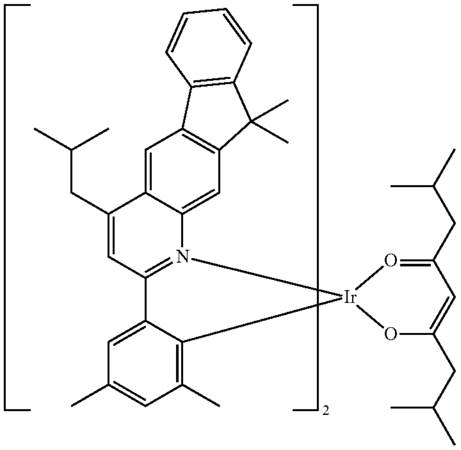
D-91
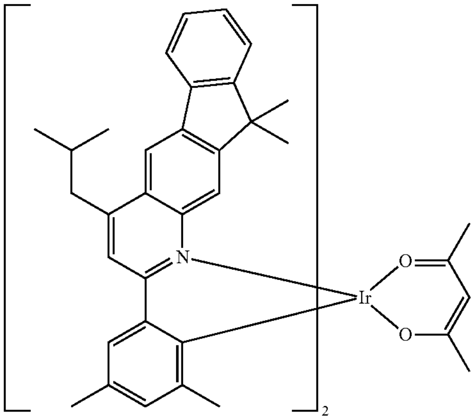

-continued
D-92
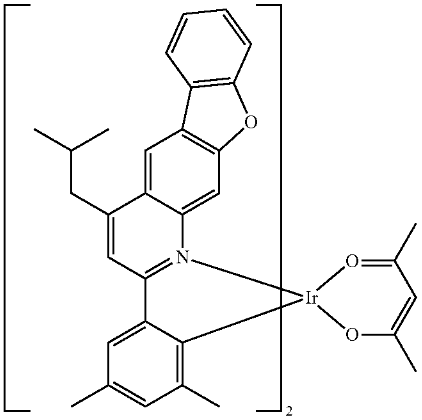
D-93
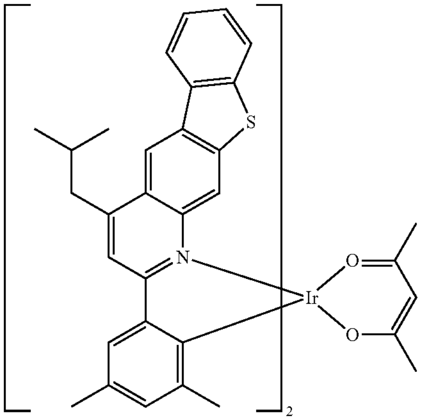
D-94
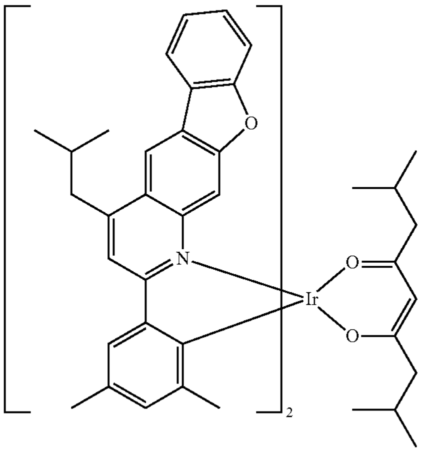
-continued
D-95
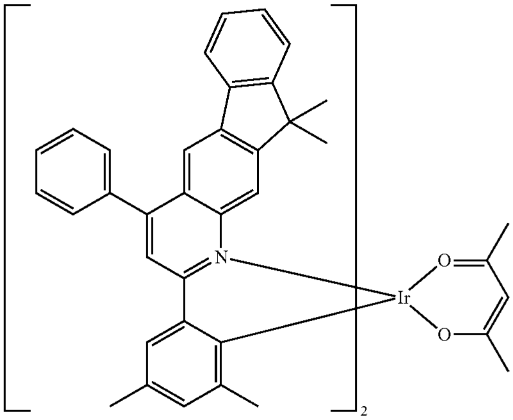
D-96
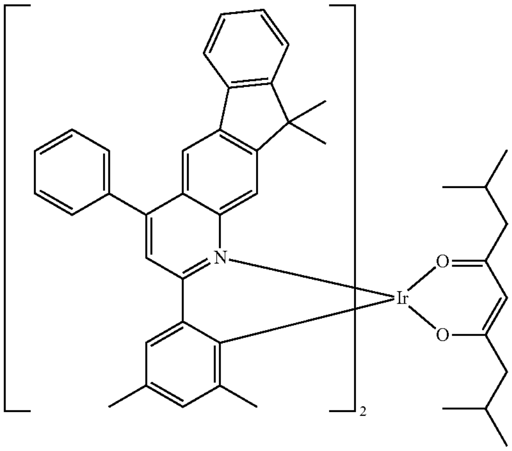
D-97
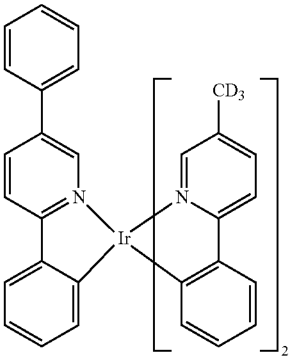
D-98
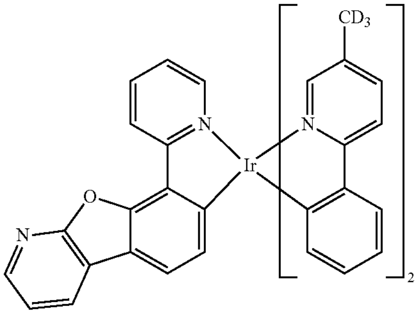

-continued
D-99
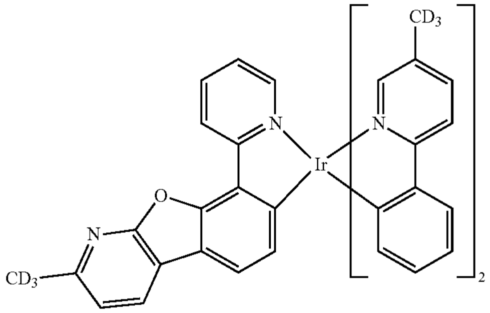
D-100
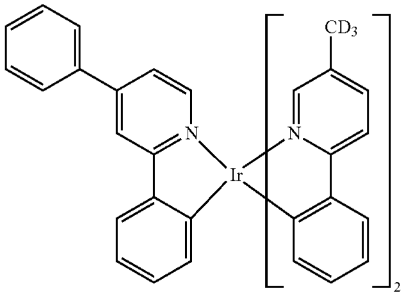
D-101
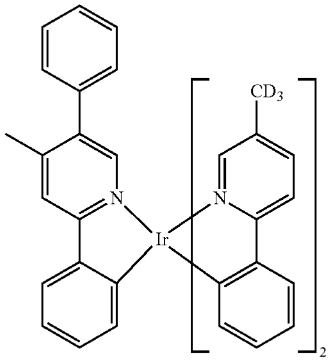
D-102
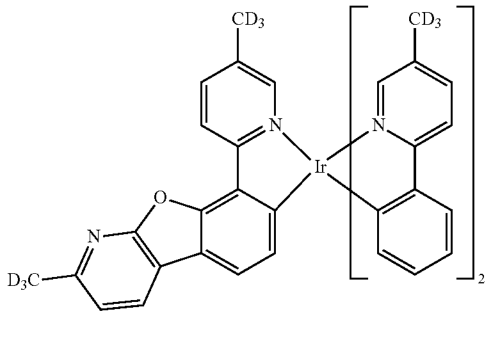
-continued
D-103
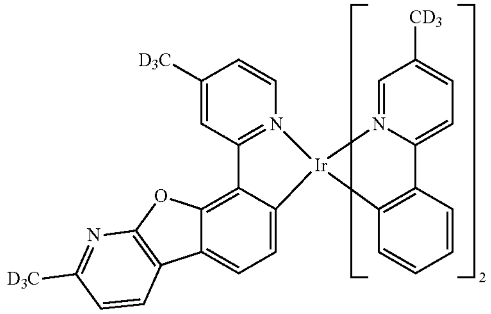
D-104
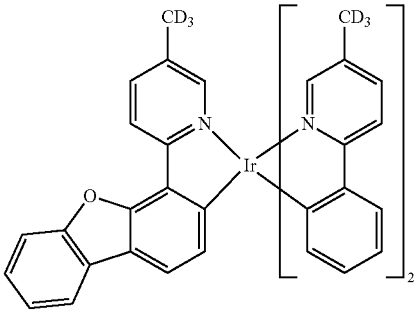
D-105
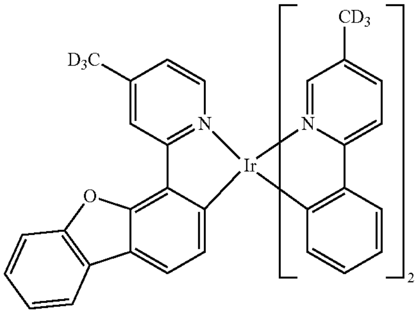
D-106
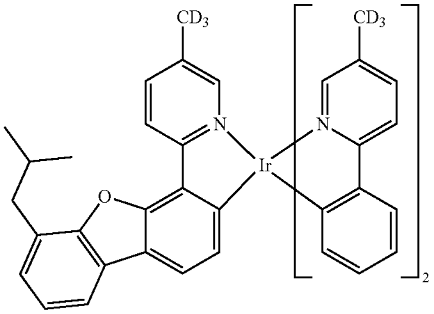
D-107
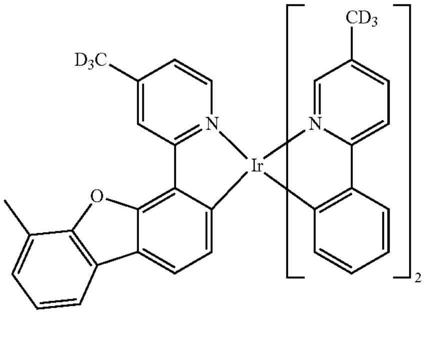

-continued
D-108
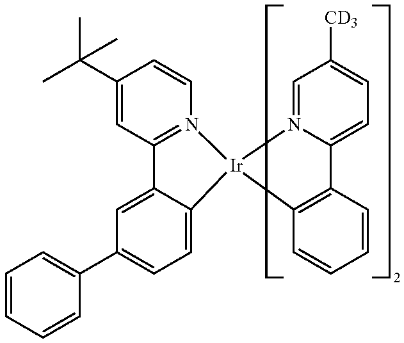
D-109
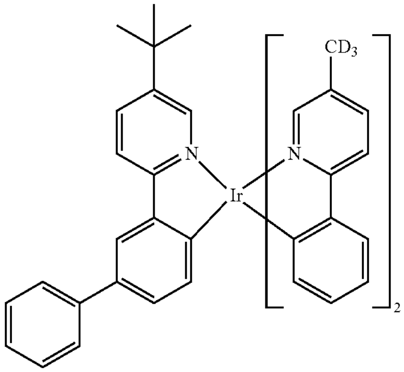
D-110
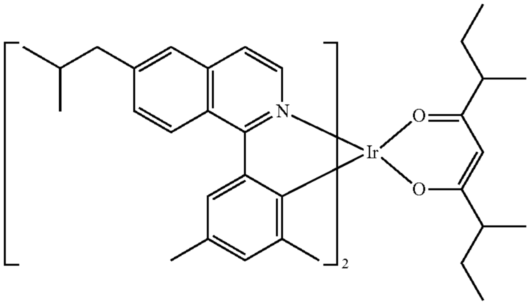
D-111
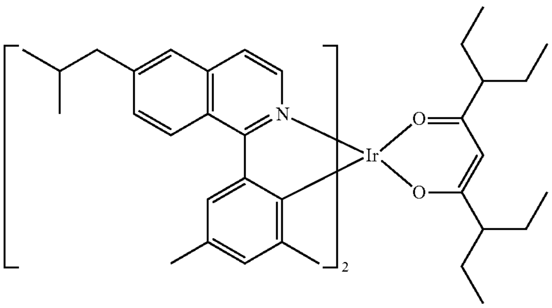
-continued
D-112
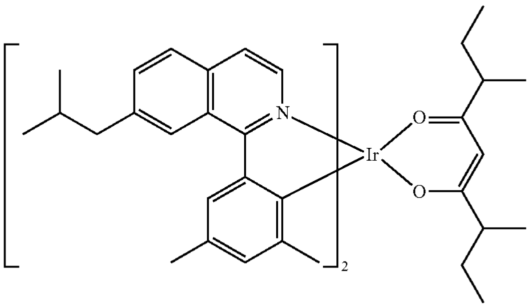
D-113
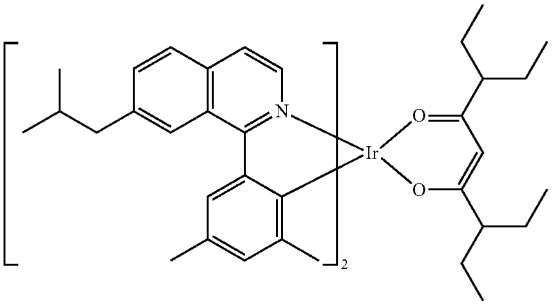
D-114
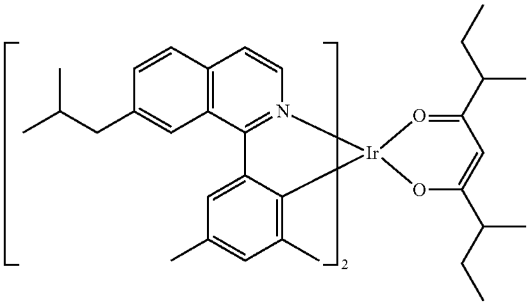
D-115
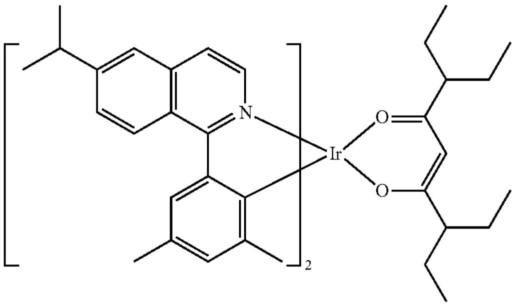
D-116
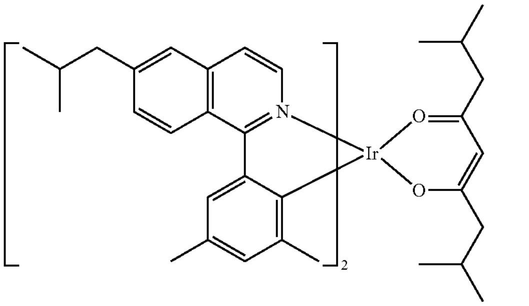

-continued
D-117
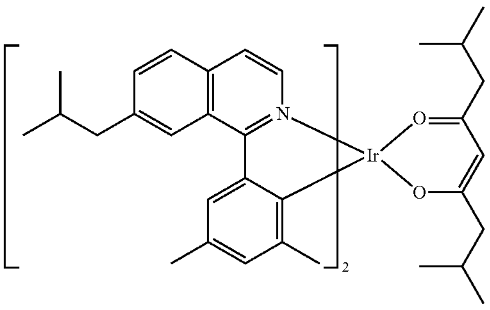
D-118
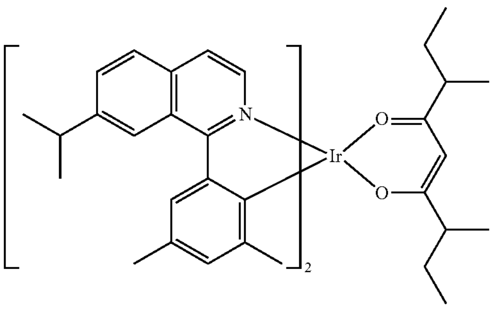
D-119
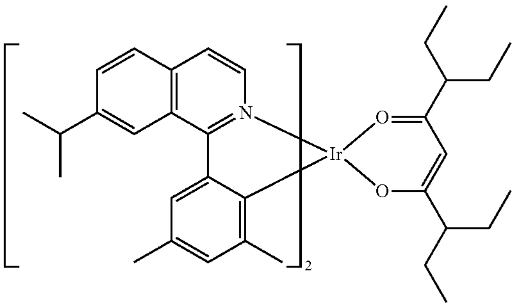
D-120
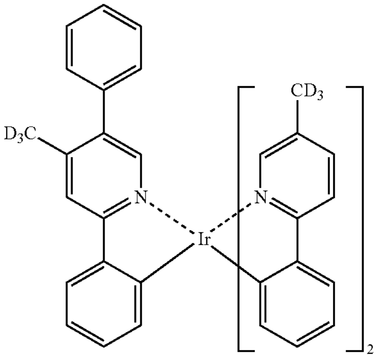
-continued
D-121
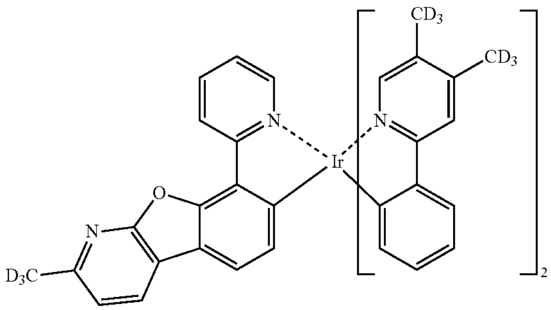
D-122
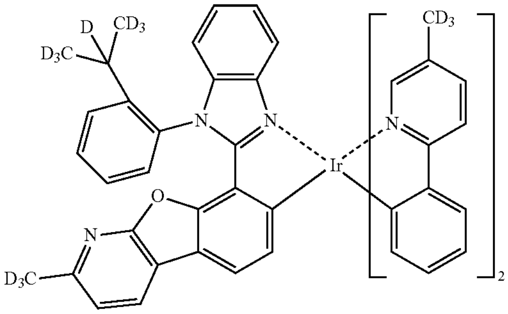
D-123
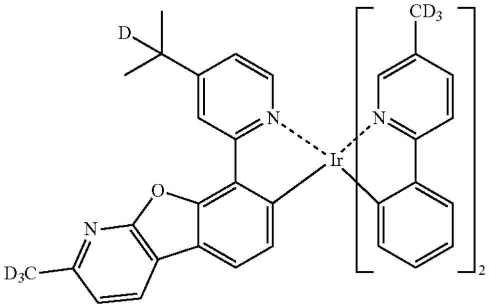
D-124
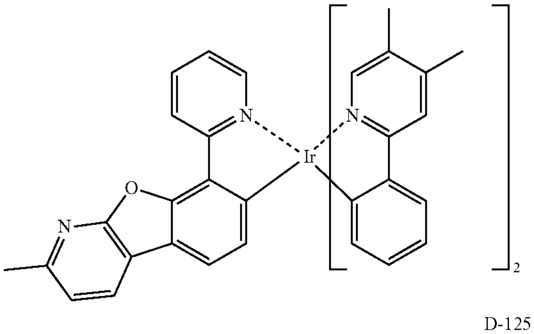
D-125
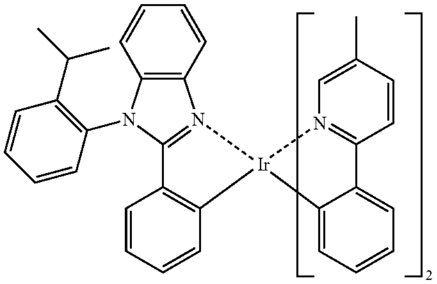

-continued
D-126
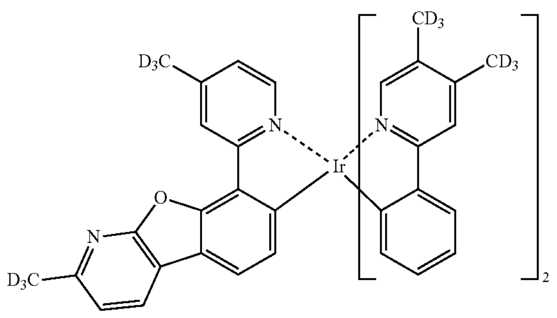
D-127
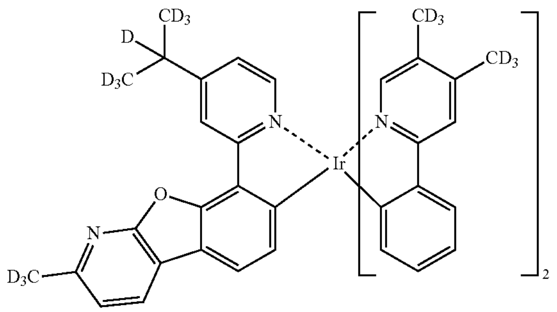
D-128
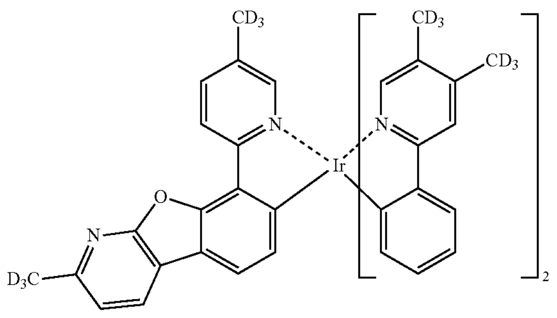
D-129
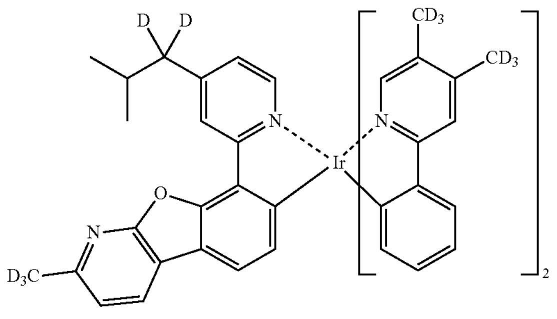
-continued
D-130
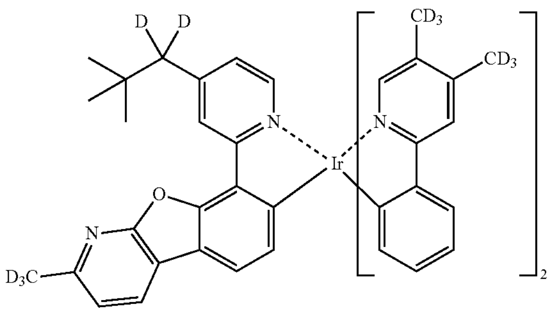
D-131
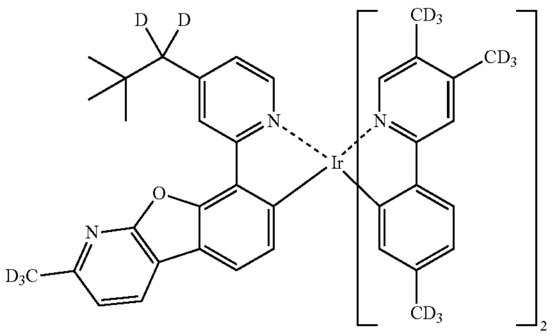
D-132
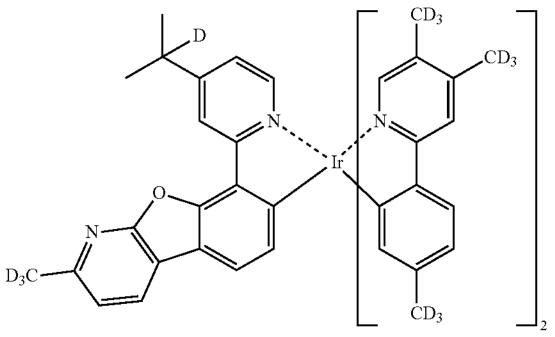
D-133
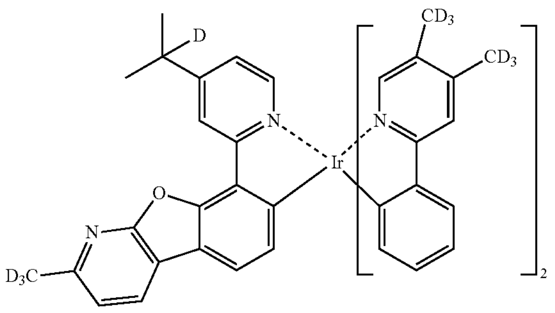

-continued
D-134
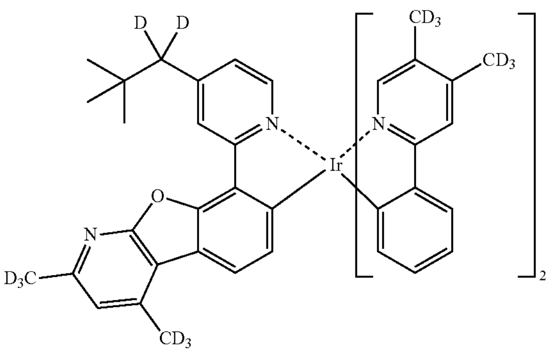
D-135
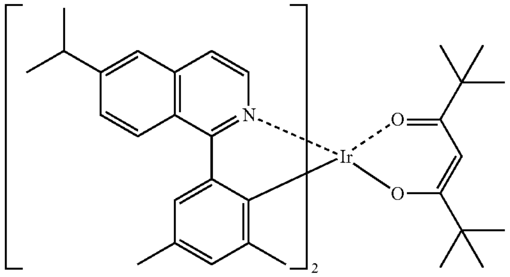
D-136
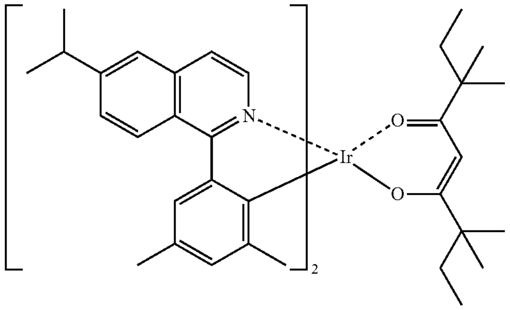
D-137
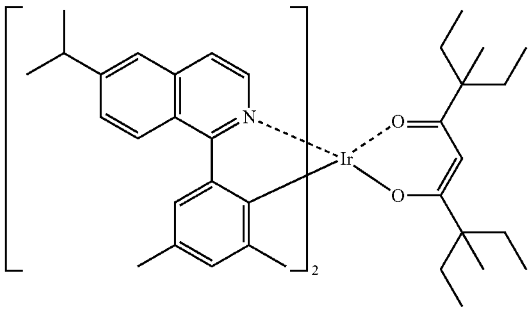
-continued
D-138
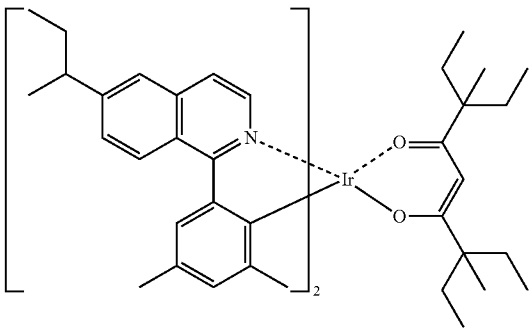
D-139
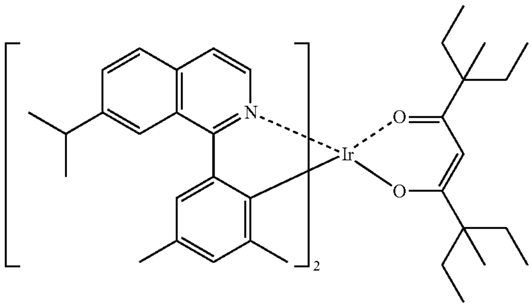
D-140
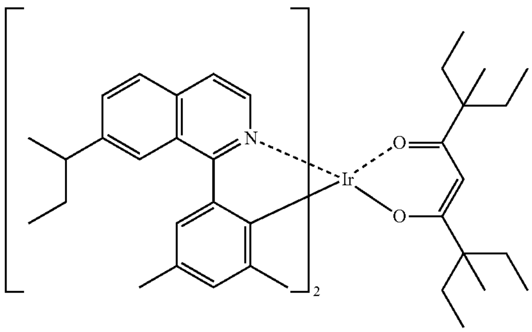
D-141
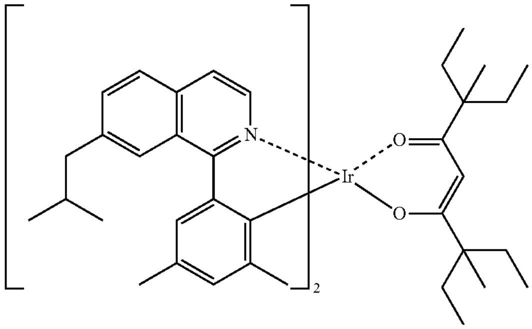

-continued
D-142
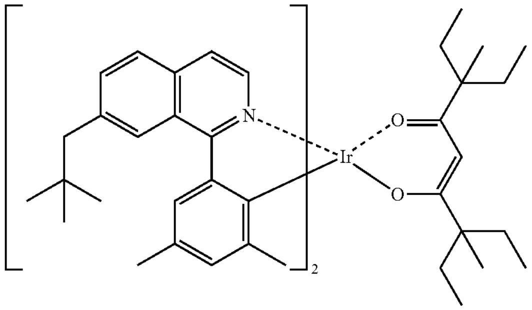
D-143
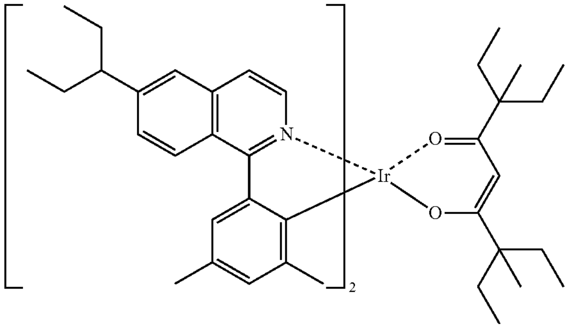
D-144
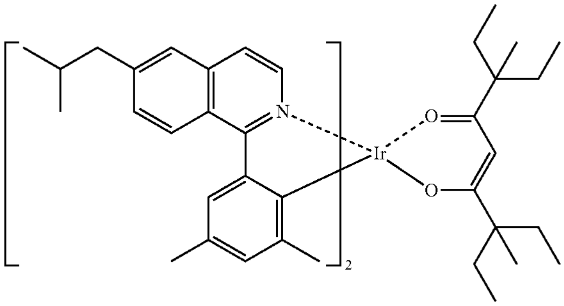
D-145
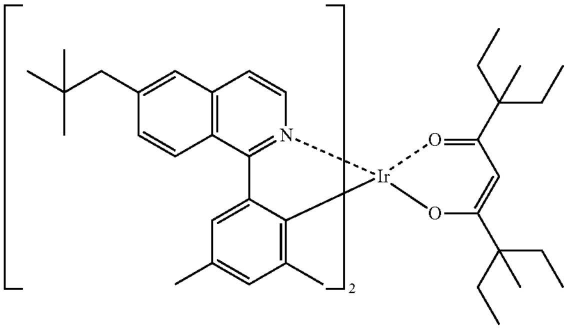
-continued
D-146
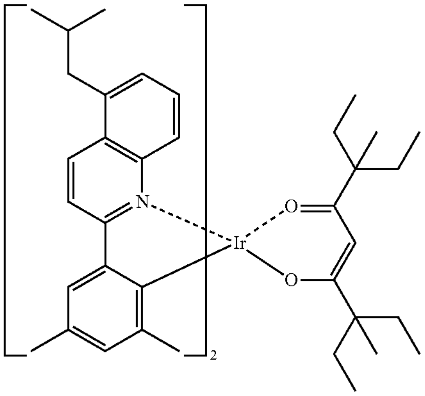
D-147
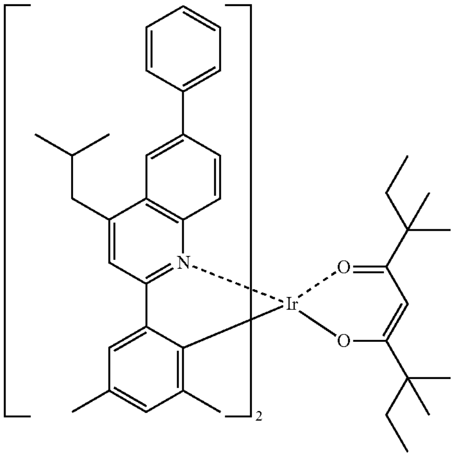
D-148
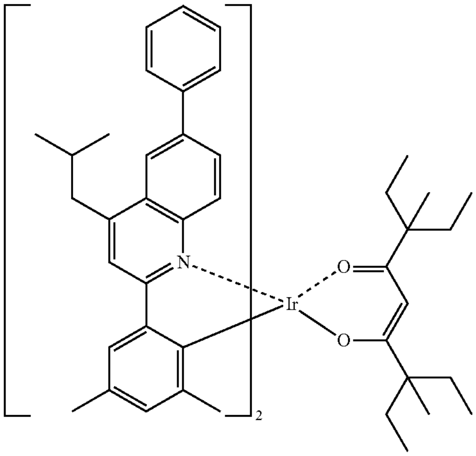

-continued

D-149

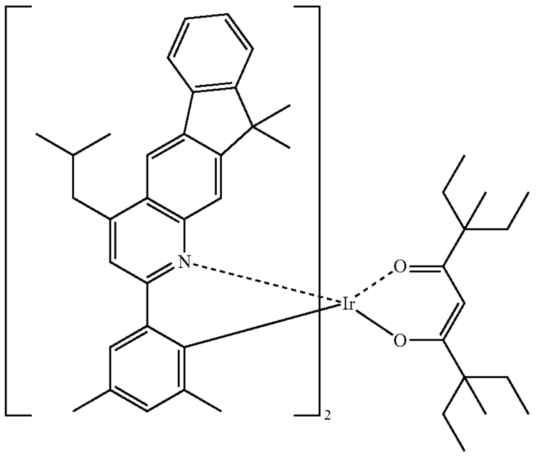

In order to form each layer of the organic electroluminescent device of the present disclosure, dry film-forming methods such as vacuum evaporation, sputtering, plasma, ion plating methods, etc., or wet film-forming methods such as spin coating, dip coating, flow coating methods, etc., can be used. When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

When forming a layer by the first host material and the second host material according to one embodiment, the layer can be formed by the above-listed methods, and can often be formed by co-deposition or mixture-deposition. The co-deposition is a mixed deposition method in which two or more materials are put into respective individual crucible sources and a current is applied to both cells simultaneously to evaporate the materials; and the mixed deposition is a method in which two or more materials are mixed in one crucible source before deposition, and then a current is applied to one cell to evaporate the materials.

According to one embodiment, when the first host material and the second host material exist in the same layer or different layers in the organic electroluminescent device, the layers by the two host compounds may be separately formed. For example, after depositing the first host material, a second host material may be deposited.

According to one embodiment, the present disclosure can provide display devices comprising a plurality of host materials including a first host material represented by the formula 1 and a second host material represented by the formula 2, and the organic electroluminescent compound represented by the formula 1-1' and/or the organic electroluminescent compound represented by the formula 1-2'. In addition, by using the organic electroluminescent device of the present disclosure, display devices such as smartphones, tablets, notebooks, PCs, TVs, or display devices for vehicles, or lighting devices such as outdoor or indoor lighting can be prepared.

Hereinafter, the preparation method of compounds according to the present disclosure will be explained with reference to the synthesis method of a representative compound or intermediate compound in order to understand the present disclosure in detail.

[Example 1] Synthesis of Compound H2-86

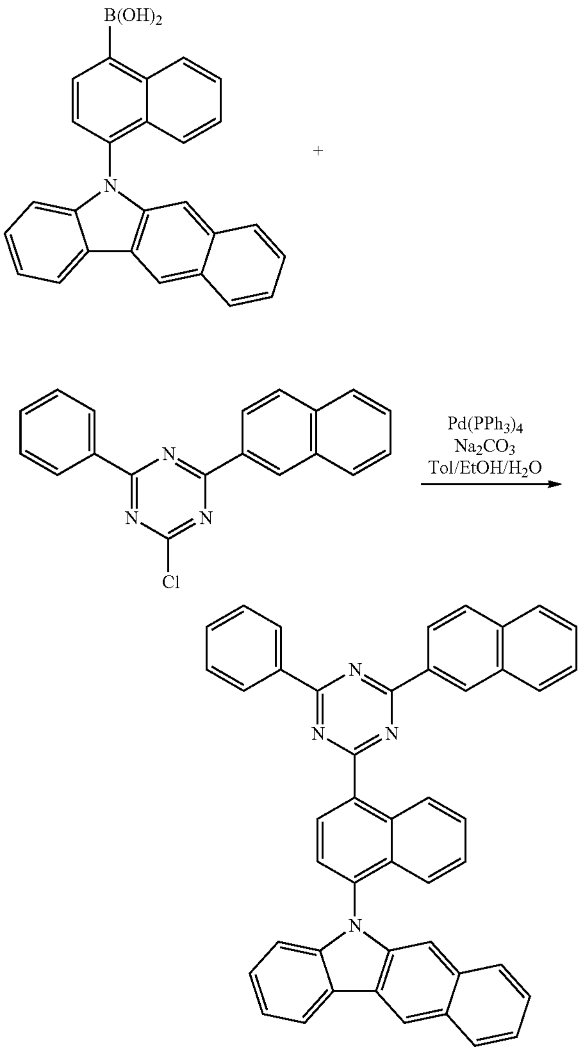

H2-86

(4-(9H-carbazol-9-yl)naphthalen-1-yl)boronic acid (4.0 g, 10.33 mmol), 2-chloro-4-(naphthalen-2-yl)-6-phenyl-1,3,5-triazine (3.6 g, 11.36 mmol), tetrakis (tiphenylphosphine) palladium(0) ($Pd(PPh_3)_4$) (410 mg, 0.35 mmol), and sodium carbonate ($Na_2CO_3$) (2.7 g, 25.82 mmol) were added to 52 mL of toluene (Tol), 13 mL of ethanol (EtOH), and 13 mL of $H_2O$ followed by dissolving. Then, it was stirred under reflux for 6 hours. After completion of the reaction, the mixture was cooled to room temperature, the layers were separated by adding ethyl acetate (EA) and $H_2O$ thereto, and the solid was formed by using MeOH followed by filtering. Next, it was separated and recrystallized by column chromatograph to obtain compound H2-86 (2.4 g, yield: 38%).

| | MW | M.P |
|---|---|---|
| H2-86 | 624.23 | 285.0° C. |

[Example 2] Synthesis of Compound H2-26

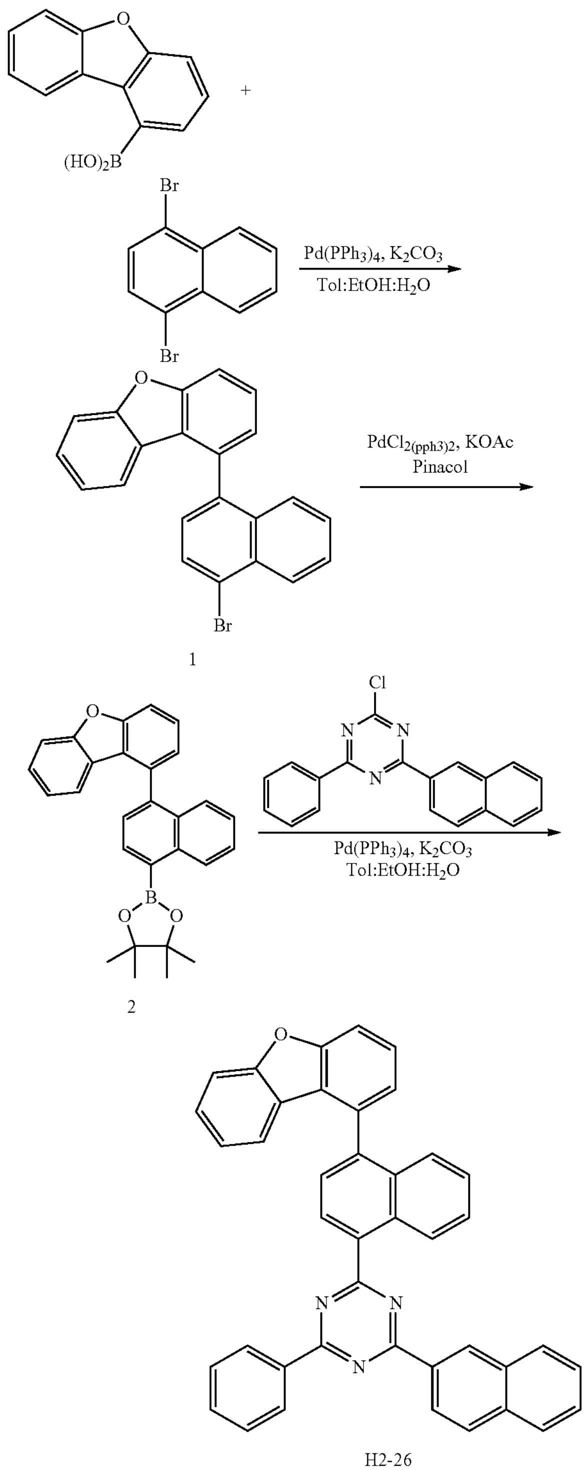

1

2

H2-26

1) Synthesis of Compound 1

Dibenzo[b,d]furan-1-yl boronic acid (20 g, 94.33 mmol), 1,4-dibromonaphthalene (54 g, 188.6 mmol), $Pd(PPh_3)_4$ (5.4 g, 4.716 mmol), and $K_2CO_3$ (26 g, 188.6 mmol) were added to 380 mL of toluene, 95 mL of EtOH, and 95 mL of $H_2O$, and stirred under reflux for 3 hours. After completion of the reaction, the mixture was cooled to room temperature, and the organic layer was extracted with distilled water and EA. The extracted organic layer was distilled under reduced pressure, and then separated by column chromatography using methylene chloride/hexane (MC/Hex) to obtain compound 1 (20 g, yield: 55%).

2) Synthesis of Compound 2

Bis(tiphenylphosphine)palladium(II) dichloride ($PdCl_2(PPh_3)_2$) (3.7 g, 53.59 mmol), KOAc (10.5 g, 107.1 mmol), Pinacol (17.7 g, 69.66 mmol), and 270 mL of 1,4-dioxane were added to compound 1 (20 g, 53.59 mmol), and then stirred under reflux for 2 hours. After completion of the reaction, the mixture was filtered with a celite filter, and then extracted with MC. Thereafter, the organic layer was concentrated. Next, it was separated by column chromatography using MC/Hex to obtain compound 2 (20 g, yield: 88%).

3) Synthesis of Compound H2-26

64 mL of toluene, 16 mL of EtOH, and 16 mL of $H_2O$ were added to compound 2 (6 g, 14.16 mmol), 2-chloro-4-(naphthalene-2-yl)-6-phenyl-1,3,5-triazine (5 g, 15.73 mmol), $Pd(PPh_3)_4$ (0.9 g, 0.786 mmol), and $K_2CO_3$ (4.3 g, 31.47 mmol), and then stirred under reflux for 2 hours. After completion of the reaction, the mixture was cooled to room temperature, and the organic layer was extracted with distilled water and EA. The extracted organic layer was distilled under reduced pressure, and then separated by column chromatography using MC/Hex to obtain compound H2-26 (4 g, yield: 44%).

| | MW | M.P |
|---|---|---|
| H2-26 | 575.6 | 131.3° C. |

[Example 3] Synthesis of Compound H2-80

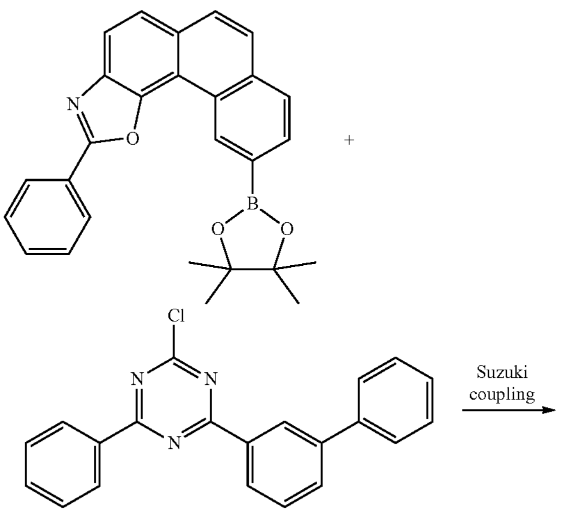

-continued

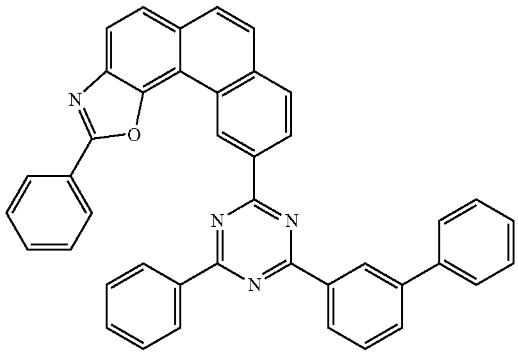

H2-80

30 mL of toluene, 7 mL of EtOH, and 10 mL of $H_2O$ were added to 2-phenyl-10-(4,4,5,5-tetramethyl-1,3,2-dioxaborolan-2-yl)phenanthro[3,4-d]oxazole (4.0 g, 9.5 mmol), 2-([1, 1'-biphenyl]-3-yl)-4-chloro-6-phenyl-1,3,5-triazine (3.9 g, 11.4 mmol), $Pd(PPh_3)_4$ (0.5 g, 0.5 mmol), and $K_2CO_3$ (2.6 g, 19 mmol), and then stirred under reflux for 6 hours. After completion of the reaction, the mixture was cooled to room temperature, and then stirred at room temperature. The resulting solid was filtered under reduced pressure by adding MeOH thereto. Next, it was separated by column chromatography using MC to obtain compound H2-80 (4.6 g, yield: 80%).

| | MW | M.P |
|---|---|---|
| H2-80 | 602.7 | 227° C. |

[Example 4] Synthesis of Compound H2-76

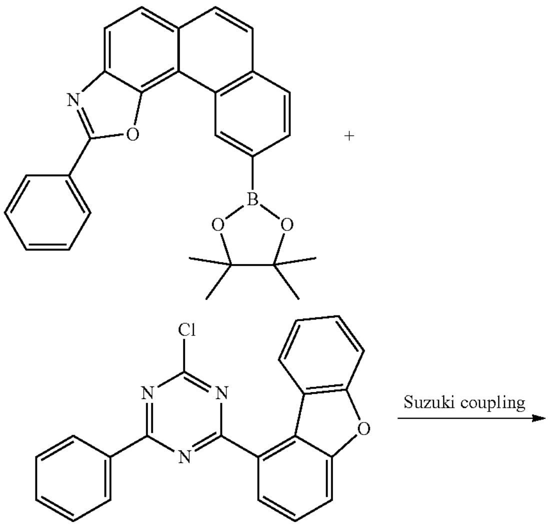

-continued

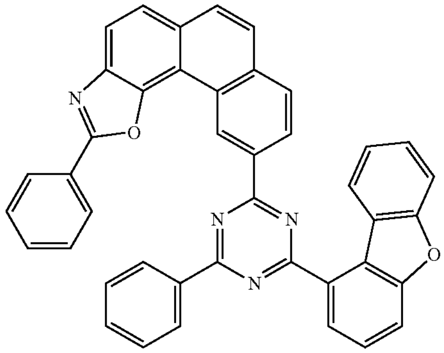

H2-76

36 mL of toluene, 8 mL of EtOH, and 12 mL of $H_2O$ were added to 2-phenyl-10-(4,4,5,5-tetramethyl-1,3,2-dioxaborolan-2-yl)phenanthro[3,4-d]oxazole (3.0 g, 7.1 mmol), 2-chloro-4-(dibenzo[b,d]furan-1-yl)-6-phenyl-1,3,5-triazine (3.4 g, 9.26 mmol), $Pd(PPh_3)_4$ (0.4 g, 0.36 mmol), and $K_2CO_3$ (2.0 g, 14 mmol), and then stirred under reflux for 6 hours. After completion of the reaction, the mixture was cooled to room temperature, and stirred at room temperature. The resulting solid was filtered under reduced pressure by adding MeOH thereto. Next, it was separated by column chromatography using MC to obtain compound H2-76 (3.3 g, yield: 75%).

| | MW | M.P |
|---|---|---|
| H2-76 | 616.7 | 282° C. |

[Example 5] Synthesis of Compound H-2-78

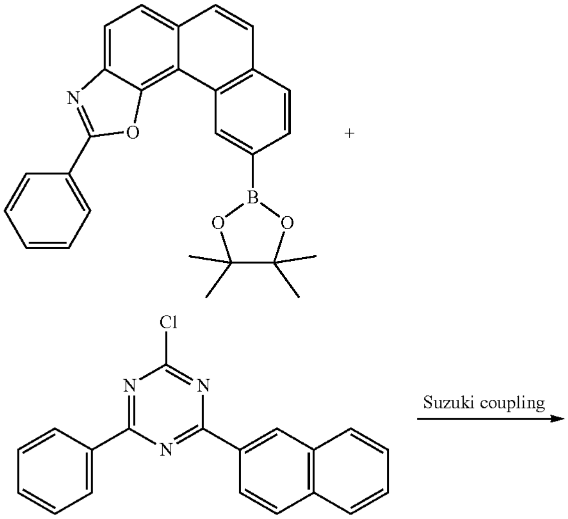

-continued

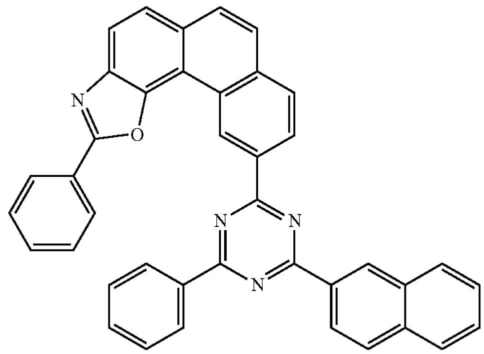

H2-78

30 mL of toluene, 7 mL of EtOH, and 10 mL of $H_2O$ were added to 2-phenyl-10-(4,4,5,5-tetramethyl-1,3,2-dioxaborolan-2-yl)phenanthro[3,4-d]oxazole (4.0 g, 9.5 mmol), 2-chloro-4-(naphthalen-2-yl)-6-phenyl-1,3,5-triazine (3.6 g, 11.4 mmol). $Pd(PPh_3)_4$ (0.5 g, 0.5 mmol), and $K_2CO_3$ (2.6 g, 19 mmol), and then stirred under reflux for 4 hours. After completion of the reaction, the mixture was cooled to room temperature, and stirred at room temperature. The solid formed by adding MeOH was filtered under reduced pressure. Next, it was separated by column chromatography using MC to obtain compound H2-78 (3.45 g, yield: 63%).

| | MW | M.P |
|---|---|---|
| H2-78 | 576.6 | 268° C. |

[Example 6] Synthesis of Compound H2-27

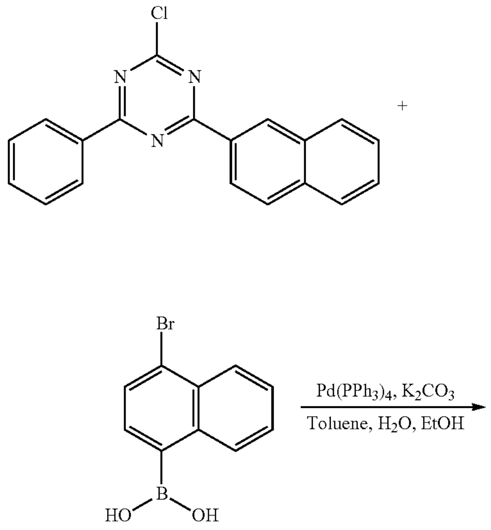

-continued

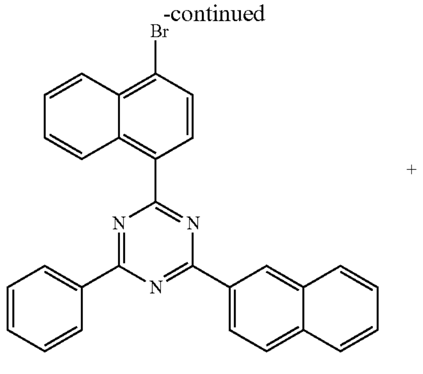

6-1

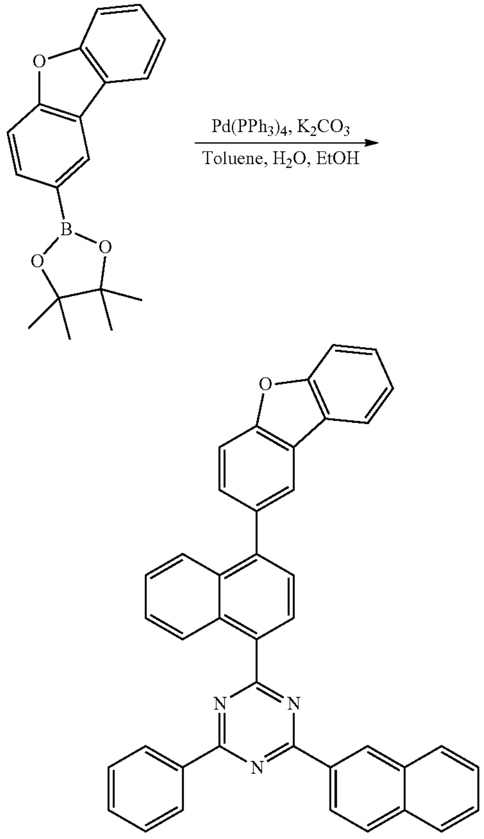

H2-27

1) Synthesis of Compound 6-1

2-chloro-4-(naphthalen-2-yl)-6-phenyl-1,3,5-triazine (24.7 g, 77.7 mmol), (4-bromonaphthalen-1-yl)boronic acid (15.0 g, 59.8 mmol), $K_2CO_3$ (20.7 g, 149.5 mmol), $Pd(PPh_3)_4$ (3.4 g, 3.0 mmol), 200 mL of toluene, 50 mL of ethanol, and 50 mL of $H_2O$ were added to a flask, and dissolved. Thereafter, the mixture was refluxed at 130° C. for 2 hours. After completion of the reaction, the organic layer was extracted with ethyl acetate, the residual water was removed with magnesium sulfate and dried. Next, it was separated by column chromatography to obtain compound 6-1 (15 g, yield: 51.3%).

2) Synthesis of Compound H2-27

Compound 6-1 (7.5 g, 15.4 mmol), 2-(dibenzo[b,d]furan-2-yl)-4,4,5,5-tetramethyl-1,3,2-dioxaborolane (5.0 g, 16.9 mmol), $K_2CO_3$ (5.3 g, 38.4 mmol), $Pd(PPh_3)_4$ (888 mg, 0.768 mmol), 45 mL of toluene, 15 mL of ethanol, and 15 mL of $H_2O$ were added to a flask, and dissolved. Thereafter, the mixture was refluxed at 130° C. for 6 hours. After completion of the reaction, the organic layer was extracted with ethyl acetate, and the residual water was removed with magnesium sulfate and dried. Next, it was separated by column chromatography to obtain compound H2-27 (4.5 g, yield: 51%).

[Example 7] Synthesis of Compound H2-96

| | MW | M.P |
|---|---|---|
| H2-27 | 575.66 | 213° C. |

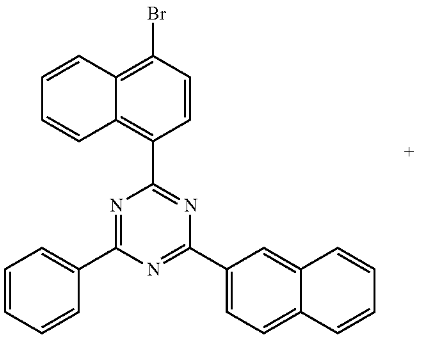

6-1

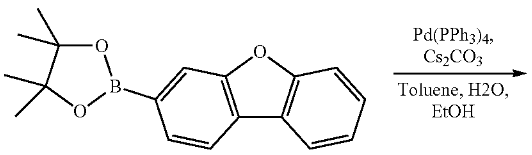

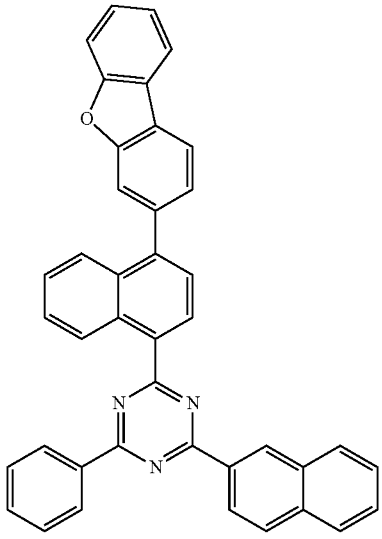

H2-96

Compound 6-1 (6.5 g 13.3 mmol), 2-(dibenzo[b,d]furan-3-yl)-4,4,5,5-tetramethyl-1,3,2-dioxaborolane (3.9 g, 13.3 mmol), $K_2CO_3$ (4.5 g, 32.5 mmol), $Pd(PPh_3)_4$ (0.77 g, 0.67 mmol), 40 mL of toluene, 13 mL of ethanol, and 13 mL of $H_2O$ were added to a flask, and dissolved. Thereafter, the mixture was refluxed at 130° C. for 6 hours. After completion of the reaction, the organic layer was extracted with ethyl acetate, and the residual water was removed with magnesium sulfate followed by drying. Next, it was separated by column chromatography to obtain compound H2-96 (6.5 g, yield: 85%).

| | MW | M.P |
|---|---|---|
| H2-96 | 575.66 | 194° C. |

[Example 8] Synthesis of Compound H2-11

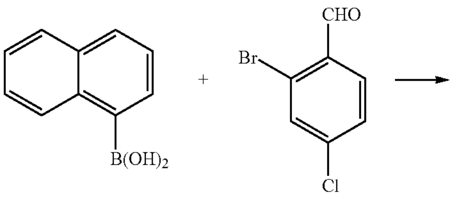

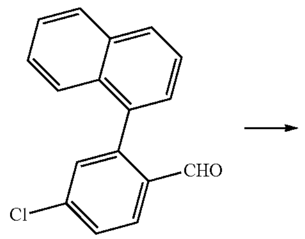

8-1

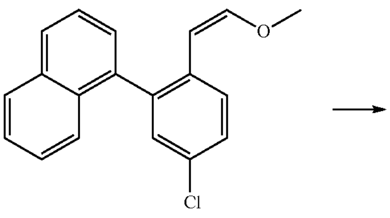

8-2

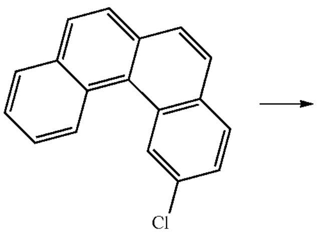

8-3

-continued

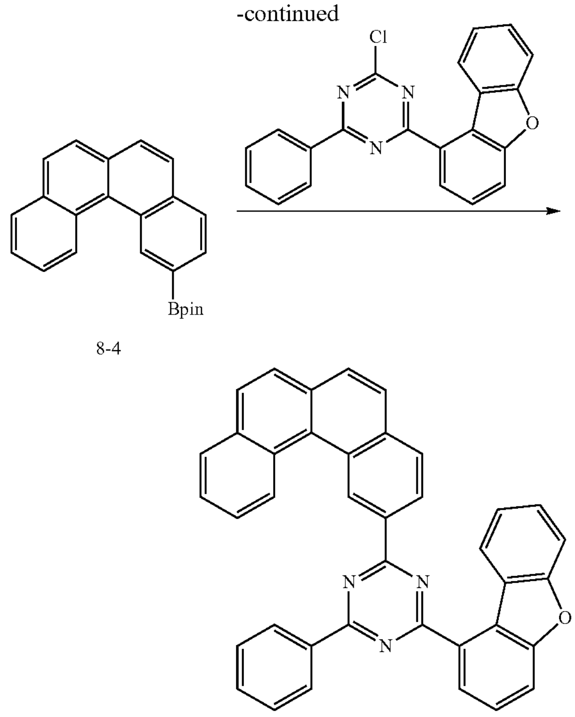

8-4

H2-11

1) Synthesis of Compound 8-1

Naphthalen-1-yl boronic acid (40 g, 232 mmol), 2-bromo-4-chlorobenzaldehyde (51 g, 232 mmol), $Pd(PPh_3)_4$ (13.4 g, 11.6 mmol), sodium carbonate (62 g, 582 mmol), 900 mL of toluene, 200 mL of ethanol, and 300 mL of distilled water were added to the reaction vessel, and then stirred at 140° C. for 5 hours. After completion of the reaction, the precipitated solid was washed with distilled water and methanol. Next, it was purified by column chromatography to obtain compound 8-1 (50 g, yield: 80%).

2) Synthesis of Compound 8-2

Compound 8-1 (50 g, 187.5 mmol), (methoxymethyl) triphenylphosphonium chloride (83 g, 243.7 mmol), and 935 mL of THF were added to the reaction vessel and stirred for 10 minutes. Thereafter, potassium t-butoxide (1M in THF, 250 mL) was slowly added dropwise under the condition of 0° C. Next, it was stirred at room temperature for 3 hours by slowly increasing the temperature. The reaction was completed by adding distilled water to the reaction mixture, and then the organic layer was extracted with ethyl acetate and dried with magnesium sulfate, followed by removing the solvent using a rotary evaporator. Next, it was purified by column chromatography to obtain compound 8-2 (52 g, yield: 95%).

3) Synthesis of Compound 8-3

Compound 8-2 (62 g, 210 mmol), Eaton's reagent (21 mL), and chlorobenzene (1,000 mL) were added to the reaction vessel, and refluxed for 2 hours. After completion of the reaction, the mixture was cooled to room temperature, and the organic layer was extracted with MC, followed by drying over magnesium sulfate, and the solvent was removed using a rotary evaporator. Next, it was purified by column chromatography to obtain compound 8-3 (12.5 g, yield: 23%).

4) Synthesis of Compound 8-4

Compound 8-3 (12.5 g, 47.6 mmol), bis(pinacolato)diborane (15.7 g, 61.9 mmol), tris(dibenzylideneacetone)dipalladium ($Pd_2(dba)_3$) (2.2 g, 2.38 mmol), 2-dicyclohexylphosphino-2',6'-dimethoxybiphenyl (s-phos) (1.96 g, 4.76 mmol), KOAc (14 g, 143 mmol) and 240 mL of 1,4-dioxane were added to the reaction vessel, and stirred at 150 t for 3 hours. After completion of the reaction, the mixture was cooled to room temperature, and then the organic layer was extracted with ethyl acetate, and dried with magnesium sulfate, followed by removing the solvent using a rotary evaporator. Next, it was purified by column chromatography to obtain compound 8-4 (11.1 g, yield: 66%).

5) Synthesis of Compound H2-11

Compound 8-4 (4 g, 11.3 mmol), 2-chloro-4-(dibenzo[b,d]furan-1-yl)-6-phenyl-1,3,5-triazine (5.3 g, 14.7 mmol), $Pd(PPh_3)_4$ (0.65 g, 0.6 mmol), calcium carbonate (3.1 g, 22.6 mmol), toluene (33 mL), ethanol (5 mL) and distilled water (11 mL) were added to the reaction vessel, and stirred at 140° C. for 7 hours. After completion of the reaction, the mixture was added dropwise to methanol, and the resulting solid was filtered. The resulting solid was purified by column chromatography to obtain compound H2-11 (4.1 g, yield: 66%).

| | MW | M.P |
|---|---|---|
| H2-11 | 549.6 | 208° C. |

[Example 9] Synthesis of Compound H2-16

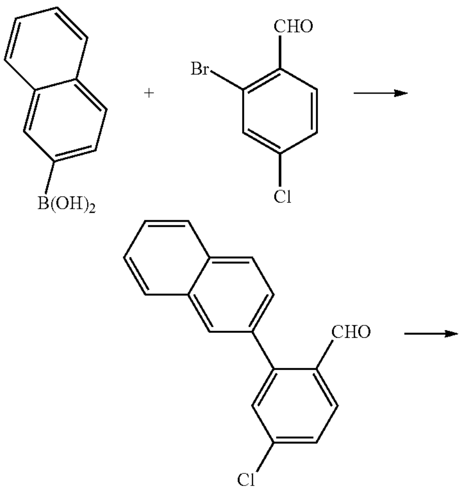

9-1

-continued

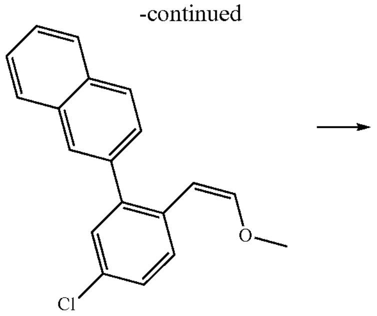

9-2

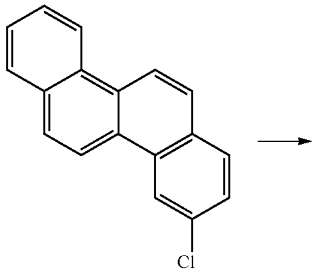

9-3

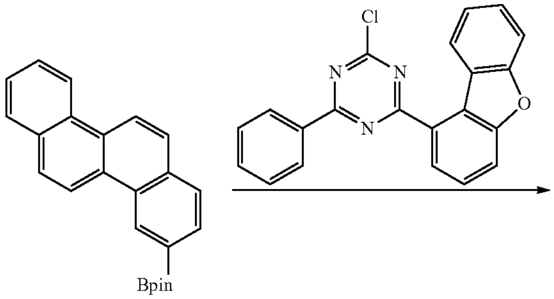

9-4

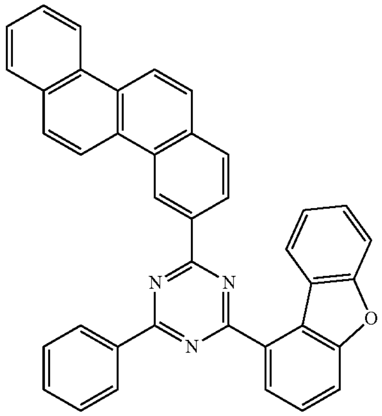

H2-16

1) Synthesis of Compound 9-1

Naphthalen-2-yl boronic acid (50 g, 291 mmol), 2-bromo-4-chlorobenzaldehyde (63 g, 291 mmol), $Pd(PPh_3)_4$ (16.8 g, 14.5 mmol), sodium carbonate (77 g, 727 mmol), 1,080 mL of toluene, 240 mL of ethanol, and 380 mL of distilled water were added to the reaction vessel, and stirred at 140° C. for 5 hours. After completion of the reaction, the precipitated solid was washed with distilled water and methanol. Next, it was purified by column chromatography to obtain compound 9-1 (71 g, yield: 92%).

2) Synthesis of Compound 9-2

Compound 9-1 (71 g, 268 mmol), (methoxymethyl)triphenylphosphonium chloride (110 g, 321 mmol) and 1,300 mL of THF were added to the reaction vessel, and stirred for 10 minutes. Potassium t-butoxide (1M in THF, 300 mL) was slowly added dropwise under the condition of 0° C. to the mixture. Next, it was stirred at room temperature for 3 hours by slowly increasing the temperature. The reaction was completed by adding distilled water to the reaction mixture, and then the organic layer was extracted with ethyl acetate, and dried with magnesium sulfate, followed by removing the solvent using a rotary evaporator. Next, it was purified by column chromatography to obtain compound 9-2 (71 g, yield: 90%).

3) Synthesis of Compound 9-3

Compound 9-2 (70 g, 238 mmol), Eaton's reagent (7 mL) and 1,180 mL of chlorobenzene were added to the reaction vessel, and refluxed for 1 hour. After completion of the reaction, the mixture was cooled to room temperature, and then the organic layer was extracted with MC, and dried with magnesium sulfate, followed by removing the solvent using a rotary evaporator. Next, it was purified by column chromatography to obtain compound 9-3 (60 g, yield: 96%).

4) Synthesis of Compound 9-4

Compound 9-3 (35 g, 133.2 mmol), bis(pinacolato)diborane (44 g, 173 mmol), $Pd_2(dba)_3$ (6.1 g, 6.66 mmol), s-phos (5.5 g, 13.3 mmol), KOAc (39.2 g, 400 mmol), and 666 mL of 1,4-dioxane were added to the reaction vessel, and stirred at 150° C. for 3 hours. After completion of the reaction, the mixture was cooled to room temperature, and then the organic layer was extracted with ethyl acetate, and dried with magnesium sulfate, followed by removing the solvent using a rotary evaporator. Next, it was purified by column chromatography to obtain compound 9-4 (38 g, yield: 81%).

5) Synthesis of Compound H2-16

Compound 9-4 (5 g, 14.1 mmol), 2-chloro-4-(dibenzo[b,d]furan-1-yl)-6-phenyl-1,3,5-triazine (6.6 g, 18.3 mmol), $Pd(PPh_3)$, (0.8 g, 0.7 mmol), calcium carbonate (3.9 g, 28.2 mmol), 42 mL of toluene, 10 mL of ethanol, and 14 mL of distilled water were added to the reaction vessel, and stirred at 140° C. for 8 hours. After completion of the reaction, the reaction mixture was added dropwise to methanol, and the resulting solid was filtered. The resulting solid was purified by column chromatography to obtain compound H2-16 (6.8 g, yield: 88%).

| | MW | M.P |
|---|---|---|
| H2-16 | 549.6 | 267° C. |

[Example 10] Synthesis of Compound H2-46

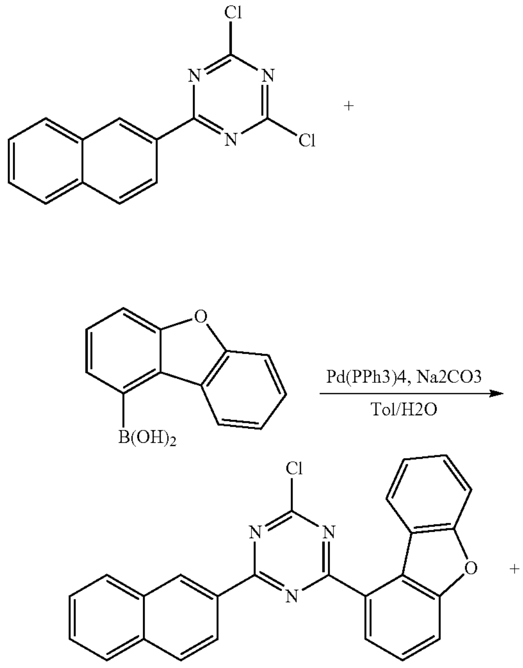

10-1

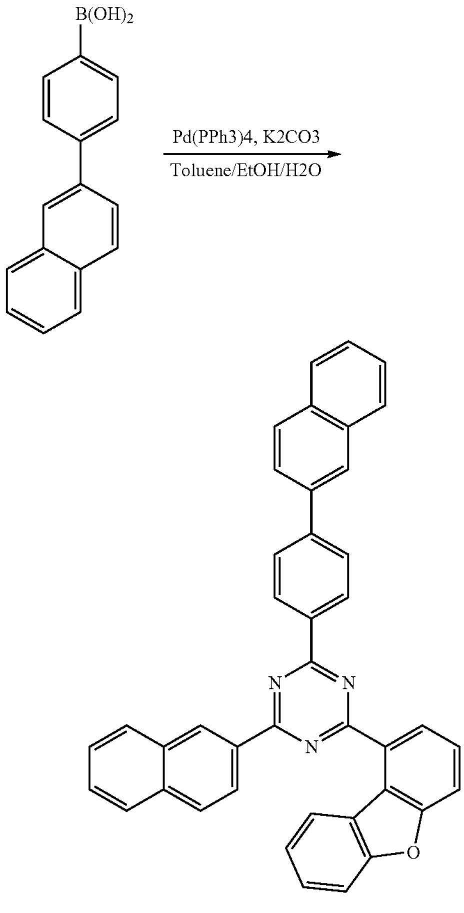

H2-46

1) Synthesis of Compound 10-1

2,4-dichloro-6-(naphthalen-2-yl)-1,3,5-triazine (58 g, 212 mmol), dibenzo[b,d]furan-1-yl boronic acid (30 g, 141 mmol), $Na_2CO_3$ (45 g, 424 mmol), $Pd(PPh_3)_4$ (4.9 g, 7.05 mmol), 1.4 L of toluene, and 352 mL of $H_2O$ were added to a flask and dissolved, followed by refluxing at 100° C. for 18 hours. After completion of the reaction, the organic layer was extracted with ethyl acetate, and the residual water was removed with magnesium sulfate followed by drying. Next, it was separated by column chromatography to obtain compound 10-1 (30 g, yield: 52%).

2) Synthesis of Compound H2-46

Compound 10-1 (6 g 14.7 mmol), 4-(naphthalen-2-yl)-phenylboronic acid (5.8 g, 17.64 mmol), $K_2CO_3$ (5.0 g, 36.75 mmol), $Pd(PPh_3)_4$ (0.85 mg, 0.73 mmol), 70 mL of toluene, 35 mL of EtOH, and 35 mL of $H_2O$ were added to a flask and dissolved, followed by refluxing at 130° C. for 4 hours. After completion of the reaction, the organic layer was extracted with ethyl acetate, and the residual water was removed with magnesium sulfate followed by drying. Next, it was separated by column chromatography to obtain compound H2-46 (4.9 g, yield: 58%).

| | MW | M.P |
|---|---|---|
| H2-46 | 575.20 | 192.9° C. |

[Example 11] Synthesis of Compound H2-66

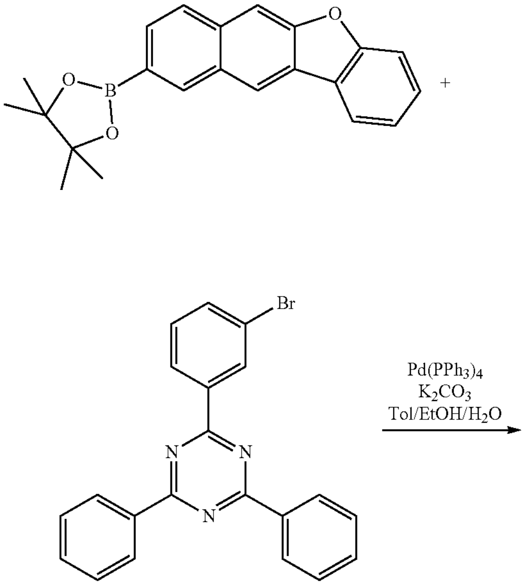

-continued

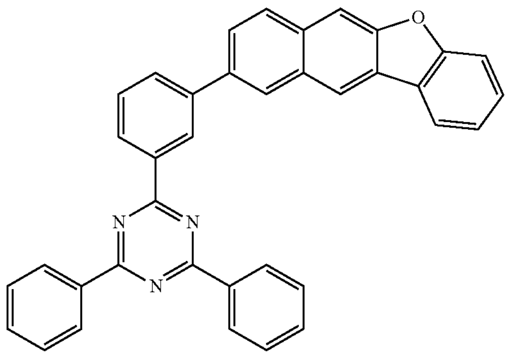

H2-66

4,4,5,5-tetramethyl-2-(naphtho[2,3-b]benzofuran-9-yl)-1,3,2-dioxaborolane (4.5 g, 13.07 mmol), 2-(3-bromophenyl)-4,6-diphenyl-1,3,5-triazine (5.0 g, 13.07 mmol), $Pd(PPh_3)_4$ (750 mg, 0.65 mmol), and $K_2CO_3$ (5.4 g, 39.22 mmol) were dissolved in 80 mL of toluene, 20 mL of EtOH, and 20 mL of $H_2O$, and stirred under reflux for 2 hours. After completion of the reaction, the mixture was cooled to room temperature, and the solid was formed by adding MeOH thereto followed by filtering. Next, it was separated by column chromatography to obtain compound H2-66 (3.7 g, yield: 53%).

| | MW | M.P |
|---|---|---|
| H2-66 | 525.6 | 272.4° C. |

[Example 12] Synthesis of Compound H1-41

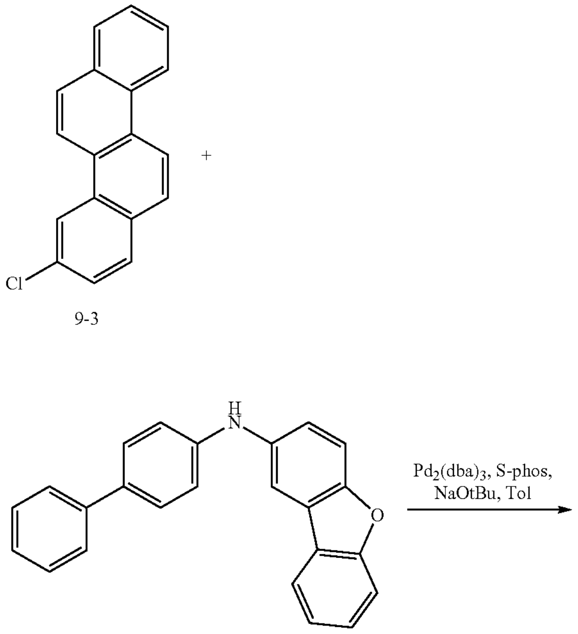

9-3

-continued

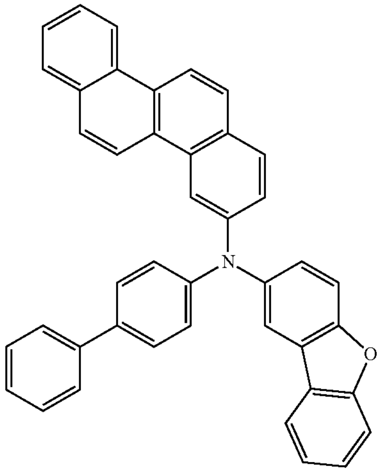

H1-41

Compound 9-3 (5.0 g, 19.0 mmol), N-([1,1'-biphenyl]-4-yl)dibenzo[b,d]furan-2-amine (6.4 g, 19.0 mmol), $Pd_2(dba)_3$ (871 mg, 0.95 mmol), S-phos (781 mg, 1.90 mmol), NaOtBu (3.7 g, 38.1 mmol), and 100 mL of toluene were added to a flask and dissolved, followed by stirring under reflux for 1 hour. After completion of the reaction, the organic layer was extracted with EA/$H_2O$. Then, it was separated by column chromatography to obtain compound H1-41 (7.3 g, yield: 68%).

| | MW | M.P |
|---|---|---|
| H1-41 | 561.67 | 243.0° C. |

[Example 13] Synthesis of Compound H1-31

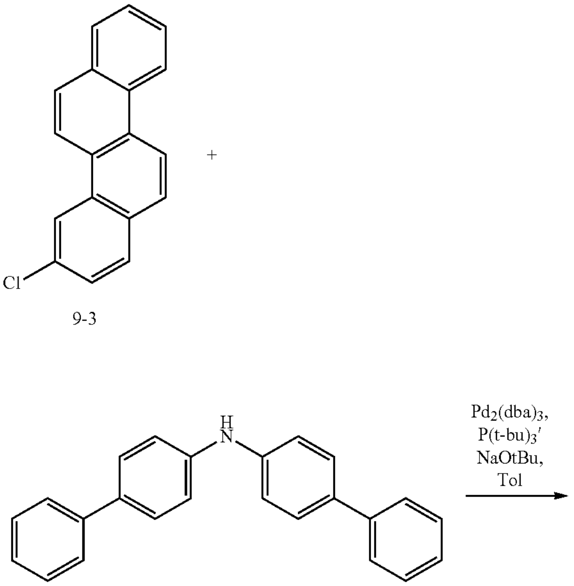

9-3

-continued

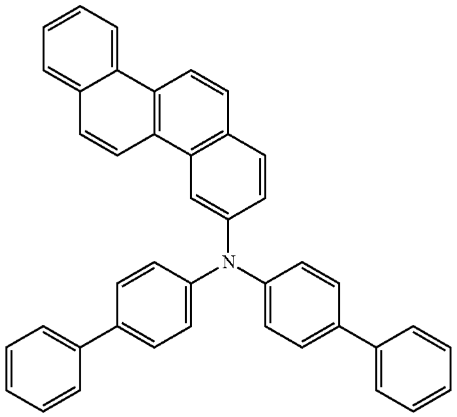

H1-31

Compound 9-3 (5.0 g, 19.0 mmol), di([1,1'-biphenyl]-4-yl)amine (6.1 g, 19.0 mmol), $Pd_2(dba)_3$ (0.9 g, 0.95 mmol), $P(t\text{-}bu)_3$ (1.0 mL, 1.90 mmol), NaOtBu (2.7 g, 28.5 mmol), and 95 mL of toluene were added to a flask and dissolved, followed by stirring under reflux for 2 hours. After completion of the reaction, the organic layer was extracted with $EA/H_2O$. Next, it was separated by column chromatography to obtain compound H1-31 (8.4 g, yield: 81%).

| | MW | M.P |
|---|---|---|
| H1-31 | 547.7 | 247° C. |

[Example 14] Synthesis of Compound H2-67

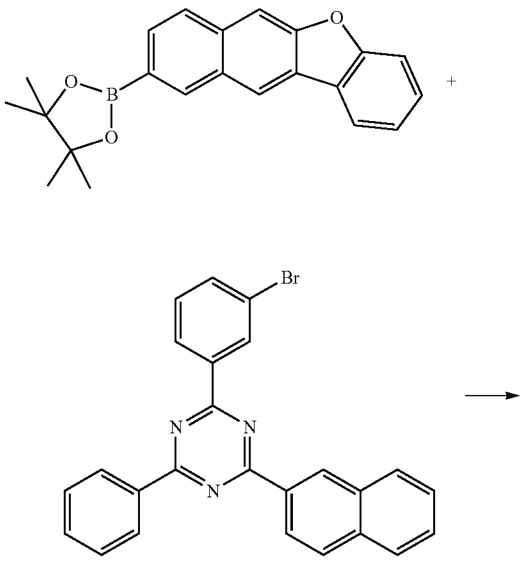

-continued

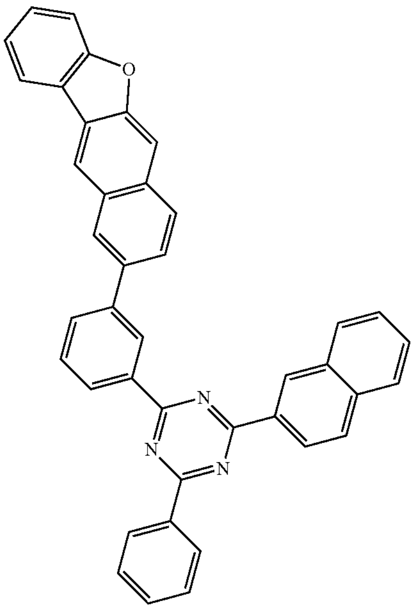

H2-67

4,4,5,5-tetramethyl-2-(naphtho[2,3-b]benzofuran-9-yl)-1,3,2-dioxaborolane (3.1 g, 9.0 mmol), 2-(3-bromophenyl)-4-(naphthalen-2-yl)-6-phenyl-1,3,5-triazine (4.3 g, 9.9 mmol), $Pd(PPh_3)_4$ (0.5 g, 0.45 mmol), calcium carbonate (3.7 g, 27.0 mmol), 60 mL of toluene, 15 mL of ethanol, and 15 mL of distilled water were added to a flask, and stirred at 120° C. for 5 hours.

After completion of the reaction, the mixture was added dropwise to methanol, and the resulting solid was filtered. The resulting solid was purified by column chromatography to obtain compound H2-67 (2.9 g, yield: 55%).

| | MW | M.P |
|---|---|---|
| H2-67 | 575.6 | 242° C. |

[Example 15] Synthesis of Compound H2-126

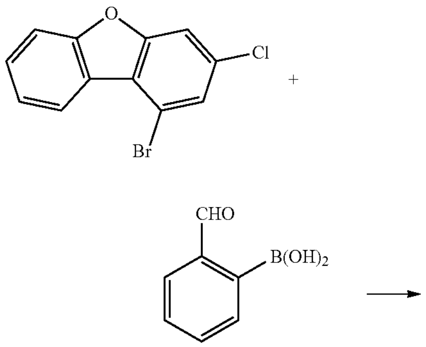

-continued

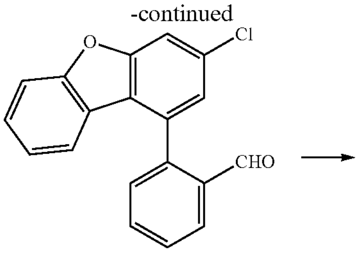

15-1

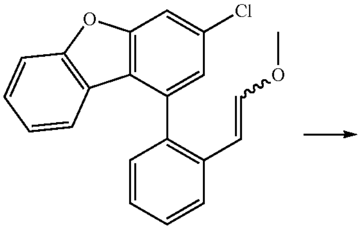

15-2

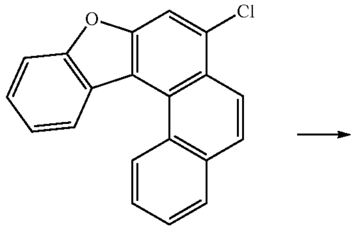

15-3

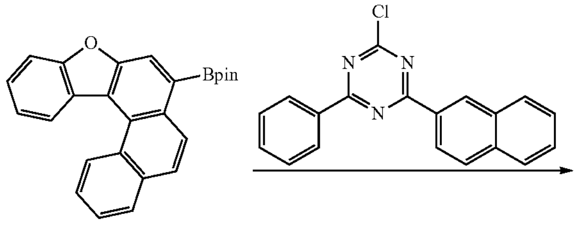

15-4

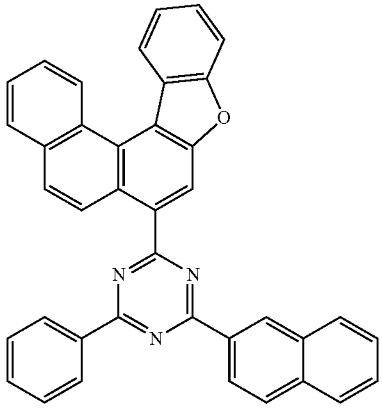

H2-126

1) Synthesis of Compound 15-1

1-bromo-3-chlorodibenzo[b,d]furan (39.2 g, 139.3 mmol), (2-formylphenyl)boronic acid (52.2 g, 348.1 mmol), $Pd(PPh_3)_4$ (16.1 g, 13.9 mmol), $Cs_2CO_3$ (136.1 g, 418 mmol), toluene (840 mL), ethanol (160 mL), and distilled water (210 mL) were added to the reaction vessel, and then stirred at 140° C. for 5 hours. After completion of the reaction, the mixture was cooled to room temperature, and the organic layer was extracted with ethyl acetate. The extracted organic layer was dried over magnesium sulfate, and then the solvent was removed using a rotary evaporator. Next, it was purified by column chromatography to obtain compound 15-1 (32.1 g, yield: 75%).

2) Synthesis of Compound 15-2

Compound 15-1 (31.6 g, 103 mmol), (methoxymethyl) triphenylphosphonium chloride (45.9 g, 133.9 mmol), and THF (515 mL) were added to the reaction vessel, and stirred for 10 minutes, and then potassium ter-butoxide (1M in THF, 150 mL) was slowly added dropwise under the condition of 0° C. thereto. It was stirred at room temperature for 3 hours by slowly increasing the temperature. Distilled water was added to the reaction solution to complete the reaction, and the organic layer was extracted with ethyl acetate. The extracted organic layer was dried over magnesium sulfate, and the solvent was removed using a rotary evaporator. Next, it was purified by column chromatography to obtain compound 15-2 (31.2 g, yield: 90%).

3) Synthesis of Compound 15-3

Compound 15-2 (29.8 g, 89.0 mmol), boron trifluoride etherate (22.4 mL), and MC (890 mL) were added to the reaction vessel and stirred for 3 hours. After completion of the reaction, the organic layer was extracted with MC together with $H_2O$. The extracted organic layer was dried over magnesium sulfate, and then the solvent was removed using a rotary evaporator. Next, it was purified by column chromatography to obtain compound 15-3 (24.2 g, yield: 90%).

4) Synthesis of Compound 15-4

Compound 15-3 (18.0 g, 59.5 mmol), bis(pinacolato) diborane (19.7 g, 77.3 mmol), $Pd_2(dba)_3$ (2.8 g, 2.9 mmol), s-phos (2.4 g, 5.9 mmol), KOAc (17.5 g, 178.5 mmol) and 1,4-dioxane (300 mL) were added to the reaction vessel, and stirred at 150° C. for 6 hours. After completion of the reaction, the mixture was cooled to room temperature, and the organic layer was extracted with ethyl acetate. The extracted organic layer was dried over magnesium sulfate, and then the solvent was removed using a rotary evaporator. Next, it was purified by column chromatography to obtain compound 15-4 (18.4 g, yield: 78%).

5) Synthesis of Compound H2-126

Compound 15-4 (4.0 g, 10.1 mmol), 2-chloro-4-(naphthalen-2-yl)-6-phenyl-1,3,5-triazine (3.9 g, 12.2 mmol), $Pd(PPh_3)_4$ (0.6 g, 0.51 mmol), potassium carbonate (2.8 g, 20.2 mmol), toluene (30 mL), ethanol (7 mL,) and distilled water (10 mL) were added to the reaction vessel and stirred at 130° C. for 6 hours. After completion of the reaction, methanol was added dropwise to the mixture, and the resulting solid was filtered. The resulting solid was purified by column chromatography to obtain compound H2-126 (4.5 g, yield: 81%).

| | MW | M.P |
|---|---|---|
| H2-126 | 549.6 | 228° C. |

[Example 16] Synthesis of Compound H2-128

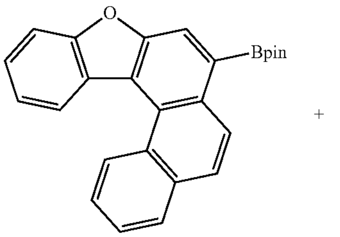

15-4

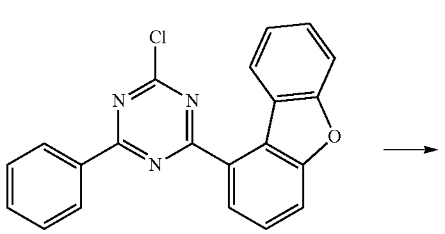

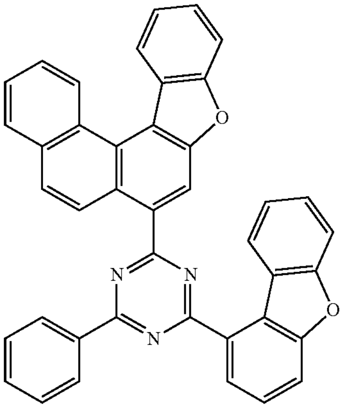

H2-128

Compound 15-4 (4.0 g, 10.1 mmol), 2-chloro-4-(dibenzo[b,d]furan-1-yl)-6-phenyl-1,3,5-triazine (4.4 g, 12.2 mmol), $Pd(PPh_3)_4$ (0.6 g, 0.5 mmol), potassium carbonate (2.8 g, 20.2 mmol), toluene (30 mL), ethanol (7 mL), and distilled water (10 mL) were added to the reaction vessel, and stirred at 130° C. for 6 hours. After completion of the reaction, methanol was added dropwise to the mixture, and the resulting solid was filtered. The resulting solid was purified by column chromatography to obtain compound H2-128 (3.13 g, yield: 53%).

| | MW | M.P |
|---|---|---|
| H2-128 | 589.6 | 250° C. |

[Example 17] Synthesis of Compound H2-131

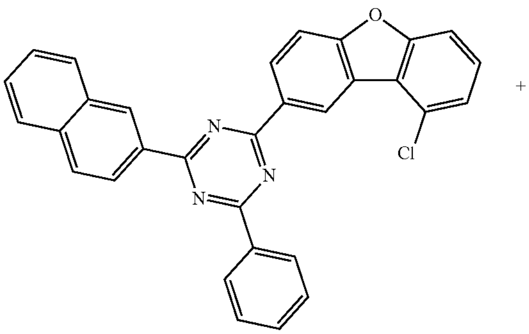

17-1

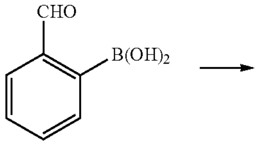

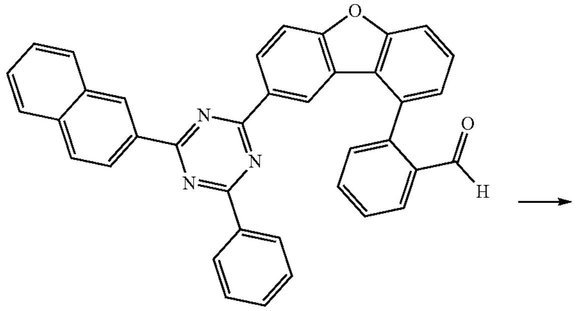

17-2

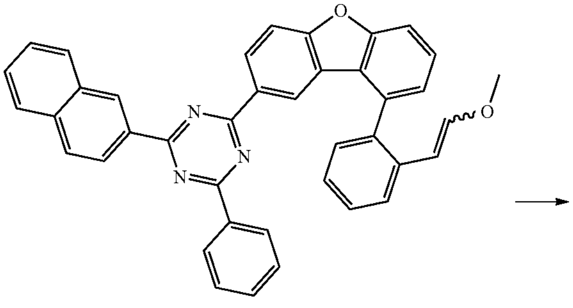

17-3

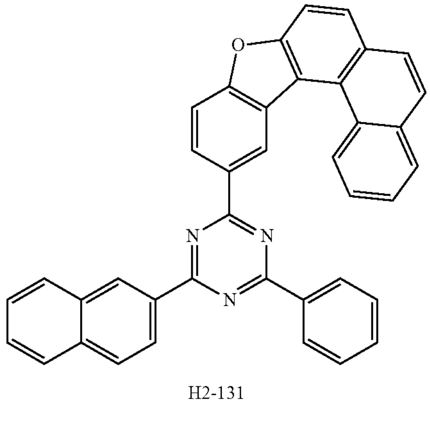

H2-131

1) Synthesis of Compound 17-2

Compound 17-1 (5.0 g, 10.3 mmol), (2-formylphenyl) boronic acid (2.3 g, 15.5 mmol), $Pd_2(dba)_3$ (0.47 g, 0.52 mmol), s-phos (0.43 g, 1.03 mmol), $K_3PO_4$ (5.5 g, 25.8 mmol), and xylene (52 mL) were added to the reaction vessel, and stirred at 165° C. for 6 hours. After completion of the reaction, the mixture was cooled to room temperature, and then the organic layer was extracted with ethyl acetate. The extracted organic layer was dried with magnesium sulfate, and then the solvent was removed using a rotary evaporator. Next, it was purified by column chromatography to obtain compound 17-2 (4.55 g, yield: 80%).

2) Synthesis of Compound 17-3

Compound 17-2 (4.55 g, 8.22 mmol), (methoxymethyl) triphenylphosphonium chloride (3.66 g, 10.7 mmol), and THF (41 mL) were added to the reaction vessel, and stirred for 10 minutes, and then potassium tert-butoxide (1M in THF, 11 mL) was slowly added dropwise under the condition of 0° C. thereto. It was stirred at room temperature for 3 hours by slowly increasing the temperature. The reaction was terminated by adding distilled water to the reaction solution, and the organic layer was extracted with ethyl acetate. The extracted organic layer was dried over magnesium sulfate, and then the solvent was removed using a rotary evaporator. Next, it was purified by column chromatography to obtain compound 17-3 (3.06 g, yield: 64%).

3) Synthesis of Compound H2-131

Compound 17-3 (2.3 g, 3.95 mmol), Eaton's reagent (0.23 mL), and chlorobenzene (23 mL) were added to the reaction vessel and refluxed for 2 hours. After completion of the reaction, the mixture was cooled to room temperature, and the organic layer was extracted with MC. The extracted organic layer was dried over magnesium sulfate, and then the solvent was removed using a rotary evaporator. Next, it was purified by column chromatography to obtain compound H2-131 (1.93 g, yield: 89%).

| | MW | M.P |
|---|---|---|
| H2-131 | 549.62 | 204° C. |

[Example 18] Synthesis of Compound H1-111

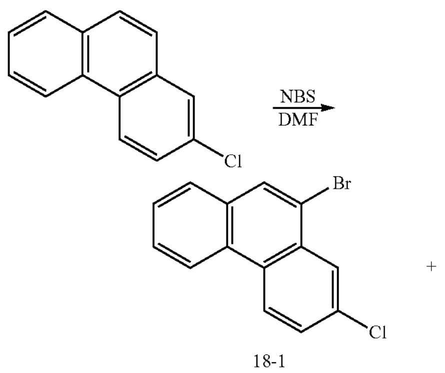

18-1

-continued

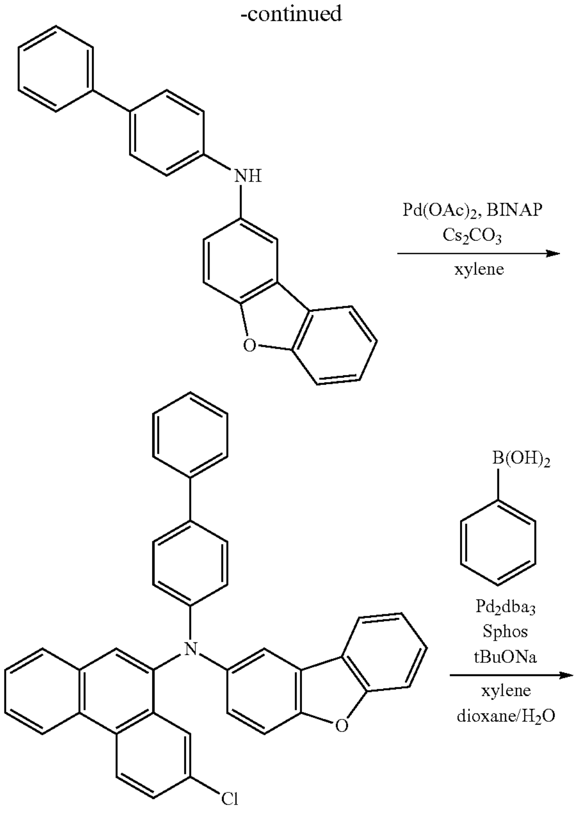

18-2

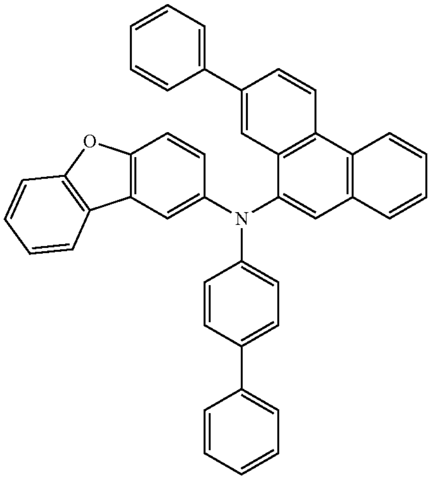

H1-111

1) Synthesis of Compound 18-1

2-chlorophenanthrene (71 g, 333 mmol) and N-bromosuccinimide (NBS) (475 g, 2.67 mol) were dissolved in 1.5 L of DMF and then stirred at 150° C. for 2 hours. After completion of the reaction, the mixture was cooled to room temperature, and filtered through a celite filter to make a solid. Next, it was separated by column chromatography to obtain compound 18-1 (30 g, yield: 30%).

2) Synthesis of Compound 18-2

Compound 18-1 (10 g, 34.29 mmol), N-([1,1'-biphenyl]-4-yl)dibenzo{b,d}furan-2-amine (11.5 g, 34.29 mmol), $Pd(OAC)_2$ (0.23 g, 1.03 mmol), BINAP (2.1 g, 3.43 mmol), $Cs_2C03$ (28 g, 85.7 mmol) were dissolved in 171 mL of o-xylene and then stirred under reflux for 4 hours. After completion of the reaction, the mixture was cooled to room temperature, and filtered through a celite filter to make a solid. Next, it was separated by column chromatography to obtain compound 18-2 (4.6 g, yield: 24.5%).

3) Synthesis of Compound H1-111

Compound 18-2 (4 g, 7.3 mmol), phenylboronic acid (1.4 g, 10.95 mmol). $Pd_2(dba)_3$ (82 mg, 0.09 mmol), S-Phos (74 mg, 30.18 mmol), and NaOtBu (216 mg, 2.25 mmol) were dissolved in 5 mL of o-xylene, 1 mL of 1,4-dioxane, and 1 mL of $H_2O$ 1 mL, and then stirred under reflux for 18 hours. After completion of the reaction, the mixture was cooled to room temperature, and filtered through a celite filter to make a solid. Next, it was separated by column chromatography to obtain compound H1-111 (3.5 g, yield: 72.6%).

| | MW | M.P |
|---|---|---|
| H1-111 | 587.72 | 159.7° C. |

[Example 19] Synthesis of Compound H1-127

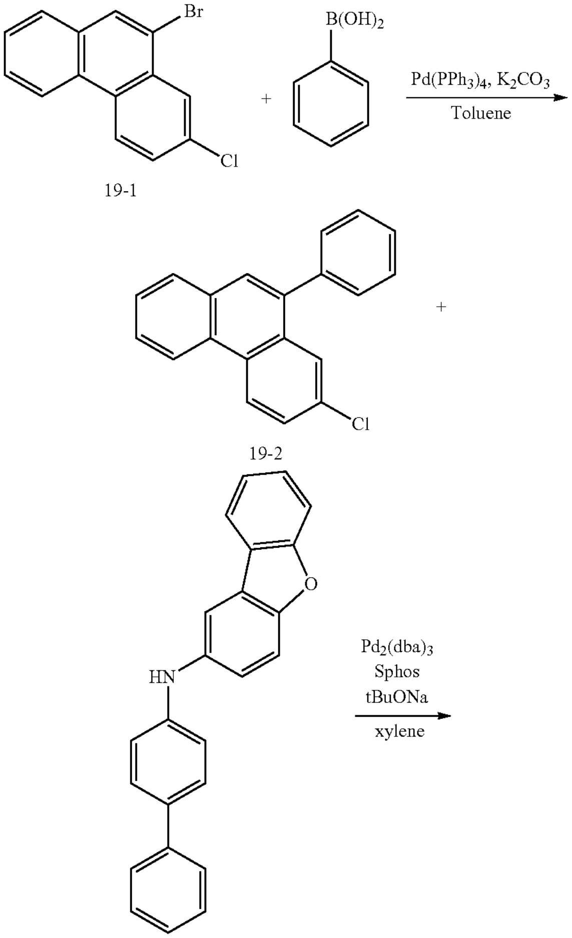

19-1

19-2

-continued

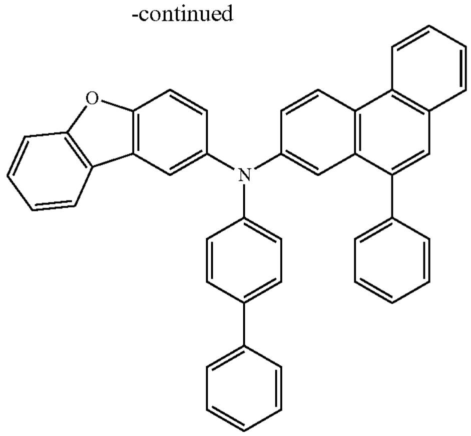

H1-127

1) Synthesis of Compound 19-2

Compound 19-1 (6 g, 23.3 mmol), phenylboronic acid (3 g, 24.5 mmol), $Pd(PPh_3)_4$ (773 mg, 0.669 mmol), and $K_2CO_3$ (7.7 g, 55.75 mmol) were dissolved in 100 mL of toluene, 50 mL of ethanol, and 50 mL of $H_2O$ and then stirred under reflux for 4 hours. After completion of the reaction, the mixture was cooled to room temperature, and filtered through a celite filter to make a solid. Next, it was separated by column chromatography to obtain compound 19-2 (6 g, yield: 86.5%).

2) Synthesis of Compound H1-127

Compound 19-2 (6 g, 20.7 mmol), N-([1,1'-biphenyl]-4-yl)dibenzo{b,d}furan-2-amine (7.7 g, 22.8 mmol), $Pd_2(dba)_3$ (948 mg, 1.035 mmol), S-Phos (849 mg, 2.07 mmol), and NaOtBu (2.98 g, 31.05 mmol) were dissolved in 100 mL of o-xylene and then stirred under reflux for 2 hours. After completion of the reaction, the mixture was cooled to room temperature, and filtered through a celite filter to make a solid. Next, it was separated by column chromatography to obtain compound H1-127 (5.8 g, yield: 47.6%).

| | MW | M.P |
|---|---|---|
| H1-127 | 587.72 | 202.7° C. |

[Example 20] Synthesis of Compound H2-143

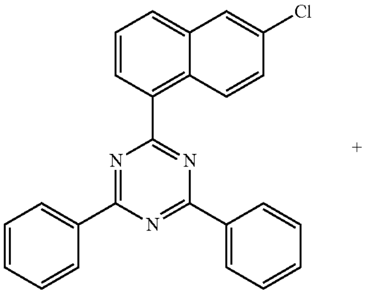

20-1

-continued

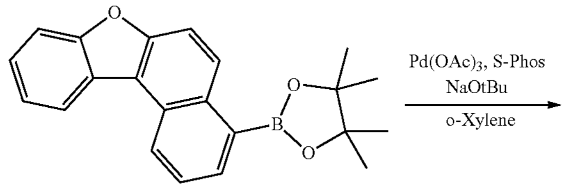

20-2

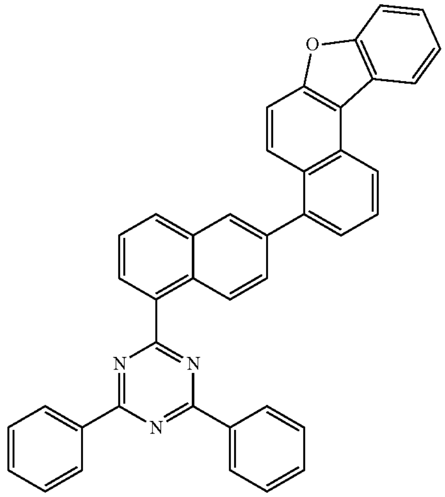

H2-143

Compound 20-1 (4.0 g, 10.16 mmol), compound 20-2 (4.2 g, 12.19 mmol), $Pd(OAC)_2$ (0.07 g, 0.30 mmol), S-Phos (0.25 g, 0.60 mmol), and NaOtBu (1.5 g, 15.24 mmol) were dissolved in 101 mL of o-xylene, and then stirred under reflux for 24 hours. After completion of the reaction, the mixture was cooled to room temperature, and stirred by adding $H_2O$ hereto, followed by filtering. Next, it was filtered through a silica filter to make a solid, and then recrystallized to obtain compound H2-143 (4.8 g, yield: 82.05%).

| | MW | M.P |
|---|---|---|
| H2-143 | 575.67 | 256° C. |

[Example 21] Synthesis of Compound H1-131

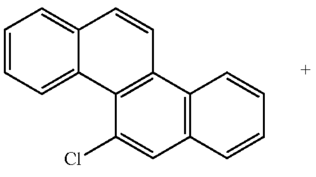

-continued

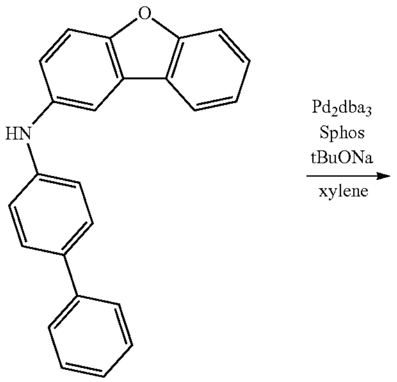

21-1

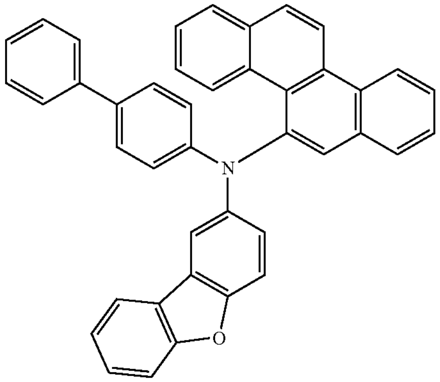

H1-131

5-chlorochrysene (5 g, 19 mmol), compound 21-1 (6.4 g, 19 mmol), $Pd_2(dba)_3$ (0.87 g, 0.95 mmol), S-Phos (0.78 g, 1.9 mmol), tBuONa (4.56 g, 47.5 mmol), and 95 mL of xylene were added to a flask, and dissolved, followed by stirring under reflux for 4 hours. After completion of the reaction, the organic layer was extracted with ethyl acetate. Next, it was separated by column chromatography to obtain compound H1-131 (5.3 g, yield: 49.7%).

| | MW | M.P |
|---|---|---|
| H1-131 | 561.67 | 130.6° C. |

[Example 22] Synthesis of Compound H1-132

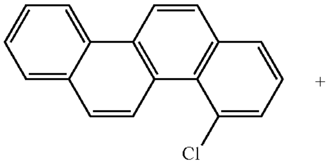

-continued

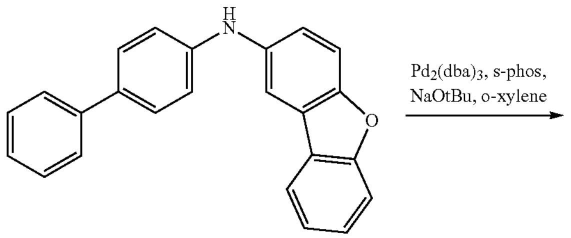

21-1

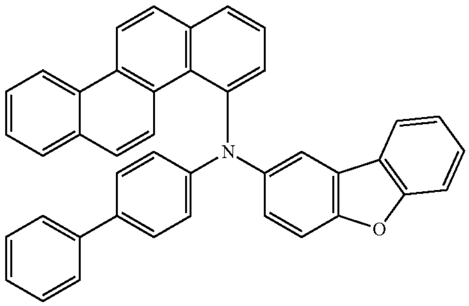

H1-132

Compound 22-1 (3.0 g, 11.4 mmol), compound 21-1 (3.8 g, 11.4 mmol), $Pd_2(dba)_3$ (0.52 g, 0.57 mmol), S-phos (0.47 g, 1.14 mmol), NaOtBu (2.7 g, 28.5 mmol), and 57 mL of o-xylene were added to a flask, and dissolved, followed by stirring under reflux for 6 hours. After completion of the reaction, the organic layer was extracted with EA/$H_2O$. Next, it was separated by column chromatography to obtain compound H1-132 (3.0 g, yield: 47%).

| | MW | M.P |
|---|---|---|
| H1-132 | 561.7 | 150° C. |

[Example 23] Synthesis of Compound H1-124

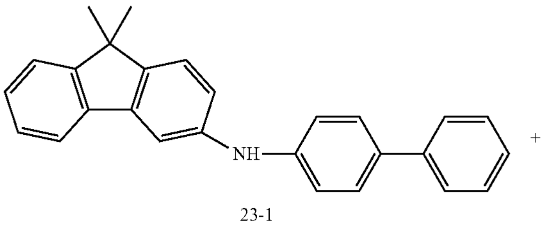

23-1

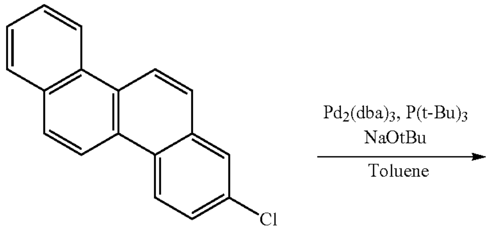

23-2

-continued

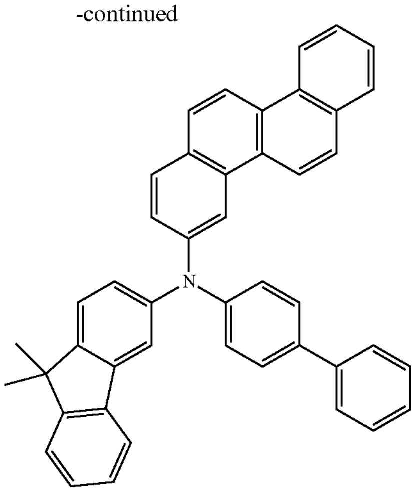

H1-124

Compound 23-1 (10.0 g, 27.66 mmol), compound 23-2 (8.0 g, 30.43 mmol), $Pd_2(dba)_3$ (1.3 g, 1.38 mmol), $P(t\text{-}Bu)_3$ (xylene 50%) (0.56 g/0.9 ml, 2.77 mmol, 0.82 density), and NaOtBu (4.0 g, 41.49 mmol) were added to a flask, and dissolved in 140 mL of toluene, and then stirred under reflux for 1.5 hours. After completion of the reaction, the mixture was cooled to room temperature, and the layers were separated. Then, it was filtered through a celite filter and then a silica filter to make a solid, and then recrystallized to obtain compound H1-124 (9.5 g, yield: 58.6%).

| | MW | M.P |
|---|---|---|
| H1-124 | 587.8 | 288° C. |

[Example 24] Synthesis of Compound H1-117

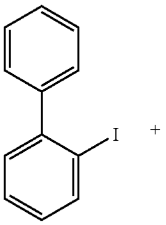

24-1

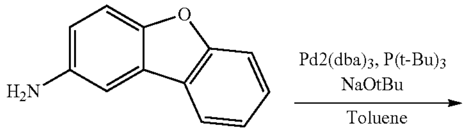

24-2

-continued

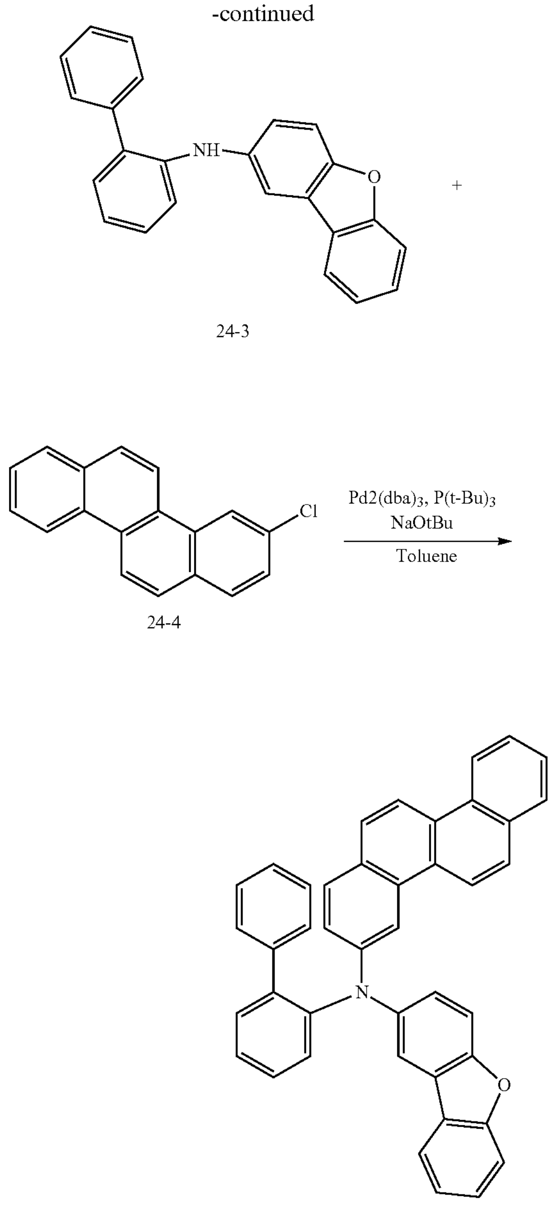

24-3

24-4

H1-117

1) Synthesis of Compound 24-3

Compound 24-1 (10.0 g, 35.70 mmol), compound 24-2 (8.5 g, 46.41 mmol), $Pd_2(dba)_3$ (1.6 g, 1.78 mmol), $P(tBu)_3$ (xylene 50%) (0.7 g/1.7 mL, 3.57 mmol, 0.82 density), and NaOtBu (5.1 g, 53.55 mmol) were dissolved in 180 mL of toluene and then stirred under reflux for 3 hours. After completion of the reaction, the mixture was cooled to room temperature. Then, it filtered through a celite filter and then a silica filter to make a solid, and then recrystallized to obtain compound 24-3 (5.4 g, yield: 45.1%).

2) Synthesis of Compound H1-117

Compound 24-3 (5.4 g, 16.10 mmol), compound 24-4 (4.6 g, 17.71 mmol), $Pd_2(dba)_3$ (0.7 g, 0.81 mmol), $P(tBu)_3$ (xylene 50%) (0.3 g/0.7 mL, 1.61 mmol, 0.82 density), and NaOtBu (2.3 g, 24.15 mmol) were dissolved in 80 mL of toluene, and then stirred under reflux for 2 hours. After completion of the reaction, the mixture was cooled to room temperature, and the layers were separated. Then, it filtered through a celite filter and then a silica filter to make a solid, and then recrystallized to obtain compound H1-117 (7.7 g, yield: 85.5%).

[Example 25] Synthesis of Compound H1-133

| | MW | M.P |
|---|---|---|
| H1-117 | 561.68 | 216° C. |

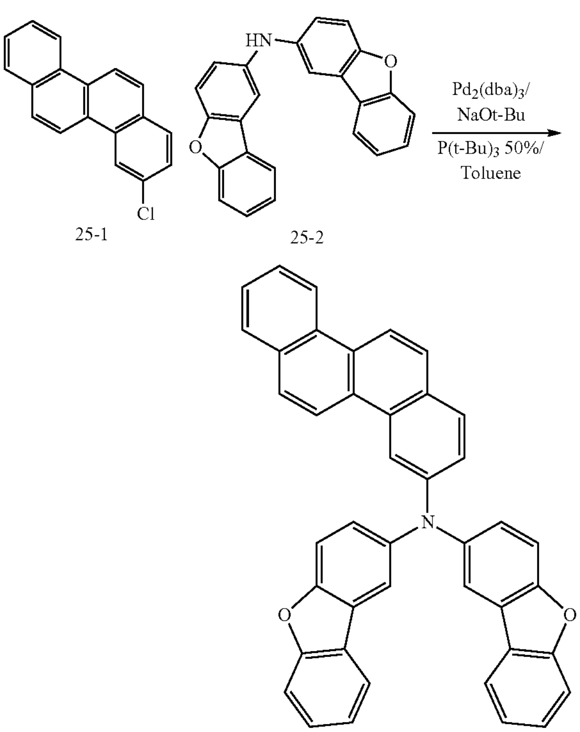

25-1

25-2

H1-133

70 mL of toluene was added to compound 25-1 (4.5 g, 17.17 mmol), compound 25-2 (5 g, 14.31 mmol), $Pd_2(dba)_3$ (0.65 g, 0.715 mmol), NaOt-Bu (2 g, 21.47 mmol), and $P(t-Bu)_3$ (xylene 50%) (0.7 mL, 1.431 mmol), and then stirred under reflux for 3 hours. After completion of the reaction, the mixture was cooled to room temperature, and filtered through a celite filter using MC. The organic layer was distilled under reduced pressure and filtered through a $SiO_2$ filter to obtain compound H1-133 (0.85 g, yield: 10%).

| | MW | M.P |
|---|---|---|
| H1-133 | 575.6 | 184.4° C. |

[Example 26] Compound H1-114

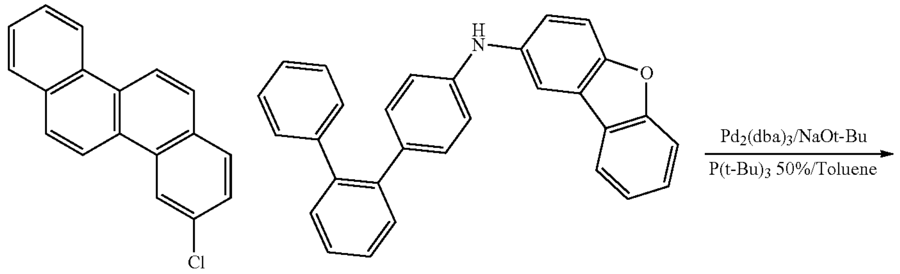

26-1 26-2

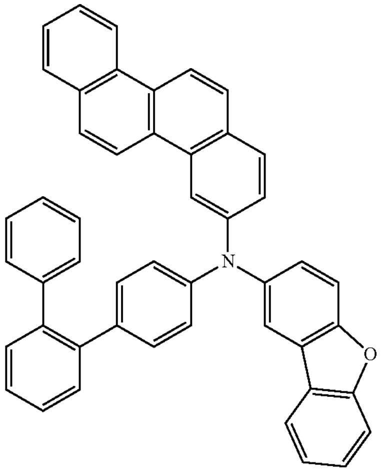

H1-114

60 mL of toluene was added to compound 26-1 (3.8 g, 14.58 mmol), compound 26-2 (5 g, 12.15 mmol), $Pd_2(dba)_3$ (0.55 g, 0.607 mmol), NaOt-Bu (1.8 g, 18.22 mmol), and $P(t-Bu)_3$ (xylene 50%) (0.6 mL, 1.215 mmol), and then stirred under reflux for 3 hours. After completion of the reaction, the mixture was cooled to room temperature, and filtered through a celite filter using MC. The organic layer was distilled under reduced pressure and filtered through a $SiO_2$ filter to obtain compound H1-114 (5.7 g, 73%).

| | MW | M.P |
|---|---|---|
| H1-114 | 637.7 | 248.3° C. |

[Example 27] Synthesis of Compound H1-122

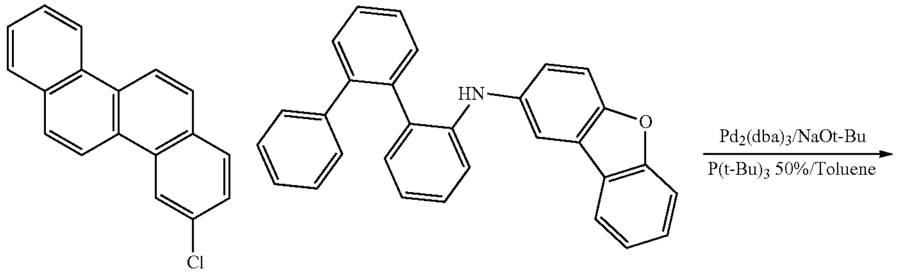

27-1 27-2

-continued

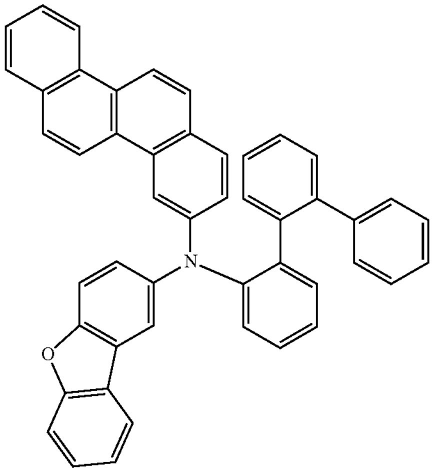

H1-122

60 mL of toluene was added to compound 27-1 (3.8 g, 14.58 mmol), compound 27-2 (5 g, 12.15 mmol), $Pd_2(dba)_3$ (0.55 g, 0.607 mmol), NaOt-Bu (1.8 g 18.22 mmol), and $P(t-Bu)_3$ (xylene 50%) (0.6 mL, 1.215 mmol), and then stirred under reflux for 3 hours. After completion of the reaction, the mixture was cooled to room temperature, and filtered through a celite filter using MC. The organic layer was distilled under reduced pressure and filtered through a $SiO_2$ filter to obtain compound H1-122 (2.5 g, yield: 32%).

| | MW | M.P |
|---|---|---|
| H1-122 | 637.7 | 228.3° C. |

[Example 28] Synthesis of Compound H1-125

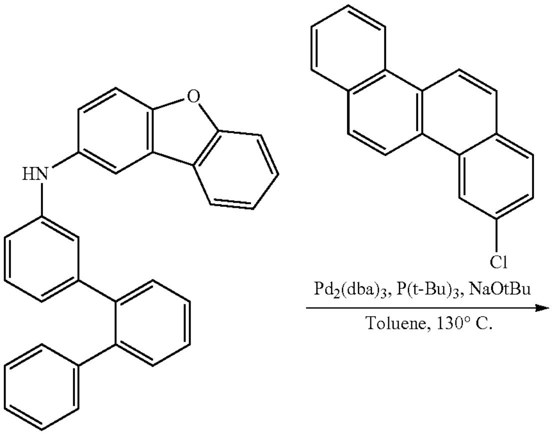

28-1

-continued

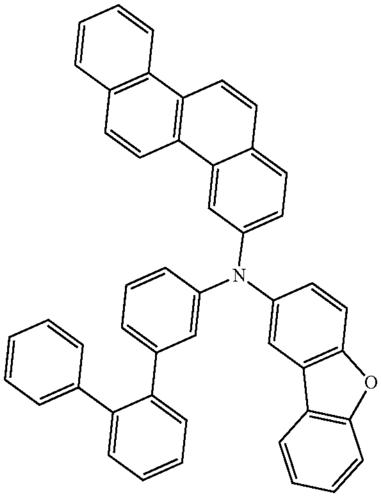

H1-125

Compound 28-1 (6.37 g, 15.50 mmol), 2-chlorochrysene (4.5 g, 17.10 mmol), $Pd_2(dba)_3$ (0.71 g, 0.78 mmol), P(t-Bu)$_3$ (0.75 mL, 1.55 mmol), NaOt-Bu (2.97 g, 31.0 mmol), and 150 mL of toluene were added to the reaction vessel, and stirred under reflux at 130° C. for 1 hour. After completion of the reaction, the mixture was cooled to room temperature, and the solid was filtered and washed with ethyl acetate. The filtrate was distilled under reduced pressure and purified by column chromatography to obtain compound H1-125 (4.3 g, yield: 43%).

| | MW | M.P |
|---|---|---|
| H1-125 | 637.78 | 138.0° C. |

[Example 29] Synthesis of Compound H1-113

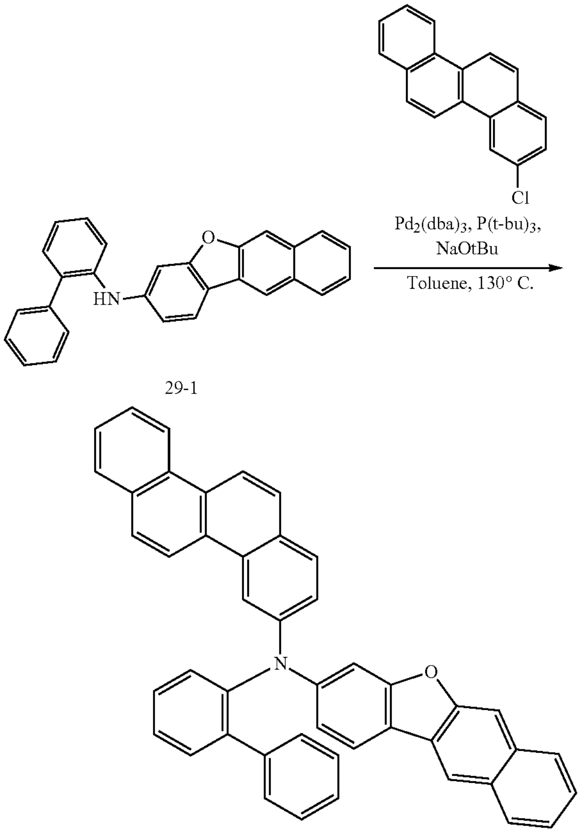

29-1

H1-113

Compound 29-1 (4.0 g, 10.40 mmol), 2-chlorochrysene (2.9 g, 11.40 mmol), $Pd_2(dba)_3$ (0.47 g, 0.52 mmol), $P(t\text{-}Bu)_3$ (0.5 mL, 1.04 mmol), NaOt-Bu (1.99 g, 20.80 mmol), and 55 mL of toluene were added to the reaction vessel, and stirred under reflux at 130° C. for 1 hour. After completion of the reaction, the mixture was cooled to room temperature, and the solid was filtered and washed with ethyl acetate. The filtrate was distilled under reduced pressure and purified by column chromatography to obtain compound H1-113 (4.7 g, yield: 68%).

| | MW | M.P |
|---|---|---|
| H1-113 | 611.70 | 280.0° C. |

Hereinafter, the preparation method of an organic electroluminescent device comprising the plurality of host materials according to the present disclosure, and the property thereof will be explained in order to understand the present disclosure in detail.

[Device Examples 1 to 25] Preparation of OLEDs Comprising the Plurality of Host Materials According to the Present Disclosure OLEDs according to the present disclosure were produced. First, a transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and thereafter was stored in isopropyl alcohol and then used. Thereafter, the ITO substrate was mounted on a substrate holder of a vacuum vapor deposition apparatus. Then, compound HI-1 was introduced into a cell of the vacuum vapor deposition apparatus, and compound HT-1 was introduced into another cell. The two materials were evaporated at different rates and compound HI-1 was deposited in a doping amount of 3 wt % based on the total amount of compounds HI-1 and HT-1 to form a hole injection layer having a thickness of 10 nm. Next, compound HT-1 was deposited as a first hole transport layer having a thickness of 80 nm on the hole injection layer. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows: the respective host compounds described in the following Table 1 were introduced into two cells of the vacuum vapor deposition apparatus as hosts, respectively, and compound D-39 was introduced into another cell as a dopant. The two host materials were evaporated at a rate of 1:1 and the dopant material was evaporated at a different rate, simultaneously, and was deposited in a doping amount of 3 wt % based on the total amount of the hosts and dopant to form a light-emitting layer having a thickness of 40 nm on the second hole transport layer. Next, compounds ETL-1 and EIL-1 as electron transport materials were deposited at a weight ratio of 50:50 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, OLEDs were produced. Each compound used for all the materials were purified by vacuum sublimation under 10-6 torr.

[Comparative Examples 1 to 8] Preparation of OLEDs Comprising a Single Host Compound OLEDs were manufactured in the same manner as in Device Examples 1 to 25, except that the second host compound of the following Table 1 alone was used as the host of the light-emitting layer.

[Comparative Examples 9 to 11] Preparation of OLEDs Comprising a Single Host Compound OLEDs were manufactured in the same manner as in Device Examples 1 to 25, except that the first host compound of the following Table 1 alone was used as the host of the light-emitting layer.

The driving voltage, the luminous efficiency, and the light-emitting color at a luminance of 1,000 nits, and the time taken for luminance to decrease from 100% to 95% at a luminance of 5,000 nits (lifespan; T95) of the organic electroluminescent devices according to Device Examples 1 to 25 and Comparative Examples 1 to 11 produced as described above, are measured, and the results thereof are shown in Table 1 below:

TABLE 1

| | First host compound | Second host compound | Driving Voltage (V) | Luminous Efficiency (cd/A) | Light-Emitting Color | Lifespan (T95, hr) |
|---|---|---|---|---|---|---|
| Device Example 1 | H1-31 | H2-11 | 3.4 | 32.2 | Red | 462 |
| Device Example 2 | H1-31 | H2-26 | 3.4 | 31.8 | Red | 442 |
| Device Example 3 | H1-41 | H2-16 | 3.3 | 32.4 | Red | 322 |
| Device Example 4 | H1-41 | H2-11 | 3.2 | 32.6 | Red | 547 |
| Device Example 5 | H1-41 | H2-27 | 3.2 | 33.4 | Red | 398 |
| Device Example 6 | H1-41 | H2-66 | 3.4 | 32.7 | Red | 468 |
| Device Example 7 | H1-41 | H2-26 | 3.3 | 32.9 | Red | 410 |
| Device Example 8 | H1-89 | H2-125 | 3.6 | 33.1 | Red | 130 |
| Device Example 9 | H1-89 | H2-46 | 3.4 | 34.0 | Red | 186 |
| Device Example 10 | H1-89 | H2-76 | 3.6 | 35.2 | Red | 233 |
| Device Example 11 | H1-89 | H2-86 | 3.4 | 33.1 | Red | 226 |
| Device Example 12 | H1-89 | H2-16 | 3.7 | 34.9 | Red | 303 |
| Device Example 13 | H1-89 | H2-67 | 3.5 | 33.2 | Red | 232 |
| Device Example 14 | H1-31 | H2-128 | 3.3 | 34.6 | Red | 354 |
| Device Example 15 | H1-31 | H2-103 | 3.5 | 32.9 | Red | 311 |
| Device Example 16 | H1-89 | H2-128 | 3.4 | 34.6 | Red | 115 |
| Device Example 17 | H1-89 | H2-103 | 3.7 | 35.0 | Red | 116 |
| Device Example 18 | H1-49 | H2-132 | 3.4 | 34.9 | Red | 262 |
| Device Example 19 | H1-134 | H2-132 | 3.5 | 32.7 | Red | 232 |
| Device Example 20 | H1-119 | H2-132 | 3.5 | 35.9 | Red | 194 |
| Device Example 21 | H1-117 | H2-132 | 3.1 | 37.2 | Red | 262 |
| Device Example 22 | H1-120 | H2-132 | 3.4 | 36.2 | Red | 440 |
| Device Example 23 | H1-118 | H2-132 | 3.4 | 37.3 | Red | 208 |
| Device Example 24 | H1-136 | H2-132 | 3.2 | 37.3 | Red | 210 |
| Device Example 25 | H1-133 | H2-132 | 3.1 | 36.4 | Red | 188 |
| Comparative Example 1 | — | H2-16 | 3.7 | 30.6 | Red | 182 |
| Comparative Example 2 | — | H2-76 | 3.5 | 30.8 | Red | 55 |
| Comparative Example 3 | — | H2-46 | 3.1 | 27.7 | Red | 35 |
| Comparative Example 4 | — | H2-125 | 3.5 | 26.8 | Red | 31.2 |
| Comparative Example 5 | — | H2-26 | 3.6 | 29.4 | Red | 31.7 |
| Comparative Example 6 | — | H2-27 | 3.3 | 26.2 | Red | 20.8 |
| Comparative Example 7 | — | H2-128 | 3.0 | 26.1 | Red | 51.1 |
| Comparative Example 8 | — | H2-103 | 3.6 | 29.3 | Red | 38.0 |
| Comparative Example 9 | H1-31 | | 4.7 | 9.5 | Red | 10.8 |
| Comparative Example 10 | H1-41 | | 4.3 | 8.8 | Red | 7.7 |
| Comparative Example 11 | H1-89 | | 7.8 | 4.6 | Red | 10.8 |

From Table 1 above, it can be seen that the organic electroluminescent device including a specific combination of compounds according to the present disclosure as host materials exhibits high luminous efficiency and, in particular, significantly improves the lifespan property, compared to the organic electroluminescent device including a single host material (Comparative Examples 1 to 11).

The compounds used in Device Examples 1 to 25 and Comparative Examples 1 to 11 above are specifically shown in the following Table 2:

TABLE 2

| | | |
|---|---|---|
| Hole Injection Layer/ Hole Transport Layer | 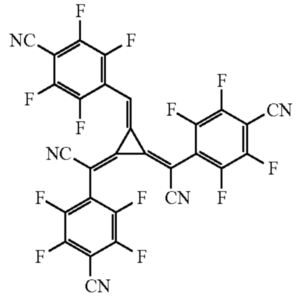 HI-1 | 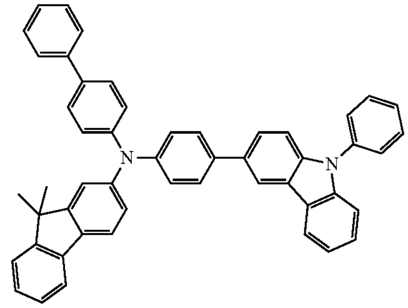 HT-1 |
| | 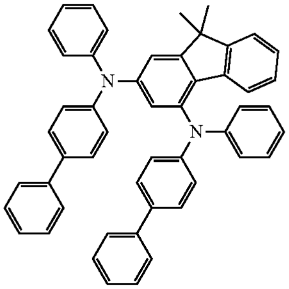 HT-2 | |
| Light-Emitting Layer | | |
| | 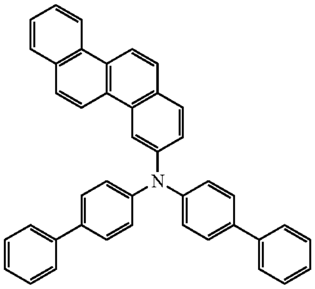 H1-31 | 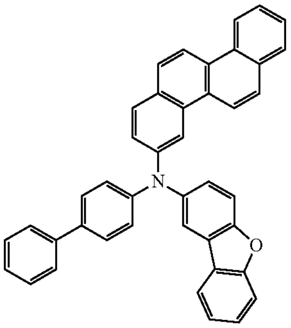 H1-41 |
| | 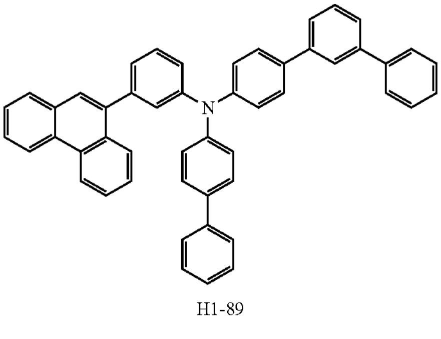 H1-89 | 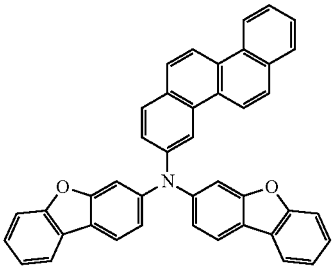 H1-134 |

TABLE 2-continued
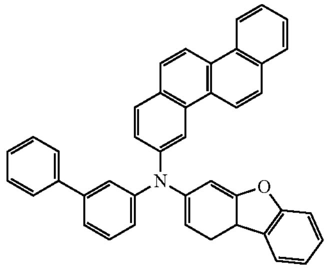
H1-119
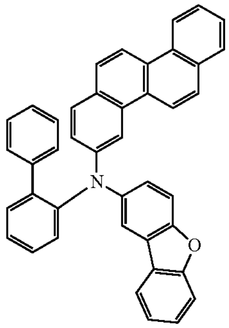
H1-117
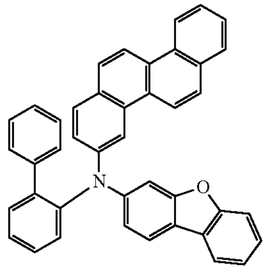
H1-120
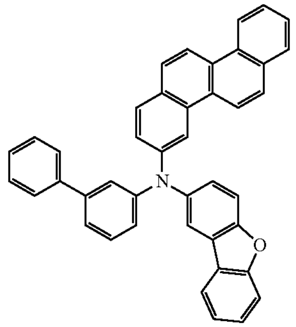
H1-118
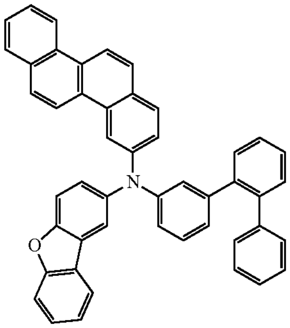
H1-136
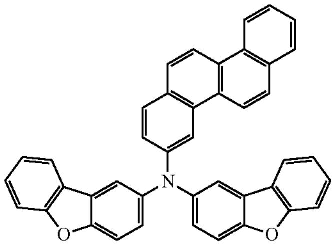
H1-133
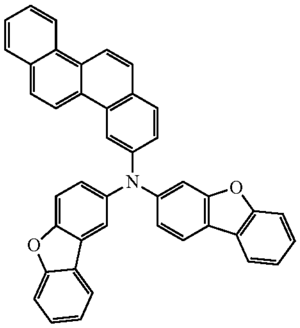
H1-49
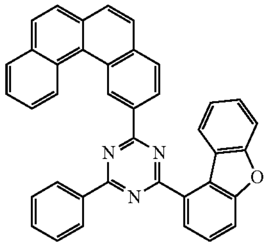
H2-11

TABLE 2-continued
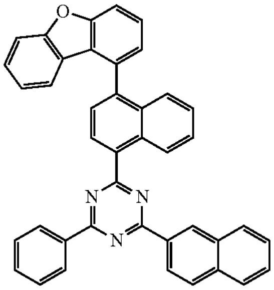
H2-26
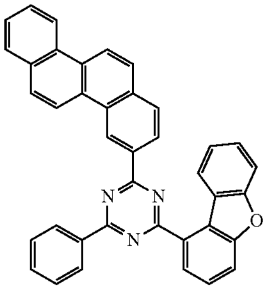
H2-16
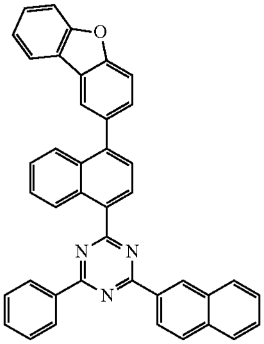
H2-27
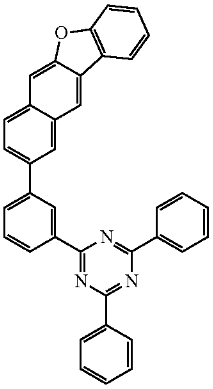
H2-66
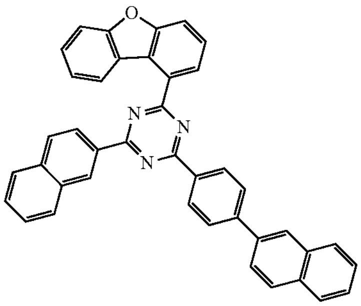
H2-46
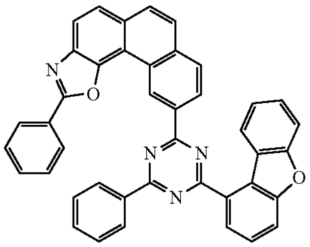
H2-76
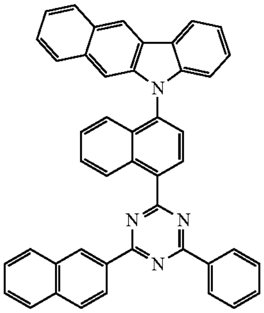
H2-86
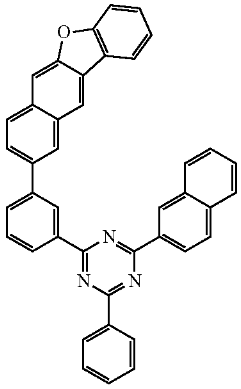
H2-67

TABLE 2-continued

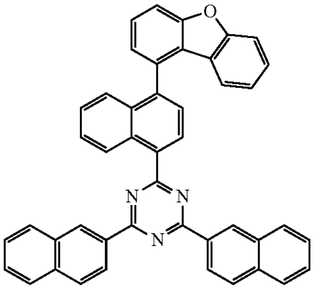

H2-125

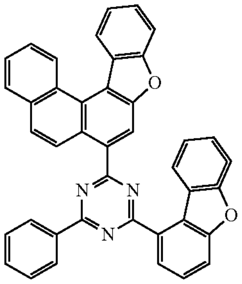

H2-128

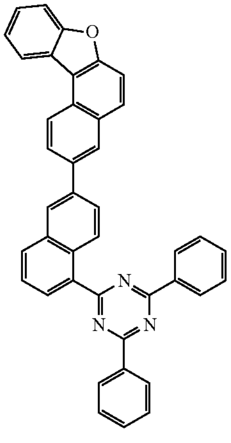

H2-103

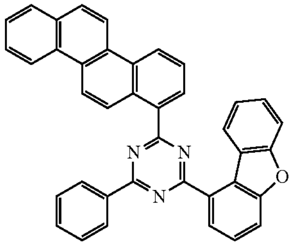

H2-132

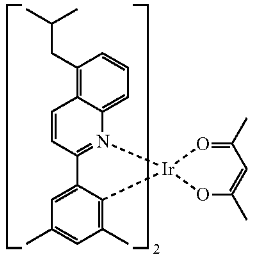

D-39

Electron Transport Layer/ Electron Injection Layer

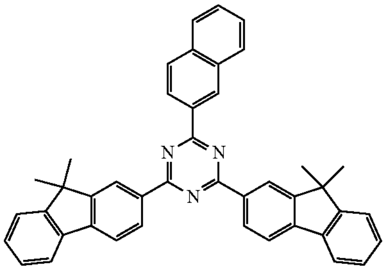

ETL-1

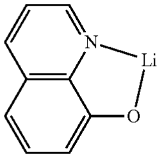

EIL-1

[Device Examples 26 and 27] Preparation of OLEDs According to the Present Disclosure which Emit Red Light OLEDs according to the present disclosure were produced. First, a transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and thereafter was stored in isopropanol and then used. Thereafter, the ITO substrate was mounted on a substrate holder of a vacuum vapor deposition apparatus. Then, compound HI-2 was introduced into a cell of the vacuum vapor deposition apparatus. After evacuating until the degree of vacuum in the chamber reached 10-7 torr, the compound was evaporated by applying an electric current to the cell, thereby forming a hole injection layer having a thickness of 60 nm on the ITO substrate. Then, the compound described in the following Table 3 was introduced into another cell of the vacuum vapor deposition apparatus, and evaporated by applying an electric current to the cell, thereby forming a hole transport layer having a thickness of 20 nm on the hole injection layer. After forming the hole injection layer and the hole transport layer, a light-emitting layer was formed thereon as follows: Compound RH was introduced into one cell of the vacuum vapor deposition apparatus as a host, and compound D-39 was introduced into another cell as a dopant. The two materials were evaporated at different rates and the dopant was deposited in a doping amount of 3 wt % based on the total amount of the host and dopant to form a light-emitting layer having a thickness of 40 nm on the hole transport layer. Next, compounds ETL-1 and EIL-1 as electron transport materials were deposited at a weight ratio of 50:50 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, OLEDs were produced. Each compound used for all the materials was purified by vacuum sublimation under $10^{-6}$ torr.

[Comparative Example 12] Preparation of an OLED not According to the Present Disclosure which Emits Red Light An OLED was manufactured in the same manner as in Device Example 26, except that the compound shown in the following Table 3 was used as the material for the hole transport layer.

The time taken for luminance to decrease from 100% to 50% at a luminance of 5,000 nits (lifespan; T50) of the organic electroluminescent devices according to Device Examples 26 and 27 and Comparative Example 12 produced as described above, was measured, and the results thereof are shown in Table 3 below:

TABLE 3

| | Material for hole transport layer | Lifespan (T50, hr) |
|---|---|---|
| Comparative Example 12 | Ref. 1 | 77 |
| Device Example 26 | H1-31 | 183 |
| Device Example 27 | H1-41 | 372 |

From Table 3 above, it can be confirmed that it can be confirmed that the organic electroluminescent device which uses the organic electroluminescent compound according to the present disclosure as a material for a hole transport layer, exhibits a superior lifespan property, compared to the organic electroluminescent device according to Comparative Example 12 which uses the conventional hole transport material.

The compounds used in Device Examples 26 and 27 and Comparative Example 12 above are specifically shown in the following Table 4:

TABLE 4

Hole Injection Layer/ Hole Transport Layer

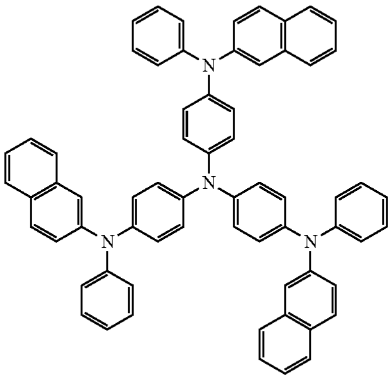 [SMILES: c1ccc(N(c2ccc(N(c3ccc(N(c4ccccc4)c4ccc5ccccc5c4)cc3)c3ccc(N(c4ccccc4)c4ccc5ccccc5c4)cc3)cc2)c2ccc3ccccc3c2)cc1]

HI-2

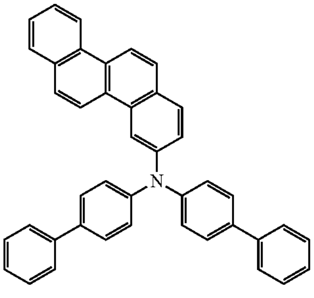

H1-31

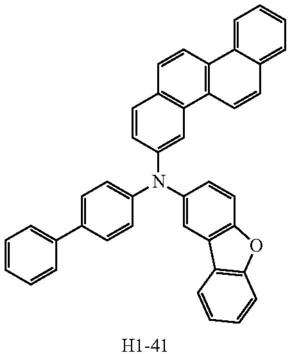 [SMILES: c1ccc(-c2ccc(N(c3ccc4ccc5c6ccccc6ccc5c4c3)c3ccc4oc5ccccc5c4c3)cc2)cc1]

H1-41

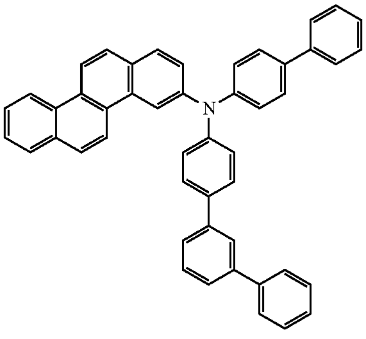

Ref.1

TABLE 4-continued

| | | |
|---|---|---|
| Light-Emitting Layer | 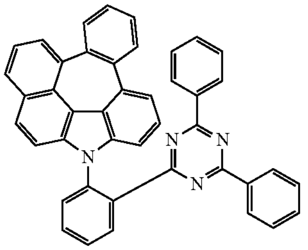 RH | 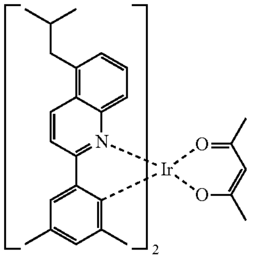 D-39 |
| Electron Transport Layer/ Electron Injection Layer | 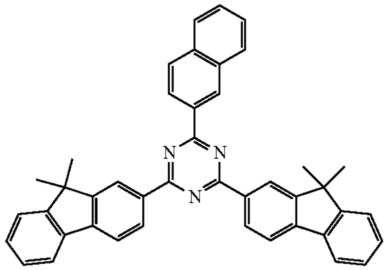 ETL-1 | 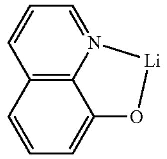 EIL-1 |

The invention claimed is:

1. A plurality of host materials comprising a first host material and a second host material, wherein the first host material comprises a compound represented by the following formula 1-2 and the second host material comprises a compound represented by the following formula 2:

(1-2)

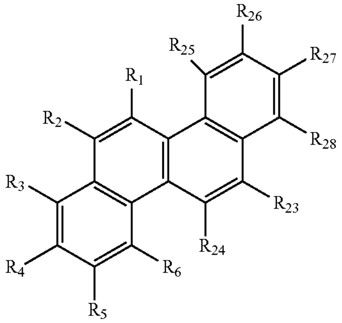

$R_1$ to $R_6$ each independently represent, hydrogen, deuterium, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl (C6-C30)arylsilyl, a substituted or unsubstituted (C1-C30)alkyldi(C6-C30)arylsilyl, a substituted or unsubstituted tri(C6-C30)arylsilyl, or $*-L_1-NAr_1Ar_2$; provided that at least one of $R_1$ to $R_6$ is $*-L_1-NAr_1Ar_2$;

$L_1$ represents a single bond, a substituted or unsubstituted (C6-C30)arylene, or a substituted or unsubstituted (3- to 30-membered) heteroarylene;

$Ar_1$ and $Ar_2$ each independently represent, a substituted or unsubstituted (C6-C30)aryl, or a substituted or unsubstituted (3- to 30-membered)heteroaryl;

$R_{23}$ and $R_{24}$ each independently represent, hydrogen, deuterium, a substituted or unsubstituted (C6-C30)aryl, or a substituted or unsubstituted (3- to 30-membered) heteroaryl; and $R_{25}$ to $R_{28}$ each independently hydrogen, deuterium, halogen, cyano, a substituted or unsubstituted (C1-C30) alkyl, a substituted or unsubstituted (C3-C30)cycloalkyl, a substituted or unsubstituted (3-to 7-membered) heterocycloalkyl, a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di-(C6-C30)arylamino, a substituted or unsubstituted (C1-C30)alkyl(C6-C30) arylamino, a substituted or unsubstituted mono- or di-(3-to 30-membered)heteroarylamino, a substituted or unsubstituted (C1-C30)alkyl(3-to 30-membered)heteroarylamino, a substituted or unsubstituted (C2-C30) alkenyl(C6-C30)arylamino, a substituted or unsubstituted (C2-C30)alkenyl(3-to 30-membered) heteroarylamino, or a substituted or unsubstituted (C6-C30)aryl (3-to 30-membered)heteroarylamino;

$$(Ar_{11}-L_{11})_a-HAr \quad (2)$$

wherein,

HAr represents a substituted or unsubstituted nitrogen-containing (3-to 20-membered)heteroaryl;

$L_{11}$ represents a single bond, a substituted or unsubstituted (C6-C30)arylene, or a substituted or unsubstituted (3- to 30-membered)heteroarylene;

$Ar_{11}$ represents a substituted or unsubstituted (C1-C30) alkyl, a substituted or unsubstituted (C3-C30)cycloalkyl, a substituted or unsubstituted (3-to 7-membered) heterocycloalkyl, a substituted or unsubstituted fused ring of (C3-C30) aliphatic ring and (C6-C30) aromatic ring, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted di(C1-C30)alkyl (C6-C30)arylsilyl, a substituted or unsubstituted (C1-C30)alkyldi(C6-C30)arylsilyl, a substituted or unsubstituted tri(C6-C30)arylsilyl, or $*-L_1-NAr_1Ar_2$;

$L_{21}$ represents a single bond, a substituted or unsubstituted (C6-C30)arylene, or a substituted or unsubstituted (3- to 30-membered)heteroarylene, $Ar_{21}$ and $Ar_{22}$ each independently represent, a substituted or unsubstituted (C1-C30)alkyl, a substituted or unsubstituted (C2-C30)alkenyl, a substituted or unsubstituted (C6-C30)aryl, or a substituted or unsubstituted (3- to 30-membered)heteroaryl; and a represents an integer of 1 to 3, and when a represents an integer of 2 or more, each of $-(L_{11}-Ar_{11})$ may be the same or different.

2. The plurality of host materials according to claim 1, wherein $L_1$, $L_{11}$, and $L_{21}$ each independently represent, a single bond, a substituted or unsubstituted phenylene, a substituted or unsubstituted p-biphenylene, a substituted or unsubstituted m-biphenylene, a substituted or unsubstituted o-biphenylene, a substituted or unsubstituted terphenylene, a substituted or unsubstituted naphthalenylene, a substituted or unsubstituted phenylnaphthalenylene, a substituted or unsubstituted naphthylphenylene, a substituted or unsubstituted binaphthalenylene, a substituted or unsubstituted pyrimidylphenylene, a substituted or unsubstituted phenanthrenylene, a substituted or unsubstituted triphenylenylene, a substituted or unsubstituted chrysenylene, a substituted or unsubstituted fluorenylene, a substituted or unsubstituted pyridylene, a substituted or unsubstituted pyrimidylene, a substituted or unsubstituted dibenzofuranylene, a substituted or unsubstituted phenanthrooxazolylene, a substituted or unsubstituted phenanthrothiazolylene, a substituted or unsubstituted triazinylene, a substituted or unsubstituted quinoxalinylene, a substituted or unsubstituted quinazolinylene, or a substituted or unsubstituted benzoquinoxalinylene.

3. The plurality of host materials according to claim 1, wherein $Ar_1$, $Ar_2$, $Ar_{21}$, and $Ar_{22}$ each independently represent, a substituted or unsubstituted phenyl, a substituted or unsubstituted naphthyl, a substituted or unsubstituted p-biphenyl, a substituted or unsubstituted m-biphenyl, a substituted or unsubstituted o-biphenyl, a substituted or unsubstituted p-terphenyl, a substituted or unsubstituted m-terphenyl, a substituted or unsubstituted o-terphenyl, a substituted or unsubstituted fluorenyl, a substituted or unsubstituted spirobifluorenyl, a substituted or unsubstituted phenanthrenyl, a substituted or unsubstituted chrysenyl, a substituted or unsubstituted dibenzofuranyl, a substituted or unsubstituted dibenzothiophenyl, a substituted or unsubstituted carbazolyl, a substituted or unsubstituted benzofluorenyl, or a substituted or unsubstituted dihydrophenanthrenyl.

4. The plurality of host materials according to claim 1, wherein the compound represented by the formula 1-2 is selected from the following compounds:

H1-31

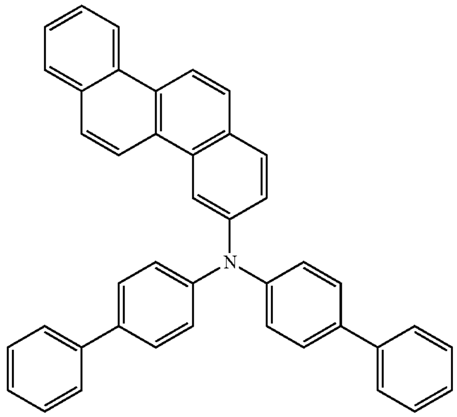

H1-32

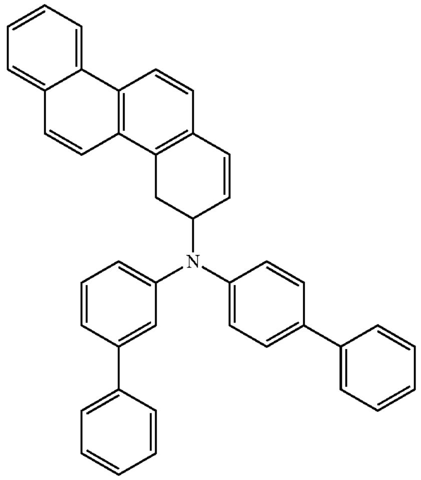

H1-33

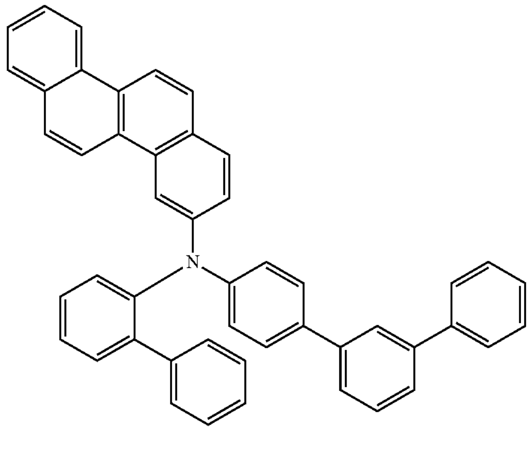

-continued
H1-34
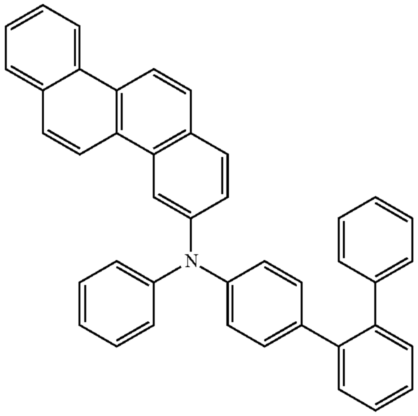
H1-35
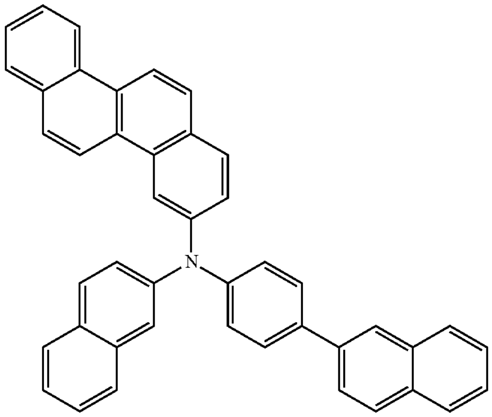
H1-36
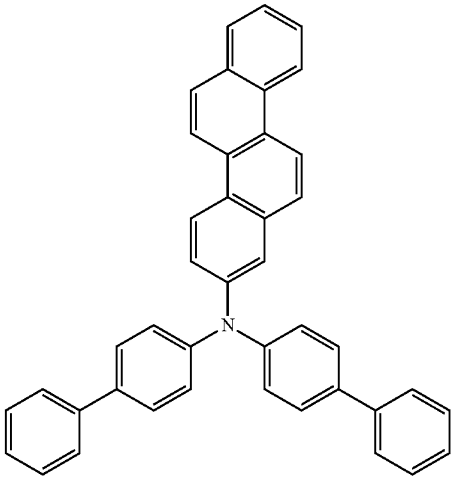
-continued
H1-37
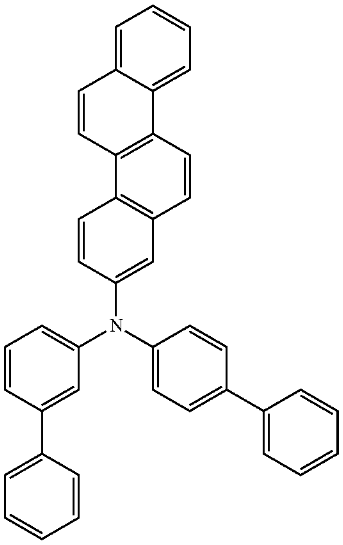
H1-38
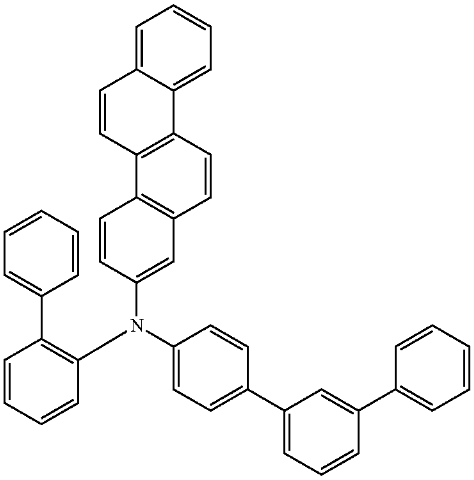
H1-39
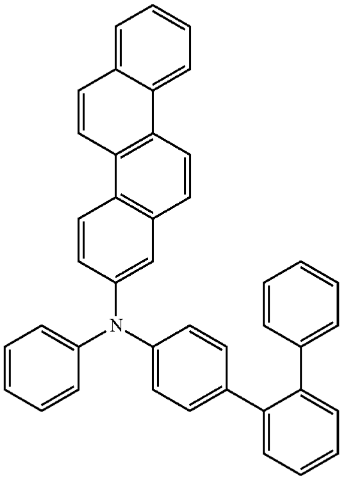

H1-40
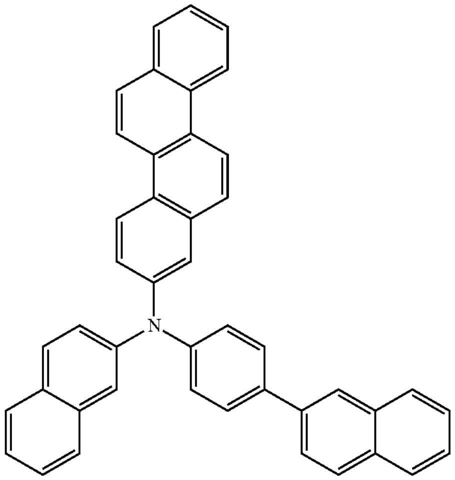
H1-41
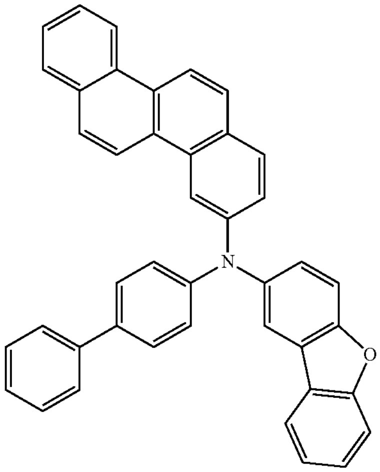
H1-42
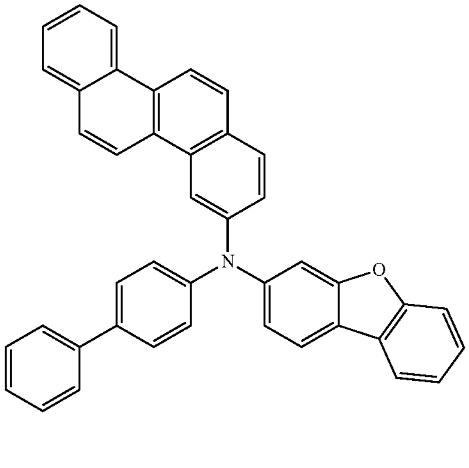
H1-43
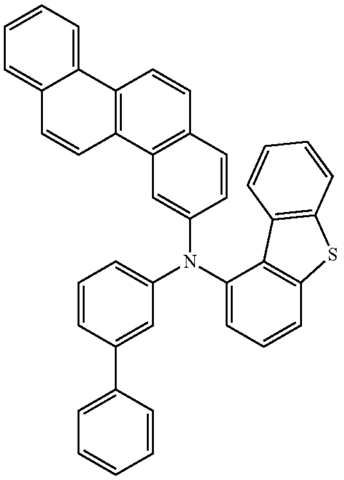
H1-44
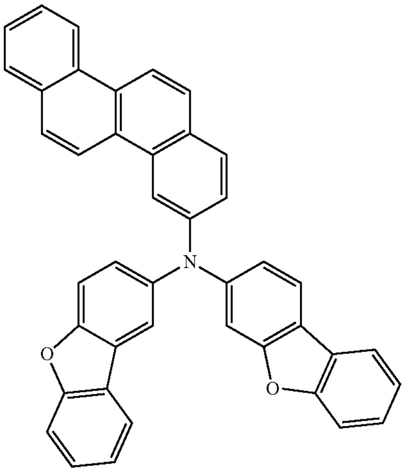
H1-45
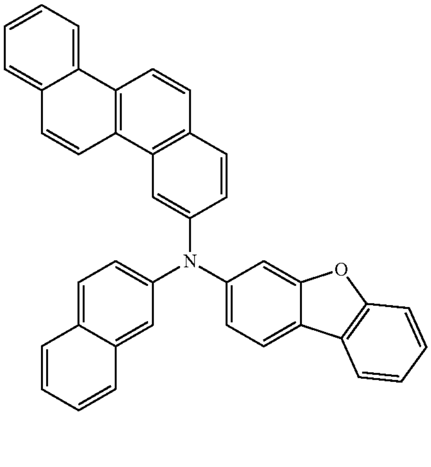

-continued
H1-46
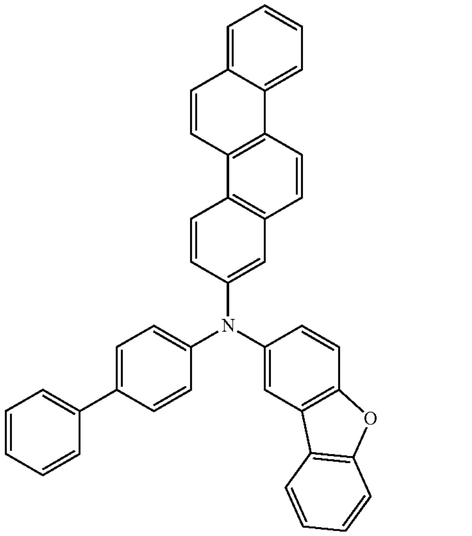
H1-47
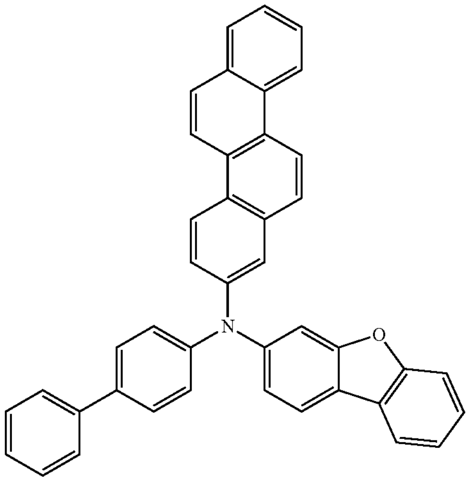
H1-48
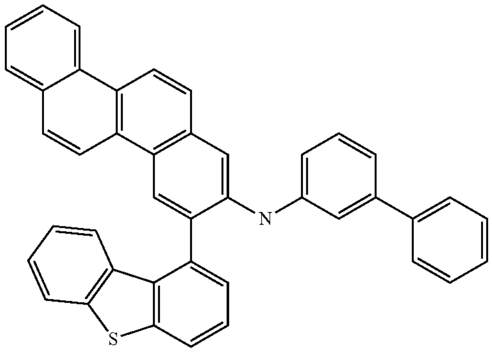
-continued
H1-49
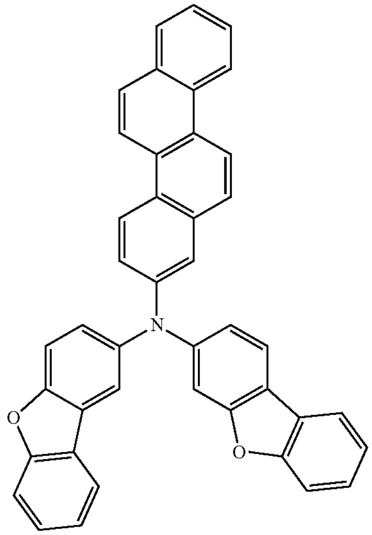
H1-50
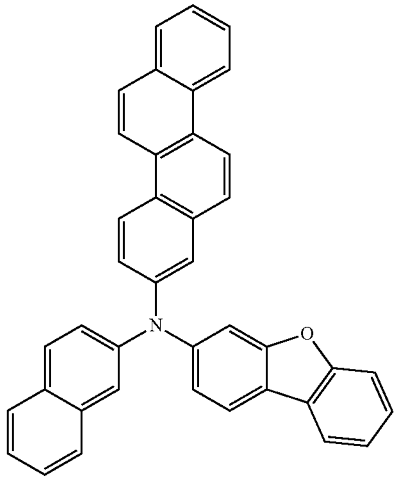
H1-51
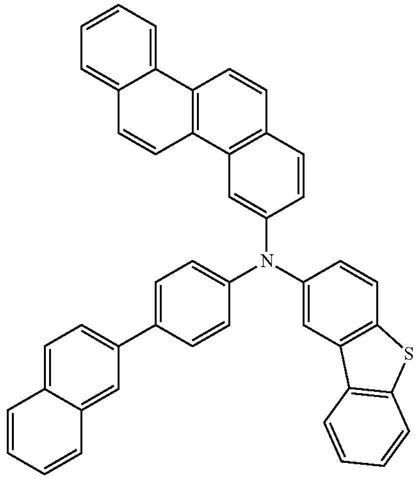

-continued
H1-52
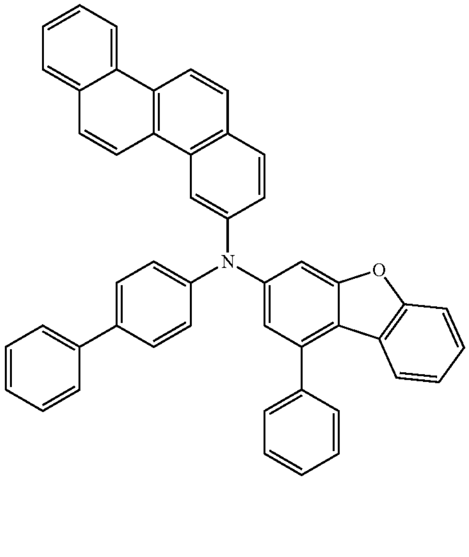
H1-53
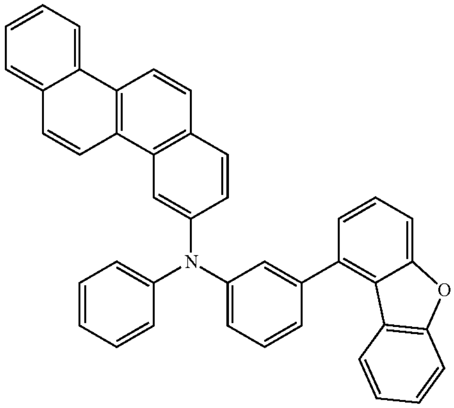
H1-54
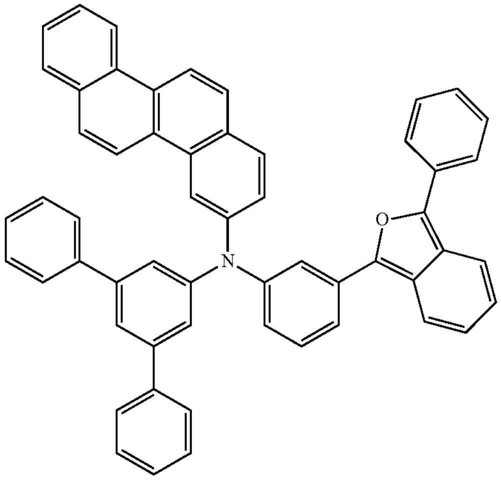
-continued
H1-55
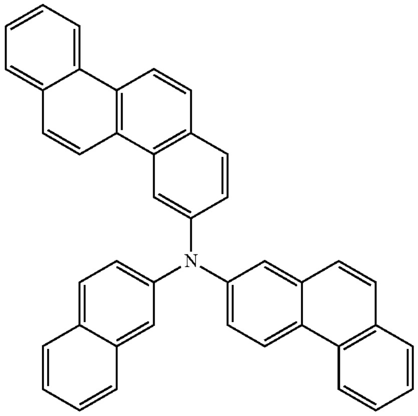
H1-56
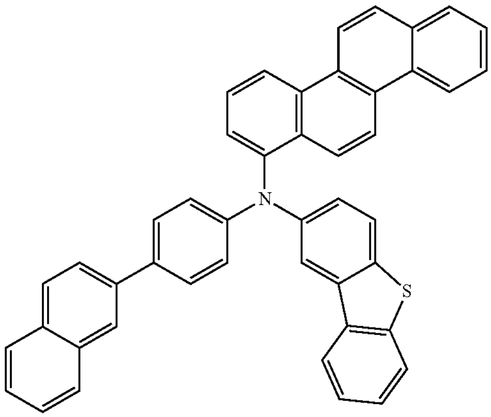
H1-57
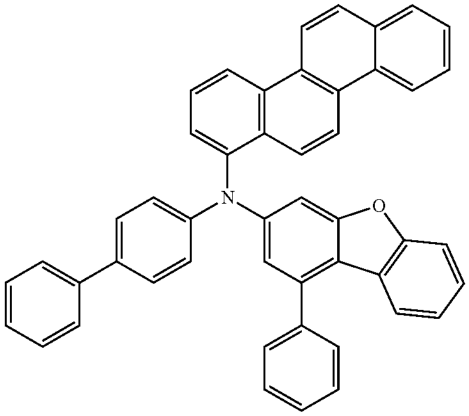

-continued
H1-58
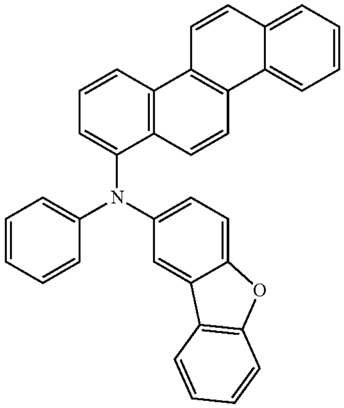
H1-59
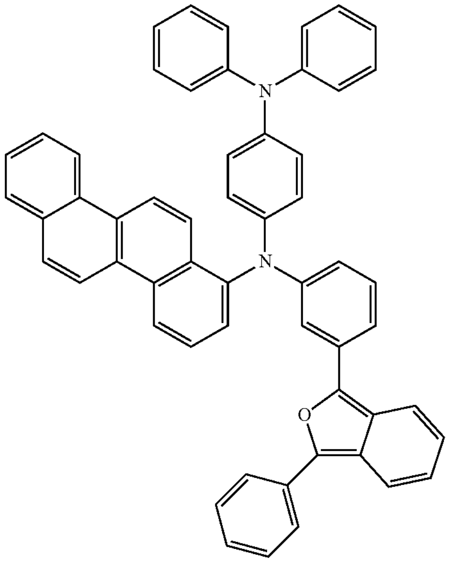
H1-60
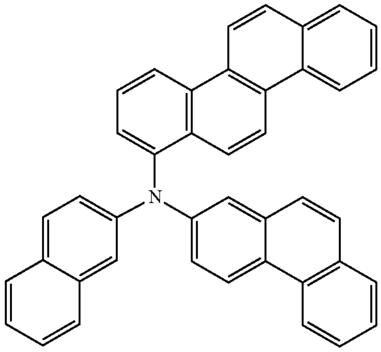
-continued
H1-61
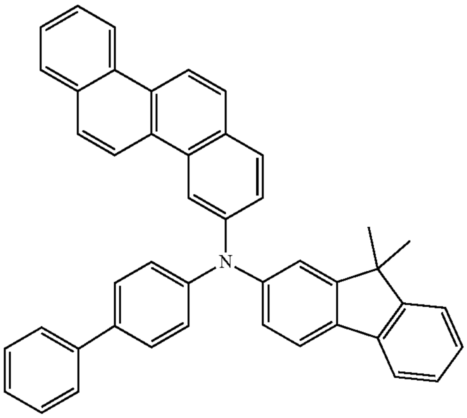
H1-62
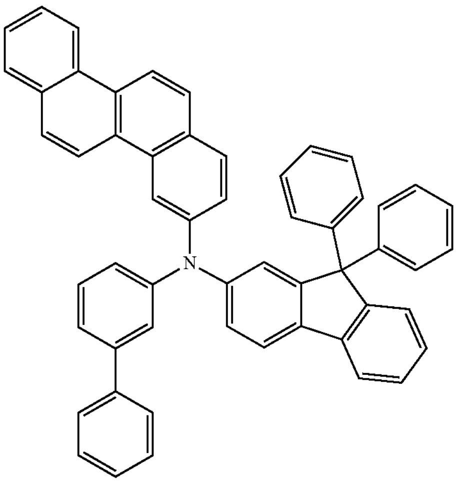
H1-63
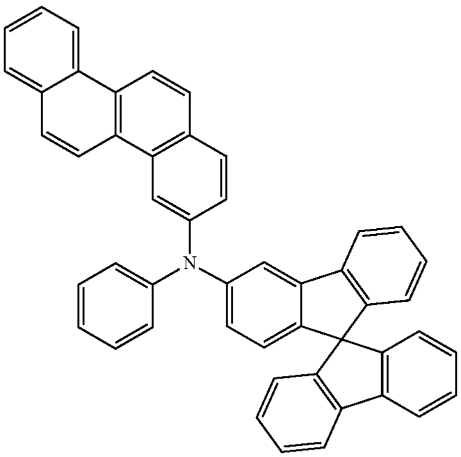

-continued
H1-64
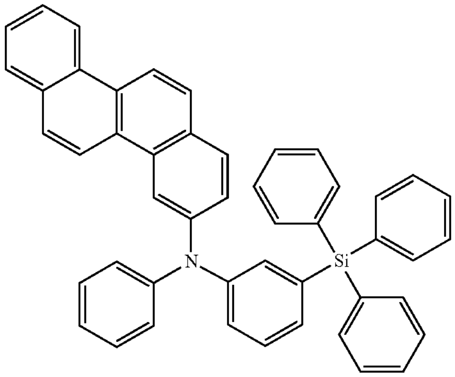
H1-65
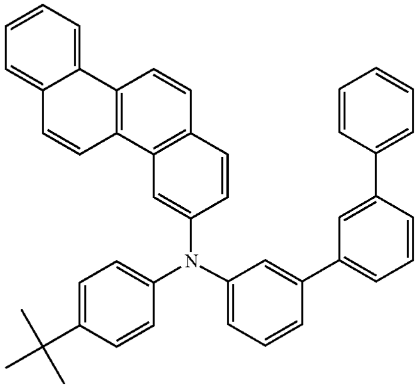
H1-66
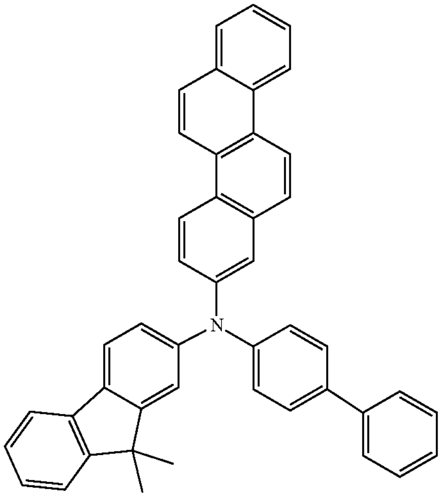
-continued
H1-67
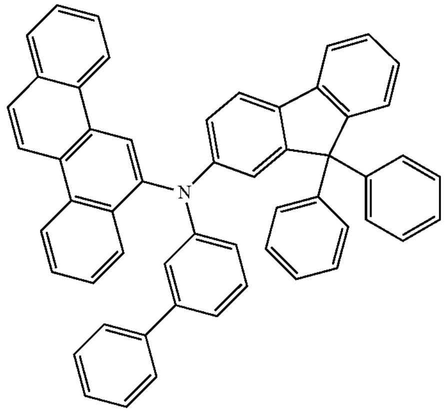
H1-68
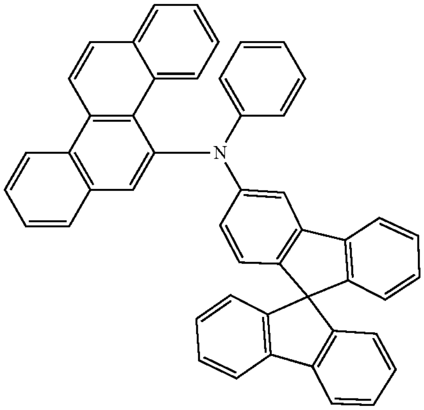
H1-69
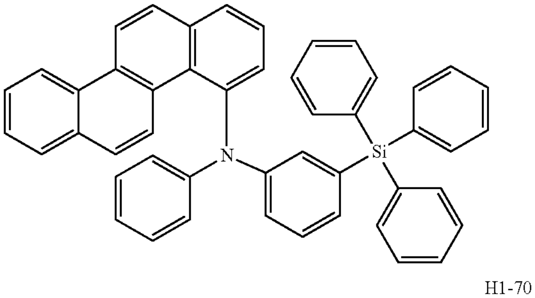
H1-70
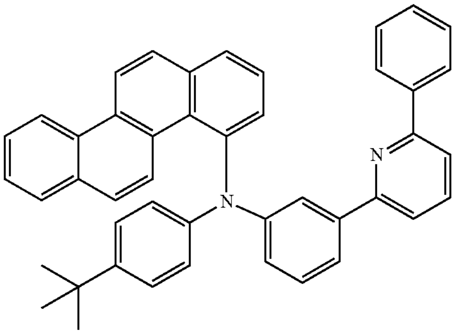

-continued
H1-71
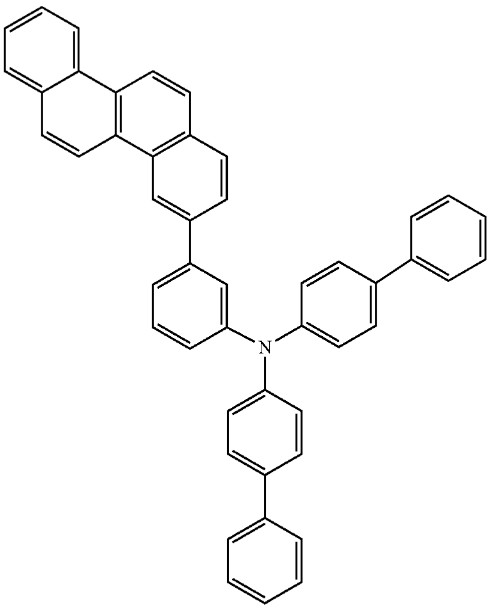
H1-72
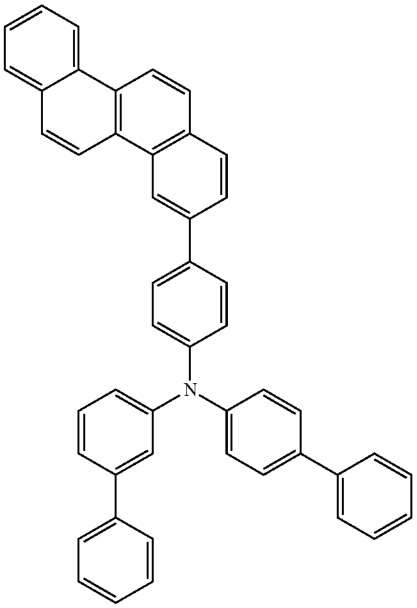
-continued
H1-73
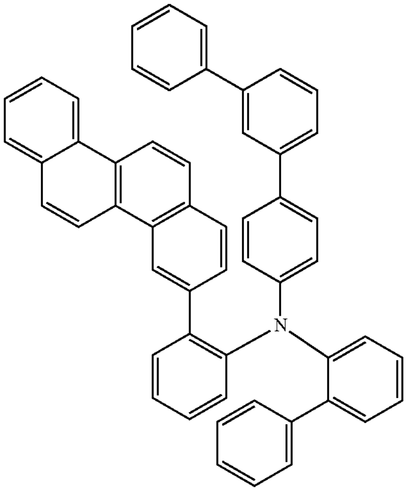
H1-74
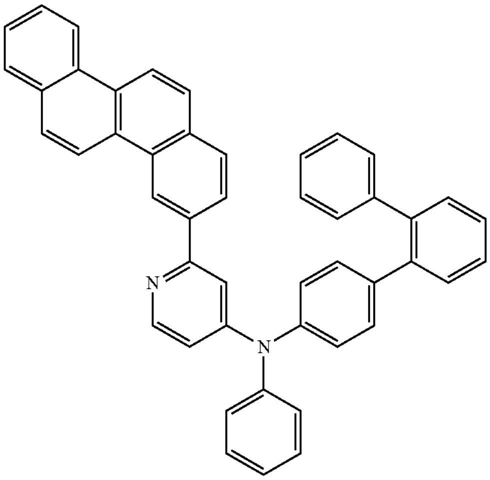
H1-75
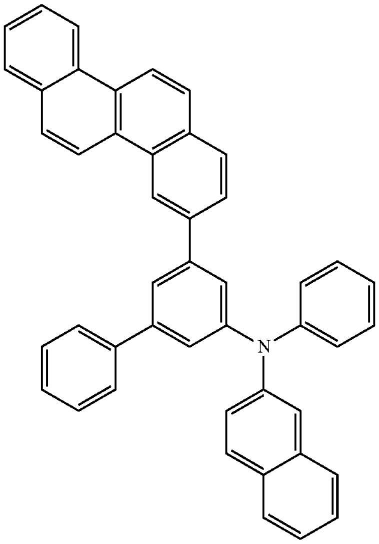

-continued
H1-76
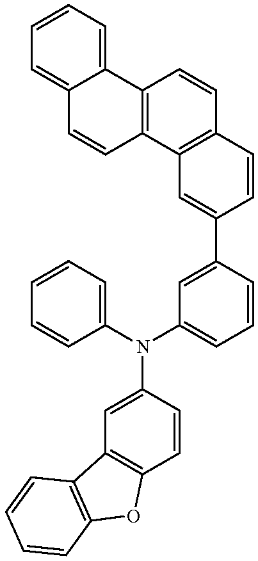
H1-77
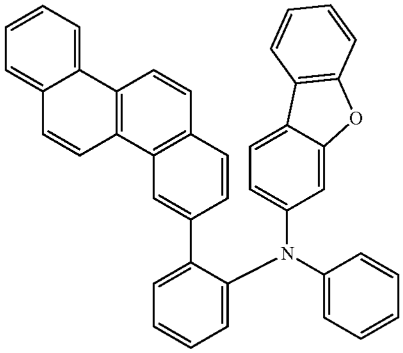
H1-78
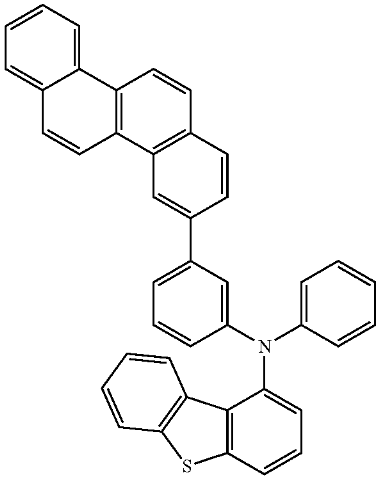
-continued
H1-79
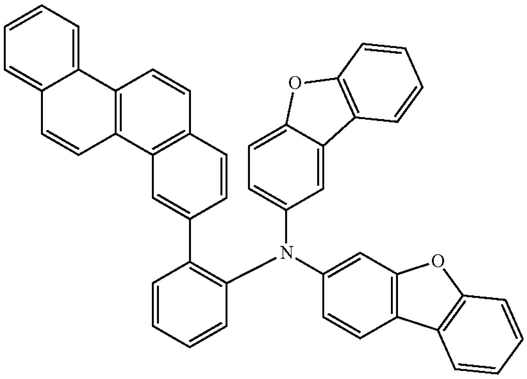
H1-80
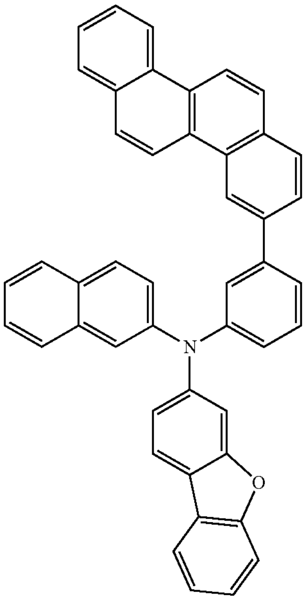
H1-81
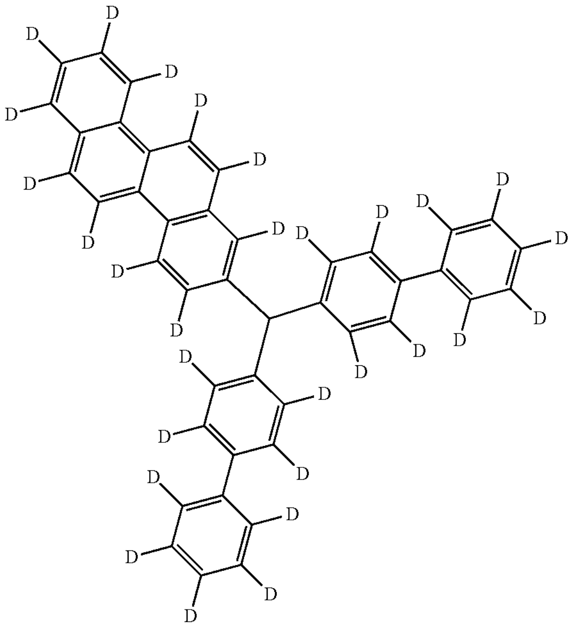

-continued
H1-82
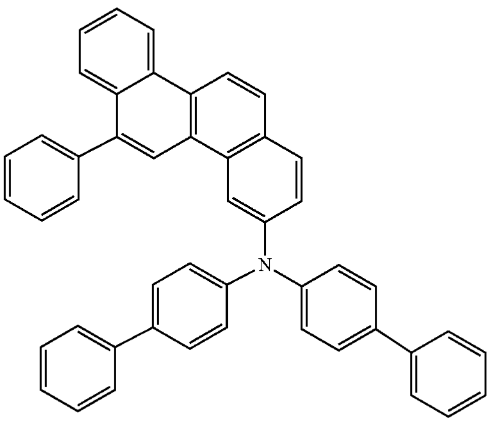
H1-83
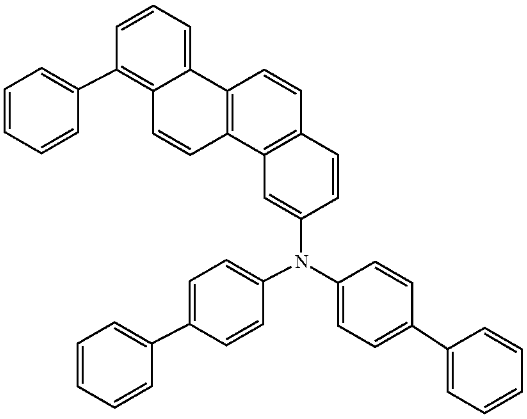
H1-84
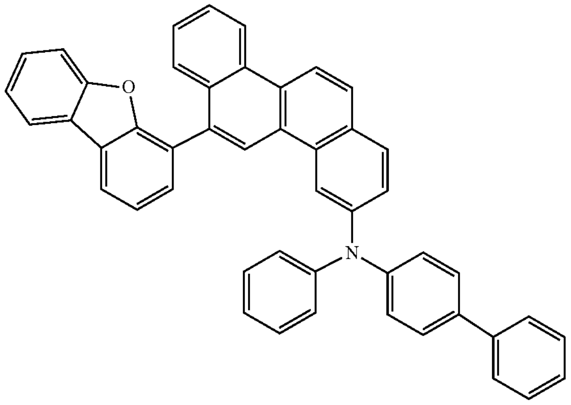
-continued
H1-85
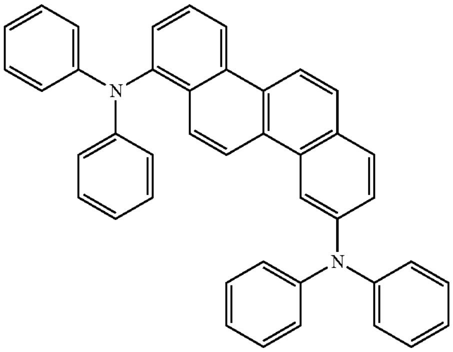
H1-86
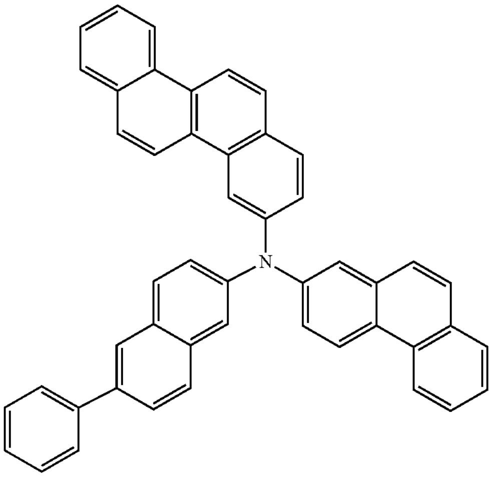
H1-87
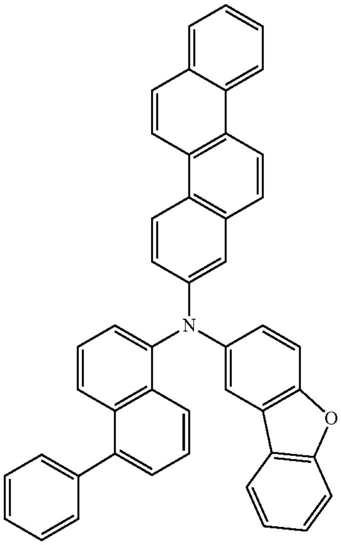

-continued
H1-88
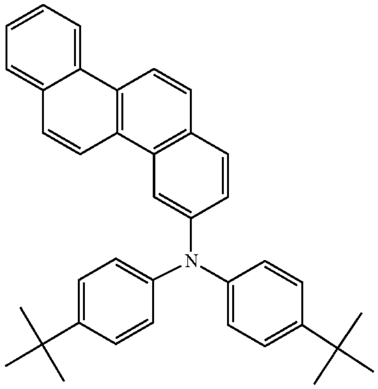
H1-112
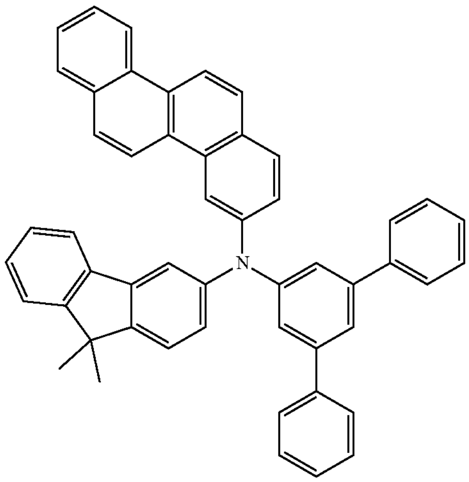
H1-113
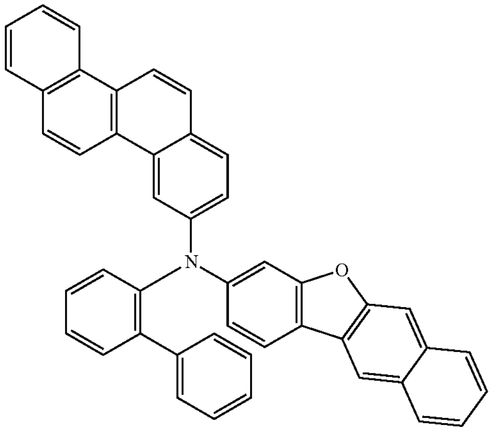
-continued
H1-114
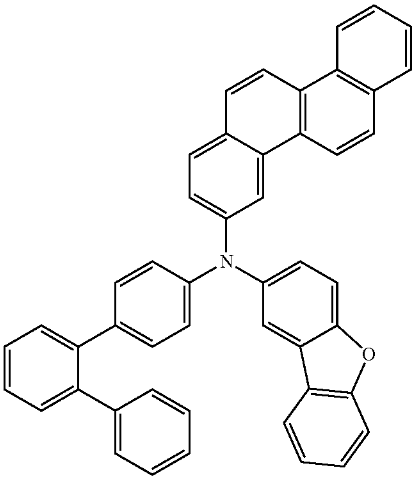
H1-115
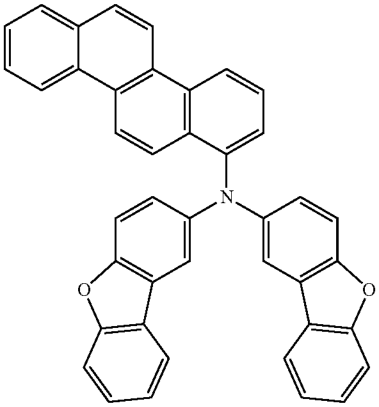
H1-116
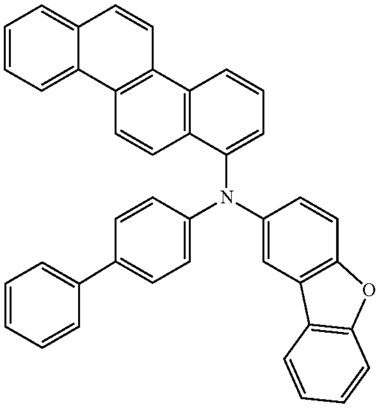

-continued
H1-117
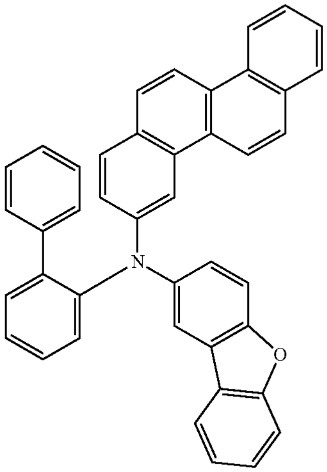
H1-118
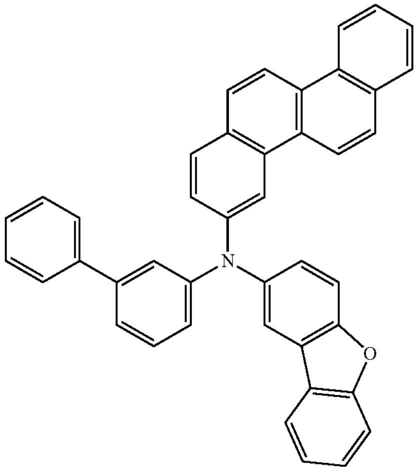
H1-119
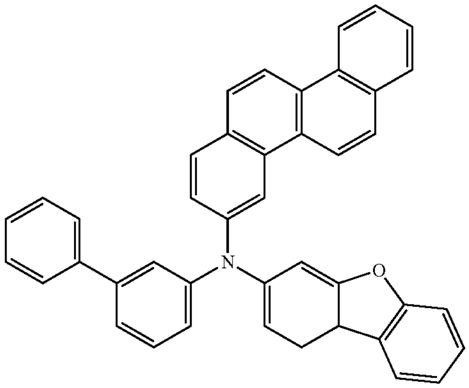
-continued
H1-120
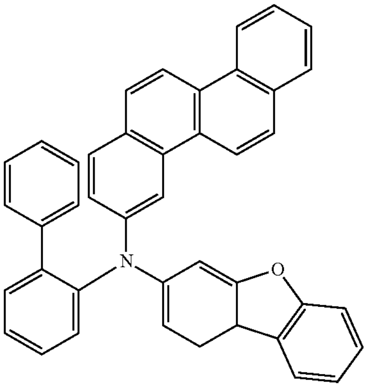
H1-121
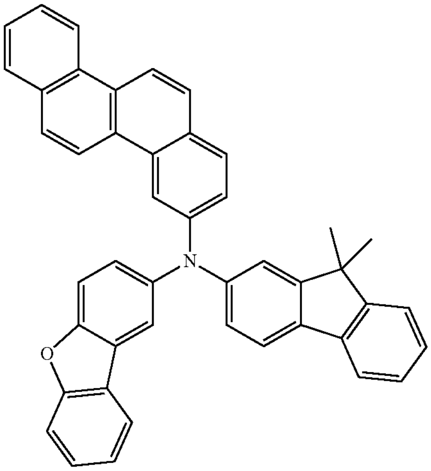
H1-122
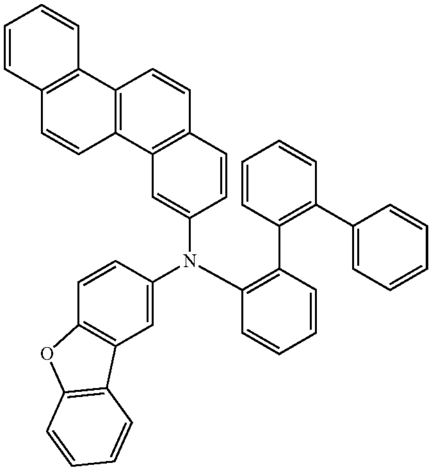

-continued
H1-123
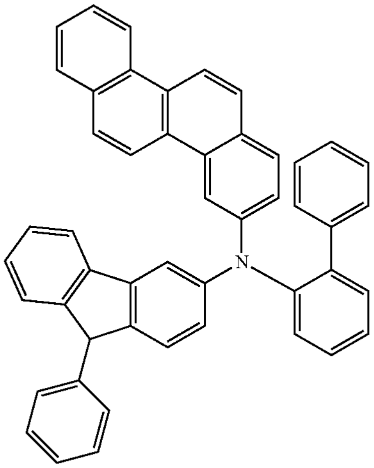
H1-124
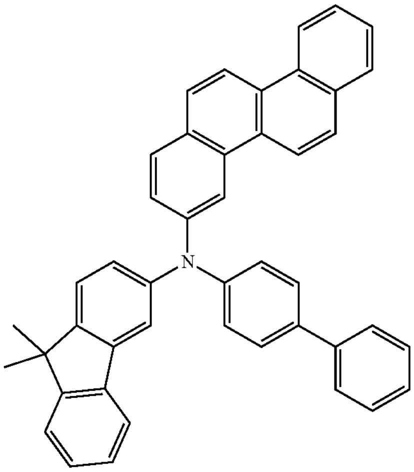
H1-125
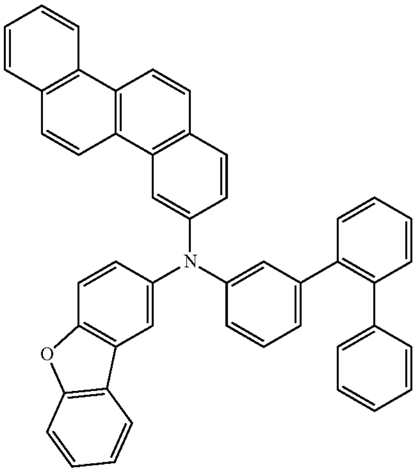
-continued
H1-126
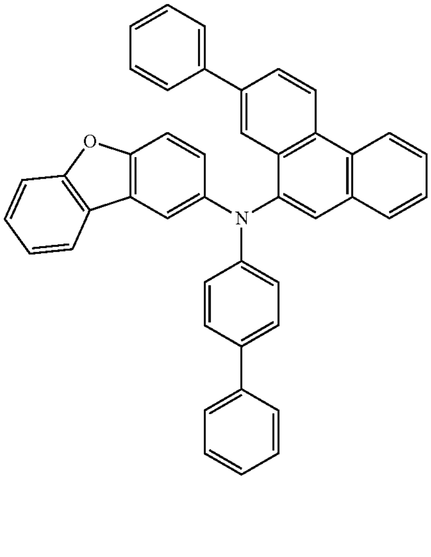
H1-127
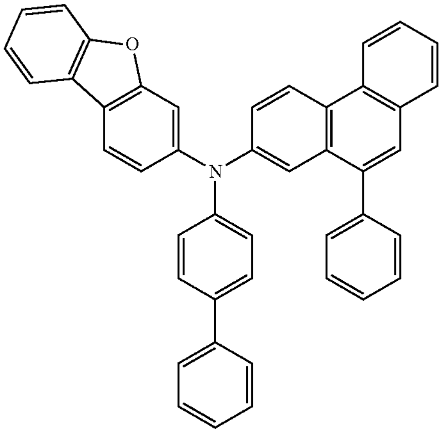
H1-128
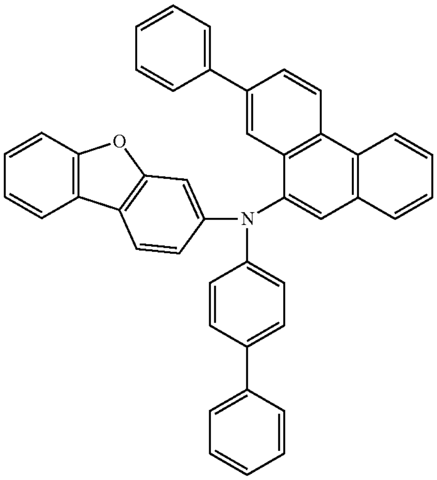

-continued
H1-129
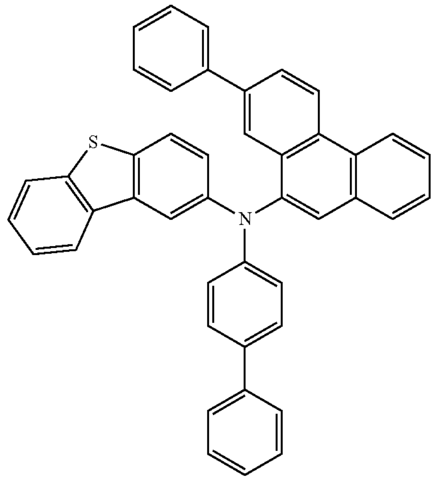
H1-130
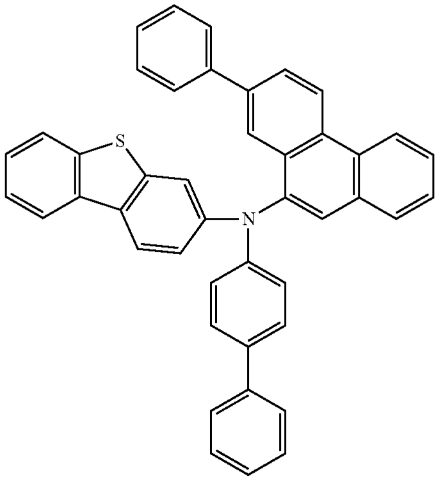
H1-131
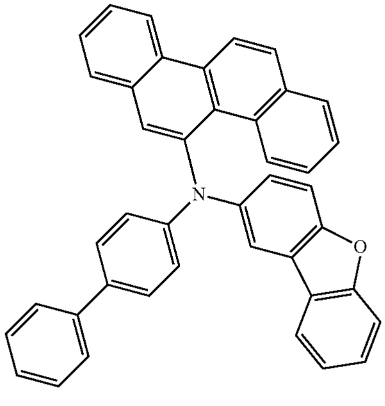
-continued
H1-132
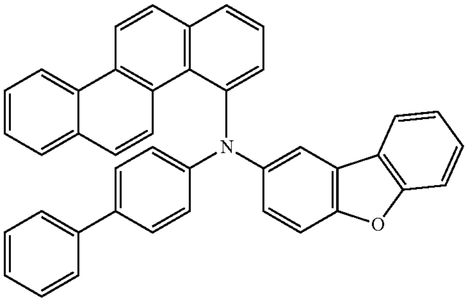
H1-133
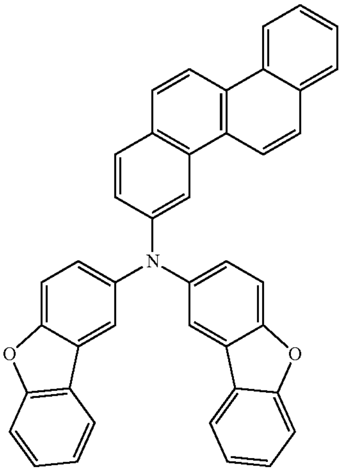
H1-134
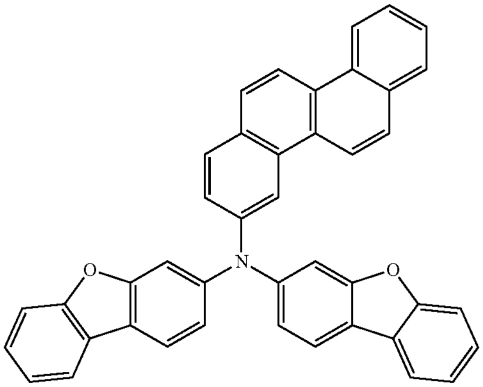
H1-135
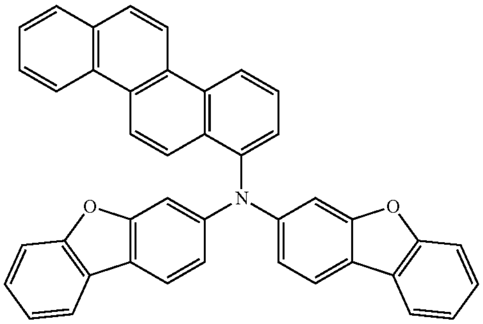

-continued
H1-136
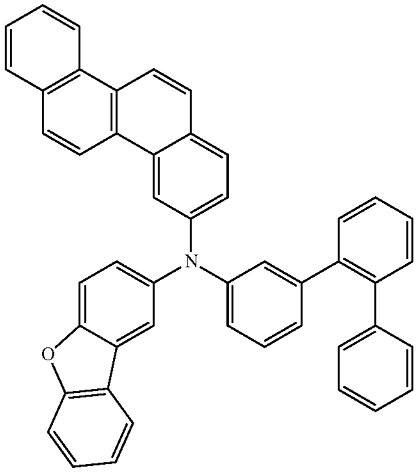
H1-137
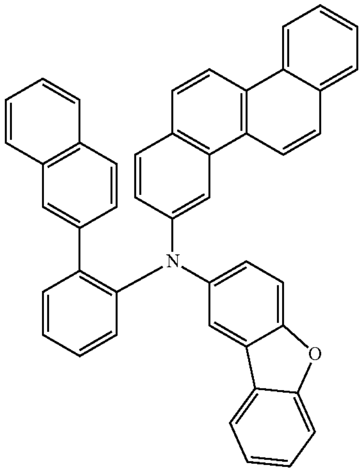
H1-138
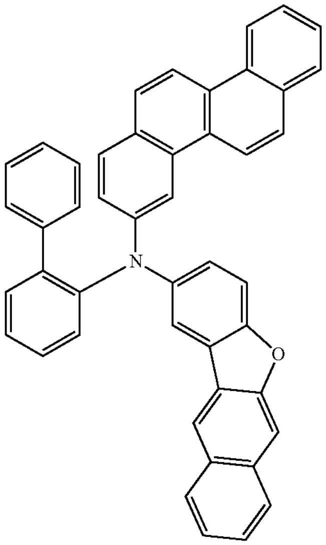
-continued
H1-139
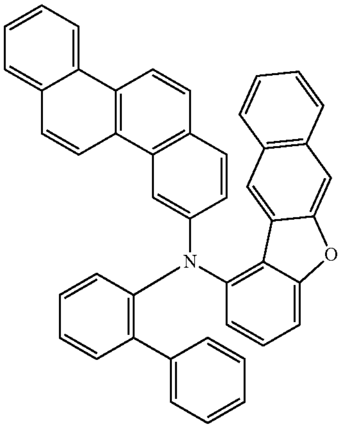
H1-140
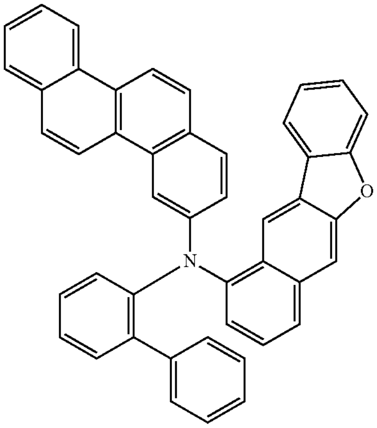
H1-141
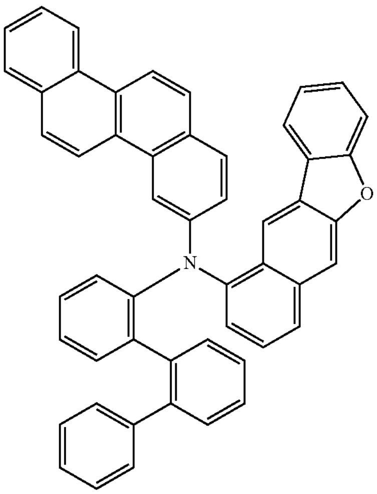

-continued
H1-142
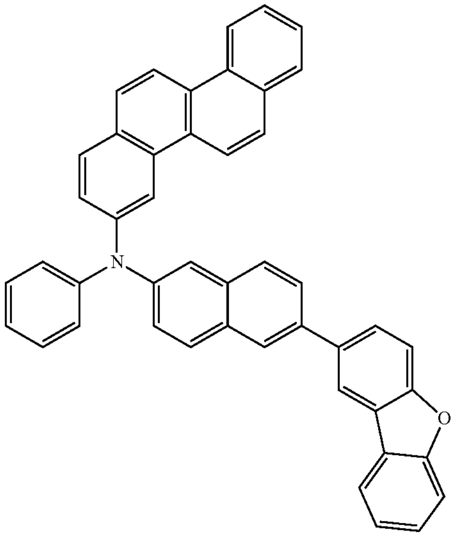
H1-143
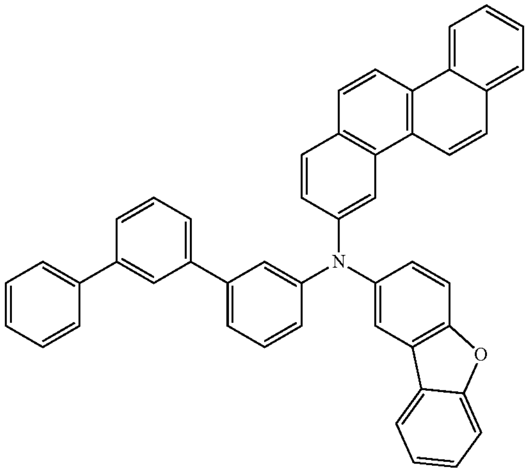
H1-144
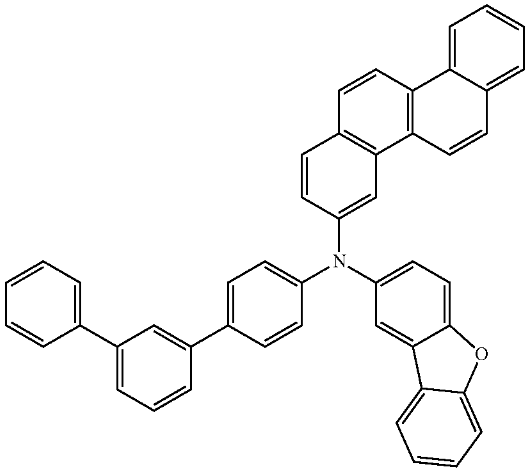
and
-continued
H1-145
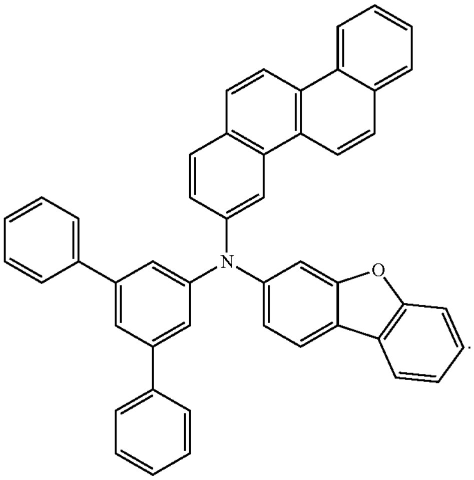
.
5. The plurality of host materials according to claim 1, wherein the compound represented by the formula 2 is selected from the following compounds:
H2-1
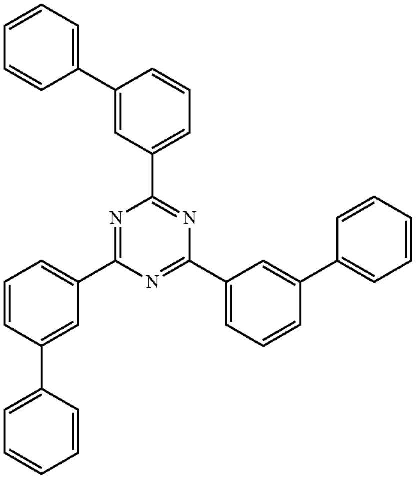

-continued
H2-2
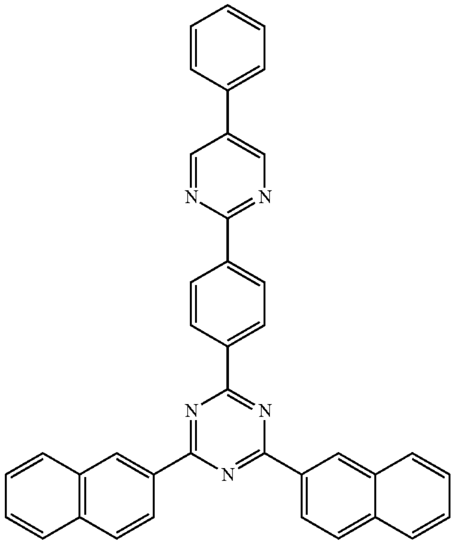
H2-3
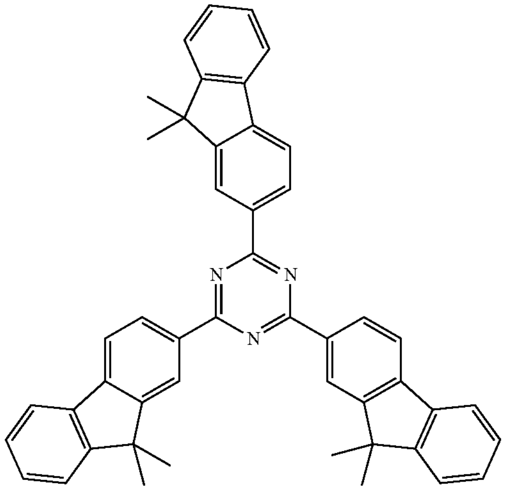
H2-4
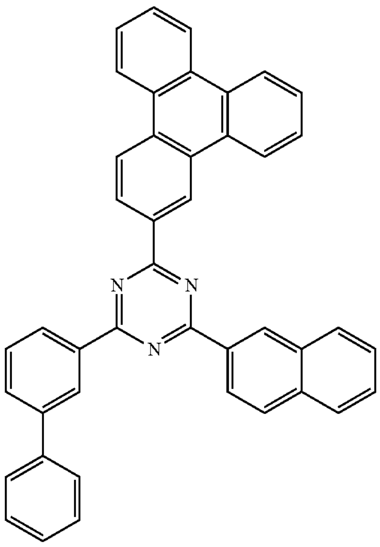
-continued
H2-5
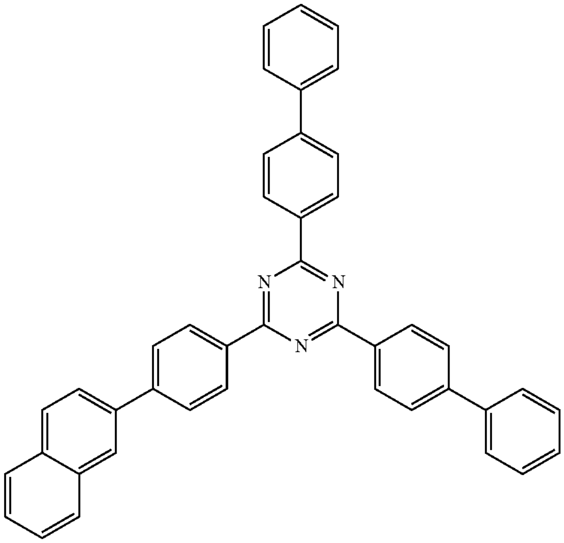
H2-6
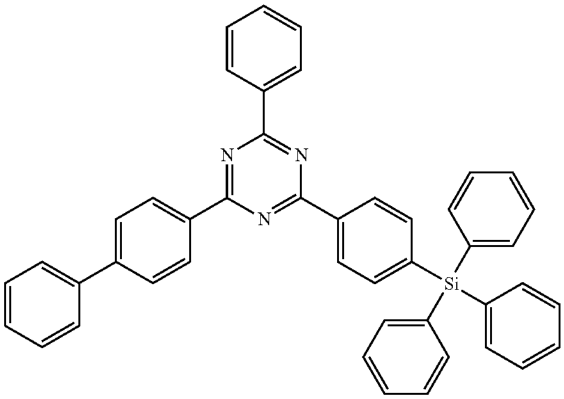
H2-7
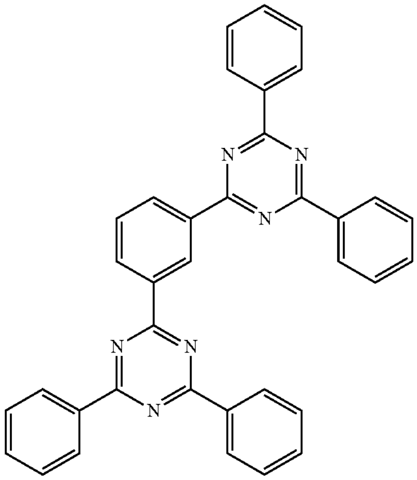

-continued
H2-8
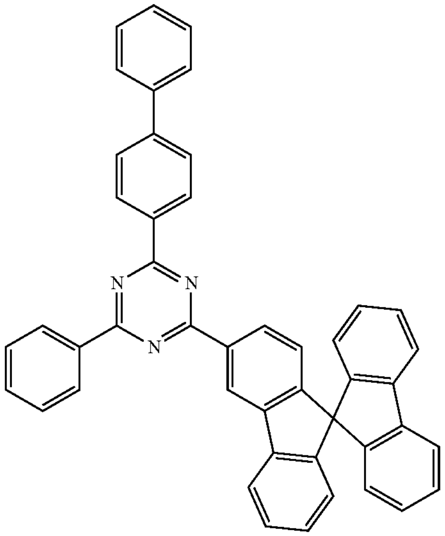
H2-9
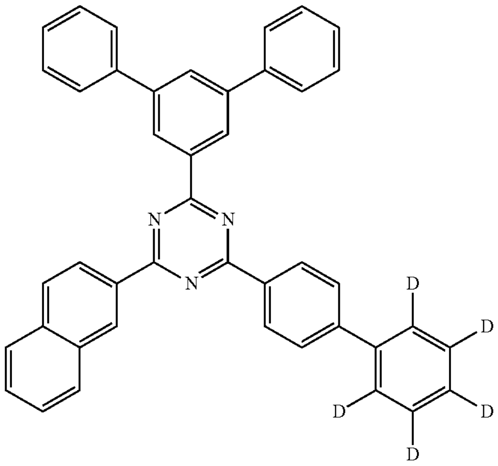
H2-10
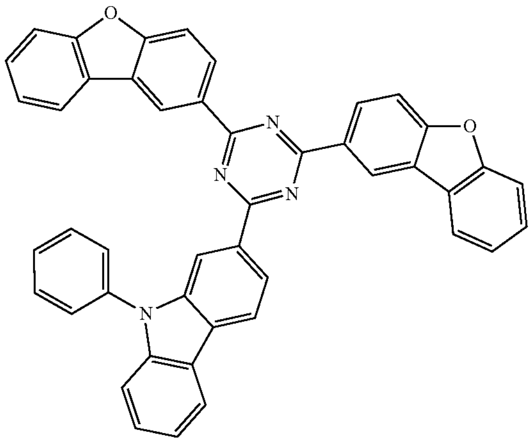
-continued
H2-11
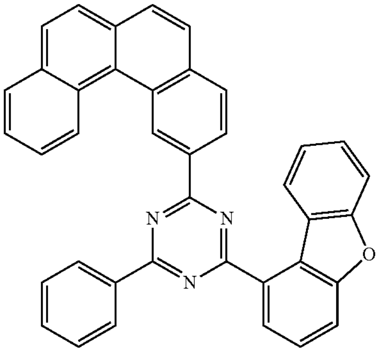
H2-12
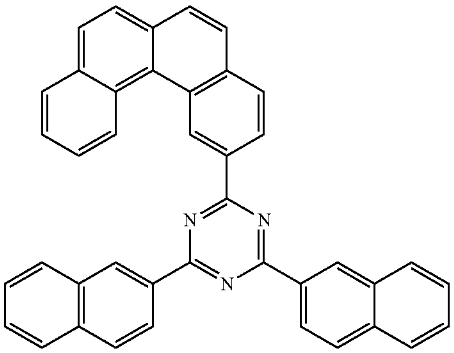
H2-13
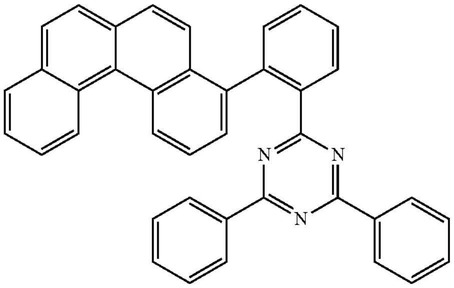
H2-14
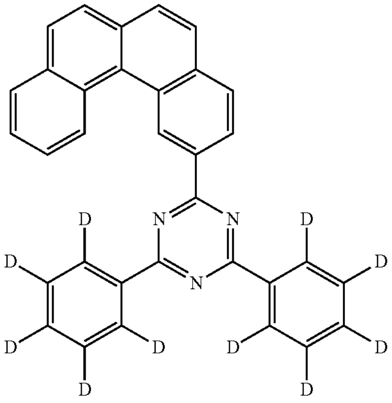

-continued
H2-15
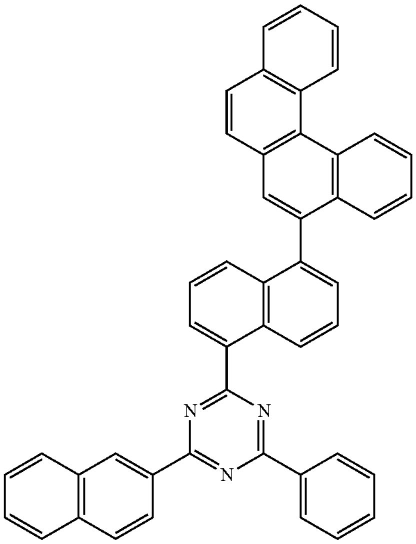
H2-16
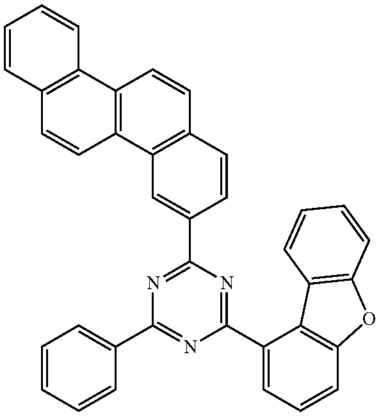
H2-17
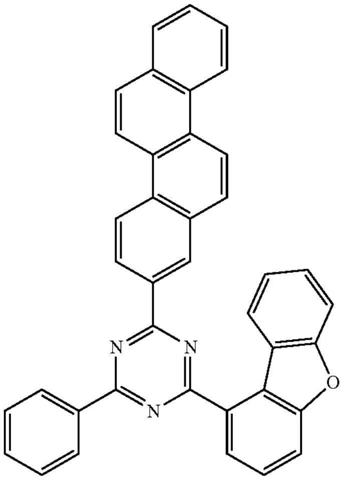
-continued
H2-18
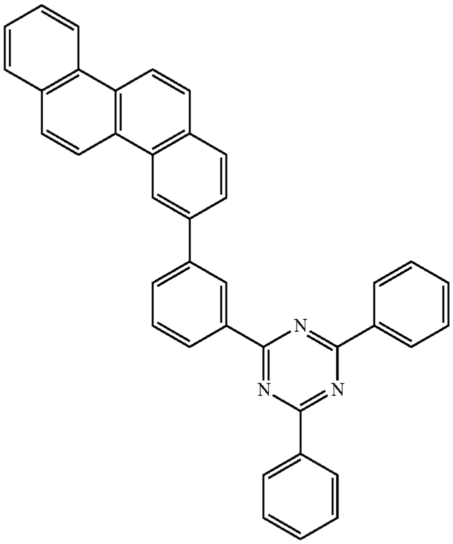
H2-19
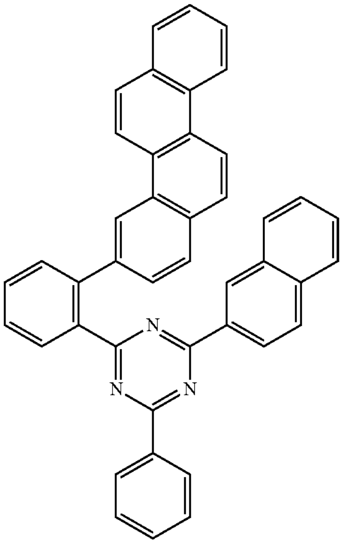
H2-20
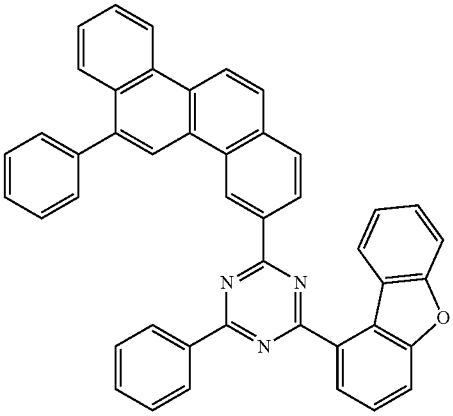

-continued
H2-21
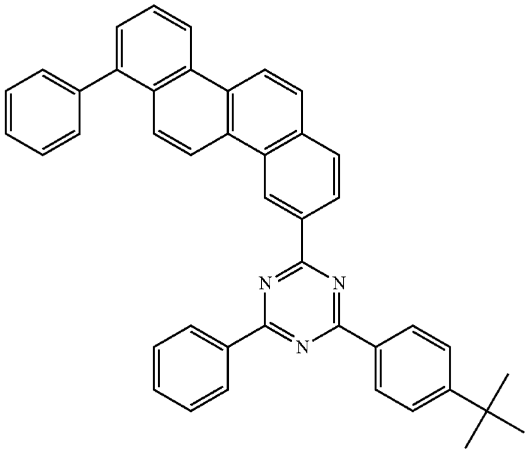
H2-22
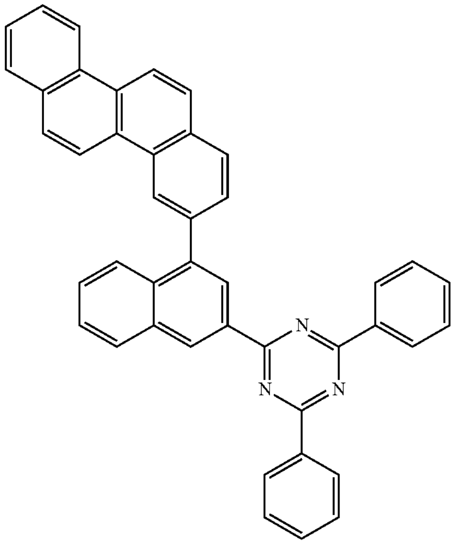
H2-23
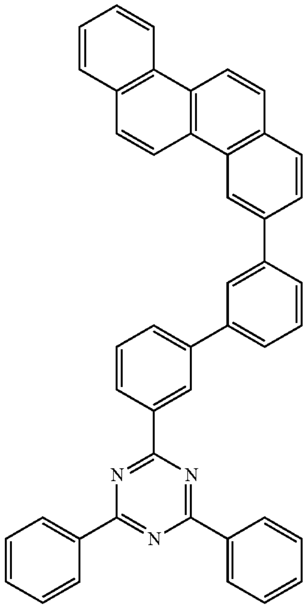
-continued
H2-24
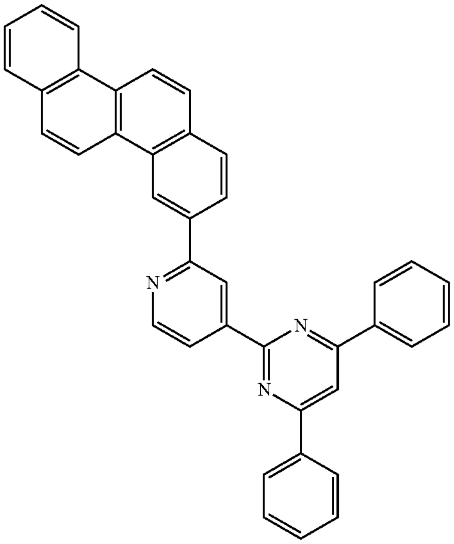
H2-25
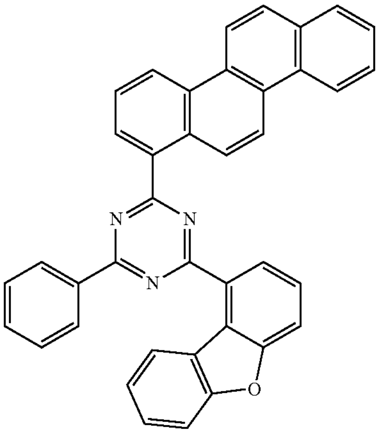
H2-26
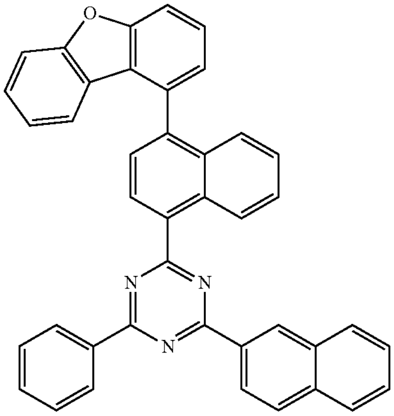

-continued
H2-27
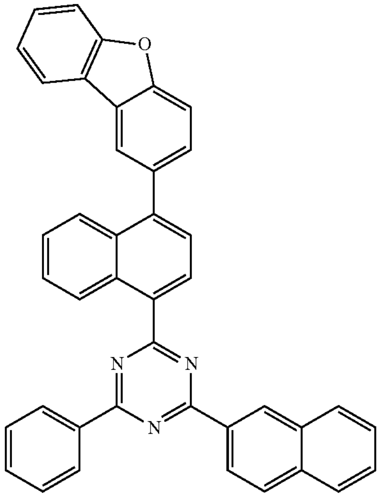
H2-28
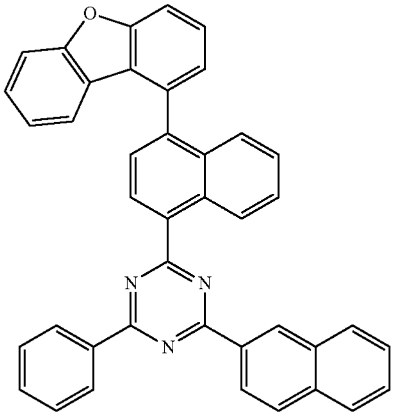
H2-29
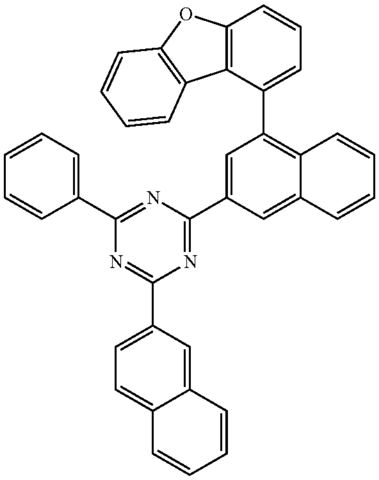
-continued
H2-30
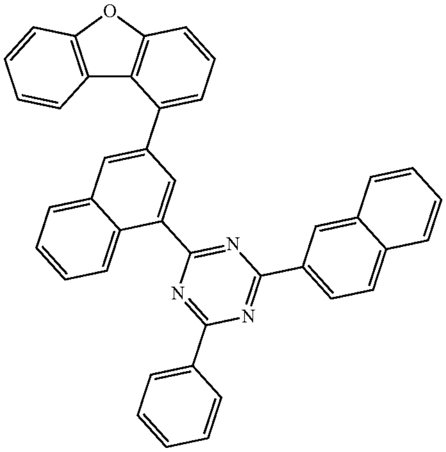
H2-31
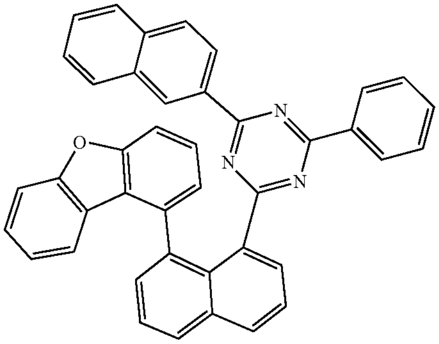
H2-32
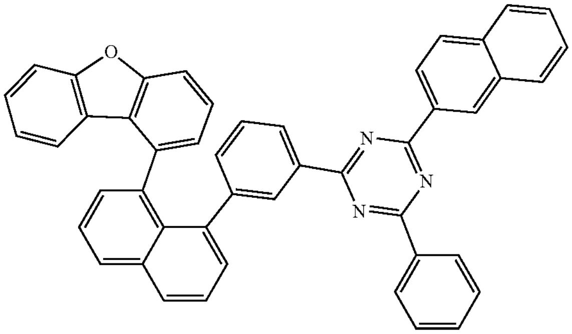
H2-33
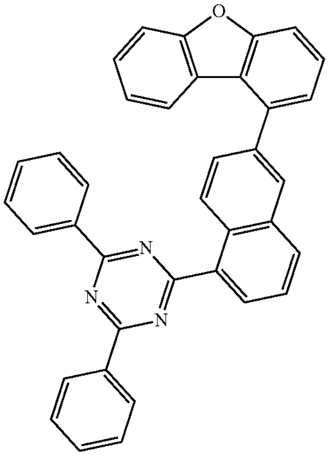

-continued
H2-34
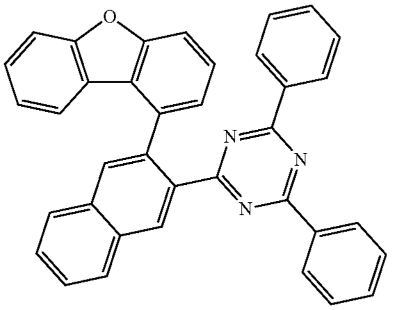
H2-35
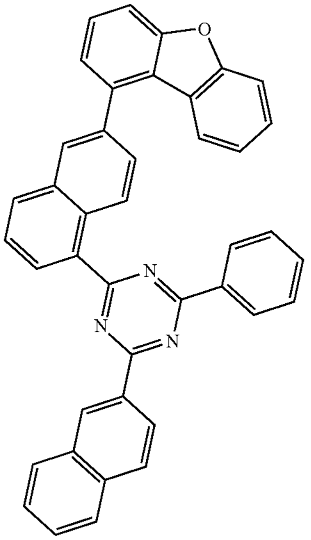
H2-36
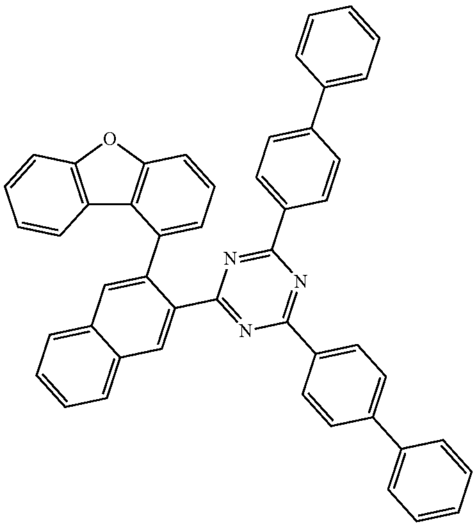
-continued
H2-37
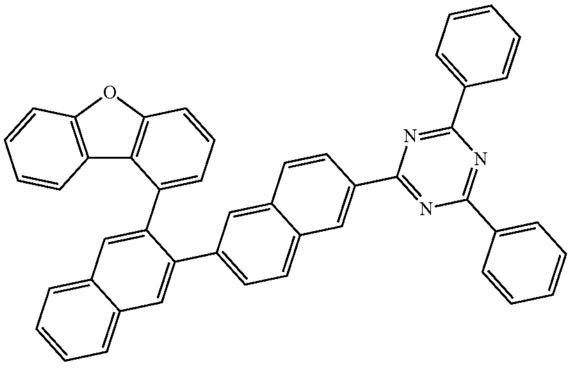
H2-38
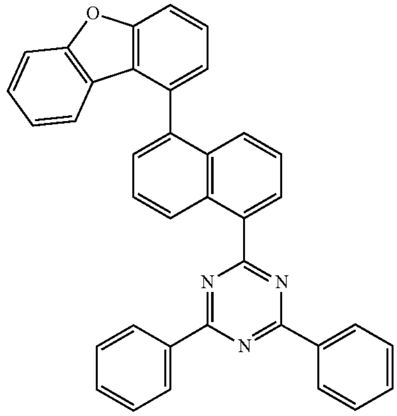
H2-39
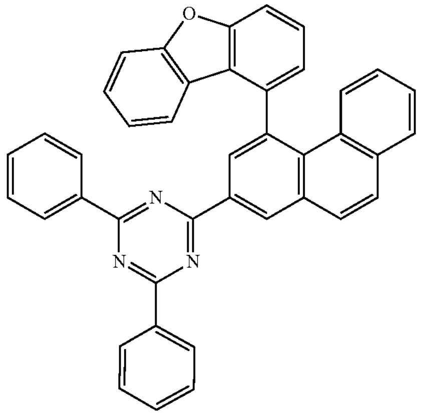

-continued
H2-40
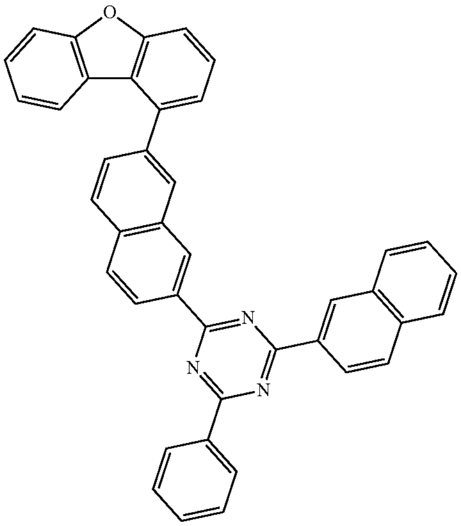
H2-41
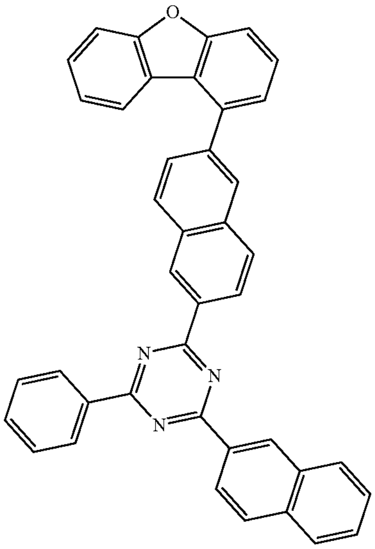
-continued
H2-42
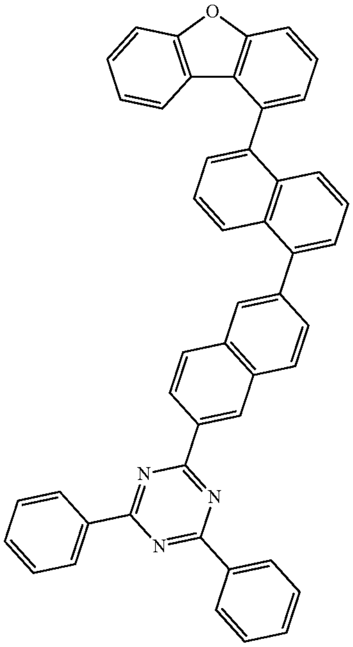
H2-43
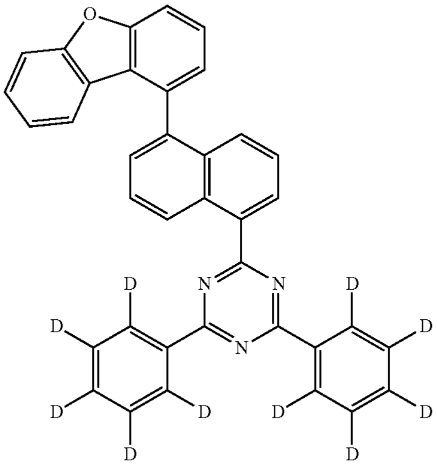
H2-44
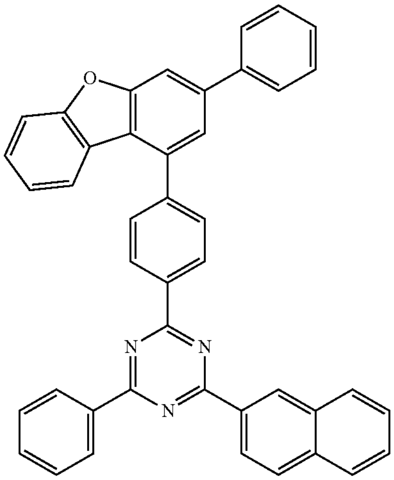

-continued
H2-45
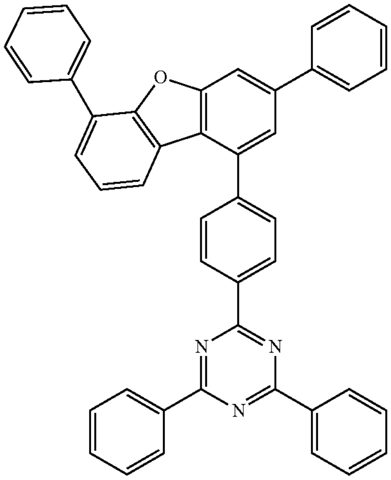
H2-46
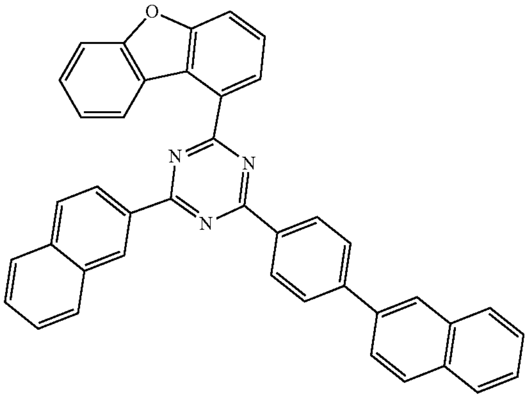
H2-47
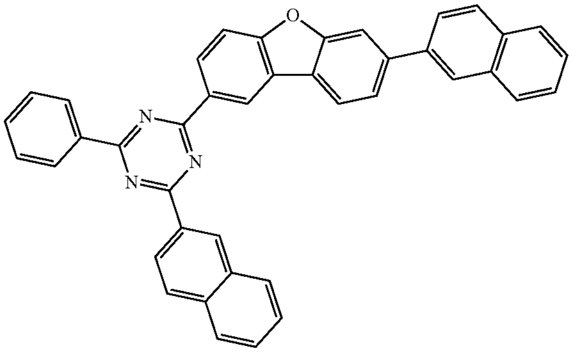
-continued
H2-48
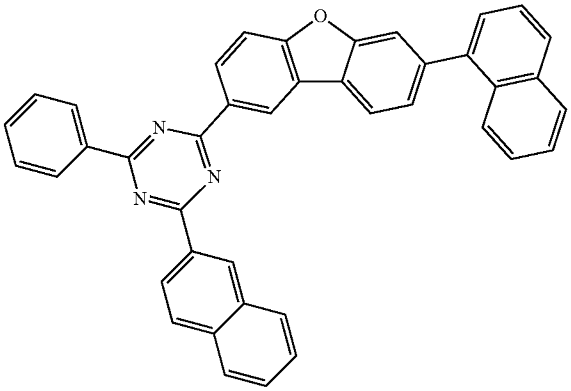
H2-49
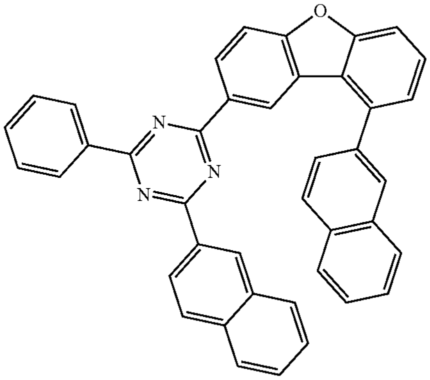
H2-50
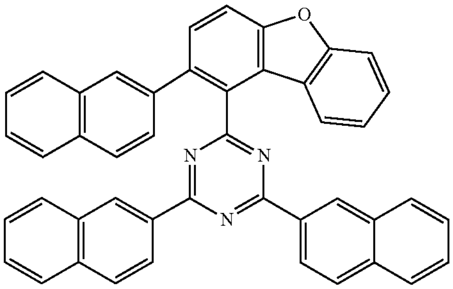
H2-51
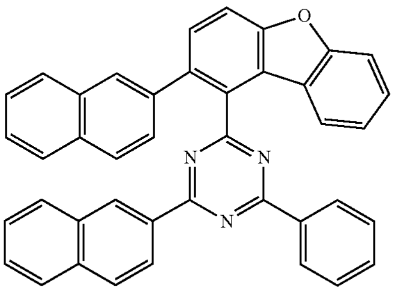

-continued
H2-52
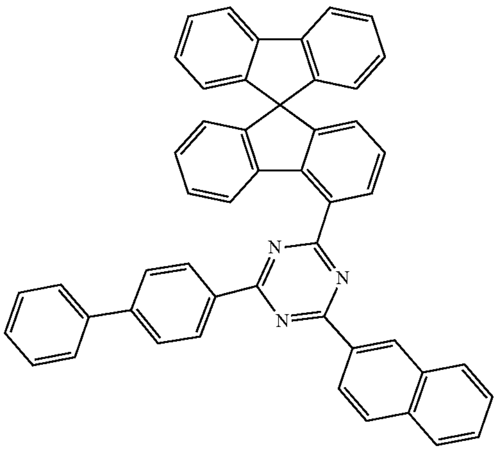
H2-53
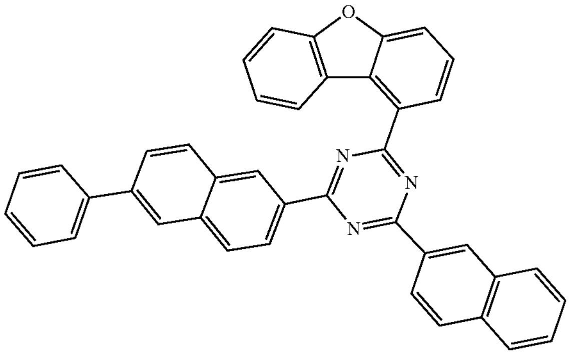
H2-54
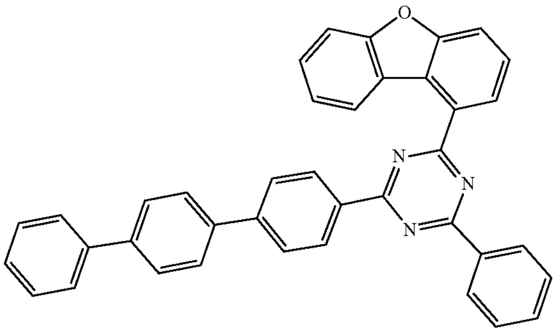
H2-55
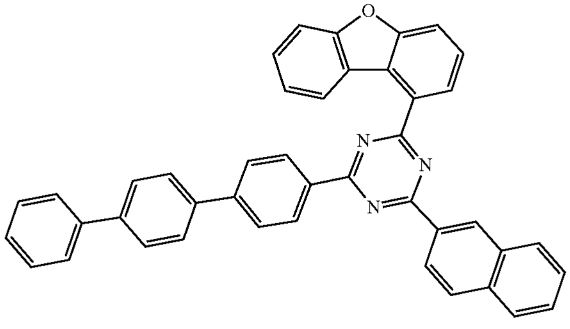
-continued
H2-56
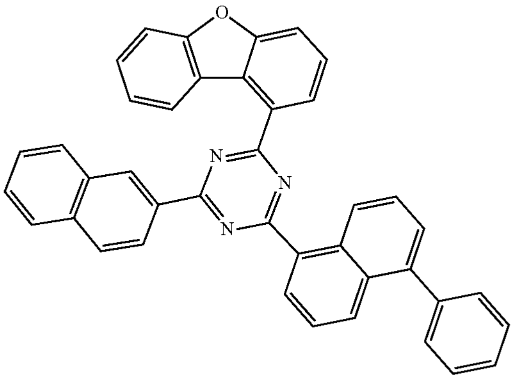
H2-57
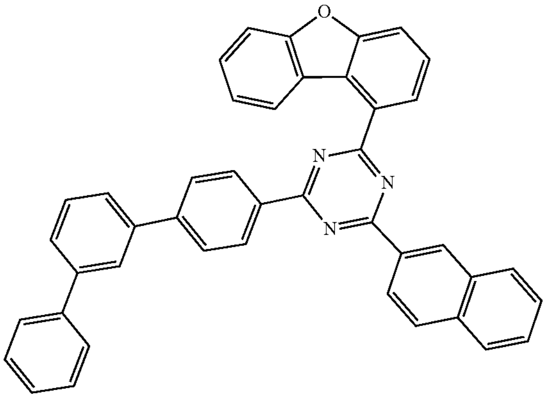
H2-58
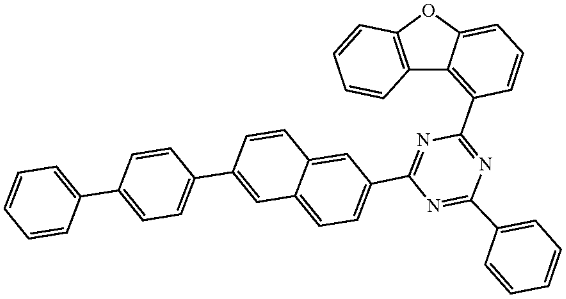
H2-59
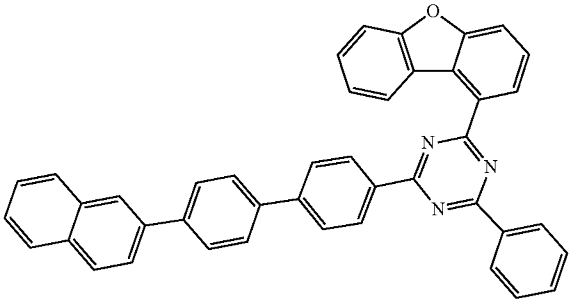

-continued
H2-60
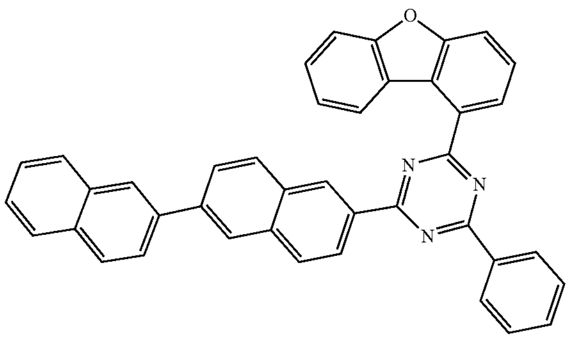
H2-61
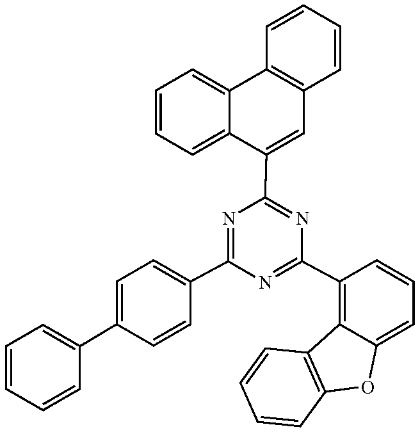
H2-62
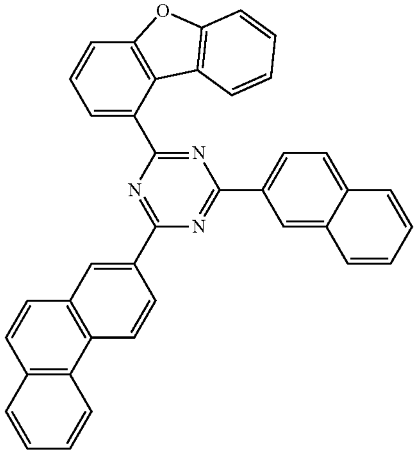
H2-63
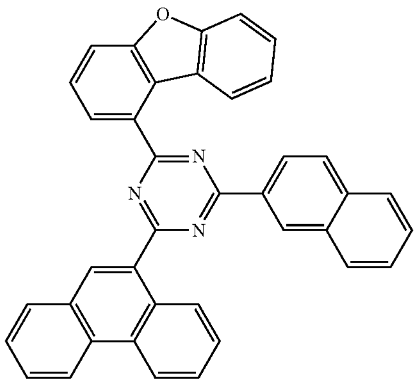
-continued
H2-64
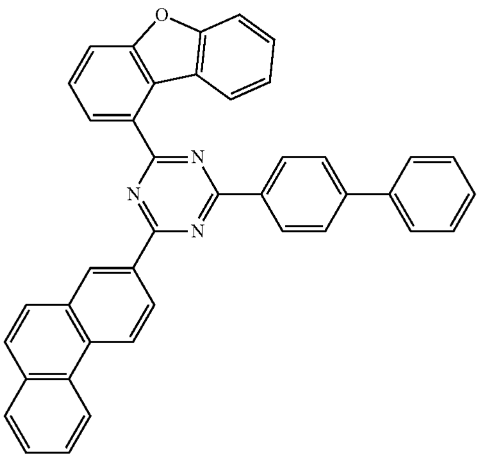
H2-65
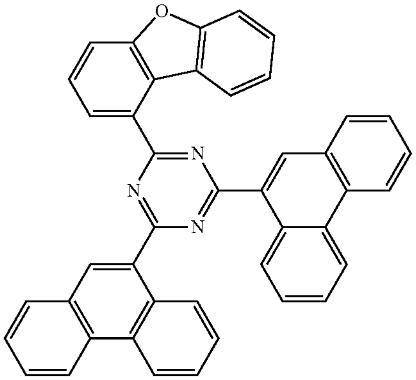
H2-66
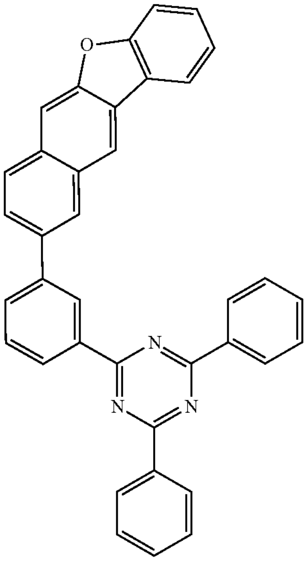

-continued
H2-67
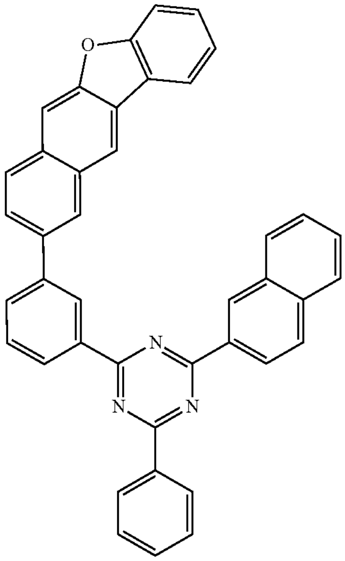
H2-68
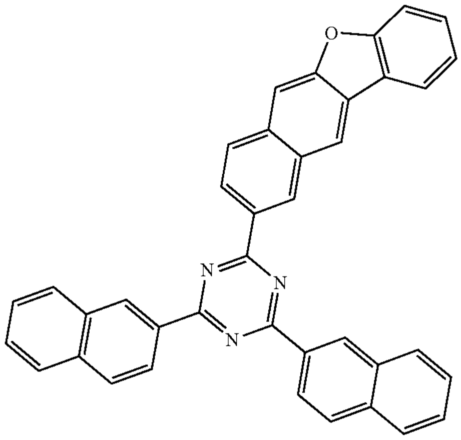
H2-69
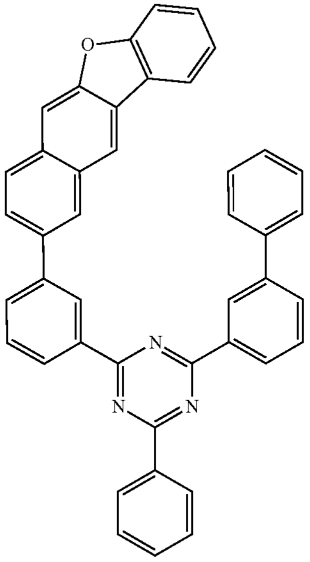
-continued
H2-70
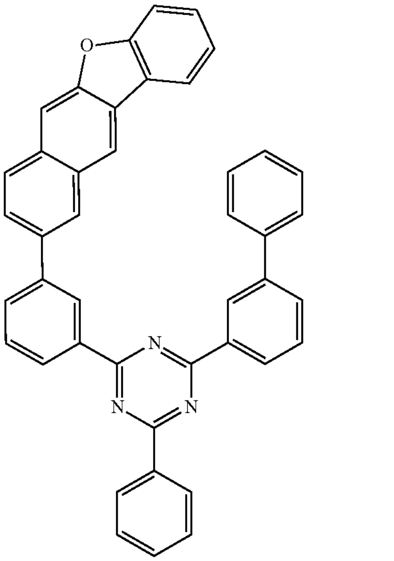
H2-71
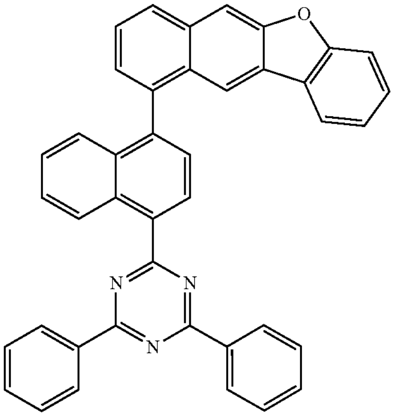
H2-72
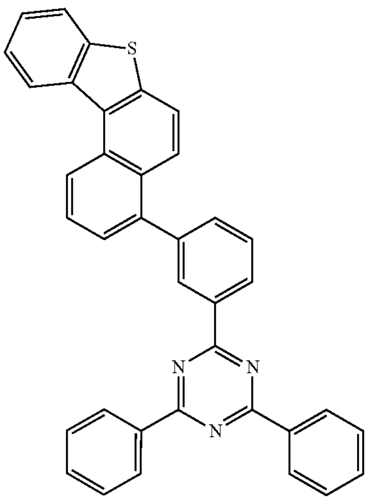

-continued
H2-73
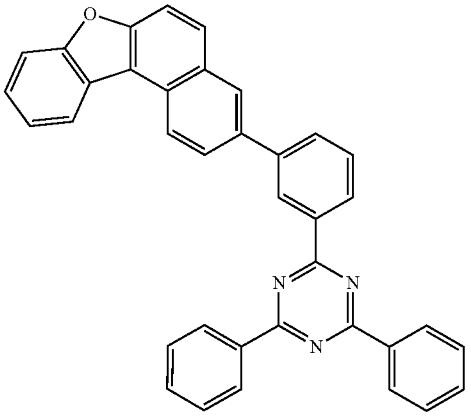
H2-74
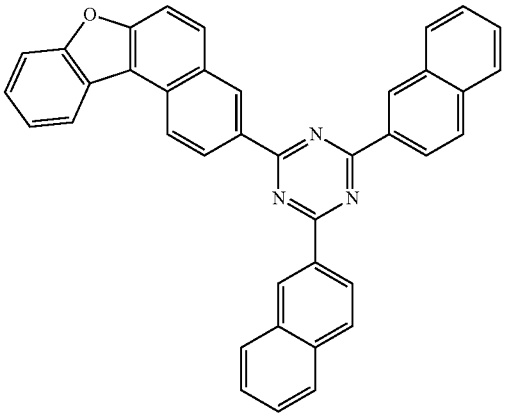
H2-75
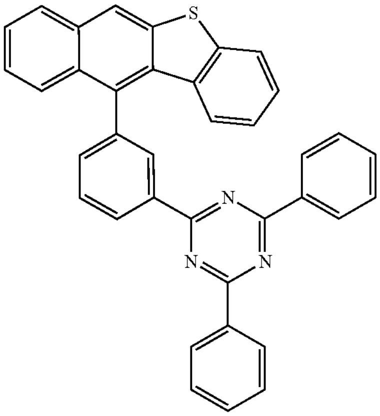
H2-76
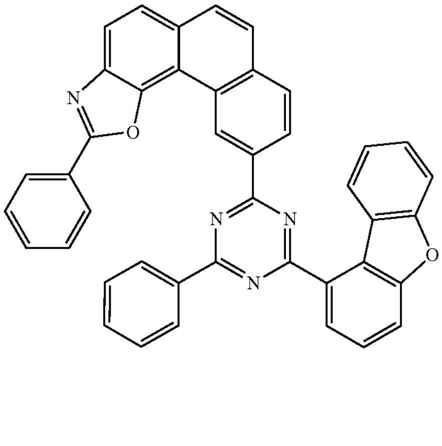
-continued
H2-77
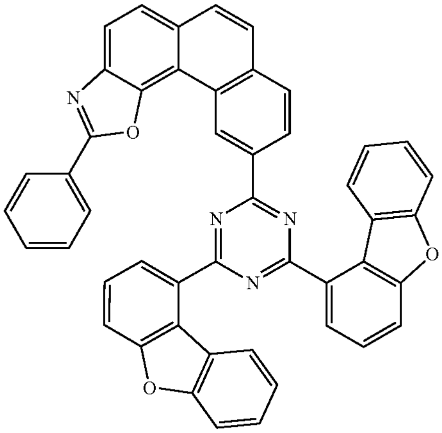
H2-78
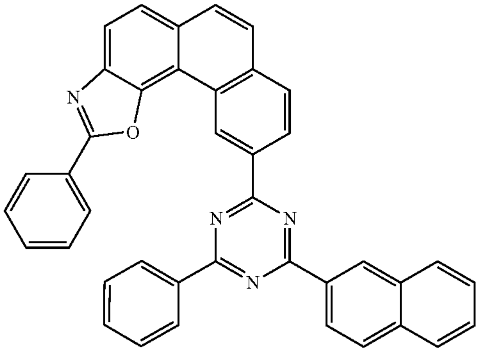
H2-79
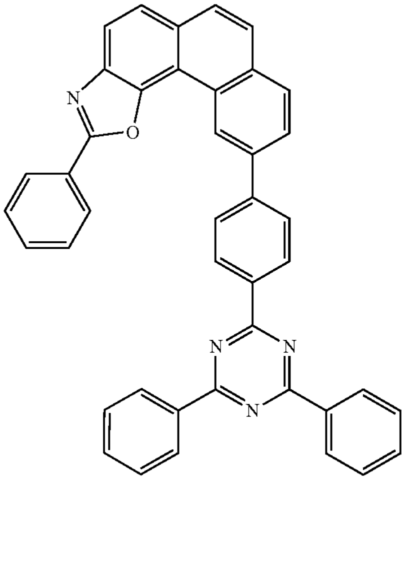

-continued
H2-80
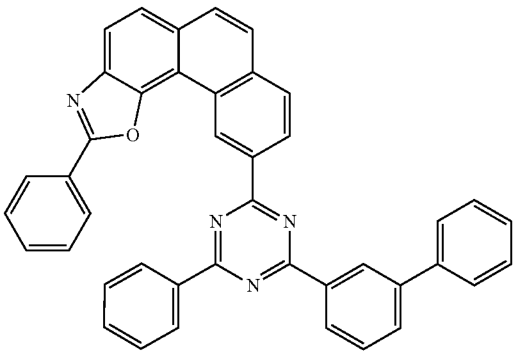
H2-81
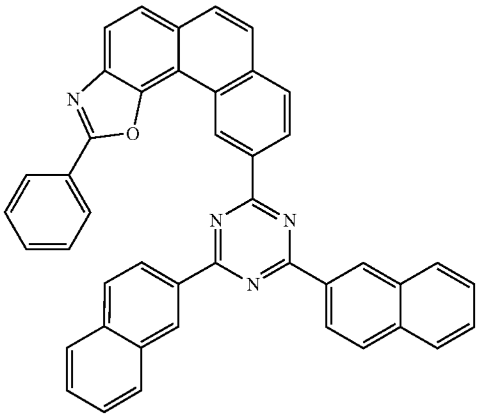
H2-82
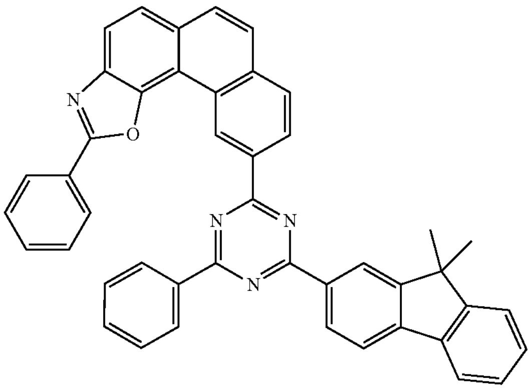
H2-83
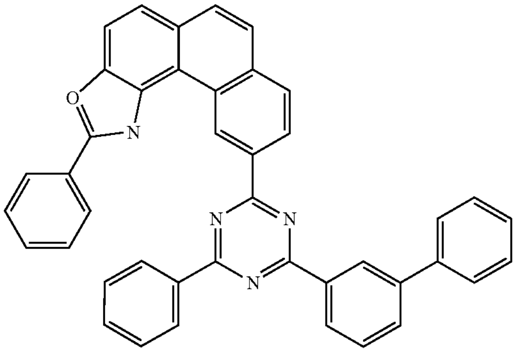
-continued
H2-84
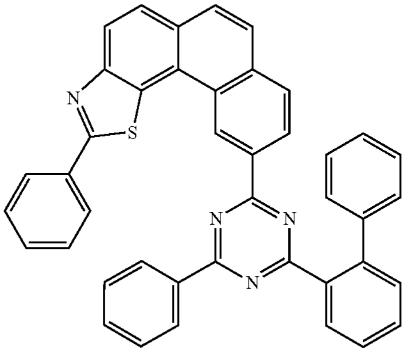
H2-85
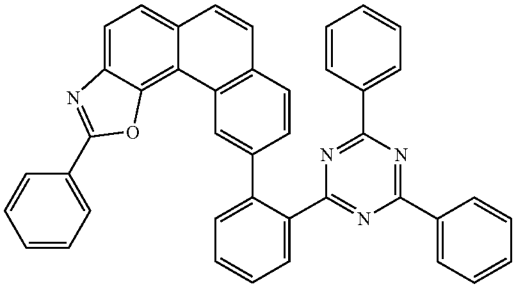
H2-86
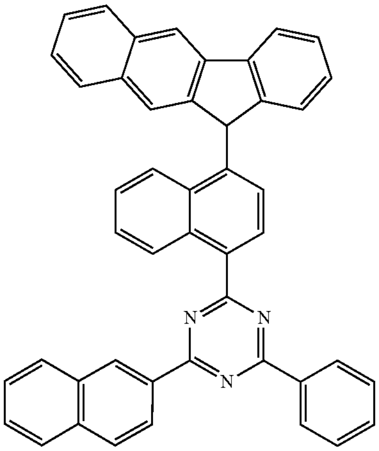
H2-87
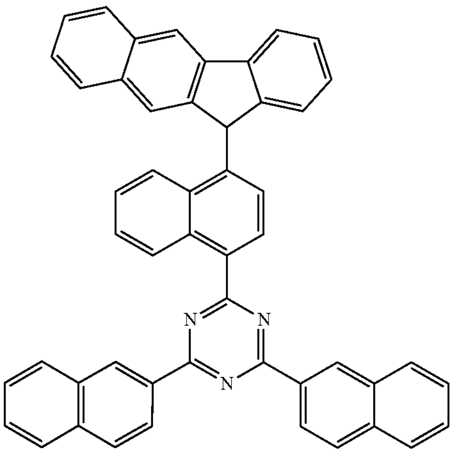

H2-88
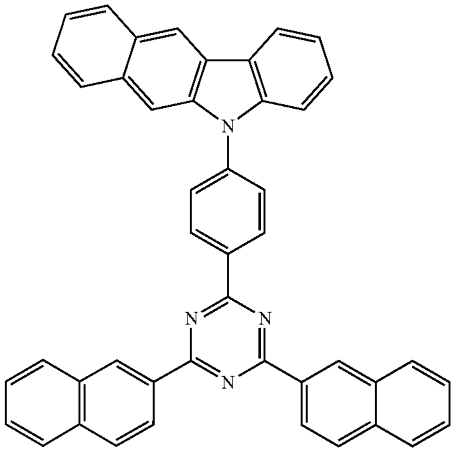
H2-89
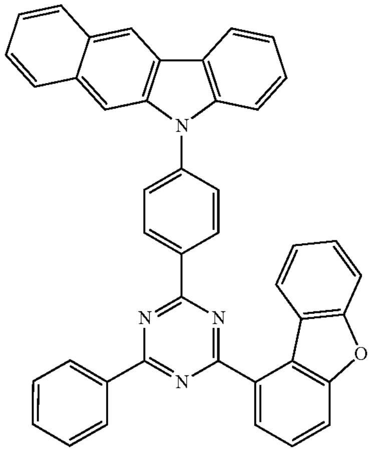
H2-90
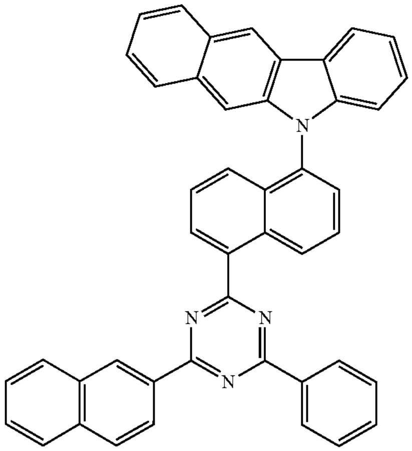
H2-91
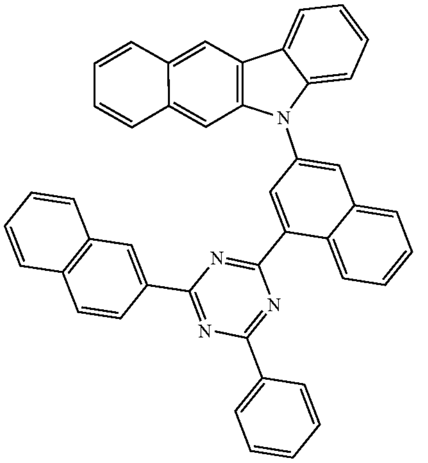
H2-92
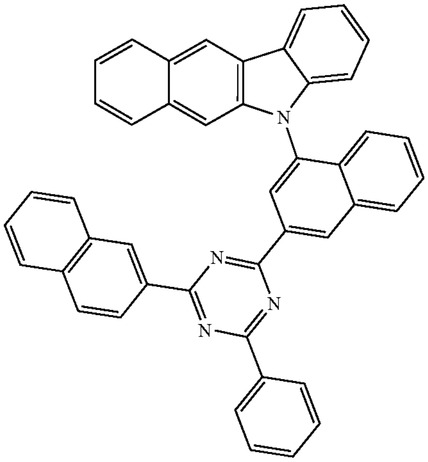
H2-93
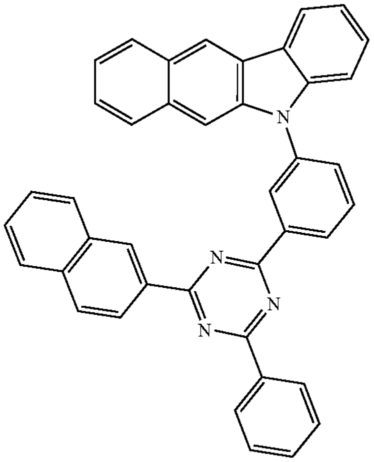

-continued
H2-94
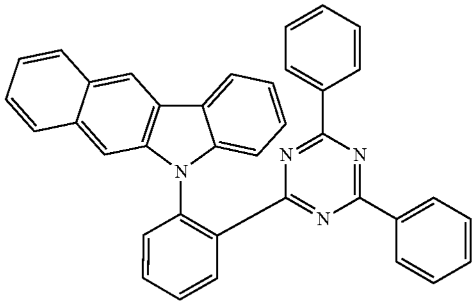
H2-95
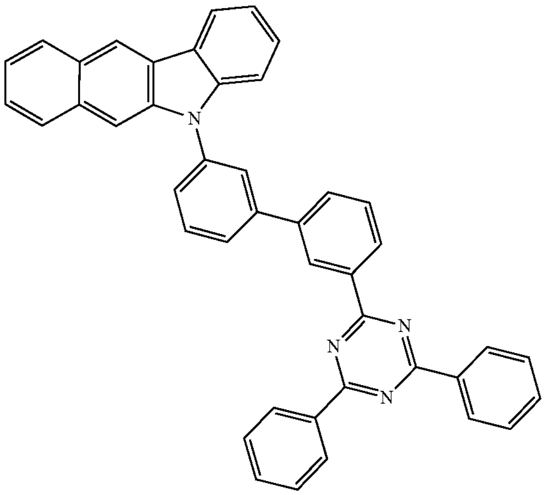
H2-96
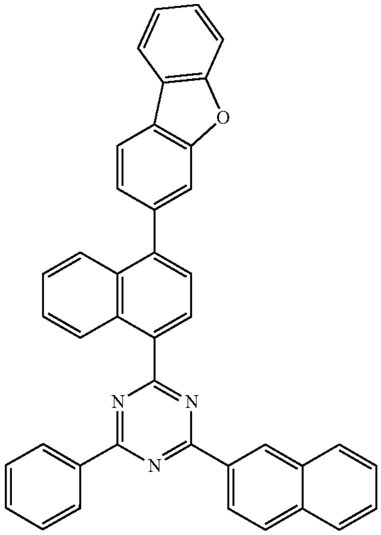
-continued
H2-97
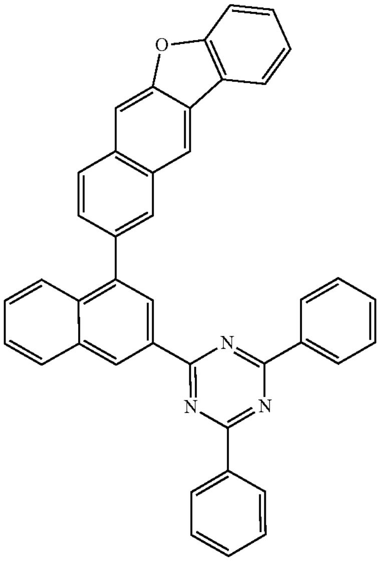
H2-98
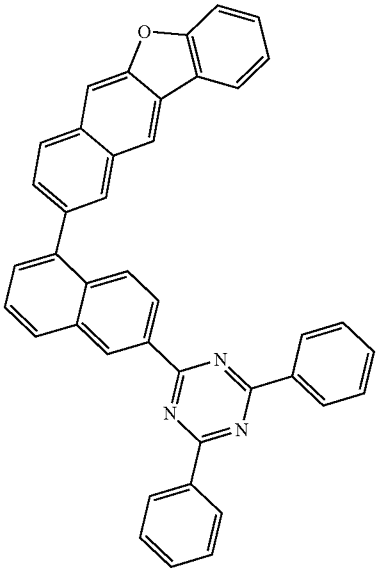
H2-99
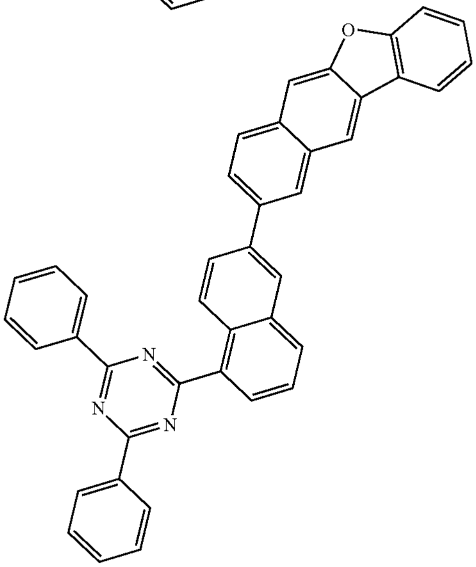

-continued
H2-100
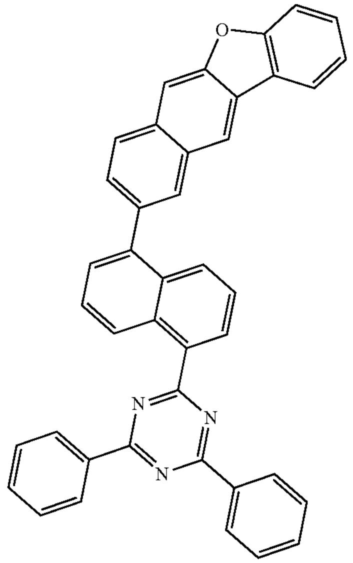
H2-101
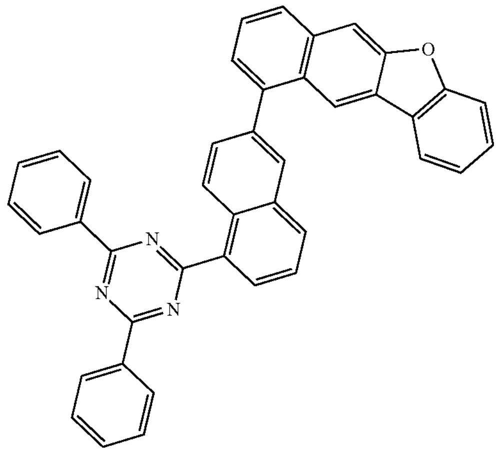
H2-102
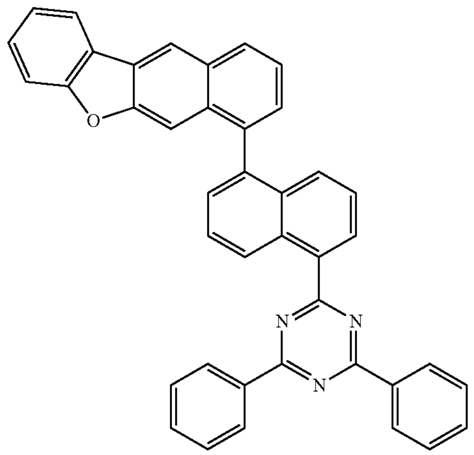
-continued
H2-103
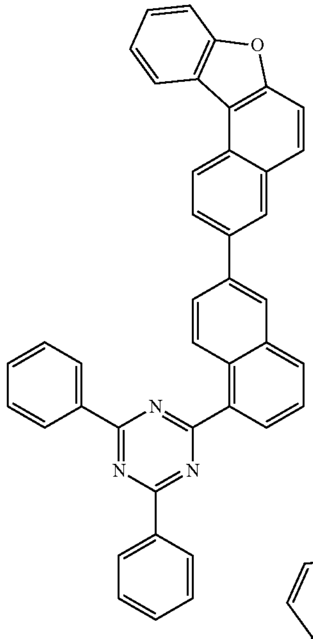
H2-104
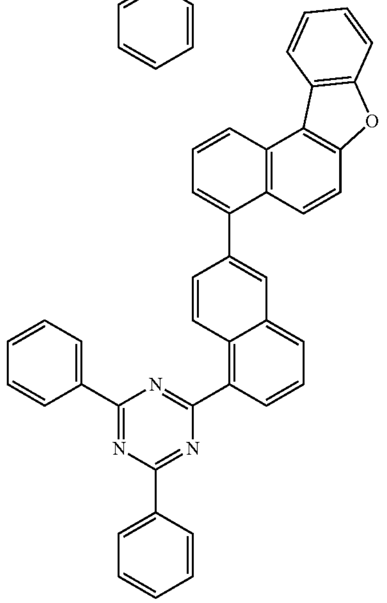
H2-105
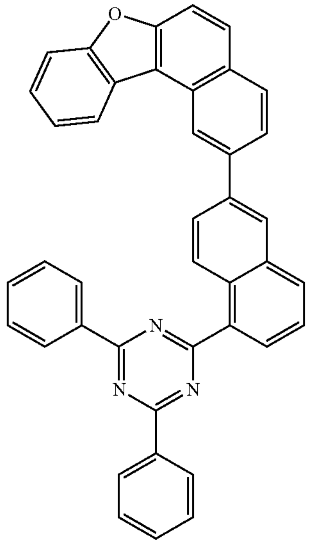

-continued
H2-106
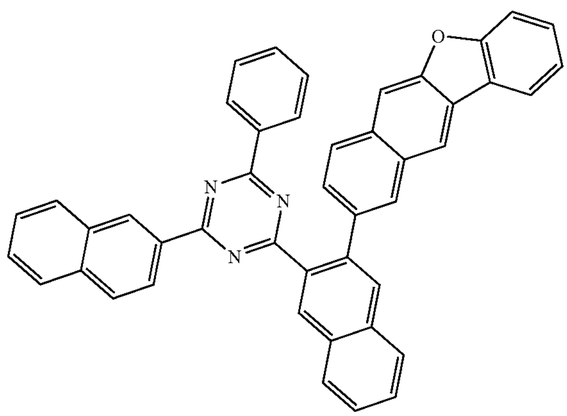
H2-107
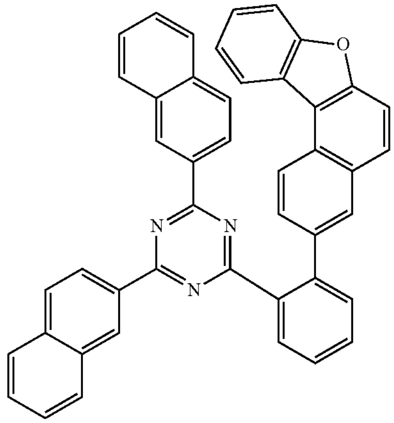
H2-108
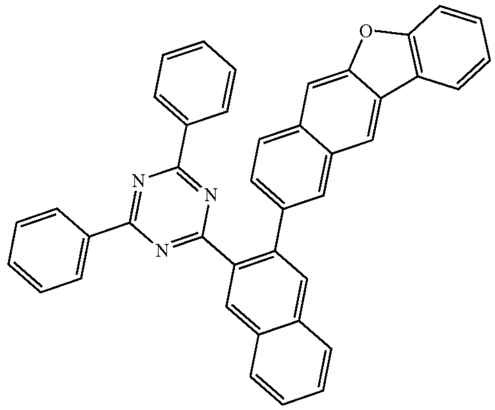
H2-109
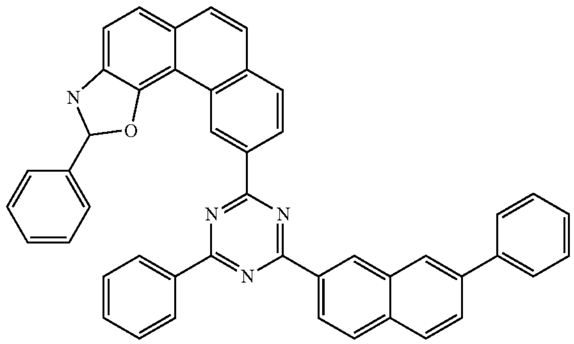
-continued
H2-110
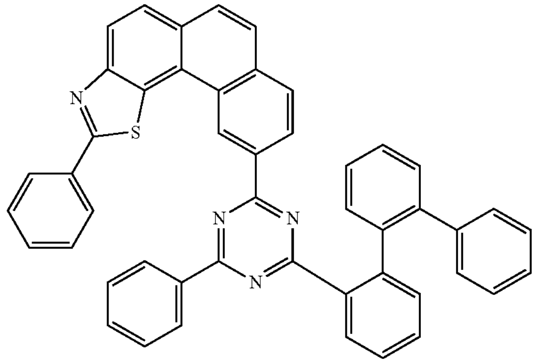
H2-111
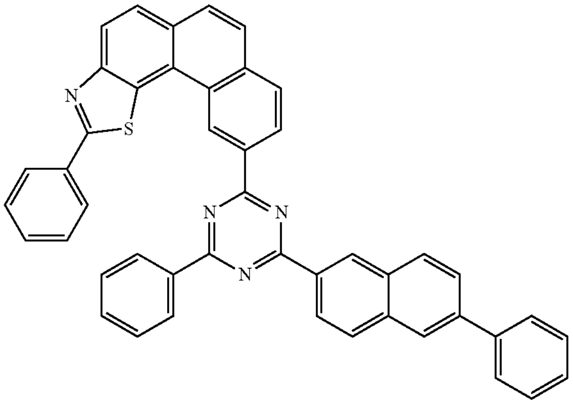
H2-112
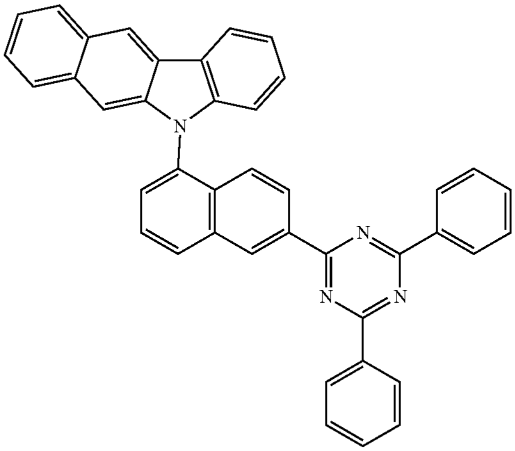

-continued
H2-113
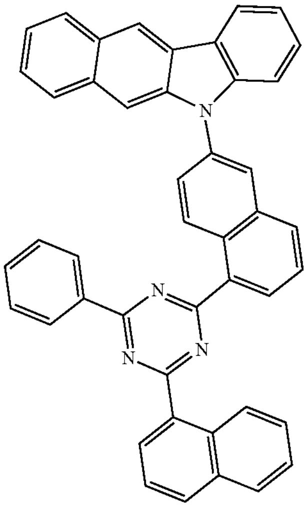
H2-114
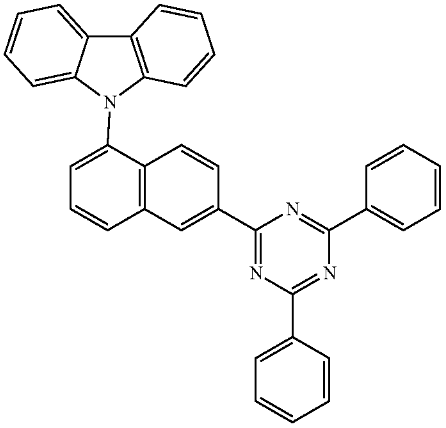
H2-115
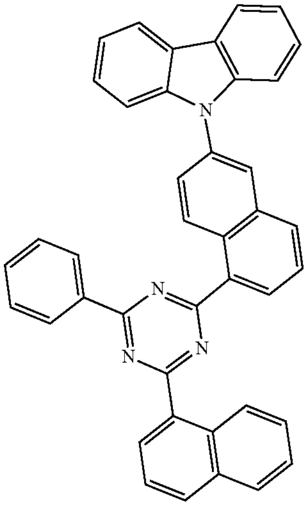
-continued
H2-116
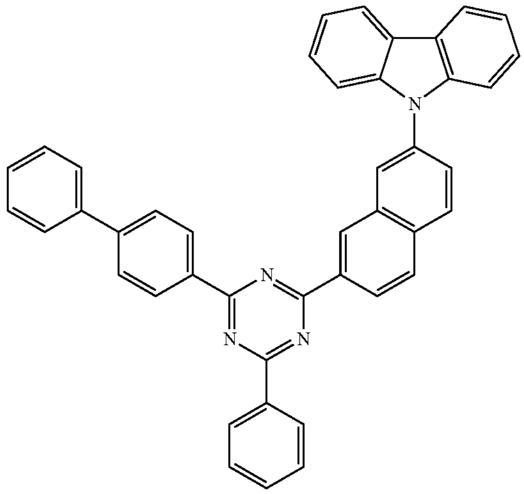
H2-117
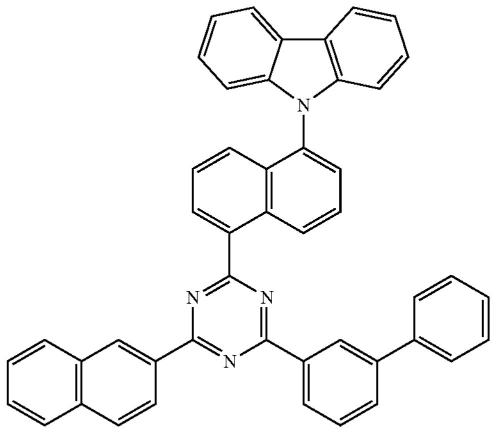
H2-118
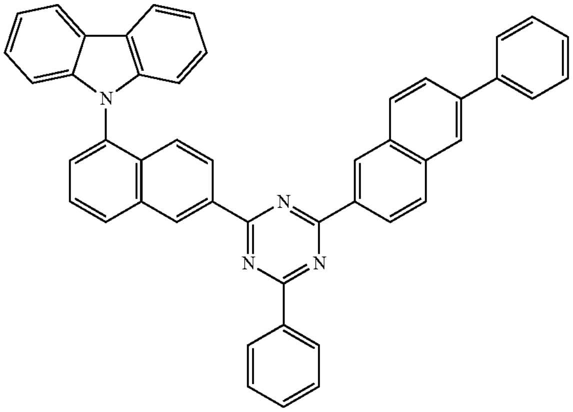

-continued
H2-119
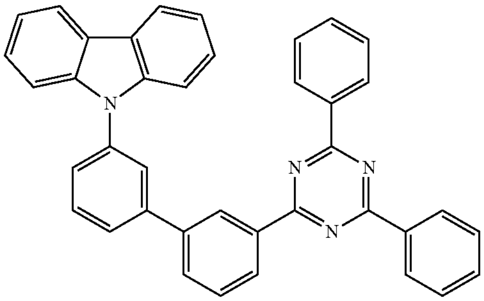
H2-120
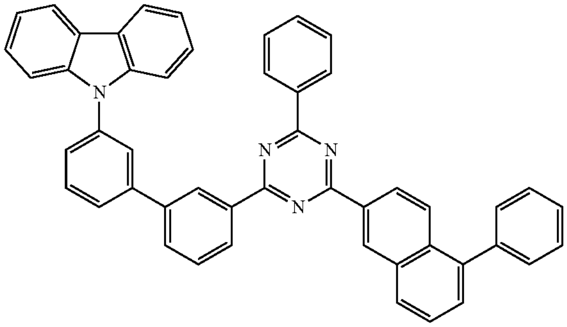
H2-121
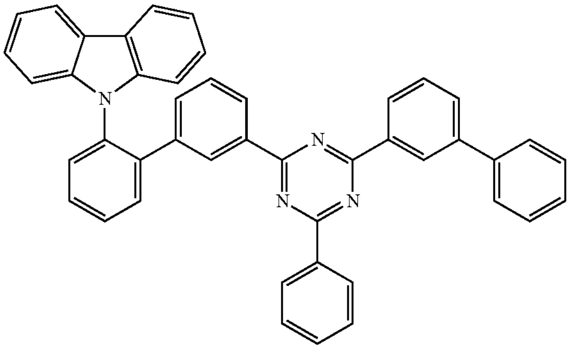
H2-122
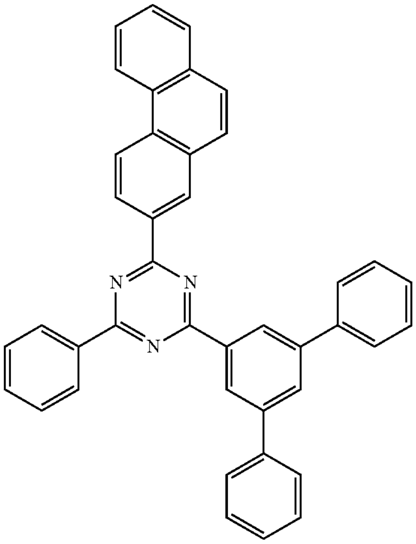
-continued
H2-123
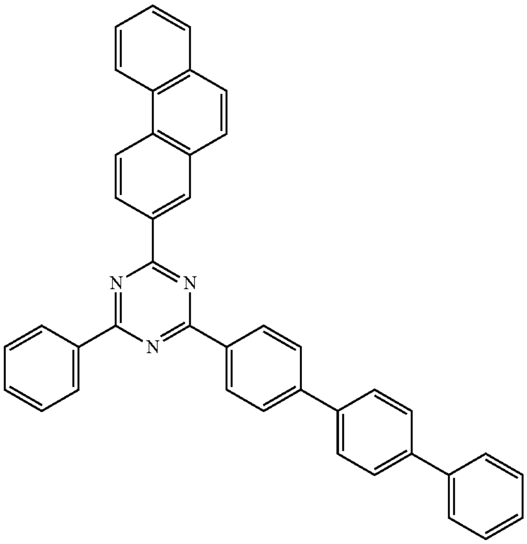
H2-124
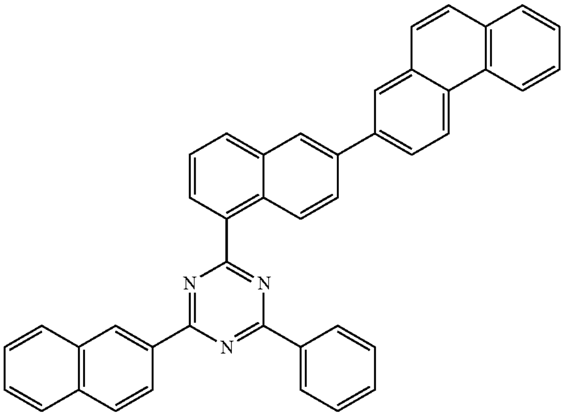
H2-125
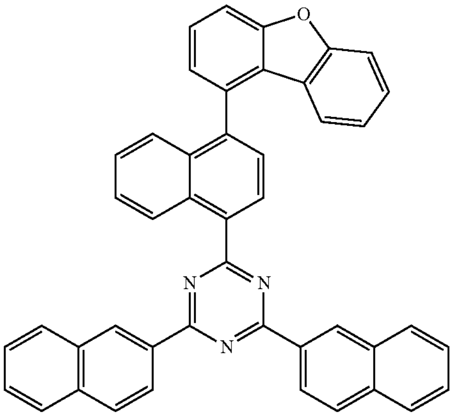

-continued
H2-126
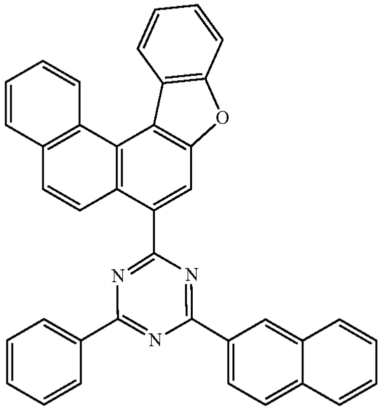
H2-127
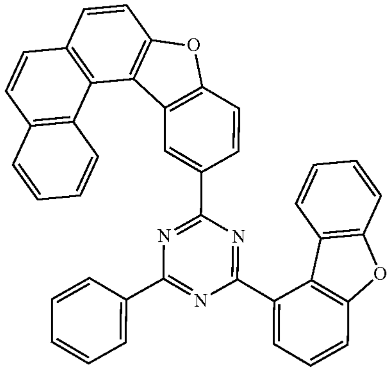
H2-128
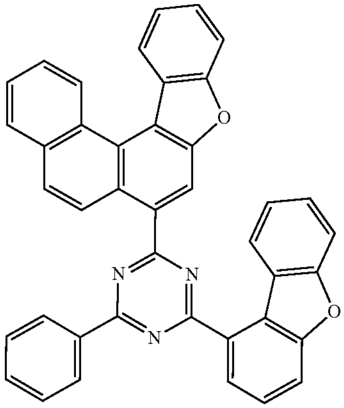
-continued
H2-129
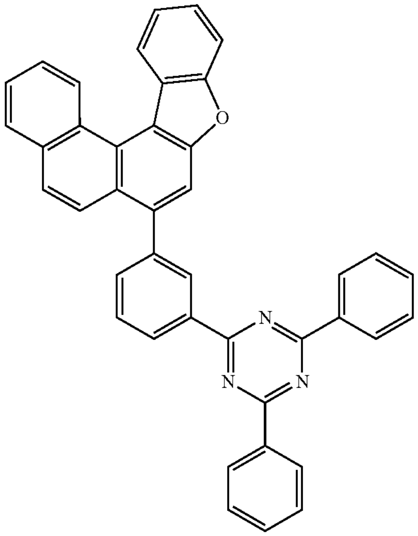
H2-130
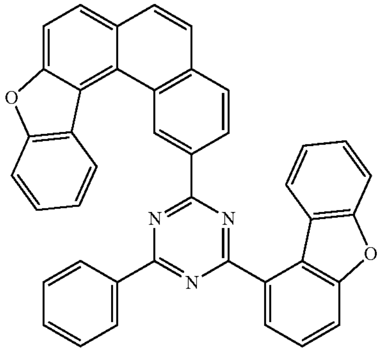
H2-131
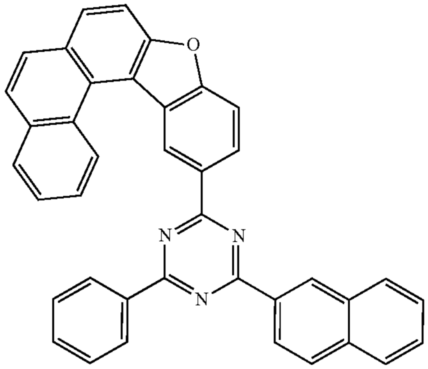
H2-132
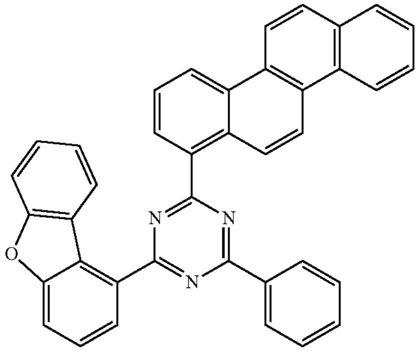

-continued
H2-133
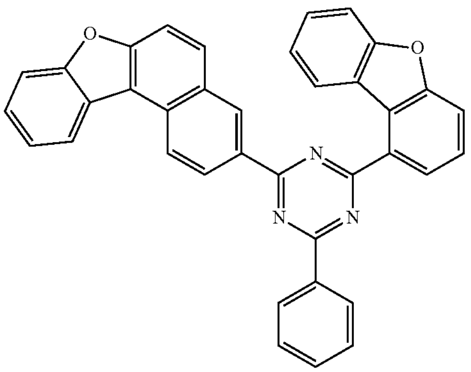
H2-134
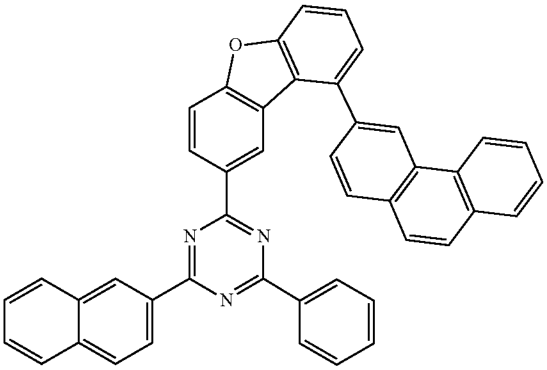
H2-135
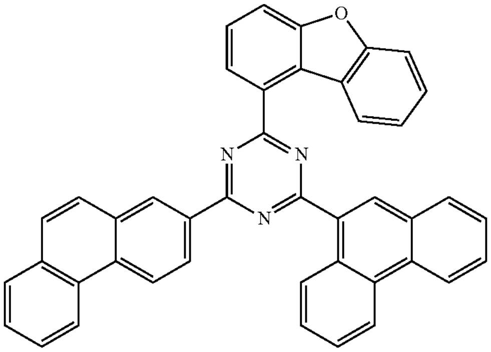
H2-136
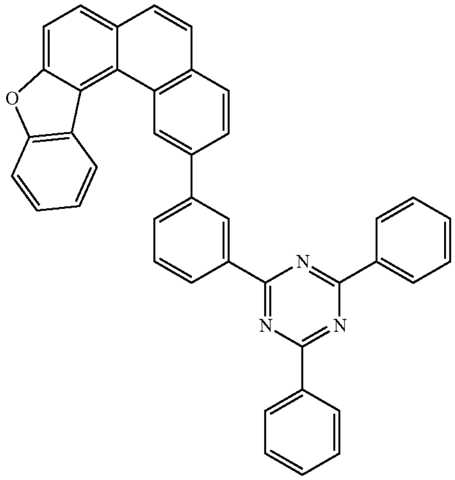
-continued
H2-137
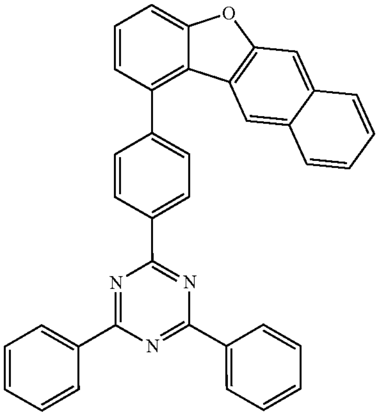
H2-138
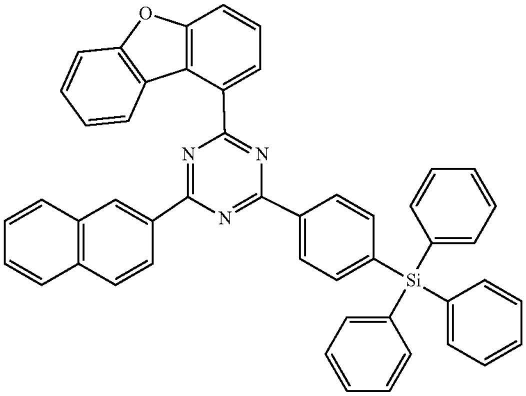
H2-139
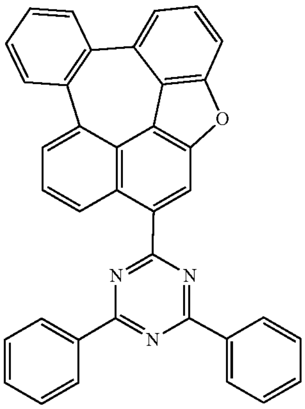

-continued
H2-140
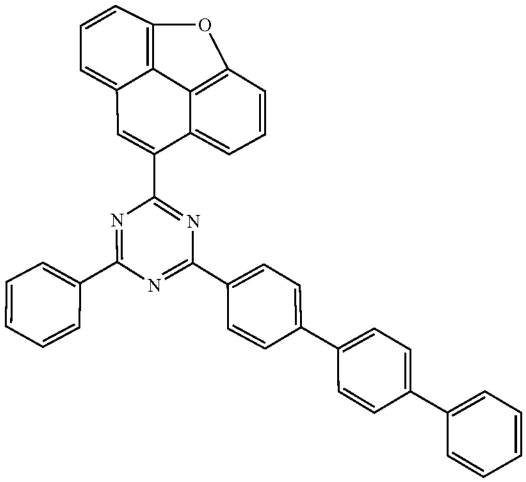
H2-141
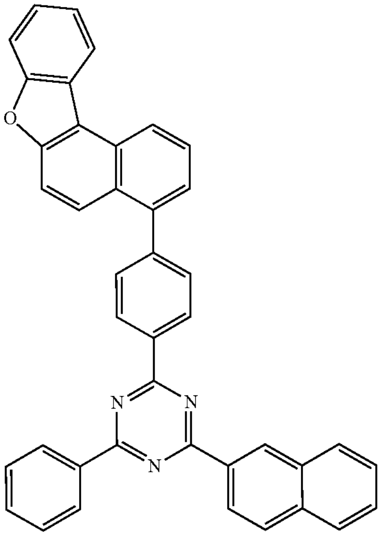
H2-142
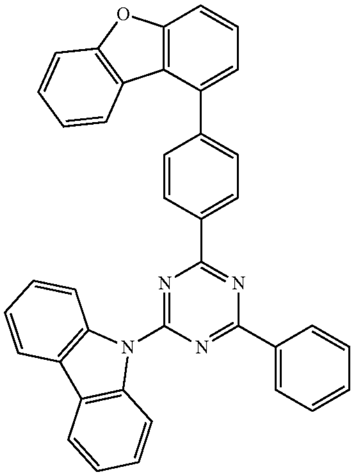
-continued
H2-143
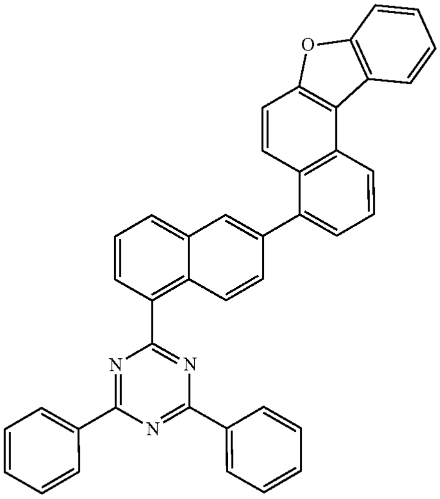
H2-144
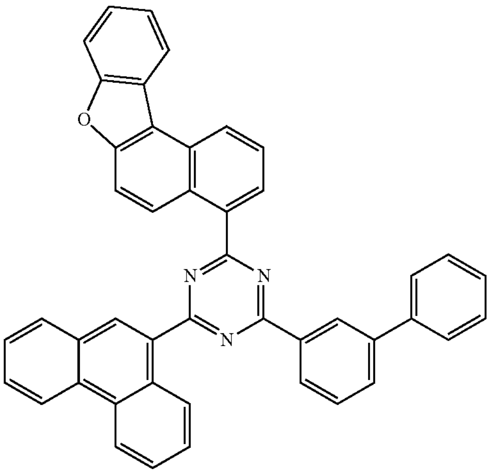
and
H2-145
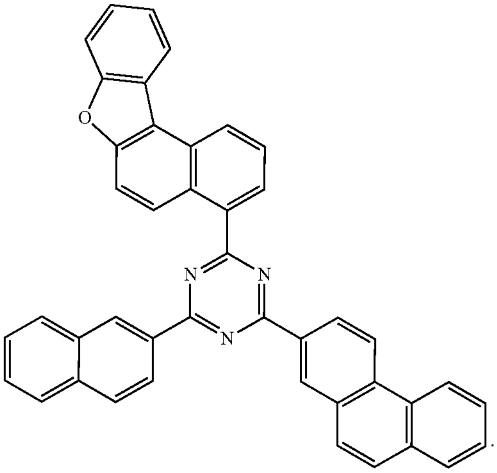
6. An organic electroluminescent device comprising: an anode; a cathode; and at least one light-emitting layer(s) between the anode and the cathode, wherein the at least one light-emitting layer(s) comprises the plurality of host materials according to claim 1.
* * * * *